US012747457B2

(12) United States Patent
Jakimo et al.

(10) Patent No.: US 12,747,457 B2
(45) Date of Patent: Sep. 29, 2026

(54) COMPOSITIONS COMPRISING A CAS12I POLYPEPTIDE AND USES THEREOF

(71) Applicant: ARBOR BIOTECHNOLOGIES, INC., Cambridge, MA (US)

(72) Inventors: Noah Michael Jakimo, Cambridge, MA (US); Pratyusha Hunnewell, Needham, MA (US); Brendan Jay Hilbert, Natick, MA (US); David A. Scott, San Francisco, CA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 677 days.

(21) Appl. No.: 17/931,027

(22) Filed: Sep. 9, 2022

(65) Prior Publication Data

US 2023/0287456 A1 Sep. 14, 2023

Related U.S. Application Data

(60) Provisional application No. 63/270,513, filed on Oct. 21, 2021, provisional application No. 63/242,940, filed on Sep. 10, 2021.

(51) Int. Cl.

| | |
|---|---|
| ***C12N 9/22*** | (2006.01) |
| ***C12N 9/78*** | (2006.01) |
| ***C12N 15/11*** | (2006.01) |
| ***C12N 15/90*** | (2006.01) |

(52) U.S. Cl.

CPC ............. *C12N 15/907* (2013.01); *C12N 9/22* (2013.01); *C12N 9/78* (2013.01); *C12N 15/11* (2013.01); *C12Y 301/21001* (2013.01); *C12Y 305/04004* (2013.01); *C07K 2319/00* (2013.01); *C07K 2319/09* (2013.01); *C12N 2310/20* (2017.05)

(58) Field of Classification Search

CPC ........ C12Y 305/04004; C07K 2319/00; C12N 2310/20

See application file for complete search history.

(56) References Cited

U.S. PATENT DOCUMENTS

| | | | |
|---|---|---|---|
| 10,808,245 | B2 | 10/2020 | Chong et al. |
| 2021/0017506 | A1 | 1/2021 | Guffy et al. |
| 2021/0261955 | A1 | 8/2021 | Slaymaker et al. |

FOREIGN PATENT DOCUMENTS

| | | | | |
|---|---|---|---|---|
| CN | 113151215 | A * | 7/2021 | C12N 15/113 |
| WO | 2019178427 | A1 | 9/2019 | |
| WO | WO-2019226953 | A1 * | 11/2019 | A61K 31/713 |
| WO | WO-2021202800 | A1 * | 10/2021 | C12N 15/102 |

OTHER PUBLICATIONS

CN-113151215-A English Translation (Year: 2021).*

(Continued)

*Primary Examiner* — Kimberly Chong
*Assistant Examiner* — Africa M Mcleod
(74) *Attorney, Agent, or Firm* — K&L Gates LLP

(57) ABSTRACT

The present invention relates to compositions comprising a Cas12i polypeptide, a deaminase polypeptide, and an RNA guide, processes for characterizing the compositions, cells comprising the compositions, Cas12i fusion proteins, Cas12i complexes, and methods of using the compositions.

42 Claims, 19 Drawing Sheets

Specification includes a Sequence Listing.

(56) References Cited

OTHER PUBLICATIONS

Yan, Fancheng, et al. "CRISPR-Cas12 and Cas13: The Lesser Known Siblings of CRISPR-Cas9." Cell Biology and Toxicology, vol. 35, Aug. 29, 2019, https://doi.org/10.1007/s10565-019-09489-1. (Year: 2019).*

Aronsson et al., "Self-sorting heterdimeric coiled coil peptides with defined and tuneable self-assembly properties," Sci Rep (2015) vol. 5, Article 14063, 10 pages.

Chen et al., "Fusion Protein Linkers: Property, Design and Functionality," Adv Drug Deliv Rev (2013) vol. 65, No. 10, pp. 1357-1369.

George et al., "An analysis of protein domain linkers: their classification and role in protein folding," Protein Engineering (2003) vol. 15, No. 11, pp. 871-879.

International Search Report and Written Opinion issued in PCT/US2022/076216, mailed Jul. 20, 2023, 13 pages.

Van Rosmalen et al., "Tuning the Flexibility of Glycine-Serine Linkers to Allow Rational Design of Multidomain Proteins," Biochemistry (2017) vol. 56, pp. 6565-6574.

Yan et al., "Functionally diverse type V CRISPR-Cas systems," Science 363(6422):88-91 (Dec. 2018).

* cited by examiner

SEQUENCE LISTING

```
Sequence total quantity: 141
SEQ ID NO: 1          moltype = DNA  length = 3162
FEATURE               Location/Qualifiers
source                1..3162
                      mol_type = other DNA
                      organism = synthetic construct
SEQUENCE: 1
atgagcagcg cgatcaaaag ctacaagagc gttctgcgtc cgaacgagcg taagaaccaa  60
ctgctgaaaa gcaccattca gtgcctggaa gacggtagcg cgttcttttt caagatgctg  120
caaggcctgt ttggtggcat caccccggag attgttcgtt tcagcaccga acaggagaaa  180
cagcaacagg atatcgcgct gtggtgcgcg gttaactggt tccgtccggt gagccaagac  240
agcctgaccc acaccattgc gagcgataac ctggtggaga agtttgagga atactatggt  300
ggcaccgcga gcgacgcgat caaacagtac ttcagcgcga gcattggcga aagctactat  360
tggaacgact gccgtcaaca gtactatgat ctgtgccgtg agctgggtgt tgaggtgagc  420
gacctgaccc atgatctgga gatcctgtgc cgtgaaaagt gcctggcggt tgcgaccgag  480
agcaaccaga acaacagcat cattagcgtt ctgtttggca ccggcgaaaa agaggaccgt  540
agcgtgaaac tgcgtatcac caagaaaatt ctggaggcga tcagcaacct gaaagaaatc  600
ccgaagaacg ttgcgccgat tcaagagatc attctgaacg tggcgaaagc gaccaaggaa  660
accttccgtc aggtgtatgc gggtaacctg ggtgcgccga gcaccctgga gaaatttatc  720
gcgaaggacg gccaaaaaga gttcgatctg aagaaactgc agaccgacct gaagaaagtt  780
attcgtggta aaagcaagga gcgtgattgg tgctgccagg aagagctgcg tagctacgtg  840
gagcaaaaca ccatccagta tgacctgtgg gcgtggggcg aaatgttcaa caaagcgcac  900
accgcgctga aatcaagag cacccgtaac tacaactttg cgaagcaacg tctggaacag  960
ttcaaagaga ttcagagcct gaacaacctg ctggttgtga agaagctgaa cgactttttc  1020
gatagcgaat ttttcagcgg cgaggaaacc tacaccatct gcgttcacca tctgggtggc  1080
aaggacctga gcaaactgta taaggcgtgg gaggatgatc cggcggaccc ggaaaacgcg  1140
attgtggttc tgtgcgacga tctgaaaaac aactttaaga aagagccgat ccgtaacatt  1200
ctgcgttaca tcttcaccat tcgtcaagaa tgcagcgcgc aggacatcct ggcggcggcg  1260
aagtacaacc aacagctgga tcgttataaa agccaaaagg cgaacccgag cgttctgggt  1320
aaccagggct ttacctggac caacgcggtg atcctgccgg agaaggcgca gcgtaacgac  1380
cgtccgaaca gcctggatct gcgtatttgg ctgtacctga aactgcgtca cccggacggt  1440
cgttggaaga aacaccatat cccgttctac gatacccgtt tcttccaaga aatttatgcg  1500
gcgggcaaca gcccggttga cacctgccag tttcgtaccc cgcgtttcgg ttatcacctg  1560
```

-continued

```
ccgaaactga ccgatcagac cgcgatccgt gttaacaaga aacatgtgaa agcggcgaag  1620
accgaggcgc gtattcgtct ggcgatccaa cagggcaccc tgccggtgag caacctgaag  1680
atcaccgaaa ttagcgcgac catcaacagc aaaggtcaag tgcgtattcc ggttaagttt  1740
gacgtgggtc gtcaaaaagg caccctgcag atcggtgacc gtttctgcgg ctacgatcaa  1800
aaccagaccg cgagccacgc gtatagcctg tgggaagtgg ttaaagaggg tcaataccat  1860
aaagagctgg gctgctttgt tcgtttcatc agcagcggtg acatcgtgag cattaccgag  1920
aaccgtggca accaatttga tcagctgagc tatgaaggtc tggcgtaccc gcaatatgcg  1980
gactggcgta agaaagcgag caagttcgtg agcctgtggc agatcaccaa gaaaaacaag  2040
aaaaaggaaa tcgtgaccgt tgaagcgaaa gagaagtttg acgcgatctg caagtaccag  2100
ccgcgtctgt ataaattcaa caaggagtac gcgtatctgc tgcgtgatat tgttcgtggc  2160
aaaagcctgg tggaactgca acagattcgt caagagatct ttcgtttcat tgaacaggac  2220
tgcggtgtta cccgtctggg cagcctgagc ctgagcaccc tggaaaccgt gaaagcggtt  2280
aagggtatca tttacagcta ttttagcacc gcgctgaacg cgagcaagaa caacccgatc  2340
agcgacgaac agcgtaaaga gtttgatccg gaactgttcg cgctgctgga aaagctggag  2400
ctgattcgta cccgtaaaaa gaaacaaaaa gtggaacgta tcgcgaacag cctgattcag  2460
acctgcctgg agaacaacat caagttcatt cgtggtgaag gcgacctgag caccaccaac  2520
aacgcgacca agaaaaaggc gaacagccgt agcatggatt ggttggcgcg tggtgttttt  2580
aacaaaatcc gtcaactggc gccgatgcac aacattaccc tgttcggttg cggcagcctg  2640
tacaccagcc accaggaccc gctggtgcat cgtaacccgg ataaagcgat gaagtgccgt  2700
tgggcggcga tcccggttaa ggacattggc gattgggtgc tgcgtaagct gagccaaaac  2760
ctgcgtgcga aaaacatcgg caccggcgag tactatcacc aaggtgttaa agagttcctg  2820
agccattatg aactgcagga cctggaggaa gagctgctga agtggcgtag cgatcgtaaa  2880
agcaacattc cgtgctgggt gctgcagaac cgtctggcgg agaagctggg caacaaagaa  2940
gcggtggttt acatcccggt tcgtggtggc cgtatttatt ttgcgaccca caaggtggcg  3000
accggtgcgg tgagcatcgt tttcgaccaa aaacaagtgt gggtttgcaa cgcggatcat  3060
gttgcggcgg cgaacatcgc gctgaccgtg aagggtattg gcgaacaaag cagcgacgaa  3120
gagaacccgg atggtagccg tatcaaactg cagctgacca gc                    3162

SEQ ID NO: 2           moltype = AA  length = 1054
FEATURE                Location/Qualifiers
source                 1..1054
                       mol_type = protein
                       organism = synthetic construct
SEQUENCE: 2
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNIGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTV KGIGEQSSDE ENPDGSRIKL QLTS                              1054

SEQ ID NO: 3           moltype = AA  length = 1054
FEATURE                Location/Qualifiers
source                 1..1054
                       mol_type = protein
                       organism = synthetic construct
SEQUENCE: 3
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG RWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGEQSSDE ENPDGSRIKL QLTS                              1054

SEQ ID NO: 4           moltype = AA  length = 1054
```

```
FEATURE                Location/Qualifiers
source                 1..1054
                       mol_type = protein
                       organism = synthetic construct
SEQUENCE: 4
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGEQSSDE ENPDGSRIKL QLTS                             1054

SEQ ID NO: 5           moltype = AA  length = 1054
FEATURE                Location/Qualifiers
source                 1..1054
                       mol_type = protein
                       organism = synthetic construct
SEQUENCE: 5
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGEQSSDE ENPDGGRIKL QLTS                             1054

SEQ ID NO: 6           moltype = AA  length = 1054
FEATURE                Location/Qualifiers
source                 1..1054
                       mol_type = protein
                       organism = synthetic construct
SEQUENCE: 6
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELRCRVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGRQSSDE ENPDGGRIKL QLTS                             1054

SEQ ID NO: 7           moltype = AA  length = 1054
FEATURE                Location/Qualifiers
source                 1..1054
                       mol_type = protein
                       organism = synthetic construct
```

-continued

```
SEQUENCE: 7
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELRCRVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLATMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGRQSSDE ENPDGGRIKL QLTS                              1054

SEQ ID NO: 8           moltype = AA  length = 1093
FEATURE                Location/Qualifiers
source                 1..1093
                       mol_type = protein
                       organism = synthetic construct
SEQUENCE: 8
MSNKEKNASE TRKAYTTKMI PRSHDRMKLL GNFMDYLMDG TPIFFELWNQ FGGGIDRDII  60
SGTANKDKIS DDLLLAVNWF KVMPINSKPQ GVSPSNLANL FQQYSGSEPD IQAQEYFASN  120
FDTEKHQWKD MRVEYERLLA ELQLSRSDMH HDLKLMYKEK CIGLSLSTAH YITSVMFGTG  180
AKNNRQTKHQ FYSKVIQLLE ESTQINSVEQ LASIILKAGD CDSYRKLRIR CSRKGATPSI  240
LKIVQDYELG TNHDDEVNVP SLIANLKEKL GRFEYECEWK CMEKIKAFLA SKVGPYYLGS  300
YSAMLENALS PIKGMTTKNC KFVLKQIDAK NDIKYENEPF GKIVEGFFDS PYFESDTNVK  360
WVLHPHHIGE SNIKTLWEDL NAIHSKYEED IASLSEDKKE KRIKVYQGDV CQTINTYCEE  420
VGKEAKTPLV QLLRYLYSRK DDIAVDKIID GITFLSKKHK VEKQKINPVI QKYPSFNFGN  480
NSKLLGKIIS PKDKLKHNLK CNRNQVDNYI WIEIKVLNTK TMRWEKHHYA LSSTRFLEEV  540
YYPATSENPP DALAARFRTK TNGYEGKPAL SAEQIEQIRS APVGLRKVKK RQMRLEAARQ  600
QNLLPRYTWG KDFNINICKR GNNFEVTLAT KVKKKKEKNY KVVLGYDANI VRKNTYAAIE  660
AHANGDGVID YNDLPVKPIE SGFVTVESQV RDKSYDQLSY NGVKLLYCKP HVESRRSFLE  720
KYRNGTMKDN RGNNIQIDFM KDFEAIADDE TSLYYFNMKY CKLLQSSIRN HSSQAKEYRE  780
EIFELLRDGK LSVLKLSSLS NLSFVMFKVA KSLIGTYFGH LLKKPKNSKS DVKAPPITDE  840
DKQKADPEMF ALRLALEEKR LNKVKSKKEV IANKIVAKAL ELRDKYGPVL IKGENISDTT  900
KKGKKSSTNS FLMDWLARGV ANKVKEMVMM HQGLEFVEVN PNFTSHQDPF VHKNPENTFR  960
ARYSRCTPSE LTEKNRKEIL SFLSDKPSKR PTNAYYNEGA MAFLATYGLK KNDVLGVSLE  1020
KFKQIMANIL HQRSEDQLLF PSRGGMFYLA TYKLDADATS VNWNGKQFWV CNADLVAAYN  1080
VGLVDIQKDF KKK                                                     1093

SEQ ID NO: 9           moltype = AA  length = 1074
FEATURE                Location/Qualifiers
source                 1..1074
                       mol_type = protein
                       organism = synthetic construct
SEQUENCE: 9
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKTTN CSFMIKREND EYKLVINRKI SVDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 10          moltype = AA  length = 1074
FEATURE                Location/Qualifiers
source                 1..1074
                       mol_type = protein
                       organism = synthetic construct
SEQUENCE: 10
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
```

```
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 11          moltype = AA  length = 1098
FEATURE                Location/Qualifiers
source                 1..1098
                       mol_type = protein
                       organism = synthetic construct
SEQUENCE: 11
MSISNNNILP YNPKLLPDDR KHKMLVDTFN QLDLIRNNLH DMIIALYGAL KYDNIKQFAS  60
KEKPHISADA LCSINWFRLV KTNERKPAIE SNQIISKFIQ YSGHTPDKYA LSHITGNHEP  120
SHKWIDCREY AINYARIMHL SFSQFQDLAT ACLNCKILIL NGTLTSSWAW GANSALFGGS  180
DKENFSVKAK ILNSFIENLK DEMNTTKFQV VEKVCQQIGS SDAADLFDLY RSTVKDGNRG  240
PATGRNPKVM NLFSQDGEIS SEQREDFIES FQKVMQEKNS KQIIPHLDKL KYHLVKQSGL  300
YDIYSWAAAI KNANSTIVAS NSSNLNTILN KTEKQQTFEE LRKDEKIVAC SKILLSVNDT  360
LPEDLHYNPS TSNLGKNLDV FFDLLNENSV HTIENKEEKN KIVKECVNQY MEECKGLNKP  420
PMPVLLTFIS DYAHKHQAQD FLSAAKMNFI DLKIKSIKVV PTVHGSSPYT WISNLSKKNK  480
DGKMIRTPNS SLIGWIIPPE EIHDQKFAGQ NPIIWAVLRV YCNNKWEMHH FPFSDSRFFT  540
EVYAYKPNLP YLPGGENRSK RFGYRHSTNL SNESRQILLD KSKYAKANKS VLRCMENMTH  600
NVVFDPKTSL NIRIKTDKNN SPVLDDKGRI TFVMQINHRI LEKYNNTKIE IGDRILAYDQ  660
NQSENHTYAI LQRTEEGSHA HQFNGWYVRV LETGKVTSIV QGLSGPIDQL NYDGMPVTSH  720
KFNCWQADRS AFVSQFASLK ISETETFDEA YQAINAQGAY TWNLFYLRIL RKALRVCHME  780
NINQFREEIL AISKNRLSPM SLGSLSQNSL KMIRAFKSII NCYMSRMSFV DELQKKEGDL  840
ELHTIMRLTD NKLNDKRVEK INRASSFLTN KAHSMGCKMI VGESDLPVAD SKTSKKQNVD  900
RMDWCARALS HKVEYACKLM GLAYRGIPAY MSSHQDPLVH LVESKRSVLR PRFVVADKSD  960
VKQHHLDNLR RMLNSKTKVG TAVYYREAVE LMCEELGIHK TDMAKGKVSL SDFVDKFIGE  1020
KAIFPQRGGR FYMSTKRLTT GAKLICYSGS DVWLSDADEI AAINIGMFVV CDQTGAFKKK  1080
KKEKLDDEEC DILPFRPM                                                1098

SEQ ID NO: 12          moltype = RNA  length = 36
FEATURE                Location/Qualifiers
source                 1..36
                       mol_type = other RNA
                       organism = synthetic construct
SEQUENCE: 12
gttggaatga ctaatttttg tgcccaccgt tggcac                             36

SEQ ID NO: 13          moltype = RNA  length = 24
FEATURE                Location/Qualifiers
source                 1..24
                       mol_type = other RNA
                       organism = synthetic construct
SEQUENCE: 13
aatttttgtg cccatcgttg gcac                                          24

SEQ ID NO: 14          moltype = RNA  length = 23
FEATURE                Location/Qualifiers
source                 1..23
                       mol_type = other RNA
                       organism = synthetic construct
SEQUENCE: 14
atttttgtgc ccatcgttgg cac                                           23

SEQ ID NO: 15          moltype = RNA  length = 36
FEATURE                Location/Qualifiers
source                 1..36
                       mol_type = other RNA
                       organism = synthetic construct
SEQUENCE: 15
gttgcaaaac ccaagaaatc cgtctttcat tgacgg                             36

SEQ ID NO: 16          moltype = RNA  length = 34
FEATURE                Location/Qualifiers
source                 1..34
                       mol_type = other RNA
```

```
                         organism = synthetic construct
SEQUENCE: 16
gcaacaccta agaaatccgt ctttcattga cggg                           34

SEQ ID NO: 17            moltype = RNA  length = 23
FEATURE                  Location/Qualifiers
source                   1..23
                         mol_type = other RNA
                         organism = synthetic construct
SEQUENCE: 17
agaaatccgt ctttcattga cgg                                       23

SEQ ID NO: 18            moltype = RNA  length = 36
FEATURE                  Location/Qualifiers
source                   1..36
                         mol_type = other RNA
                         organism = synthetic construct
SEQUENCE: 18
ctagcaatga cctaatagtg tgtccttagt tgacat                         36

SEQ ID NO: 19            moltype = RNA  length = 36
FEATURE                  Location/Qualifiers
source                   1..36
                         mol_type = other RNA
                         organism = synthetic construct
SEQUENCE: 19
cctacaatac ctaagaaatc cgtcctaagt tgacgg                         36

SEQ ID NO: 20            moltype = RNA  length = 22
FEATURE                  Location/Qualifiers
source                   1..22
                         mol_type = other RNA
                         organism = synthetic construct
SEQUENCE: 20
atagtgtgtc cttagttgac at                                        22

SEQ ID NO: 21            moltype = RNA  length = 36
FEATURE                  Location/Qualifiers
source                   1..36
                         mol_type = other RNA
                         organism = synthetic construct
SEQUENCE: 21
gttggaatga ctaattttg tgcccaccgt tggcac                          36

SEQ ID NO: 22            moltype = RNA  length = 36
FEATURE                  Location/Qualifiers
source                   1..36
                         mol_type = other RNA
                         organism = synthetic construct
SEQUENCE: 22
cccacaatac ctgagaaatc cgtcctacgt tgacgg                         36

SEQ ID NO: 23            moltype = RNA  length = 36
FEATURE                  Location/Qualifiers
source                   1..36
                         mol_type = other RNA
                         organism = synthetic construct
SEQUENCE: 23
tctcaacgat agtcagacat gtgtcctcag tgacac                         36

SEQ ID NO: 24            moltype = RNA  length = 22
FEATURE                  Location/Qualifiers
source                   1..22
                         mol_type = other RNA
                         organism = synthetic construct
SEQUENCE: 24
agacatgtgt cctcagtgac ac                                        22

SEQ ID NO: 25            moltype = AA  length = 1054
FEATURE                  Location/Qualifiers
source                   1..1054
                         mol_type = protein
                         organism = synthetic construct
SEQUENCE: 25
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
```

```
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYAQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGEQSSDE ENPDGSRIKL QLTS                             1054

SEQ ID NO: 26          moltype = AA  length = 1368
FEATURE                Location/Qualifiers
source                 1..1368
                       mol_type = protein
                       organism = synthetic construct
SEQUENCE: 26
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 27          moltype = AA  length = 1368
FEATURE                Location/Qualifiers
source                 1..1368
                       mol_type = protein
                       organism = synthetic construct
SEQUENCE: 27
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 28          moltype = AA  length = 176
FEATURE                Location/Qualifiers
source                 1..176
                       mol_type = protein
                       organism = synthetic construct
```

```
SEQUENCE: 28
MDPATFTYQF KNVRWAKGRR ETYLCYVVKR RDSATSFSLD FGYLRNKNGC HVELLFLRYI  60
SDWDLDPGRC YRVTWFTSWS PCYDCARHVA DFLRGNPNLS LRIFTARLYF CEDRKAEPEG  120
LRRLAEAGVQ IAIMTFKDYF YCWNTFVENH ERTFKAWEGL HENSVRLSRQ LRRILQ      176

SEQ ID NO: 29           moltype = AA  length = 199
FEATURE                 Location/Qualifiers
source                  1..199
                        mol_type = protein
                        organism = synthetic construct
SEQUENCE: 29
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSAGCAGEV RAFLQENTHV  120
RLRIFAARIY DYDYLYKEAL QMLRDAGAQV SIMTYDEFKH CWDTFVDHQG CPFQPWDGLD  180
EHSQALSGRL RAILQNQGN                                              199

SEQ ID NO: 30           moltype = AA  length = 167
FEATURE                 Location/Qualifiers
source                  1..167
                        mol_type = protein
                        organism = synthetic construct
SEQUENCE: 30
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD                167

SEQ ID NO: 31           moltype = AA  length = 84
FEATURE                 Location/Qualifiers
source                  1..84
                        mol_type = protein
                        organism = synthetic construct
SEQUENCE: 31
MTNLSDIIEK ETGKQLVIQE SILMLPEEVE EVIGNKPESD ILVHTAYDES TDENVMLLTS  60
DAPEYKPWAL VIQDSNGENK IKML                                        84

SEQ ID NO: 32           moltype = AA  length = 4
FEATURE                 Location/Qualifiers
source                  1..4
                        mol_type = protein
                        organism = synthetic construct
SEQUENCE: 32
SGGS                                                              4

SEQ ID NO: 33           moltype = AA  length = 7
FEATURE                 Location/Qualifiers
source                  1..7
                        mol_type = protein
                        organism = synthetic construct
SEQUENCE: 33
PKKKRKV                                                           7

SEQ ID NO: 34           moltype = AA  length = 14
FEATURE                 Location/Qualifiers
source                  1..14
                        mol_type = protein
                        organism = synthetic construct
SEQUENCE: 34
MKIEEGKGHH HHHH                                                   14

SEQ ID NO: 35           moltype = AA  length = 15
FEATURE                 Location/Qualifiers
source                  1..15
                        mol_type = protein
                        organism = synthetic construct
SEQUENCE: 35
GGGGSGGGGS GGGGS                                                  15

SEQ ID NO: 36           moltype = AA  length = 16
FEATURE                 Location/Qualifiers
source                  1..16
                        mol_type = protein
                        organism = synthetic construct
SEQUENCE: 36
KRPAATKKAG QAKKKK                                                 16

SEQ ID NO: 37           moltype = AA  length = 18
FEATURE                 Location/Qualifiers
source                  1..18
                        mol_type = protein
```

```
                      organism = synthetic construct
SEQUENCE: 37
EGRGSLLTCG DVEENPGP                                             18

SEQ ID NO: 38         moltype = AA  length = 19
FEATURE               Location/Qualifiers
source                1..19
                      mol_type = protein
                      organism = synthetic construct
SEQUENCE: 38
MKRTADGSEF ESPKKKRKV                                            19

SEQ ID NO: 39         moltype = AA  length = 19
FEATURE               Location/Qualifiers
source                1..19
                      mol_type = protein
                      organism = synthetic construct
SEQUENCE: 39
ATNFSLLKQA GDVEENPGP                                            19

SEQ ID NO: 40         moltype = AA  length = 32
FEATURE               Location/Qualifiers
source                1..32
                      mol_type = protein
                      organism = synthetic construct
SEQUENCE: 40
SGGSSGGSSG SETPGTSESA TPESSGGSSG GS                             32

SEQ ID NO: 41         moltype = AA  length = 1385
FEATURE               Location/Qualifiers
source                1..1385
                      mol_type = protein
                      organism = synthetic construct
SEQUENCE: 41
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSM TNLSDIIEKE TGKQLVIQES ILMLPEEVEE VIGNKPESDI  240
LVHTAYDEST DENVMLLTSD APEYKPWALV IQDSNGENKI KMLSGGSSGG SSGSETPGTS  300
ESATPESSGG SSGGSMSSAI KSYKSVLRPN ERKNQLLKST IQCLEDGSAF FFKMLQGLFG  360
GITPEIVRFS TEQEKQQQDI ALWCAVNWFR PVSQDSLTHT IASDNLVEKF EEYYGGTASD  420
AIKQYFSASI GESYYWNDCR QQYYDLCREL GVEVSDLTHD LEILCREKCL AVATESNQNN  480
SIISVLFGTG EKEDRSVKLR ITKKILEAIS NLKEIPKNVA PIQEIILNVA KATKETFRQV  540
YAGNLGAPST LEKFIAKDGQ KEFDLKKLQT DLKKVIRGKS KERDWCCQEE LRSYVEQNTI  600
QYDLWAWGEM FNKAHTALKI KSTRNYNFAK QRLEQFKEIQ SLNNLLVVKK LNDFFDSEFF  660
SGEETYTICV HHLGGKDLSK LYKAWEDDPA DPENAIVVLC DDLKNNFKKE PIRNILRYIF  720
TIRQECSAQD ILAAAKYNQQ LDRYKSQKAN PSVLGNQGFT WTNAVILPEK AQRNDRPNSL  780
DLRIWLYLKL RHPDGRWKKH HIPFYDTRFF QEIYAAGNSP VDTCQFRTPR FGYHLPKLTD  840
QTAIRVNKKH VKAAKTEARI RLAIQQGTLP VSNLKITEIS ATINSKGQVR IPVKFRVGRQ  900
KGTLQIGDRF CGYAQNQTAS HAYSLWEVVK EGQYHKELGC FVRFISSGDI VSITENRGNQ  960
FDQLSYEGLA YPQYADWRKK ASKFVSLWQI TKKNKKKEIV TVEAKEKFDA ICKYQPRLYK  1020
FNKEYAYLLR DIVRGKSLVE LQQIRQEIFR FIEQDCGVTR LGSLSLSTLE TVKAVKGIIY  1080
SYFSTALNAS KNNPISDEQR KEFDPELFAL LEKLELIRTR KKKQKVERIA NSLIQTCLEN  1140
NIKFIRGEGD LSTTNNATKK KANSRSMDWL ARGVFNKIRQ LAPMHNITLF GCGSLYTSHQ  1200
DPLVHRNPDK AMKCRWAAIP VKDIGDWVLR KLSQNLRAKN RGTGEYYHQG VKEFLSHYEL  1260
QDLEEELLKW RSDRKSNIPC WVLQNRLAEK LGNKEAVVYI PVRGGRIYFA THKVATGAVS  1320
IVFDQKQVWV CNADHVAAAN IALTGKGIGE QSSDEENPDG SRIKLQLTSK RPAATKKAGQ  1380
AKKKK                                                           1385

SEQ ID NO: 42         moltype = AA  length = 1396
FEATURE               Location/Qualifiers
source                1..1396
                      mol_type = protein
                      organism = synthetic construct
SEQUENCE: 42
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSS GGSSGSETPG TSESATPESS GGSSGGSMSS AIKSYKSVLR  240
PNERKNQLLK STIQCLEDGS AFFFKMLQGL FGGITPEIVR FSTEQEKQQQ DIALWCAVNW  300
FRPVSQDSLT HTIASDNLVE KFEEYYGGTA SDAIKQYFSA SIGESYYWND CRQQYYDLCR  360
ELGVEVSDLT HDLEILCREK CLAVATESNQ NNSIISVLFG TGEKEDRSVK LRITKKILEA  420
ISNLKEIPKN VAPIQEIILN VAKATKETFR QVYAGNLGAP STLEKFIAKD GQKEFDLKKL  480
QTDLKKVIRG KSKERDWCCQ EELRSYVEQN TIQYDLWAWG EMFNKAHTAL KIKSTRNYNF  540
AKQRLEQFKE IQSLNNLLVV KKLNDFFDSE FFSGEETYTI CVHHLGGKDL SKLYKAWEDD  600
PADPENAIVV LCDDLKNNFK KEPIRNILRY IFTIRQECSA QDILAAAKYN QQLDRYKSQK  660
ANPSVLGNQG FTWTNAVILP EKAQRNDRPN SLDLRIWLYL KLRHPDGRWK KHHIPFYDTR  720
FFQEIYAAGN SPVDTCQFRT PRFGYHLPKL TDQTAIRVNK KHVKAAKTEA RIRLAIQQGT  780
LPVSNLKITE ISATINSKGQ VRIPVKFRVG RQKGTLQIGD RFCGYAQNQT ASHAYSLWEV  840
```

VKEGQYHKEL GCFVRFISSG DIVSITENRG NQFDQLSYEG LAYPQYADWR KKASKFVSLW 900
QITKKNKKKE IVTVEAKEKF DAICKYQPRL YKFNKEYAYL LRDIVRGKSL VELQQIRQEI 960
FRFIEQDCGV TRLGSLSLST LETVKAVKGI IYSYFSTALN ASKNNPISDE QRKEFDPELF 1020
ALLEKLELIR TRKKKQKVER IANSLIQTCL ENNIKFIRGE GDLSTTNNAT KKKANSRSMD 1080
WLARGVFNKI RQLAPMHNIT LFGCGSLYTS HQDPLVHRNP DKAMKCRWAA IPVKDIGDWV 1140
LRKLSQNLRA KNRGTGEYYH QGVKEFLSHY ELQDLEEELL KWRSDRKSNI PCWVLQNRLA 1200
EKLGNKEAVV YIPVRGGRIY FATHKVATGA VSIVFDQKQV WVCNADHVAA ANIALTGKGI 1260
GEQSSDEENP DGSRIKLQLT SKRPAATKKA GQAKKKKGGG GSGGGGSGGG GSMTNLSDII 1320
EKETGKQLVI QESILMLPEE VEEVIGNKPE SDILVHTAYD ESTDENVMLL TSDAPEYKPW 1380
ALVIQDSNGE NKIKML 1396

SEQ ID NO: 43 moltype = AA length = 1403
FEATURE Location/Qualifiers
source 1..1403
mol_type = protein
organism = synthetic construct
SEQUENCE: 43
MKIEEGKGHH HHHHMSSAIK SYKSVLRPNE RKNQLLKSTI QCLEDGSAFF FKMLQGLFGG 60
ITPEIVRFST EQEKQQQDIA LWCAVNWFRP VSQDSLTHTI ASDNLVEKFE EYYGGTASDA 120
IKQYFSASIG ESYYWNDCRQ QYYDLCRELG VEVSDLTHDL EILCREKCLA VATESNQNNS 180
IISVLFGTGE KEDRSVKLRI TKKILEAISN LKEIPKNVAP IQEIILNVAK ATKETFRQVY 240
AGNLGAPSTL EKFIAKDGQK EFDLKKLQTD LKKVIRGKSK ERDWCCQEEL RSYVEQNTIQ 300
YDLWAWGEMF NKAHTALKIK STRNYNFAKQ RLEQFKEIQS LNNLLVVKKL NDFFDSEFFS 360
GEETYTICVH HLGGKDLSKL YKAWEDDPAD PENAIVVLCD DLKNNFKKEP IRNILRYIFT 420
IRQECSAQDI LAAAKYNQQL DRYKSQKANP SVLGNQGFTW TNAVILPEKA QRNDRPNSLD 480
LRIWLYLKLR HPDGRWKKHH IPFYDTRFFQ EIYAAGNSPV DTCQFRTPRF GYHLPKLTDQ 540
TAIRVNKKHV KAAKTEARIR LAIQQGTLPV SNLKITEISA TINSKGQVRI PVKFRVGRQK 600
GTLQIGDRFC GYAQNQTASH AYSLWEVVKE GQYHKELGCF VRFISSGDIV SITENRGNQF 660
DQLSYEGLAY PQYADWRKKA SKFVSLWQIT KKNKKKEIVT VEAKEKFDAI CKYQPRLYKF 720
NKEYAYLLRD IVRGKSLVEL QQIRQEIFRF IEQDCGVTRL GSLSLSTLET VKAVKGIIYS 780
YFSTALNASK NNPISDEQRK EFDPELFALL EKLELIRTRK KKQKVERIAN SLIQTCLENN 840
IKFIRGEGDL STTNNATKKK ANSRSMDWLA RGVFNKIRQL APMHNITLFG CGSLYTSHQD 900
PLVHRNPDKA MKCRWAAIPV KDIGDWVLRK LSQNLRAKNR GTGEYYHQGV KEFLSHYELQ 960
DLEEELLKWR SDRKSNIPCW VLQNRLAEKL GNKEAVVYIP VRGGRIYFAT HKVATGAVSI 1020
VFDQKQVWVC NADHVAAANI ALTGKGIGEQ SSDEENPDGS RIKLQLTSKR PAATKKAGQA 1080
KKKKSGGSSG GSSGSETPGT SESATPESSG GSSGGSMDPA TFTYQFKNVR WAKGRRETYL 1140
CYVVKRRDSA TSFSLDFGYL RNKNGCHVEL LFLRYISDWD LDPGRCYRVT WFTSWSPCYD 1200
CARHVADFLR GNPNLSLRIF TARLYFCEDR KAEPEGLRRL AEAGVQIAIM TFKDYFYCWN 1260
TFVENHERTF KAWEGLHENS VRLSRQLRRI LQSGGSMTNL SDIIEKETGK QLVIQESILM 1320
LPEEVEEVIG NKPESDILVH TAYDESTDEN VMLLTSDAPE YKPWALVIQD SNGENKIKML 1380
SGGSMKRTAD GSEFESPKKK RKV 1403

SEQ ID NO: 44 moltype = AA length = 1408
FEATURE Location/Qualifiers
source 1..1408
mol_type = protein
organism = synthetic construct
SEQUENCE: 44
MKRTADGSEF ESPKKKRKVM EASPASGPRH LMDPHIFTSN FNNGIGRHKT YLCYEVERLD 60
NGTSVKMDQH RGFLHNQAKN LLCGFYGRHA ELRFLDLVPS LQLDPAQIYR VTWFISWSPC 120
FSAGCAGEVR AFLQENTHVR LRIFAARIYD YDYLYKEALQ MLRDAGAQVS IMTYDEFKHC 180
WDTFVDHQGC PFQPWDGLDE HSQALSGRLR AILQNQGNSG GSMTNLSDII EKETGKQLVI 240
QESILMLPEE VEEVIGNKPE SDILVHTAYD ESTDENVMLL TSDAPEYKPW ALVIQDSNGE 300
NKIKMLSGGS SGGSSGSETP GTSESATPES SGGSSGGSMS SAIKSYKSVL RPNERKNQLL 360
KSTIQCLEDG SAFFFKMLQG LFGGITPEIV RFSTEQEKQQ QDIALWCAVN WFRPVSQDSL 420
THTIASDNLV EKFEEYYGGT ASDAIKQYFS ASIGESYYWN DCRQQYYDLC RELGVEVSDL 480
THDLEILCRE KCLAVATESN QNNSIISVLF GTGEKEDRSV KLRITKKILE AISNLKEIPK 540
NVAPIQEIIL NVAKATKETF RQVYAGNLGA PSTLEKFIAK DGQKEFDLKK LQTDLKKVIR 600
GKSKERDWCC QEELRSYVEQ NTIQYDLWAW GEMFNKAHTA LKIKSTRNYN FAKQRLEQFK 660
EIQSLNNLLV VKKLNDFFDS EFFSGEETYT ICVHHLGGKD LSKLYKAWED DPADPENAIV 720
VLCDDLKNNF KKEPIRNILR YIFTIRQECS AQDILAAAKY NQQLDRYKSQ KANPSVLGNQ 780
GFTWTNAVIL PEKAQRNDRP NSLDLRIWLY LKLRHPDGRW KKHHIPFYDT RFFQEIYAAG 840
NSPVDTCQFR TPRFGYHLPK LTDQTAIRVN KKHVKAAKTE ARIRLAIQQG TLPVSNLKIT 900
EISATINSKG QVRIPVKFRV GRQKGTLQIG DRFCGYAQNQ TASHAYSLWE VVKEGQYHKE 960
LGCFVRFISS GDIVSITENR GNQFDQLSYE GLAYPQYADW RKKASKFVSL WQITKKNKKK 1020
EIVTVEAKEK FDAICKYQPR LYKFNKEYAY LLRDIVRGKS LVELQQIRQE IFRFIEQDCG 1080
VTRLGSLSLS TLETVKAVKG IIYSYFSTAL NASKNNPISD EQRKEFDPEL FALLEKLELI 1140
RTRKKKQKVE RIANSLIQTC LENNIKFIRG EGDLSTTNNA TKKKANSRSM DWLARGVFNK 1200
IRQLAPMHNI TLFGCGSLYT SHQDPLVHRN PDKAMKCRWA AIPVKDIGDW VLRKLSQNLR 1260
AKNRGTGEYY HQGVKEFLSH YELQDLEEEL LKWRSDRKSN IPCWVLQNRL AEKLGNKEAV 1320
VYIPVRGGRI YFATHKVATG AVSIVFDQKQ VWVCNADHVA AANIALTGKG IGEQSSDEEN 1380
PDGSRIKLQL TSKRPAATKK AGQAKKKK 1408

SEQ ID NO: 45 moltype = AA length = 1419
FEATURE Location/Qualifiers
source 1..1419
mol_type = protein
organism = synthetic construct
SEQUENCE: 45

```
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSSGGSSGSE TPGTSESATP  240
ESSGGSSGGS MSSAIKSYKS VLRPNERKNQ LLKSTIQCLE DGSAFFFKML QGLFGGITPE  300
IVRFSTEQEK QQQDIALWCA VNWFRPVSQD SLTHTIASDN LVEKFEEYYG GTASDAIKQY  360
FSASIGESYY WNDCRQQYYD LCRELGVEVS DLTHDLEILC REKCLAVATE SNQNNSIISV  420
LFGTGEKEDR SVKLRITKKI LEAISNLKEI PKNVAPIQEI ILNVAKATKE TFRQVYAGNL  480
GAPSTLEKFI AKDGQKEFDL KKLQTDLKKV IRGKSKERDW CCQEELRSYV EQNTIQYDLW  540
AWGEMFNKAH TALKIKSTRN YNFAKQRLEQ FKEIQSLNNL LVVKKLNDFF DSEFFSGEET  600
YTICVHHLGG KDLSKLYKAW EDDPADPENA IVVLCDDLKN NFKKEPIRNI LRYIFTIRQE  660
CSAQDILAAA KYNQQLDRYK SQKANPSVLG NQGFTWTNAV ILPEKAQRND RPNSLDLRIW  720
LYLKLRHPDG RWKKHHIPFY DTRFFQEIYA AGNSPVDTCQ FRTPRFGYHL PKLTDQTAIR  780
VNKKHVKAAK TEARIRLAIQ QGTLPVSNLK ITEISATINS KGQVRIPVKF RVGRQKGTLQ  840
IGDRFCGYAQ NQTASHAYSL WEVVKEGQYH KELGCFVRFI SSGDIVSITE NRGNQFDQLS  900
YEGLAYPQYA DWRKKASKFV SLWQITKKNK KKEIVTVEAK EKFDAICKYQ PRLYKFNKEY  960
AYLLRDIVRG KSLVELQQIR QEIFRFIEQD CGVTRLGSLS LSTLETVKAV KGIIYSYFST  1020
ALNASKNNPI SDEQRKEFDP ELFALLEKLE LIRTRKKKQK VERIANSLIQ TCLENNIKFI  1080
RGEGDLSTTN NATKKKANSR SMDWLARGVF NKIRQLAPMH NITLFGCGSL YTSHQDPLVH  1140
RNPDKAMKCR WAAIPVKDIG DWVLRKLSQN LRAKNRGTGE YYHQGVKEFL SHYELQDLEE  1200
ELLKWRSDRK SNIPCWVLQN RLAEKLGNKE AVVYIPVRGG RIYFATHKVA TGAVSIVFDQ  1260
KQVWVCNADH VAAANIALTG KGIGEQSSDE ENPDGSRIKL QLTSKRPAAT KKAGQAKKKK  1320
GGGGSGGGGS GGGGSMTNLS DIIEKETGKQ LVIQESILML PEEVEEVIGN KPESDILVHT  1380
AYDESTDENV MLLTSDAPEY KPWALVIQDS NGENKIKML                        1419

SEQ ID NO: 46          moltype = AA  length = 1426
FEATURE                Location/Qualifiers
source                 1..1426
                       mol_type = protein
                       organism = synthetic construct
SEQUENCE: 46
MKIEEGKGHH HHHHMSSAIK SYKSVLRPNE RKNQLLKSTI QCLEDGSAFF FKMLQGLFGG  60
ITPEIVRFST EQEKQQQDIA LWCAVNWFRP VSQDSLTHTI ASDNLVEKFE EYYGGTASDA  120
IKQYFSASIG ESYYWNDCRQ QYYDLCRELG VEVSDLTHDL EILCREKCLA VATESNQNNS  180
IISVLFGTGE KEDRSVKLRI TKKILEAISN LKEIPKNVAP IQEIILNVAK ATKETFRQVY  240
AGNLGAPSTL EKFIAKDGQK EFDLKKLQTD LKKVIRGKSK ERDWCCQEEL RSYVEQNTIQ  300
YDLWAWGEMF NKAHTALKIK STRNYNFAKQ RLEQFKEIQS LNNLLVVKKL NDFFDSEFFS  360
GEETYTICVH HLGGKDLSKL YKAWEDDPAD PENAIVVLCD DLKNNFKKEP IRNILRYIFT  420
IRQECSAQDI LAAAKYNQQL DRYKSQKANP SVLGNQGFTW TNAVILPEKA QRNDRPNSLD  480
LRIWLYLKLR HPDGRWKKHH IPFYDTRFFQ EIYAAGNSPV DTCQFRTPRF GYHLPKLTDQ  540
TAIRVNKKHV KAAKTEARIR LAIQQGTLPV SNLKITEISA TINSKGQVRI PVKFRVGRQK  600
GTLQIGDRFC GYAQNQTASH AYSLWEVVKE GQYHKELGCF VRFISSGDIV SITENRGNQF  660
DQLSYEGLAY PQYADWRKKA SKFVSLWQIT KKNKKKEIVT VEAKEKFDAI CKYQPRLYKF  720
NKEYAYLLRD IVRGKSLVEL QQIRQEIFRF IEQDCGVTRL GSLSLSTLET VKAVKGIIYS  780
YFSTALNASK NNPISDEQRK EFDPELFALL EKLELIRTRK KKQKVERIAN SLIQTCLENN  840
IKFIRGEGDL STTNNATKKK ANSRSMDWLA RGVFNKIRQL APMHNITLFG CGSLYTSHQD  900
PLVHRNPDKA MKCRWAAIPV KDIGDWVLRK LSQNLRAKNR GTGEYYHQGV KEFLSHYELQ  960
DLEEELLKWR SDRKSNIPCW VLQNRLAEKL GNKEAVVYIP VRGGRIYFAT HKVATGAVSI  1020
VFDQKQVWVC NADHVAAANI ALTGKGIGEQ SSDEENPDGS RIKLQLTSKR PAATKKAGQA  1080
KKKKSGGSSG GSSGSETPGT SESATPESSG GSSGGSMEAS PASGPRHLMD PHIFTSNFNN  1140
GIGRHKTYLC YEVERLDNGT SVKMDQHRGF LHNQAKNLLC GFYGRHAELR FLDLVPSLQL  1200
DPAQIYRVTW FISWSPCFSA GCAGEVRAFL QENTHVRLRI FAARIYDYDY LYKEALQMLR  1260
DAGAQVSIMT YDEFKHCWDT FVDHQGCPFQ PWDGLDEHSQ ALSGRLRAIL QNQGNSGGSM  1320
TNLSDIIEKE TGKQLVIQES ILMLPEEVEE VIGNKPESDI LVHTAYDEST DENVMLLTSD  1380
APEYKPWALV IQDSNGENKI KMLSGGSMKR TADGSEFESP KKKRKV                1426

SEQ ID NO: 47          moltype = AA  length = 1699
FEATURE                Location/Qualifiers
source                 1..1699
                       mol_type = protein
                       organism = synthetic construct
SEQUENCE: 47
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSM TNLSDIIEKE TGKQLVIQES ILMLPEEVEE VIGNKPESDI  240
LVHTAYDEST DENVMLLTSD APEYKPWALV IQDSNGENKI KMLSGGSSGG SSGSETPGTS  300
ESATPESSGG SSGGSMDKKY SIGLAIGTNS VGWAVITDEY KVPSKKFKVL GNTDRHSIKK  360
NLIGALLFDS GETAEATRLK RTARRRYTRR KNRICYLQEI FSNEMAKVDD SFFHRLEESF  420
LVEEDKKHER HPIFGNIVDE VAYHEKYPTI YHLRKKLVDS TDKADLRLIY LALAHMIKFR  480
GHFLIEGDLN PDNSDVDKLF IQLVQTYNQL FEENPINASG VDAKAILSAR LSKSRRLENL  540
IAQLPGEKKN GLFGNLIALS LGLTPNFKSN FDLAEDAKLQ LSKDTYDDDL DNLLAQIGDQ  600
YADLFLAAKN LSDAILLSDI LRVNTEITKA PLSASMIKRY DEHHQDLTLL KALVRQQLPE  660
KYKEIFFDQS KNGYAGYIDG GASQEEFYKF IKPILEKMDG TEELLVKLNR EDLLRKQRTF  720
DNGSIPHQIH LGELHAILRR QEDFYPFLKD NREKIEKILT FRIPYYVGPL ARGNSRFAWM  780
TRKSEETITP WNFEEVVDKG ASAQSFIERM TNFDKNLPNE KVLPKHSLLY EYFTVYNELT  840
KVKYVTEGMR KPAFLSGEQK KAIVDLLFKT NRKVTVKQLK EDYFKKIECF DSVEISGVED  900
RFNASLGTYH DLLKIIKDKD FLDNEENEDI LEDIVLTLTL FEDREMIEER LKTYAHLFDD  960
KVMKQLKRRR YTGWGRLSRK LINGIRDKQS GKTILDFLKS DGFANRNFMQ LIHDDSLTFK  1020
```

-continued

```
EDIQKAQVSG QGDSLHEHIA NLAGSPAIKK GILQTVKVVD ELVKVMGRHK PENIVIEMAR  1080
ENQTTQKGQK NSRERMKRIE EGIKELGSQI LKEHPVENTQ LQNEKLYLYY LQNGRDMYVD  1140
QELDINRLSD YDVDAIVPQS FLKDDSIDNK VLTRSDKNRG KSDNVPSEEV VKKMKNYWRQ  1200
LLNAKLITQR KFDNLTKAER GGLSELDKAG FIKRQLVETR QITKHVAQIL DSRMNTKYDE  1260
NDKLIREVKV ITLKSKLVSD FRKDFQFYKV REINNYHHAH DAYLNAVVGT ALIKKYPKLE  1320
SEFVYGDYKV YDVRKMIAKS EQEIGKATAK YFFYSNIMNF FKTEITLANG EIRKRPLIET  1380
NGETGEIVWD KGRDFATVRK VLSMPQVNIV KKTEVQTGGF SKESILPKRN SDKLIARKKD  1440
WDPKKYGGFD SPTVAYSVLV VAKVEKGKSK KLKSVKELLG ITIMERSSFE KNPIDFLEAK  1500
GYKEVKKDLI IKLPKYSLFE LENGRKRMLA SAGELQKGNE LALPSKYVNF LYLASHYEKL  1560
KGSPEDNEQK QLFVEQHKHY LDEIIEQISE FSKRVILADA NLDKVLSAYN KHRDKPIREQ  1620
AENIIHLFTL TNLGAPAAFK YFDTTIDRKR YTSTKEVLDA TLIHQSITGL YETRIDLSQL  1680
GGDKRPAATK KAGQAKKKK                                               1699

SEQ ID NO: 48          moltype = AA  length = 1710
FEATURE                Location/Qualifiers
source                 1..1710
                       mol_type = protein
                       organism = synthetic construct
SEQUENCE: 48
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSS GGSSGSETPG TSESATPESS GGSSGGSMDK KYSIGLAIGT  240
NSVGWAVITD EYKVPSKKFK VLGNTDRHSI KKNLIGALLF DSGETAEATR LKRTARRRYT  300
RRKNRICYLQ EIFSNEMAKV DDSFFHRLEE SFLVEEDKKH ERHPIFGNIV DEVAYHEKYP  360
TIYHLRKKLV DSTDKADLRL IYLALAHMIK FRGHFLIEGD LNPDNSDVDK LFIQLVQTYN  420
QLFEENPINA SGVDAKAILS ARLSKSRRLE NLIAQLPGEK KNGLFGNLIA LSLGLTPNFK  480
SNFDLAEDAK LQLSKDTYDD DLDNLLAQIG DQYADLFLAA KNLSDAILLS DILRVNTEIT  540
KAPLSASMIK RYDEHHQDLT LLKALVRQQL PEKYKEIFFD QSKNGYAGYI DGGASQEEFY  600
KFIKPILEKM DGTEELLVKL NREDLLRKQR TFDNGSIPHQ IHLGELHAIL RRQEDFYPFL  660
KDNREKIEKI LTFRIPYYVG PLARGNSRFA WMTRKSEETI TPWNFEEVVD KGASAQSFIE  720
RMTNFDKNLP NEKVLPKHSL LYEYFTVYNE LTKVKYVTEG MRKPAFLSGE QKKAIVDLLF  780
KTNRKVTVKQ LKEDYFKKIE CFDSVEISGV EDRFNASLGT YHDLLKIIKD KDFLDNEENE  840
DILEDIVLTL TLFEDREMIE ERLKTYAHLF DDKVMKQLKR RRYTGWGRLS RKLINGIRDK  900
QSGKTILDFL KSDGFANRNF MQLIHDDSLT FKEDIQKAQV SGQGDSLHEH IANLAGSPAI  960
KKGILQTVKV VDELVKVMGR HKPENIVIEM ARENQTTQKG QKNSRERMKR IEEGIKELGS  1020
QILKEHPVEN TQLQNEKLYL YYLQNGRDMY VDQELDINRL SDYDVDAIVP QSFLKDDSID  1080
NKVLTRSDKN RGKSDNVPSE EVVKKMKNYW RQLLNAKLIT QRKFDNLTKA ERGGLSELDK  1140
AGFIKRQLVE TRQITKHVAQ ILDSRMNTKY DENDKLIREV KVITLKSKLV SDFRKDFQFY  1200
KVREINNYHH AHDAYLNAVV GTALIKKYPK LESEFVYGDY KVYDVRKMIA KSEQEIGKAT  1260
AKYFFYSNIM NFFKTEITLA NGEIRKRPLI ETNGETGEIV WDKGRDFATV RKVLSMPQVN  1320
IVKKTEVQTG GFSKESILPK RNSDKLIARK KDWDPKKYGG FDSPTVAYSV LVVAKVEKGK  1380
SKKLKSVKEL LGITIMERSS FEKNPIDFLE AKGYKEVKKD LIIKLPKYSL FELENGRKRM  1440
LASAGELQKG NELALPSKYV NFLYLASHYE KLKGSPEDNE QKQLFVEQHK HYLDEIIEQI  1500
SEFSKRVILA DANLDKVLSA YNKHRDKPIR EQAENIIHLF TLTNLGAPAA FKYFDTTIDR  1560
KRYTSTKEVL DATLIHQSIT GLYETRIDLS QLGGDKRPAA TKKAGQAKKK KGGGGSGGGG  1620
SGGGGSMTNL SDIIEKETGK QLVIQESILM LPEEVEEVIG NKPESDILVH TAYDESTDEN  1680
VMLLTSDAPE YKPWALVIQD SNGENKIKML                                   1710

SEQ ID NO: 49          moltype = AA  length = 1717
FEATURE                Location/Qualifiers
source                 1..1717
                       mol_type = protein
                       organism = synthetic construct
SEQUENCE: 49
MKIEEGKGHH HHHHMDKKYS IGLAIGTNSV GWAVITDEYK VPSKKFKVLG NTDRHSIKKN  60
LIGALLFDSG ETAEATRLKR TARRRYTRRK NRICYLQEIF SNEMAKVDDS FFHRLEESFL  120
VEEDKKHERH PIFGNIVDEV AYHEKYPTIY HLRKKLVDST DKADLRLIYL ALAHMIKFRG  180
HFLIEGDLNP DNSDVDKLFI QLVQTYNQLF EENPINASGV DAKAILSARL SKSRRLENLI  240
AQLPGEKKNG LFGNLIALSL GLTPNFKSNF DLAEDAKLQL SKDTYDDDLD NLLAQIGDQY  300
ADLFLAAKNL SDAILLSDIL RVNTEITKAP LSASMIKRYD EHHQDLTLLK ALVRQQLPEK  360
YKEIFFDQSK NGYAGYIDGG ASQEEFYKFI KPILEKMDGT EELLVKLNRE DLLRKQRTFD  420
NGSIPHQIHL GELHAILRRQ EDFYPFLKDN REKIEKILTF RIPYYVGPLA RGNSRFAWMT  480
RKSEETITPW NFEEVVDKGA SAQSFIERMT NFDKNLPNEK VLPKHSLLYE YFTVYNELTK  540
VKYVTEGMRK PAFLSGEQKK AIVDLLFKTN RKVTVKQLKE DYFKKIECFD SVEISGVEDR  600
FNASLGTYHD LLKIIKDKDF LDNEENEDIL EDIVLTLTLF EDREMIEERL KTYAHLFDDK  660
VMKQLKRRRY TGWGRLSRKL INGIRDKQSG KTILDFLKSD GFANRNFMQL IHDDSLTFKE  720
DIQKAQVSGQ GDSLHEHIAN LAGSPAIKKG ILQTVKVVDE LVKVMGRHKP ENIVIEMARE  780
NQTTQKGQKN SRERMKRIEE GIKELGSQIL KEHPVENTQL QNEKLYLYYL QNGRDMYVDQ  840
ELDINRLSDY DVDAIVPQSF LKDDSIDNKV LTRSDKNRGK SDNVPSEEVV KKMKNYWRQL  900
LNAKLITQRK FDNLTKAERG GLSELDKAGF IKRQLVETRQ ITKHVAQILD SRMNTKYDEN  960
DKLIREVKVI TLKSKLVSDF RKDFQFYKVR EINNYHHAHD AYLNAVVGTA LIKKYPKLES  1020
EFVYGDYKVY DVRKMIAKSE QEIGKATAKY FFYSNIMNFF KTEITLANGE IRKRPLIETN  1080
GETGEIVWDK GRDFATVRKV LSMPQVNIVK KTEVQTGGFS KESILPKRNS DKLIARKKDW  1140
DPKKYGGFDS PTVAYSVLVV AKVEKGKSKK LKSVKELLGI TIMERSSFEK NPIDFLEAKG  1200
YKEVKKDLII KLPKYSLFEL ENGRKRMLAS AGELQKGNEL ALPSKYVNFL YLASHYEKLK  1260
GSPEDNEQKQ LFVEQHKHYL DEIIEQISEF SKRVILADAN LDKVLSAYNK HRDKPIREQA  1320
ENIIHLFTLT NLGAPAAFKY FDTTIDRKRY TSTKEVLDAT LIHQSITGLY ETRIDLSQLG  1380
GDKRPAATKK AGQAKKKKSG GSSGGSSGSE TPGTSESATP ESSGGSSGGS MDPATFTYQF  1440
```

```
KNVRWAKGRR ETYLCYVVKR RDSATSFSLD FGYLRNKNGC HVELLFLRYI SDWDLDPGRC  1500
YRVTWFTSWS PCYDCARHVA DFLRGNPNLS LRIFTARLYF CEDRKAEPEG LRRLAEAGVQ  1560
IAIMTFKDYF YCWNTFVENH ERTFKAWEGL HENSVRLSRQ LRRILQSGGS MTNLSDIIEK  1620
ETGKQLVIQE SILMLPEEVE EVIGNKPESD ILVHTAYDES TDENVMLLTS DAPEYKPWAL  1680
VIQDSNGENK IKMLSGGSMK RTADGSEFES PKKKRKV                           1717

SEQ ID NO: 50          moltype = AA  length = 1722
FEATURE                Location/Qualifiers
source                 1..1722
                       mol_type = protein
                       organism = synthetic construct
SEQUENCE: 50
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSMTNLSDII EKETGKQLVI  240
QESILMLPEE VEEVIGNKPE SDILVHTAYD ESTDENVMLL TSDAPEYKPW ALVIQDSNGE  300
NKIKMLSGGS SGGSSGSETP GTSESATPES SGGSSGGSMD KKYSIGLAIG TNSVGWAVIT  360
DEYKVPSKKF KVLGNTDRHS IKKNLIGALL FDSGETAEAT RLKRTARRRY TRRKNRICYL  420
QEIFSNEMAK VDDSFFHRLE ESFLVEEDKK HERHPIFGNI VDEVAYHEKY PTIYHLRKKL  480
VDSTDKADLR LIYLALAHMI KFRGHFLIEG DLNPDNSDVD KLFIQLVQTY NQLFEENPIN  540
ASGVDAKAIL SARLSKSRRL ENLIAQLPGE KKNGLFGNLI ALSLGLTPNF KSNFDLAEDA  600
KLQLSKDTYD DDLDNLLAQI GDQYADLFLA AKNLSDAILL SDILRVNTEI TKAPLSASMI  660
KRYDEHHQDL TLLKALVRQQ LPEKYKEIFF DQSKNGYAGY IDGGASQEEF YKFIKPILEK  720
MDGTEELLVK LNREDLLRKQ RTFDNGSIPH QIHLGELHAI LRRQEDFYPF LKDNREKIEK  780
ILTFRIPYYV GPLARGNSRF AWMTRKSEET ITPWNFEEVV DKGASAQSFI ERMTNFDKNL  840
PNEKVLPKHS LLYEYFTVYN ELTKVKYVTE GMRKPAFLSG EQKKAIVDLL FKTNRKVTVK  900
QLKEDYFKKI ECFDSVEISG VEDRFNASLG TYHDLLKIIK DKDFLDNEEN EDILEDIVLT  960
LTLFEDREMI EERLKTYAHL FDDKVMKQLK RRRYTGWGRL SRKLINGIRD KQSGKTILDF  1020
LKSDGFANRN FMQLIHDDSL TFKEDIQKAQ VSGQGDSLHE HIANLAGSPA IKKGILQTVK  1080
VVDELVKVMG RHKPENIVIE MARENQTTQK GQKNSRERMK RIEEGIKELG SQILKEHPVE  1140
NTQLQNEKLY LYYLQNGRDM YVDQELDINR LSDYDVDAIV PQSFLKDDSI DNKVLTRSDK  1200
NRGKSDNVPS EEVVKKMKNY WRQLLNAKLI TQRKFDNLTK AERGGLSELD KAGFIKRQLV  1260
ETRQITKHVA QILDSRMNTK YDENDKLIRE VKVITLKSKL VSDFRKDFQF YKVREINNYH  1320
HAHDAYLNAV VGTALIKKYP KLESEFVYGD YKVYDVRKMI AKSEQEIGKA TAKYFFYSNI  1380
MNFFKTEITL ANGEIRKRPL IETNGETGEI VWDKGRDFAT VRKVLSMPQV NIVKKTEVQT  1440
GGFSKESILP KRNSDKLIAR KKDWDPKKYG GFDSPTVAYS VLVVAKVEKG KSKKLKSVKE  1500
LLGITIMERS SFEKNPIDFL EAKGYKEVKK DLIIKLPKYS LFELENGRKR MLASAGELQK  1560
GNELALPSKY VNFLYLASHY EKLKGSPEDN EQKQLFVEQH KHYLDEIIEQ ISEFSKRVIL  1620
ADANLDKVLS AYNKHRDKPI REQAENIIHL FTLTNLGAPA AFKYFDTTID RKRYTSTKEV  1680
LDATLIHQSI TGLYETRIDL SQLGGDKRPA ATKKAGQAKK KK                     1722

SEQ ID NO: 51          moltype = AA  length = 1733
FEATURE                Location/Qualifiers
source                 1..1733
                       mol_type = protein
                       organism = synthetic construct
SEQUENCE: 51
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSSGGSSGSE TPGTSESATP  240
ESSGGSSGGS MDKKYSIGLA IGTNSVGWAV ITDEYKVPSK KFKVLGNTDR HSIKKNLIGA  300
LLFDSGETAE ATRLKRTARR RYTRRKNRIC YLQEIFSNEM AKVDDSFFHR LEESFLVEED  360
KKHERHPIFG NIVDEVAYHE KYPTIYHLRK KLVDSTDKAD LRLIYLALAH MIKFRGHFLI  420
EGDLNPDNSD VDKLFIQLVQ TYNQLFEENP INASGVDAKA ILSARLSKSR RLENLIAQLP  480
GEKKNGLFGN LIALSLGLTP NFKSNFDLAE DAKLQLSKDT YDDDLDNLLA QIGDQYADLF  540
LAAKNLSDAI LLSDILRVNT EITKAPLSAS MIKRYDEHHQ DLTLLKALVR QQLPEKYKEI  600
FFDQSKNGYA GYIDGGASQE EFYKFIKPIL EKMDGTEELL VKLNREDLLR KQRTFDNGSI  660
PHQIHLGELH AILRRQEDFY PFLKDNREKI EKILTFRIPY YVGPLARGNS RFAWMTRKSE  720
ETITPWNFEE VVDKGASAQS FIERMTNFDK NLPNEKVLPK HSLLYEYFTV YNELTKVKYV  780
TEGMRKPAFL SGEQKKAIVD LLFKTNRKVT VKQLKEDYFK KIECFDSVEI SGVEDRFNAS  840
LGTYHDLLKI IKDKDFLDNE ENEDILEDIV LTLTLFEDRE MIEERLKTYA HLFDDKVMKQ  900
LKRRRYTGWG RLSRKLINGI RDKQSGKTIL DFLKSDGFAN RNFMQLIHDD SLTFKEDIQK  960
AQVSGQGDSL HEHIANLAGS PAIKKGILQT VKVVDELVKV MGRHKPENIV IEMARENQTT  1020
QKGQKNSRER MKRIEEGIKE LGSQILKEHP VENTQLQNEK LYLYYLQNGR DMYVDQELDI  1080
NRLSDYDVDA IVPQSFLKDD SIDNKVLTRS DKNRGKSDNV PSEEVVKKMK NYWRQLLNAK  1140
LITQRKFDNL TKAERGGLSE LDKAGFIKRQ LVETRQITKH VAQILDSRMN TKYDENDKLI  1200
REVKVITLKS KLVSDFRKDF QFYKVREINN YHHAHDAYLN AVVGTALIKK YPKLESEFVY  1260
GDYKVYDVRK MIAKSEQEIG KATAKYFFYS NIMNFFKTEI TLANGEIRKR PLIETNGETG  1320
EIVWDKGRDF ATVRKVLSMP QVNIVKKTEV QTGGFSKESI LPKRNSDKLI ARKKDWDPKK  1380
YGGFDSPTVA YSVLVVAKVE KGKSKKLKSV KELLGITIME RSSFEKNPID FLEAKGYKEV  1440
KKDLIIKLPK YSLFELENGR KRMLASAGEL QKGNELALPS KYVNFLYLAS HYEKLKGSPE  1500
DNEQKQLFVE QHKHYLDEII EQISEFSKRV ILADANLDKV LSAYNKHRDK PIREQAENII  1560
HLFTLTNLGA PAAFKYFDTT IDRKRYTSTK EVLDATLIHQ SITGLYETRI DLSQLGGDKR  1620
PAATKKAGQA KKKKGGGGSG GGGSGGGGSM TNLSDIIEKE TGKQLVIQES ILMLPEEVEE  1680
VIGNKPESDI LVHTAYDEST DENVMLLTSD APEYKPWALV IQDSNGENKI KML         1733

SEQ ID NO: 52          moltype = AA  length = 1740
```

```
FEATURE                 Location/Qualifiers
source                  1..1740
                        mol_type = protein
                        organism = synthetic construct
SEQUENCE: 52
MKIEEGKGHH HHHHMDKKYS IGLAIGTNSV GWAVITDEYK VPSKKFKVLG NTDRHSIKKN  60
LIGALLFDSG ETAEATRLKR TARRRYTRRK NRICYLQEIF SNEMAKVDDS FFHRLEESFL  120
VEEDKKHERH PIFGNIVDEV AYHEKYPTIY HLRKKLVDST DKADLRLIYL ALAHMIKFRG  180
HFLIEGDLNP DNSDVDKLFI QLVQTYNQLF EENPINASGV DAKAILSARL SKSRRLENLI  240
AQLPGEKKNG LFGNLIALSL GLTPNFKSNF DLAEDAKLQL SKDTYDDDLD NLLAQIGDQY  300
ADLFLAAKNL SDAILLSDIL RVNTEITKAP LSASMIKRYD EHHQDLTLLK ALVRQQLPEK  360
YKEIFFDQSK NGYAGYIDGG ASQEEFYKFI KPILEKMDGT EELLVKLNRE DLLRKQRTFD  420
NGSIPHQIHL GELHAILRRQ EDFYPFLKDN REKIEKILTF RIPYYVGPLA RGNSRFAWMT  480
RKSEETITPW NFEEVVDKGA SAQSFIERMT NFDKNLPNEK VLPKHSLLYE YFTVYNELTK  540
VKYVTEGMRK PAFLSGEQKK AIVDLLFKTN RKVTVKQLKE DYFKKIECFD SVEISGVEDR  600
FNASLGTYHD LLKIIKDKDF LDNEENEDIL EDIVLTLTLF EDREMIEERL KTYAHLFDDK  660
VMKQLKRRRY TGWGRLSRKL INGIRDKQSG KTILDFLKSD GFANRNFMQL IHDDSLTFKE  720
DIQKAQVSGQ GDSLHEHIAN LAGSPAIKKG ILQTVKVVDE LVKVMGRHKP ENIVIEMARE  780
NQTTQKGQKN SRERMKRIEE GIKELGSQIL KEHPVENTQL QNEKLYLYYL QNGRDMYVDQ  840
ELDINRLSDY DVDAIVPQSF LKDDSIDNKV LTRSDKNRGK SDNVPSEEVV KKMKNYWRQL  900
LNAKLITQRK FDNLTKAERG GLSELDKAGF IKRQLVETRQ ITKHVAQILD SRMNTKYDEN  960
DKLIREVKVI TLKSKLVSDF RKDFQFYKVR EINNYHHAHD AYLNAVVGTA LIKKYPKLES  1020
EFVYGDYKVY DVRKMIAKSE QEIGKATAKY FFYSNIMNFF KTEITLANGE IRKRPLIETN  1080
GETGEIVWDK GRDFATVRKV LSMPQVNIVK KTEVQTGGFS KESILPKRNS DKLIARKKDW  1140
DPKKYGGFDS PTVAYSVLVV AKVEKGKSKK LKSVKELLGI TIMERSSFEK NPIDFLEAKG  1200
YKEVKKDLII KLPKYSLFEL ENGRKRMLAS AGELQKGNEL ALPSKYVNFL YLASHYEKLK  1260
GSPEDNEQKQ LFVEQHKHYL DEIIEQISEF SKRVILADAN LDKVLSAYNK HRDKPIREQA  1320
ENIIHLFTLT NLGAPAAFKY FDTTIDRKRY TSTKEVLDAT LIHQSITGLY ETRIDLSQLG  1380
GDKRPAATKK AGQAKKKKSG GSSGGSSGSE TPGTSESATP ESSGGSSGGS MEASPASGPR  1440
HLMDPHIFTS NFNNGIGRHK TYLCYEVERL DNGTSVKMDQ HRGFLHNQAK NLLCGFYGRH  1500
AELRFLDLVP SLQLDPAQIY RVTWFISWSP CFSAGCAGEV RAFLQENTHV RLRIFAARIY  1560
DYDYLYKEAL QMLRDAGAQV SIMTYDEFKH CWDTFVDHQG CPFQPWDGLD EHSQALSGRL  1620
RAILQNQGNS GGSMTNLSDI IEKETGKQLV IQESILMLPE EVEEVIGNKP ESDILVHTAY  1680
DESTDENVML LTSDAPEYKP WALVIQDSNG ENKIKMLSGG SMKRTADGSE FESPKKKRKV  1740

SEQ ID NO: 53           moltype = AA  length = 1699
FEATURE                 Location/Qualifiers
source                  1..1699
                        mol_type = protein
                        organism = synthetic construct
SEQUENCE: 53
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSM TNLSDIIEKE TGKQLVIQES ILMLPEEVEE VIGNKPESDI  240
LVHTAYDEST DENVMLLTSD APEYKPWALV IQDSNGENKI KMLSGGSSGG SSGSETPGTS  300
ESATPESSGG SSGGSMDKKY SIGLAIGTNS VGWAVITDEY KVPSKKFKVL GNTDRHSIKK  360
NLIGALLFDS GETAEATRLK RTARRRYTRR KNRICYLQEI FSNEMAKVDD SFFHRLEESF  420
LVEEDKKHER HPIFGNIVDE VAYHEKYPTI YHLRKKLVDS TDKADLRLIY LALAHMIKFR  480
GHFLIEGDLN PDNSDVDKLF IQLVQTYNQL FEENPINASG VDAKAILSAR LSKSRRLENL  540
IAQLPGEKKN GLFGNLIALS LGLTPNFKSN FDLAEDAKLQ LSKDTYDDDL DNLLAQIGDQ  600
YADLFLAAKN LSDAILLSDI LRVNTEITKA PLSASMIKRY DEHHQDLTLL KALVRQQLPE  660
KYKEIFFDQS KNGYAGYIDG GASQEEFYKF IKPILEKMDG TEELLVKLNR EDLLRKQRTF  720
DNGSIPHQIH LGELHAILRR QEDFYPFLKD NREKIEKILT FRIPYYVGPL ARGNSRFAWM  780
TRKSEETITP WNFEEVVDKG ASAQSFIERM TNFDKNLPNE KVLPKHSLLY EYFTVYNELT  840
KVKYVTEGMR KPAFLSGEQK KAIVDLLFKT NRKVTVKQLK EDYFKKIECF DSVEISGVED  900
RFNASLGTYH DLLKIIKDKD FLDNEENEDI LEDIVLTLTL FEDREMIEER LKTYAHLFDD  960
KVMKQLKRRR YTGWGRLSRK LINGIRDKQS GKTILDFLKS DGFANRNFMQ LIHDDSLTFK  1020
EDIQKAQVSG QGDSLHEHIA NLAGSPAIKK GILQTVKVVD ELVKVMGRHK PENIVIEMAR  1080
ENQTTQKGQK NSRERMKRIE EGIKELGSQI LKEHPVENTQ LQNEKLYLYY LQNGRDMYVD  1140
QELDINRLSD YDVDHIVPQS FLKDDSIDNK VLTRSDKNRG KSDNVPSEEV VKKMKNYWRQ  1200
LLNAKLITQR KFDNLTKAER GGLSELDKAG FIKRQLVETR QITKHVAQIL DSRMNTKYDE  1260
NDKLIREVKV ITLKSKLVSD FRKDFQFYKV REINNYHHAH DAYLNAVVGT ALIKKYPKLE  1320
SEFVYGDYKV YDVRKMIAKS EQEIGKATAK YFFYSNIMNF FKTEITLANG EIRKRPLIET  1380
NGETGEIVWD KGRDFATVRK VLSMPQVNIV KKTEVQTGGF SKESILPKRN SDKLIARKKD  1440
WDPKKYGGFD SPTVAYSVLV VAKVEKGKSK KLKSVKELLG ITIMERSSFE KNPIDFLEAK  1500
GYKEVKKDLI IKLPKYSLFE LENGRKRMLA SAGELQKGNE LALPSKYVNF LYLASHYEKL  1560
KGSPEDNEQK QLFVEQHKHY LDEIIEQISE FSKRVILADA NLDKVLSAYN KHRDKPIREQ  1620
AENIIHLFTL TNLGAPAAFK YFDTTIDRKR YTSTKEVLDA TLIHQSITGL YETRIDLSQL  1680
GGDKRPAATK KAGQAKKKK                                             1699

SEQ ID NO: 54           moltype = AA  length = 1710
FEATURE                 Location/Qualifiers
source                  1..1710
                        mol_type = protein
                        organism = synthetic construct
SEQUENCE: 54
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
```

```
RIFTARLYFC EDRKAEPEGL RRLAEAGVQI AIMTFKDYFY CWNTFVENHE RTFKAWEGLH  180
ENSVRLSRQL RRILQSGGSS GGSSGSETPG TSESATPESS GGSSGGSMDK KYSIGLAIGT  240
NSVGWAVITD EYKVPSKKFK VLGNTDRHSI KKNLIGALLF DSGETAEATR LKRTARRRYT  300
RRKNRICYLQ EIFSNEMAKV DDSFFHRLEE SFLVEEDKKH ERHPIFGNIV DEVAYHEKYP  360
TIYHLRKKLV DSTDKADLRL IYLALAHMIK FRGHFLIEGD LNPDNSDVDK LFIQLVQTYN  420
QLFEENPINA SGVDAKAILS ARLSKSRRLE NLIAQLPGEK KNGLFGNLIA LSLGLTPNFK  480
SNFDLAEDAK LQLSKDTYDD DLDNLLAQIG DQYADLFLAA KNLSDAILLS DILRVNTEIT  540
KAPLSASMIK RYDEHHQDLT LLKALVRQQL PEKYKEIFFD QSKNGYAGYI DGGASQEEFY  600
KFIKPILEKM DGTEELLVKL NREDLLRKQR TFDNGSIPHQ IHLGELHAIL RRQEDFYPFL  660
KDNREKIEKI LTFRIPYYVG PLARGNSRFA WMTRKSEETI TPWNFEEVVD KGASAQSFIE  720
RMTNFDKNLP NEKVLPKHSL LYEYFTVYNE LTKVKYVTEG MRKPAFLSGE QKKAIVDLLF  780
KTNRKVTVKQ LKEDYFKKIE CFDSVEISGV EDRFNASLGT YHDLLKIIKD KDFLDNEENE  840
DILEDIVLTL TLFEDREMIE ERLKTYAHLF DDKVMKQLKR RRYTGWGRLS RKLINGIRDK  900
QSGKTILDFL KSDGFANRNF MQLIHDDSLT FKEDIQKAQV SGQGDSLHEH IANLAGSPAI  960
KKGILQTVKV VDELVKVMGR HKPENIVIEM ARENQTTQKG QKNSRERMKR IEEGIKELGS  1020
QILKEHPVEN TQLQNEKLYL YYLQNGRDMY VDQELDINRL SDYDVDHIVP QSFLKDDSID  1080
NKVLTRSDKN RGKSDNVPSE EVVKKMKNYW RQLLNAKLIT QRKFDNLTKA ERGGLSELDK  1140
AGFIKRQLVE TRQITKHVAQ ILDSRMNTKY DENDKLIREV KVITLKSKLV SDFRKDFQFY  1200
KVREINNYHH AHDAYLNAVV GTALIKKYPK LESEFVYGDY KVYDVRKMIA KSEQEIGKAT  1260
AKYFFYSNIM NFFKTEITLA NGEIRKRPLI ETNGETGEIV WDKGRDFATV RKVLSMPQVN  1320
IVKKTEVQTG GFSKESILPK RNSDKLIARK KDWDPKKYGG FDSPTVAYSV LVVAKVEKGK  1380
SKKLKSVKEL LGITIMERSS FEKNPIDFLE AKGYKEVKKD LIIKLPKYSL FELENGRKRM  1440
LASAGELQKG NELALPSKYV NFLYLASHYE KLKGSPEDNE QKQLFVEQHK HYLDEIIEQI  1500
SEFSKRVILA DANLDKVLSA YNKHRDKPIR EQAENIIHLF TLTNLGAPAA FKYFDTTIDR  1560
KRYTSTKEVL DATLIHQSIT GLYETRIDLS QLGGDKRPAA TKKAGQAKKK KGGGGSGGGG  1620
SGGGGSMTNL SDIIEKETGK QLVIQESILM LPEEVEEVIG NKPESDILVH TAYDESTDEN  1680
VMLLTSDAPE YKPWALVIQD SNGENKIKML                                 1710

SEQ ID NO: 55          moltype = AA  length = 1717
FEATURE                Location/Qualifiers
source                 1..1717
                       mol_type = protein
                       organism = synthetic construct
SEQUENCE: 55
MKIEEGKGHH HHHMDKKYS IGLAIGTNSV GWAVITDEYK VPSKKFKVLG NTDRHSIKKN  60
LIGALLFDSG ETAEATRLKR TARRRYTRRK NRICYLQEIF SNEMAKVDDS FFHRLEESFL  120
VEEDKKHERH PIFGNIVDEV AYHEKYPTIY HLRKKLVDST DKADLRLIYL ALAHMIKFRG  180
HFLIEGDLNP DNSDVDKLFI QLVQTYNQLF EENPINASGV DAKAILSARL SKSRRLENLI  240
AQLPGEKKNG LFGNLIALSL GLTPNFKSNF DLAEDAKLQL SKDTYDDDLD NLLAQIGDQY  300
ADLFLAAKNL SDAILLSDIL RVNTEITKAP LSASMIKRYD EHHQDLTLLK ALVRQQLPEK  360
YKEIFFDQSK NGYAGYIDGG ASQEEFYKFI KPILEKMDGT EELLVKLNRE DLLRKQRTFD  420
NGSIPHQIHL GELHAILRRQ EDFYPFLKDN REKIEKILTF RIPYYVGPLA RGNSRFAWMT  480
RKSEETITPW NFEEVVDKGA SAQSFIERMT NFDKNLPNEK VLPKHSLLYE YFTVYNELTK  540
VKYVTEGMRK PAFLSGEQKK AIVDLLFKTN RKVTVKQLKE DYFKKIECFD SVEISGVEDR  600
FNASLGTYHD LLKIIKDKDF LDNEENEDIL EDIVLTLTLF EDREMIEERL KTYAHLFDDK  660
VMKQLKRRRY TGWGRLSRKL INGIRDKQSG KTILDFLKSD GFANRNFMQL IHDDSLTFKE  720
DIQKAQVSGQ GDSLHEHIAN LAGSPAIKKG ILQTVKVVDE LVKVMGRHKP ENIVIEMARE  780
NQTTQKGQKN SRERMKRIEE GIKELGSQIL KEHPVENTQL QNEKLYLYYL QNGRDMYVDQ  840
ELDINRLSDY DVDHIVPQSF LKDDSIDNKV LTRSDKNRGK SDNVPSEEVV KKMKNYWRQL  900
LNAKLITQRK FDNLTKAERG GLSELDKAGF IKRQLVETRQ ITKHVAQILD SRMNTKYDEN  960
DKLIREVKVI TLKSKLVSDF RKDFQFYKVR EINNYHHAHD AYLNAVVGTA LIKKYPKLES  1020
EFVYGDYKVY DVRKMIAKSE QEIGKATAKY FFYSNIMNFF KTEITLANGE IRKRPLIETN  1080
GETGEIVWDK GRDFATVRKV LSMPQVNIVK KTEVQTGGFS KESILPKRNS DKLIARKKDW  1140
DPKKYGGFDS PTVAYSVLVV AKVEKGKSKK LKSVKELLGI TIMERSSFEK NPIDFLEAKG  1200
YKEVKKDLII KLPKYSLFEL ENGRKRMLAS AGELQKGNEL ALPSKYVNFL YLASHYEKLK  1260
GSPEDNEQKQ LFVEQHKHYL DEIIEQISEF SKRVILADAN LDKVLSAYNK HRDKPIREQA  1320
ENIIHLFTLT NLGAPAAFKY FDTTIDRKRY TSTKEVLDAT LIHQSITGLY ETRIDLSQLG  1380
GDKRPAATKK AGQAKKKKSG GSSGGSSGSE TPGTSESATP ESSGGSSGGS MDPATFTYQF  1440
KNVRWAKGRR ETYLCYVVKR RDSATSFSLD FGYLRNKNGC HVELLFLRYI SDWDLDPGRC  1500
YRVTWFTSWS PCYDCARHVA DFLRGNPNLS LRIFTARLYF CEDRKAEPEG LRRLAEAGVQ  1560
IAIMTFKDYF YCWNTFVENH ERTFKAWEGL HENSVRLSRQ LRRILQSGGS MTNLSDIIEK  1620
ETGKQLVIQE SILMLPEEVE EVIGNKPESD ILVHTAYDES TDENVMLLTS DAPEYKPWAL  1680
VIQDSNGENK IKMLSGGSMK RTADGSEFES PKKKRKV                         1717

SEQ ID NO: 56          moltype = AA  length = 1722
FEATURE                Location/Qualifiers
source                 1..1722
                       mol_type = protein
                       organism = synthetic construct
SEQUENCE: 56
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSMTNLSDII EKETGKQLVI  240
QESILMLPEE VEEVIGNKPE SDILVHTAYD ESTDENVMLL TSDAPEYKPW ALVIQDSNGE  300
NKIKMLSGGS SGGSSGSETP GTSESATPES SGGSSGGSMD KKYSIGLAIG TNSVGWAVIT  360
DEYKVPSKKF KVLGNTDRHS IKKNLIGALL FDSGETAEAT RLKRTARRRY TRRKNRICYL  420
QEIFSNEMAK VDDSFFHRLE ESFLVEEDKK HERHPIFGNI VDEVAYHEKY PTIYHLRKKL  480
VDSTDKADLR LIYLALAHMI KFRGHFLIEG DLNPDNSDVD KLFIQLVQTY NQLFEENPIN  540
```

-continued

```
ASGVDAKAIL SARLSKSRRL ENLIAQLPGE KKNGLFGNLI ALSLGLTPNF KSNFDLAEDA  600
KLQLSKDTYD DDLDNLLAQI GDQYADLFLA AKNLSDAILL SDILRVNTEI TKAPLSASMI  660
KRYDEHHQDL TLLKALVRQQ LPEKYKEIFF DQSKNGYAGY IDGGASQEEF YKFIKPILEK  720
MDGTEELLVK LNREDLLRKQ RTFDNGSIPH QIHLGELHAI LRRQEDFYPF LKDNREKIEK  780
ILTFRIPYYV GPLARGNSRF AWMTRKSEET ITPWNFEEVV DKGASAQSFI ERMTNFDKNL  840
PNEKVLPKHS LLYEYFTVYN ELTKVKYVTE GMRKPAFLSG EQKKAIVDLL FKTNRKVTVK  900
QLKEDYFKKI ECFDSVEISG VEDRFNASLG TYHDLLKIIK DKDFLDNEEN EDILEDIVLT  960
LTLFEDREMI EERLKTYAHL FDDKVMKQLK RRRYTGWGRL SRKLINGIRD KQSGKTILDF  1020
LKSDGFANRN FMQLIHDDSL TFKEDIQKAQ VSGQGDSLHE HIANLAGSPA IKKGILQTVK  1080
VVDELVKVMG RHKPENIVIE MARENQTTQK GQKNSRERMK RIEEGIKELG SQILKEHPVE  1140
NTQLQNEKLY LYYLQNGRDM YVDQELDINR LSDYDVDHIV PQSFLKDDSI DNKVLTRSDK  1200
NRGKSDNVPS EEVVKKMKNY WRQLLNAKLI TQRKFDNLTK AERGGLSELD KAGFIKRQLV  1260
ETRQITKHVA QILDSRMNTK YDENDKLIRE VKVITLKSKL VSDFRKDFQF YKVREINNYH  1320
HAHDAYLNAV VGTALIKKYP KLESEFVYGD YKVYDVRKMI AKSEQEIGKA TAKYFFYSNI  1380
MNFFKTEITL ANGEIRKRPL IETNGETGEI VWDKGRDFAT VRKVLSMPQV NIVKKTEVQT  1440
GGFSKESILP KRNSDKLIAR KKDWDPKKYG GFDSPTVAYS VLVVAKVEKG KSKKLKSVKE  1500
LLGITIMERS SFEKNPIDFL EAKGYKEVKK DLIIKLPKYS LFELENGRKR MLASAGELQK  1560
GNELALPSKY VNFLYLASHY EKLKGSPEDN EQKQLFVEQH KHYLDEIIEQ ISEFSKRVIL  1620
ADANLDKVLS AYNKHRDKPI REQAENIIHL FTLTNLGAPA AFKYFDTTID RKRYTSTKEV  1680
LDATLIHQSI TGLYETRIDL SQLGGDKRPA ATKKAGQAKK KK                    1722

SEQ ID NO: 57          moltype = AA  length = 1733
FEATURE                Location/Qualifiers
source                 1..1733
                       mol_type = protein
                       organism = synthetic construct
SEQUENCE: 57
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSSGGSSGSE TPGTSESATP  240
ESSGGSSGGS MDKKYSIGLA IGTNSVGWAV ITDEYKVPSK KFKVLGNTDR HSIKKNLIGA  300
LLFDSGETAE ATRLKRTARR RYTRRKNRIC YLQEIFSNEM AKVDDSFFHR LEESFLVEED  360
KKHERHPIFG NIVDEVAYHE KYPTIYHLRK KLVDSTDKAD LRLIYLALAH MIKFRGHFLI  420
EGDLNPDNSD VDKLFIQLVQ TYNQLFEENP INASGVDAKA ILSARLSKSR RLENLIAQLP  480
GEKKNGLFGN LIALSLGLTP NFKSNFDLAE DAKLQLSKDT YDDDLDNLLA QIGDQYADLF  540
LAAKNLSDAI LLSDILRVNT EITKAPLSAS MIKRYDEHHQ DLTLLKALVR QQLPEKYKEI  600
FFDQSKNGYA GYIDGGASQE EFYKFIKPIL EKMDGTEELL VKLNREDLLR KQRTFDNGSI  660
PHQIHLGELH AILRRQEDFY PFLKDNREKI EKILTFRIPY YVGPLARGNS RFAWMTRKSE  720
ETITPWNFEE VVDKGASAQS FIERMTNFDK NLPNEKVLPK HSLLYEYFTV YNELTKVKYV  780
TEGMRKPAFL SGEQKKAIVD LLFKTNRKVT VKQLKEDYFK KIECFDSVEI SGVEDRFNAS  840
LGTYHDLLKI IKDKDFLDNE ENEDILEDIV LTLTLFEDRE MIEERLKTYA HLFDDKVMKQ  900
LKRRRYTGWG RLSRKLINGI RDKQSGKTIL DFLKSDGFAN RNFMQLIHDD SLTFKEDIQK  960
AQVSGQGDSL HEHIANLAGS PAIKKGILQT VKVVDELVKV MGRHKPENIV IEMARENQTT  1020
QKGQKNSRER MKRIEEGIKE LGSQILKEHP VENTQLQNEK LYLYYLQNGR DMYVDQELDI  1080
NRLSDYDVDH IVPQSFLKDD SIDNKVLTRS DKNRGKSDNV PSEEVVKKMK NYWRQLLNAK  1140
LITQRKFDNL TKAERGGLSE LDKAGFIKRQ LVETRQITKH VAQILDSRMN TKYDENDKLI  1200
REVKVITLKS KLVSDFRKDF QFYKVREINN YHHAHDAYLN AVVGTALIKK YPKLESEFVY  1260
GDYKVYDVRK MIAKSEQEIG KATAKYFFYS NIMNFFKTEI TLANGEIRKR PLIETNGETG  1320
EIVWDKGRDF ATVRKVLSMP QVNIVKKTEV QTGGFSKESI LPKRNSDKLI ARKKDWDPKK  1380
YGGFDSPTVA YSVLVVAKVE KGKSKKLKSV KELLGITIME RSSFEKNPID FLEAKGYKEV  1440
KKDLIIKLPK YSLFELENGR KRMLASAGEL QKGNELALPS KYVNFLYLAS HYEKLKGSPE  1500
DNEQKQLFVE QHKHYLDEII EQISEFSKRV ILADANLDKV LSAYNKHRDK PIREQAENII  1560
HLFTLTNLGA PAAFKYFDTT IDRKRYTSTK EVLDATLIHQ SITGLYETRI DLSQLGGDKR  1620
PAATKKAGQA KKKGGGGSG GGGSGGGGSM TNLSDIIEKE TGKQLVIQES ILMLPEEVEE  1680
VIGNKPESDI LVHTAYDEST DENVMLLTSD APEYKPWALV IQDSNGENKI KML         1733

SEQ ID NO: 58          moltype = AA  length = 1740
FEATURE                Location/Qualifiers
source                 1..1740
                       mol_type = protein
                       organism = synthetic construct
SEQUENCE: 58
MKIEEGKGHH HHHMDKKYS IGLAIGTNSV GWAVITDEYK VPSKKFKVLG NTDRHSIKKN  60
LIGALLFDSG ETAEATRLKR TARRRYTRRK NRICYLQEIF SNEMAKVDDS FFHRLEESFL  120
VEEDKKHERH PIFGNIVDEV AYHEKYPTIY HLRKKLVDST DKADLRLIYL ALAHMIKFRG  180
HFLIEGDLNP DNSDVDKLFI QLVQTYNQLF EENPINASGV DAKAILSARL SKSRRLENLI  240
AQLPGEKKNG LFGNLIALSL GLTPNFKSNF DLAEDAKLQL SKDTYDDDLD NLLAQIGDQY  300
ADLFLAAKNL SDAILLSDIL RVNTEITKAP LSASMIKRYD EHHQDLTLLK ALVRQQLPEK  360
YKEIFFDQSK NGYAGYIDGG ASQEEFYKFI KPILEKMDGT EELLVKLNRE DLLRKQRTFD  420
NGSIPHQIHL GELHAILRRQ EDFYPFLKDN REKIEKILTF RIPYYVGPLA RGNSRFAWMT  480
RKSEETITPW NFEEVVDKGA SAQSFIERMT NFDKNLPNEK VLPKHSLLYE YFTVYNELTK  540
VKYVTEGMRK PAFLSGEQKK AIVDLLFKTN RKVTVKQLKE DYFKKIECFD SVEISGVEDR  600
FNASLGTYHD LLKIIKDKDF LDNEENEDIL EDIVLTLTLF EDREMIEERL KTYAHLFDDK  660
VMKQLKRRRY TGWGRLSRKL INGIRDKQSG KTILDFLKSD GFANRNFMQL IHDDSLTFKE  720
DIQKAQVSGQ GDSLHEHIAN LAGSPAIKKG ILQTVKVVDE LVKVMGRHKP ENIVIEMARE  780
NQTTQKGQKN SRERMKRIEE GIKELGSQIL KEHPVENTQL QNEKLYLYYL QNGRDMYVDQ  840
ELDINRLSDY DVDHIVPQSF LKDDSIDNKV LTRSDKNRGK SDNVPSEEVV KKMKNYWRQL  900
LNAKLITQRK FDNLTKAERG GLSELDKAGF IKRQLVETRQ ITKHVAQILD SRMNTKYDEN  960
```

```
DKLIREVKVI TLKSKLVSDF RKDFQFYKVR EINNYHHAHD AYLNAVVGTA LIKKYPKLES  1020
EFVYGDYKVY DVRKMIAKSE QEIGKATAKY FFYSNIMNFF KTEITLANGE IRKRPLIETN  1080
GETGEIVWDK GRDFATVRKV LSMPQVNIVK KTEVQTGGFS KESILPKRNS DKLIARKKDW  1140
DPKKYGGFDS PTVAYSVLVV AKVEKGKSKK LKSVKELLGI TIMERSSFEK NPIDFLEAKG  1200
YKEVKKDLII KLPKYSLFEL ENGRKRMLAS AGELQKGNEL ALPSKYVNFL YLASHYEKLK  1260
GSPEDNEQKQ LFVEQHKHYL DEIIEQISEF SKRVILADAN LDKVLSAYNK HRDKPIREQA  1320
ENIIHLFTLT NLGAPAAFKY FDTTIDRKRY TSTKEVLDAT LIHQSITGLY ETRIDLSQLG  1380
GDKRPAATKK AGQAKKKKSG GSSGGSSGSE TPGTSESATP ESSGGSSGGS MEASPASGPR  1440
HLMDPHIFTS NFNNGIGRHK TYLCYEVERL DNGTSVKMDQ HRGFLHNQAK NLLCGFYGRH  1500
AELRFLDLVP SLQLDPAQIY RVTWFISWSP CFSAGCAGEV RAFLQENTHV RLRIFAARIY  1560
DYDYLYKEAL QMLRDAGAQV SIMTYDEFKH CWDTFVDHQG CPFQPWDGLD EHSQALSGRL  1620
RAILQNQGNS GGSMTNLSDI IEKETGKQLV IQESILMLPE EVEEVIGNKP ESDILVHTAY  1680
DESTDENVML LTSDAPEYKP WALVIQDSNG ENKIKMLSGG SMKRTADGSE FESPKKKRKV  1740

SEQ ID NO: 59           moltype = AA  length = 1074
FEATURE                 Location/Qualifiers
source                  1..1074
                        mol_type = protein
                        organism = synthetic construct
SEQUENCE: 59
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 60           moltype = AA  length = 1405
FEATURE                 Location/Qualifiers
source                  1..1405
                        mol_type = protein
                        organism = synthetic construct
SEQUENCE: 60
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
ENSVRLSRQL RRILQSGGSM TNLSDIIEKE TGKQLVIQES ILMLPEEVEE VIGNKPESDI  240
LVHTAYDEST DENVMLLTSD APEYKPWALV IQDSNGENKI KMLSGGSSGG SSGSETPGTS  300
ESATPESSGG SSGGSMASIS RPYGTKLRPD ARKKEMLDKF FNTLTKGQRV FADLALCIYG  360
SLTLEMAKSL EPESDSELVC AIGWFRLVDK TIWSKDGIKQ ENLVKQYEAY SGKEASEVVK  420
TYLNSPSSDK YVWIDCRQKF LRFQRELGTR NLSEDFECML FEQYIRLTKG EIEGYAAISN  480
MFGNGEKEDR SKKRMYATRM KDWLEANENI TWEQYREALK NQLNAKNLEQ VVANYKGNAG  540
GADPFFKYSF SKEGMVSKKE HAQQLDKFKT VLKNKARDLN FPNKEKLKQY LEAEIGIPVD  600
ANVYSQMFSN GVSEVQPKTT RNMSFSNEKL DLLTELKDLN KGDGFEYARE VLNGFFDSEL  660
HTTEDKFNIT SRYLGGDKSN RLSKLYKIWK KEGVDCEEGI QQFCEAVKDK MGQIPIRNVL  720
KYLWQFRETV SAEDFEAAAK ANHLEEKISR VKAHPIVISN RYWAFGTSAL VGNIMPADKR  780
HQGEYAGQNF KMWLRAELHY DGKKAKHHLP FYNARFFEEV YCYHPSVAEI TPFKTKQFGC  840
EIGKDIPDYV SVALKDNPYK KATKRILRAI YNPVANTTRV DKTTNCSFMI KRENDEYKLV  900
INRKISRDRP KRIEVGRTIM GYDRNQTASD TYWIGRLVPP GTRGAYRIGE WSVQYIKSGP  960
VLSSTQGVNN STTDQLVYNG MPSSSERFKA WKKARMAFIR KLIRQLNDEG LESKGQDYIP  1020
ENPSSFDVRG ETLYVFNSNY LKALVSKHRK AKKPVEGILD EIEAWTSKDK DSCSLMRLSS  1080
LSDASMQGIA SLKSLINSYF NKNGCKTIED KEKFNPVLYA KLVEVEQRRT NKRSEKVGRI  1140
AGSLEQLALL NGVEVVIGEA DLGEVEKGKS KKQNSRNMDW CAKQVAQRLE YKLAFHGIGY  1200
FGVNPMYTSH QDPFEHRRVA DHIVMRARFE EVNVENIAEW HVRNFSNYLR ADSGTGLYYK  1260
QATMDFLKHY GLEEHAEGLE NKKIKFYDFR KILEDKNLTS VIIPKRGGRI YMATNPVTSD  1320
STPITYAGKT YNRCNADEVA AANIVISVLA PRSKKNREQD DIPLITKKAE SKSPPKDRKR  1380
SKTSQLPQKK RPAATKKAGQ AKKKK                                       1405

SEQ ID NO: 61           moltype = AA  length = 1416
FEATURE                 Location/Qualifiers
source                  1..1416
                        mol_type = protein
                        organism = synthetic construct
SEQUENCE: 61
MKRTADGSEF ESPKKKRKVM DPATFTYQFK NVRWAKGRRE TYLCYVVKRR DSATSFSLDF  60
GYLRNKNGCH VELLFLRYIS DWDLDPGRCY RVTWFTSWSP CYDCARHVAD FLRGNPNLSL  120
RIFTARLYFC EDRKAEPEGL RRLAEAGVQI AIMTFKDYFY CWNTFVENHE RTFKAWEGLH  180
```

```
ENSVRLSRQL RRILQSGGSS GGSSGSETPG TSESATPESS GGSSGGSMAS ISRPYGTKLR  240
PDARKKEMLD KFFNTLTKGQ RVFADLALCI YGSLTLEMAK SLEPESDSEL VCAIGWFRLV  300
DKTIWSKDGI KQENLVKQYE AYSGKEASEV VKTYLNSPSS DKYVWIDCRQ KFLRFQRELG  360
TRNLSEDFEC MLFEQYIRLT KGEIEGYAAI SNMFGNGEKE DRSKKRMYAT RMKDWLEANE  420
NITWEQYREA LKNQLNAKNL EQVVANYKGN AGGADPFFKY SFSKEGMVSK KEHAQQLDKF  480
KTVLKNKARD LNFPNKEKLK QYLEAEIGIP VDANVYSQMF SNGVSEVQPK TTRNMSFSNE  540
KLDLLTELKD LNKGDGFEYA REVLNGFFDS ELHTTEDKFN ITSRYLGGDK SNRLSKLYKI  600
WKKEGVDCEE GIQQFCEAVK DKMGQIPIRN VLKYLWQFRE TVSAEDFEAA AKANHLEEKI  660
SRVKAHPIVI SNRYWAFGTS ALVGNIMPAD KRHQGEYAGQ NFKMWLRAEL HYDGKKAKHH  720
LPFYNARFFE EVYCYHPSVA EITPFKTKQF GCEIGKDIPD YVSVALKDNP YKKATKRILR  780
AIYNPVANTT RVDKTTNCSF MIKRENDEYK LVINRKISRD RPKRIEVGRT IMGYDRNQTA  840
SDTYWIGRLV PPGTRGAYRI GEWSVQYIKS GPVLSSTQGV NNSTTDQLVY NGMPSSSERF  900
KAWKKARMAF IRKLIRQLND EGLESKGQDY IPENPSSFDV RGETLYVFNS NYLKALVSKH  960
RKAKKPVEGI LDEIEAWTSK DKDSCSLMRL SSLSDASMQG IASLKSLINS YFNKNGCKTI  1020
EDKEKFNPVL YAKLVEVEQR RTNKRSEKVG RIAGSLEQLA LLNGVEVVIG EADLGEVEKG  1080
KSKKQNSRNM DWCAKQVAQR LEYKLAFHGI GYFGVNPMYT SHQDPFEHRR VADHIVMRAR  1140
FEEVNVENIA EWHVRNFSNY LRADSGTGLY YKQATMDFLK HYGLEEHAEG LENKKIKFYD  1200
FRKILEDKNL TSVIIPKRGG RIYMATNPVT SDSTPITYAG KTYNRCNADE VAAANIVISV  1260
LAPRSKKNRE QDDIPLITKK AESKSPPKDR KRSKTSQLPQ KKRPAATKKA GQAKKKKGGG  1320
GSGGGGSGGG GSMTNLSDII EKETGKQLVI QESILMLPEE VEEVIGNKPE SDILVHTAYD  1380
ESTDENVMLL TSDAPEYKPW ALVIQDSNGE NKIKML                           1416

SEQ ID NO: 62           moltype = AA  length = 1423
FEATURE                 Location/Qualifiers
source                  1..1423
                        mol_type = protein
                        organism = synthetic construct
SEQUENCE: 62
MKIEEGKGHH HHHHMASISR PYGTKLRPDA RKKEMLDKFF NTLTKGQRVF ADLALCIYGS  60
LTLEMAKSLE PESDSELVCA IGWFRLVDKT IWSKDGIKQE NLVKQYEAYS GKEASEVVKT  120
YLNSPSSDKY VWIDCRQKFL RFQRELGTRN LSEDFECMLF EQYIRLTKGE IEGYAAISNM  180
FGNGEKEDRS KKRMYATRMK DWLEANENIT WEQYREALKN QLNAKNLEQV VANYKGNAGG  240
ADPFFKYSFS KEGMVSKKEH AQQLDKFKTV LKNKARDLNF PNKEKLKQYL EAEIGIPVDA  300
NVYSQMFSNG VSEVQPKTTR NMSFSNEKLD LLTELKDLNK GDGFEYAREV LNGFFDSELH  360
TTEDKFNITS RYLGGDKSNR LSKLYKIWKK EGVDCEEGIQ QFCEAVKDKM GQIPIRNVLK  420
YLWQFRETVS AEDFEAAAKA NHLEEKISRV KAHPIVISNR YWAFGTSALV GNIMPADKRH  480
QGEYAGQNFK MWLRAELHYD GKKAKHHLPF YNARFFEEVY CYHPSVAEIT PFKTKQFGCE  540
IGKDIPDYVS VALKDNPYKK ATKRILRAIY NPVANTTRVD KTTNCSFMIK RENDEYKLVI  600
NRKISRDRPK RIEVGRTIMG YDRNQTASDT YWIGRLVPPG TRGAYRIGEW SVQYIKSGPV  660
LSSTQGVNNS TTDQLVYNGM PSSSERFKAW KKARMAFIRK LIRQLNDEGL ESKGQDYIPE  720
NPSSFDVRGE TLYVFNSNYL KALVSKHRKA KKPVEGILDE IEAWTSKDKD SCSLMRLSSL  780
SDASMQGIAS LKSLINSYFN KNGCKTIEDK EKFNPVLYAK LVEVEQRRTN KRSEKVGRIA  840
GSLEQLALLN GVEVVIGEAD LGEVEKGKSK KQNSRNMDWC AKQVAQRLEY KLAFHGIGYF  900
GVNPMYTSHQ DPFEHRRVAD HIVMRARFEE VNVENIAEWH VRNFSNYLRA DSGTGLYYKQ  960
ATMDFLKHYG LEEHAEGLEN KKIKFYDFRK ILEDKNLTSV IIPKRGGRIY MATNPVTSDS  1020
TPITYAGKTY NRCNADEVAA ANIVISVLAP RSKKNREQDD IPLITKKAES KSPPKDRKRS  1080
KTSQLPQKKR PAATKKAGQA KKKKSGGSSG GSSGSETPGT SESATPESSG GSSGGSMDPA  1140
TFTYQFKNVR WAKGRRETYL CYVVKRRDSA TSFSLDFGYL RNKNGCHVEL LFLRYISDWD  1200
LDPGRCYRVT WFTSWSPCYD CARHVADFLR GNPNLSLRIF TARLYFCEDR KAEPEGLRRL  1260
AEAGVQIAIM TFKDYFYCWN TFVENHERTF KAWEGLHENS VRLSRQLRRI LQSGGSMTNL  1320
SDIIEKETGK QLVIQESILM LPEEVEEVIG NKPESDILVH TAYDESTDEN VMLLTSDAPE  1380
YKPWALVIQD SNGENKIKML SGGSMKRTAD GSEFESPKKK RKV                   1423

SEQ ID NO: 63           moltype = AA  length = 1428
FEATURE                 Location/Qualifiers
source                  1..1428
                        mol_type = protein
                        organism = synthetic construct
SEQUENCE: 63
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSMTNLSDII EKETGKQLVI  240
QESILMLPEE VEEVIGNKPE SDILVHTAYD ESTDENVMLL TSDAPEYKPW ALVIQDSNGE  300
NKIKMLSGGS SGGSSGSETP GTSESATPES SGGSSGGSMA SISRPYGTKL RPDARKKEML  360
DKFFNTLTKG QRVFADLALC IYGSLTLEMA KSLEPESDSE LVCAIGWFRL VDKTIWSKDG  420
IKQENLVKQY EAYSGKEASE VVKTYLNSPS SDKYVWIDCR QKFLRFQREL GTRNLSEDFE  480
CMLFEQYIRL TKGEIEGYAA ISNMFGNGEK EDRSKKRMYA TRMKDWLEAN ENITWEQYRE  540
ALKNQLNAKN LEQVVANYKG NAGGADPFFK YSFSKEGMVS KKEHAQQLDK FKTVLKNKAR  600
DLNFPNKEKL KQYLEAEIGI PVDANVYSQM FSNGVSEVQP KTTRNMSFSN EKLDLLTELK  660
DLNKGDGFEY AREVLNGFFD SELHTTEDKF NITSRYLGGD KSNRLSKLYK IWKKEGVDCE  720
EGIQQFCEAV KDKMGQIPIR NVLKYLWQFR ETVSAEDFEA AAKANHLEEK ISRVKAHPIV  780
ISNRYWAFGT SALVGNIMPA DKRHQGEYAG QNFKMWLRAE LHYDGKKAKH HLPFYNARFF  840
EEVYCYHPSV AEITPFKTKQ FGCEIGKDIP DYVSVALKDN PYKKATKRIL RAIYNPVANT  900
TRVDKTTNCS FMIKRENDEY KLVINRKISR DRPKRIEVGR TIMGYDRNQT ASDTYWIGRL  960
VPPGTRGAYR IGEWSVQYIK SGPVLSSTQG VNNSTTDQLV YNGMPSSSER FKAWKKARMA  1020
FIRKLIRQLN DEGLESKGQD YIPENPSSFD VRGETLYVFN SNYLKALVSK HRKAKKPVEG  1080
ILDEIEAWTS KDKDSCSLMR LSSLSDASMQ GIASLKSLIN SYFNKNGCKT IEDKEKFNPV  1140
LYAKLVEVEQ RRTNKRSEKV GRIAGSLEQL ALLNGVEVVI GEADLGEVEK GKSKKQNSRN  1200
```

```
MDWCAKQVAQ RLEYKLAFHG IGYFGVNPMY TSHQDPFEHR RVADHIVMRA RFEEVNVENI  1260
AEWHVRNFSN YLRADSGTGL YYKQATMDFL KHYGLEEHAE GLENKKIKFY DFRKILEDKN  1320
LTSVIIPKRG GRIYMATNPV TSDSTPITYA GKTYNRCNAD EVAAANIVIS VLAPRSKKNR  1380
EQDDIPLITK KAESKSPPKD RKRSKTSQLP QKKRPAATKK AGQAKKKK               1428

SEQ ID NO: 64          moltype = AA  length = 1439
FEATURE                Location/Qualifiers
source                 1..1439
                       mol_type = protein
                       organism = synthetic construct
SEQUENCE: 64
MKRTADGSEF ESPKKKRKVM EASPASGPRH LMDPHIFTSN FNNGIGRHKT YLCYEVERLD  60
NGTSVKMDQH RGFLHNQAKN LLCGFYGRHA ELRFLDLVPS LQLDPAQIYR VTWFISWSPC  120
FSAGCAGEVR AFLQENTHVR LRIFAARIYD YDYLYKEALQ MLRDAGAQVS IMTYDEFKHC  180
WDTFVDHQGC PFQPWDGLDE HSQALSGRLR AILQNQGNSG GSSGGSSGSE TPGTSESATP  240
ESSGGSSGGS MASISRPYGT KLRPDARKKE MLDKFFNTLT KGQRVFADLA LCIYGSLTLE  300
MAKSLEPESD SELVCAIGWF RLVDKTIWSK DGIKQENLVK QYEAYSGKEA SEVVKTYLNS  360
PSSDKYVWID CRQKFLRFQR ELGTRNLSED FECMLFEQYI RLTKGEIEGY AAISNMFGNG  420
EKEDRSKKRM YATRMKDWLE ANENITWEQY REALKNQLNA KNLEQVVANY KGNAGGADPF  480
FKYSFSKEGM VSKKEHAQQL DKFKTVLKNK ARDLNFPNKE KLKQYLEAEI GIPVDANVYS  540
QMFSNGVSEV QPKTTRNMSF SNEKLDLLTE LKDLNKGDGF EYAREVLNGF FDSELHTTED  600
KFNITSRYLG GDKSNRLSKL YKIWKKEGVD CEEGIQQFCE AVKDKMGQIP IRNVLKYLWQ  660
FRETVSAEDF EAAAKANHLE EKISRVKAHP IVISNRYWAF GTSALVGNIM PADKRHQGEY  720
AGQNFKMWLR AELHYDGKKA KHHLPFYNAR FFEEVYCYHP SVAEITPFKT KQFGCEIGKD  780
IPDYVSVALK DNPYKKATKR ILRAIYNPVA NTTRVDKTTN CSFMIKREND EYKLVINRKI  840
SRDRPKRIEV GRTIMGYDRN QTASDTYWIG RLVPPGTGRA YRIGEWSVQY IKSGPVLSST  900
QGVNNSTTDQ LVYNGMPSSS ERFKAWKKAR MAFIRKLIRQ LNDEGLESKG QDYIPENPSS  960
FDVRGETLYV FNSNYLKALV SKHRKAKKPV EGILDEIEAW TSKDKDSCSL MRLSSLSDAS  1020
MQGIASLKSL INSYFNKNGC KTIEDKEKFN PVLYAKLVEV EQRRTNKRSE KVGRIAGSLE  1080
QLALLNGVEV VIGEADLGEV EKGKSKKQNS RNMDWCAKQV AQRLEYKLAF HGIGYFGVNP  1140
MYTSHQDPFE HRRVADHIVM RARFEEVNVE NIAEWHVRNF SNYLRADSGT GLYYKQATMD  1200
FLKHYGLEEH AEGLENKKIK FYDFRKILED KNLTSVIIPK RGGRIYMATN PVTSDSTPIT  1260
YAGKTYNRCN ADEVAAANIV ISVLAPRSKK NREQDDIPLI TKKAESKSPP KDRKRSKTSQ  1320
LPQKKRPAAT KKAGQAKKKK GGGGSGGGGS GGGGSMTNLS DIIEKETGKQ LVIQESILML  1380
PEEVEEVIGN KPESDILVHT AYDESTDENV MLLTSDAPEY KPWALVIQDS NGENKIKML   1439

SEQ ID NO: 65          moltype = AA  length = 1446
FEATURE                Location/Qualifiers
source                 1..1446
                       mol_type = protein
                       organism = synthetic construct
SEQUENCE: 65
MKIEEGKGHH HHHHMASISR PYGTKLRPDA RKKEMLDKFF NTLTKGQRVF ADLALCIYGS  60
LTLEMAKSLE PESDSELVCA IGWFRLVDKT IWSKDGIKQE NLVKQYEAYS GKEASEVVKT  120
YLNSPSSDKY VWIDCRQKFL RFQRELGTRN LSEDFECMLF EQYIRLTKGE IEGYAAISNM  180
FGNGEKEDRS KKRMYATRMK DWLEANENIT WEQYREALKN QLNAKNLEQV VANYKGNAGG  240
ADPFFKYSFS KEGMVSKKEH AQQLDKFKTV LKNKARDLNF PNKEKLKQYL EAEIGIPVDA  300
NVYSQMFSNG VSEVQPKTTR NMSFSNEKLD LLTELKDLNK GDGFEYAREV LNGFFDSELH  360
TTEDKFNITS RYLGGDKSNR LSKLYKIWKK EGVDCEEGIQ QFCEAVKDKM GQIPIRNVLK  420
YLWQFRETVS AEDFEAAAKA NHLEEKISRV KAHPIVISNR YWAFGTSALV GNIMPADKRH  480
QGEYAGQNFK MWLRAELHYD GKKAKHHLPF YNARFFEEVY CYHPSVAEIT PFKTKQFGCE  540
IGKDIPDYVS VALKDNPYKK ATKRILRAIY NPVANTTRVD KTTNCSFMIK RENDEYKLVI  600
NRKISRDRPK RIEVGRTIMG YDRNQTASDT YWIGRLVPPG TRGAYRIGEW SVQYIKSGPV  660
LSSTQGVNNS TTDQLVYNGM PSSSERFKAW KKARMAFIRK LIRQLNDEGL ESKGQDYIPE  720
NPSSFDVRGE TLYVFNSNYL KALVSKHRKA KKPVEGILDE IEAWTSKDKD SCSLMRLSSL  780
SDASMQGIAS LKSLINSYFN KNGCKTIEDK EKFNPVLYAK LVEVEQRRTN KRSEKVGRIA  840
GSLEQLALLN GVEVVIGEAD LGEVEKGKSK KQNSRNMDWC AKQVAQRLEY KLAFHGIGYF  900
GVNPMYTSHQ DPFEHRRVAD HIVMRARFEE VNVENIAEWH VRNFSNYLRA DSGTGLYYKQ  960
ATMDFLKHYG LEEHAEGLEN KKIKFYDFRK ILEDKNLTSV IIPKRGGRIY MATNPVTSDS  1020
TPITYAGKTY NRCNADEVAA ANIVISVLAP RSKKNREQDD IPLITKKAES KSPPKDRKRS  1080
KTSQLPQKKR PAATKKAGQA KKKKSGGSSG GSSGSETPGT SESATPESSG GSSGGSMEAS  1140
PASGPRHLMD PHIFTSNFNN GIGRHKTYLC YEVERLDNGT SVKMDQHRGF LHNQAKNLLC  1200
GFYGRHAELR FLDLVPSLQL DPAQIYRVTW FISWSPCFSA GCAGEVRAFL QENTHVRLRI  1260
FAARIYDYDY LYKEALQMLR DAGAQVSIMT YDEFKHCWDT FVDHQGCPFQ PWDGLDEHSQ  1320
ALSGRLRAIL QNQGNSGGSM TNLSDIIEKE TGKQLVIQES ILMLPEEVEE VIGNKPESDI  1380
LVHTAYDEST DENVMLLTSD APEYKPWALV IQDSNGENKI KMLSGGSMKR TADGSEFESP  1440
KKKRKV                                                             1446

SEQ ID NO: 66          moltype = DNA  length = 20
FEATURE                Location/Qualifiers
source                 1..20
                       mol_type = other DNA
                       organism = synthetic construct
SEQUENCE: 66
gtgagaatgg tgcgtcctag                                              20

SEQ ID NO: 67          moltype = DNA  length = 20
FEATURE                Location/Qualifiers
source                 1..20
```

```
                          mol_type = other DNA
                          organism = synthetic construct
SEQUENCE: 67
ttgtgagaat ggtgcgtcct                                                  20

SEQ ID NO: 68             moltype = DNA  length = 20
FEATURE                   Location/Qualifiers
source                    1..20
                          mol_type = other DNA
                          organism = synthetic construct
SEQUENCE: 68
aactggccct ggctttggca                                                  20

SEQ ID NO: 69             moltype = DNA  length = 20
FEATURE                   Location/Qualifiers
source                    1..20
                          mol_type = other DNA
                          organism = synthetic construct
SEQUENCE: 69
gctttaactg gccctggctt                                                  20

SEQ ID NO: 70             moltype = DNA  length = 20
FEATURE                   Location/Qualifiers
source                    1..20
                          mol_type = other DNA
                          organism = synthetic construct
SEQUENCE: 70
gtagcctctc ccgctctggt                                                  20

SEQ ID NO: 71             moltype = DNA  length = 20
FEATURE                   Location/Qualifiers
source                    1..20
                          mol_type = other DNA
                          organism = synthetic construct
SEQUENCE: 71
ctttgtagcc tctcccgctc                                                  20

SEQ ID NO: 72             moltype = DNA  length = 20
FEATURE                   Location/Qualifiers
source                    1..20
                          mol_type = other DNA
                          organism = synthetic construct
SEQUENCE: 72
ggatggcgac ttcaggcaca                                                  20

SEQ ID NO: 73             moltype = DNA  length = 20
FEATURE                   Location/Qualifiers
source                    1..20
                          mol_type = other DNA
                          organism = synthetic construct
SEQUENCE: 73
tggatggcga cttcaggcac                                                  20

SEQ ID NO: 74             moltype = DNA  length = 20
FEATURE                   Location/Qualifiers
source                    1..20
                          mol_type = other DNA
                          organism = synthetic construct
SEQUENCE: 74
ggggaggcct ggagtcatgg                                                  20

SEQ ID NO: 75             moltype = DNA  length = 20
FEATURE                   Location/Qualifiers
source                    1..20
                          mol_type = other DNA
                          organism = synthetic construct
SEQUENCE: 75
tttggggagg cctggagtca                                                  20

SEQ ID NO: 76             moltype = DNA  length = 20
FEATURE                   Location/Qualifiers
source                    1..20
                          mol_type = other DNA
                          organism = synthetic construct
SEQUENCE: 76
agcaagggac tattcaggga                                                  20

SEQ ID NO: 77             moltype = DNA  length = 20
FEATURE                   Location/Qualifiers
```

```
source                  1..20
                        mol_type = other DNA
                        organism = synthetic construct
SEQUENCE: 77
ctttagcaag ggactattca                                              20

SEQ ID NO: 78           moltype = DNA  length = 20
FEATURE                 Location/Qualifiers
source                  1..20
                        mol_type = other DNA
                        organism = synthetic construct
SEQUENCE: 78
aaaattgagc aatctaccct                                              20

SEQ ID NO: 79           moltype = DNA  length = 20
FEATURE                 Location/Qualifiers
source                  1..20
                        mol_type = other DNA
                        organism = synthetic construct
SEQUENCE: 79
taaaattgag caatctaccc                                              20

SEQ ID NO: 80           moltype = DNA  length = 20
FEATURE                 Location/Qualifiers
source                  1..20
                        mol_type = other DNA
                        organism = synthetic construct
SEQUENCE: 80
tgggggtgac cgccggagcg                                              20

SEQ ID NO: 81           moltype = DNA  length = 20
FEATURE                 Location/Qualifiers
source                  1..20
                        mol_type = other DNA
                        organism = synthetic construct
SEQUENCE: 81
tgggggtgac cgccggagcg                                              20

SEQ ID NO: 82           moltype = DNA  length = 20
FEATURE                 Location/Qualifiers
source                  1..20
                        mol_type = other DNA
                        organism = synthetic construct
SEQUENCE: 82
gttgacattg tccacacctg                                              20

SEQ ID NO: 83           moltype = DNA  length = 20
FEATURE                 Location/Qualifiers
source                  1..20
                        mol_type = other DNA
                        organism = synthetic construct
SEQUENCE: 83
ttgttgacat tgtccacacc                                              20

SEQ ID NO: 84           moltype = DNA  length = 20
FEATURE                 Location/Qualifiers
source                  1..20
                        mol_type = other DNA
                        organism = synthetic construct
SEQUENCE: 84
ttaaactctc catggaccag                                              20

SEQ ID NO: 85           moltype = DNA  length = 20
FEATURE                 Location/Qualifiers
source                  1..20
                        mol_type = other DNA
                        organism = synthetic construct
SEQUENCE: 85
ttttaaactc tccatggacc                                              20

SEQ ID NO: 86           moltype = RNA  length = 43
FEATURE                 Location/Qualifiers
source                  1..43
                        mol_type = other RNA
                        organism = synthetic construct
SEQUENCE: 86
agaaatccgt ctttcattga cgggtgagaa tggtgcgtcc tag                    43

SEQ ID NO: 87           moltype = RNA  length = 96
```

```
FEATURE                 Location/Qualifiers
source                  1..96
                        mol_type = other RNA
                        organism = synthetic construct
SEQUENCE: 87
gttttagagc tagaaatagc aagttaaaat aaggctagtc cgttatcaac ttgaaaaagt  60
ggcaccgagt cggtgcttgt gagaatggtg cgtcct                            96

SEQ ID NO: 88           moltype = RNA  length = 43
FEATURE                 Location/Qualifiers
source                  1..43
                        mol_type = other RNA
                        organism = synthetic construct
SEQUENCE: 88
agaaatccgt ctttcattga cggaactggc cctggctttg gca                    43

SEQ ID NO: 89           moltype = RNA  length = 96
FEATURE                 Location/Qualifiers
source                  1..96
                        mol_type = other RNA
                        organism = synthetic construct
SEQUENCE: 89
gttttagagc tagaaatagc aagttaaaat aaggctagtc cgttatcaac ttgaaaaagt  60
ggcaccgagt cggtgcaact ggccctggct ttggca                            96

SEQ ID NO: 90           moltype = RNA  length = 43
FEATURE                 Location/Qualifiers
source                  1..43
                        mol_type = other RNA
                        organism = synthetic construct
SEQUENCE: 90
agaaatccgt ctttcattga cgggtagcct ctcccgctct ggt                    43

SEQ ID NO: 91           moltype = RNA  length = 96
FEATURE                 Location/Qualifiers
source                  1..96
                        mol_type = other RNA
                        organism = synthetic construct
SEQUENCE: 91
gttttagagc tagaaatagc aagttaaaat aaggctagtc cgttatcaac ttgaaaaagt  60
ggcaccgagt cggtgccttt gtagcctctc ccgctc                            96

SEQ ID NO: 92           moltype = RNA  length = 43
FEATURE                 Location/Qualifiers
source                  1..43
                        mol_type = other RNA
                        organism = synthetic construct
SEQUENCE: 92
agaaatccgt ctttcattga cggggatggc gacttcaggc aca                    43

SEQ ID NO: 93           moltype = RNA  length = 96
FEATURE                 Location/Qualifiers
source                  1..96
                        mol_type = other RNA
                        organism = synthetic construct
SEQUENCE: 93
gttttagagc tagaaatagc aagttaaaat aaggctagtc cgttatcaac ttgaaaaagt  60
ggcaccgagt cggtgctgga tggcgacttc aggcac                            96

SEQ ID NO: 94           moltype = RNA  length = 43
FEATURE                 Location/Qualifiers
source                  1..43
                        mol_type = other RNA
                        organism = synthetic construct
SEQUENCE: 94
agaaatccgt ctttcattga cggggggagg cctggagtca tgg                    43

SEQ ID NO: 95           moltype = RNA  length = 96
FEATURE                 Location/Qualifiers
source                  1..96
                        mol_type = other RNA
                        organism = synthetic construct
SEQUENCE: 95
gttttagagc tagaaatagc aagttaaaat aaggctagtc cgttatcaac ttgaaaaagt  60
ggcaccgagt cggtgctttg gggaggcctg gagtca                            96

SEQ ID NO: 96           moltype = RNA  length = 43
FEATURE                 Location/Qualifiers
source                  1..43
```

```
                        mol_type = other RNA
                        organism = synthetic construct
SEQUENCE: 96
agaaatccgt ctttcattga cggagcaagg gactattcag gga                     43

SEQ ID NO: 97           moltype = RNA  length = 96
FEATURE                 Location/Qualifiers
source                  1..96
                        mol_type = other RNA
                        organism = synthetic construct
SEQUENCE: 97
gttttagagc tagaaatagc aagttaaaat aaggctagtc cgttatcaac ttgaaaaagt  60
ggcaccgagt cggtgccttt agcaagggac tattca                             96

SEQ ID NO: 98           moltype = RNA  length = 43
FEATURE                 Location/Qualifiers
source                  1..43
                        mol_type = other RNA
                        organism = synthetic construct
SEQUENCE: 98
agaaatccgt ctttcattga cggaaaattg agcaatctac cct                     43

SEQ ID NO: 99           moltype = RNA  length = 96
FEATURE                 Location/Qualifiers
source                  1..96
                        mol_type = other RNA
                        organism = synthetic construct
SEQUENCE: 99
gttttagagc tagaaatagc aagttaaaat aaggctagtc cgttatcaac ttgaaaaagt  60
ggcaccgagt cggtgctaaa attgagcaat ctaccc                             96

SEQ ID NO: 100          moltype = RNA  length = 43
FEATURE                 Location/Qualifiers
source                  1..43
                        mol_type = other RNA
                        organism = synthetic construct
SEQUENCE: 100
agaaatccgt ctttcattga cggtgggggt gaccgccgga gcg                     43

SEQ ID NO: 101          moltype = RNA  length = 96
FEATURE                 Location/Qualifiers
source                  1..96
                        mol_type = other RNA
                        organism = synthetic construct
SEQUENCE: 101
gttttagagc tagaaatagc aagttaaaat aaggctagtc cgttatcaac ttgaaaaagt  60
ggcaccgagt cggtgctggg ggtgaccgcc ggagcg                             96

SEQ ID NO: 102          moltype = RNA  length = 43
FEATURE                 Location/Qualifiers
source                  1..43
                        mol_type = other RNA
                        organism = synthetic construct
SEQUENCE: 102
agaaatccgt ctttcattga cgggttgaca ttgtccacac ctg                     43

SEQ ID NO: 103          moltype = RNA  length = 96
FEATURE                 Location/Qualifiers
source                  1..96
                        mol_type = other RNA
                        organism = synthetic construct
SEQUENCE: 103
gttttagagc tagaaatagc aagttaaaat aaggctagtc cgttatcaac ttgaaaaagt  60
ggcaccgagt cggtgcttgt tgacattgtc cacacc                             96

SEQ ID NO: 104          moltype = RNA  length = 43
FEATURE                 Location/Qualifiers
source                  1..43
                        mol_type = other RNA
                        organism = synthetic construct
SEQUENCE: 104
agaaatccgt ctttcattga cggttaaact ctccatggac cag                     43

SEQ ID NO: 105          moltype = RNA  length = 96
FEATURE                 Location/Qualifiers
source                  1..96
                        mol_type = other RNA
                        organism = synthetic construct
SEQUENCE: 105
```

```
gttttagagc tagaaatagc aagttaaaat aaggctagtc cgttatcaac ttgaaaaagt  60
ggcaccgagt cggtgctttt aaactctcca tggacc                            96

SEQ ID NO: 106          moltype = AA  length = 16
FEATURE                 Location/Qualifiers
source                  1..16
                        mol_type = protein
                        organism = synthetic construct
SEQUENCE: 106
SGSETPGTSE SATPES                                                  16

SEQ ID NO: 107          moltype = AA  length = 14
FEATURE                 Location/Qualifiers
source                  1..14
                        mol_type = protein
                        organism = synthetic construct
SEQUENCE: 107
SEFFSGEETY TICV                                                    14

SEQ ID NO: 108          moltype = AA  length = 6
FEATURE                 Location/Qualifiers
source                  1..6
                        mol_type = protein
                        organism = synthetic construct
SEQUENCE: 108
DPADPE                                                             6

SEQ ID NO: 109          moltype = AA  length = 6
FEATURE                 Location/Qualifiers
source                  1..6
                        mol_type = protein
                        organism = synthetic construct
SEQUENCE: 109
RQECSA                                                             6

SEQ ID NO: 110          moltype = AA  length = 9
FEATURE                 Location/Qualifiers
source                  1..9
                        mol_type = protein
                        organism = synthetic construct
SEQUENCE: 110
KKNKKKEIV                                                          9

SEQ ID NO: 111          moltype = AA  length = 6
FEATURE                 Location/Qualifiers
source                  1..6
                        mol_type = protein
                        organism = synthetic construct
SEQUENCE: 111
VRGKSL                                                             6

SEQ ID NO: 112          moltype = AA  length = 12
FEATURE                 Location/Qualifiers
source                  1..12
                        mol_type = protein
                        organism = synthetic construct
SEQUENCE: 112
ALNASKNNPI SD                                                      12

SEQ ID NO: 113          moltype = AA  length = 13
FEATURE                 Location/Qualifiers
source                  1..13
                        mol_type = protein
                        organism = synthetic construct
SEQUENCE: 113
LKWRSDRKSN IPC                                                     13

SEQ ID NO: 114          moltype = AA  length = 11
FEATURE                 Location/Qualifiers
source                  1..11
                        mol_type = protein
                        organism = synthetic construct
SEQUENCE: 114
STEQEKQQQD I                                                       11

SEQ ID NO: 115          moltype = AA  length = 7
FEATURE                 Location/Qualifiers
source                  1..7
                        mol_type = protein
```

```
                      organism = synthetic construct
SEQUENCE: 115
YGGTASD                                                           7

SEQ ID NO: 116        moltype = AA  length = 9
FEATURE               Location/Qualifiers
source                1..9
                      mol_type = protein
                      organism = synthetic construct
SEQUENCE: 116
SASIGESYY                                                         9

SEQ ID NO: 117        moltype = AA  length = 12
FEATURE               Location/Qualifiers
source                1..12
                      mol_type = protein
                      organism = synthetic construct
SEQUENCE: 117
SNLKEIPKNV AP                                                     12

SEQ ID NO: 118        moltype = AA  length = 9
FEATURE               Location/Qualifiers
source                1..9
                      mol_type = protein
                      organism = synthetic construct
SEQUENCE: 118
KDGQKEFDL                                                         9

SEQ ID NO: 119        moltype = AA  length = 12
FEATURE               Location/Qualifiers
source                1..12
                      mol_type = protein
                      organism = synthetic construct
SEQUENCE: 119
GRQKGTLQIG DR                                                     12

SEQ ID NO: 120        moltype = AA  length = 25
FEATURE               Location/Qualifiers
source                1..25
                      mol_type = protein
                      organism = synthetic construct
SEQUENCE: 120
CGSLYTSHQD PLVHRNPDKA MKCRW                                       25

SEQ ID NO: 121        moltype = AA  length = 5
FEATURE               Location/Qualifiers
source                1..5
                      mol_type = protein
                      organism = synthetic construct
SEQUENCE: 121
GGGGS                                                             5

SEQ ID NO: 122        moltype = AA  length = 30
FEATURE               Location/Qualifiers
source                1..30
                      mol_type = protein
                      organism = synthetic construct
SEQUENCE: 122
GGGGSGGGGS GGGGSGGGGS GGGGSGGGGS                                  30

SEQ ID NO: 123        moltype = AA  length = 15
FEATURE               Location/Qualifiers
source                1..15
                      mol_type = protein
                      organism = synthetic construct
SEQUENCE: 123
GGGGSGGGGS GGGGS                                                  15

SEQ ID NO: 124        moltype = AA  length = 4
FEATURE               Location/Qualifiers
source                1..4
                      mol_type = protein
                      organism = synthetic construct
SEQUENCE: 124
GSSG                                                              4

SEQ ID NO: 125        moltype = AA  length = 8
FEATURE               Location/Qualifiers
source                1..8
```

```
                         mol_type = protein
                         organism = synthetic construct
SEQUENCE: 125
GSSGGSSG                                                 8

SEQ ID NO: 126           moltype = AA  length = 12
FEATURE                  Location/Qualifiers
source                   1..12
                         mol_type = protein
                         organism = synthetic construct
SEQUENCE: 126
GSSGGSSGGS SG                                            12

SEQ ID NO: 127           moltype = AA  length = 16
FEATURE                  Location/Qualifiers
source                   1..16
                         mol_type = protein
                         organism = synthetic construct
SEQUENCE: 127
GSSGGSSGGS SGGSSG                                        16

SEQ ID NO: 128           moltype =   length =
SEQUENCE: 128
000

SEQ ID NO: 129           moltype = AA  length = 12
FEATURE                  Location/Qualifiers
source                   1..12
                         mol_type = protein
                         organism = synthetic construct
SEQUENCE: 129
GSGGSGGSGG SG                                            12

SEQ ID NO: 130           moltype = AA  length = 4
FEATURE                  Location/Qualifiers
source                   1..4
                         mol_type = protein
                         organism = synthetic construct
SEQUENCE: 130
GGGS                                                     4

SEQ ID NO: 131           moltype = AA  length = 12
FEATURE                  Location/Qualifiers
source                   1..12
                         mol_type = protein
                         organism = synthetic construct
SEQUENCE: 131
DDLKNNFKKE PI                                            12

SEQ ID NO: 132           moltype = DNA  length = 50
FEATURE                  Location/Qualifiers
source                   1..50
                         mol_type = other DNA
                         organism = synthetic construct
SEQUENCE: 132
ccctggccag gctttgggga ggcctggagt catggcccca cagggcttga    50

SEQ ID NO: 133           moltype = AA  length = 1074
FEATURE                  Location/Qualifiers
source                   1..1074
                         mol_type = protein
                         organism = synthetic construct
SEQUENCE: 133
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYARN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
```

```
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 134         moltype = RNA  length = 42
FEATURE                Location/Qualifiers
source                 1..42
                       mol_type = other RNA
                       organism = synthetic construct
SEQUENCE: 134
agacatgtgt cctcagtgac acagcaaggg actattcagg ga                     42

SEQ ID NO: 135         moltype = AA  length = 45
FEATURE                Location/Qualifiers
source                 1..45
                       mol_type = protein
                       organism = synthetic construct
VARIANT                1..45
                       note = This sequence may encompass 0-15 GSG repeating units
SEQUENCE: 135
GSGGSGGSGG SGGSGGSGGS GGSGGSGGSG GSGGSGGSGG SGGSG                  45

SEQ ID NO: 136         moltype = AA  length = 60
FEATURE                Location/Qualifiers
source                 1..60
                       mol_type = protein
                       organism = synthetic construct
VARIANT                1..60
                       note = This sequence may encompass 0-15 GGGS repeating units
SEQUENCE: 136
GGGSGGGSGG GSGGGSGGGS GGGSGGGSGG GSGGGSGGGS GGGSGGGSGG GSGGGSGGGS  60

SEQ ID NO: 137         moltype = AA  length = 60
FEATURE                Location/Qualifiers
source                 1..60
                       mol_type = protein
                       organism = synthetic construct
VARIANT                1..60
                       note = This sequence may encompass 0-15 GSSG repeating units
SEQUENCE: 137
GSSGGSSGGS SGGSSGGSSG GSSGGSSGGS SGGSSGGSSG GSSGGSSGGS SGGSSGGSSG  60

SEQ ID NO: 138         moltype = AA  length = 75
FEATURE                Location/Qualifiers
source                 1..75
                       mol_type = protein
                       organism = synthetic construct
VARIANT                1..75
                       note = This sequence may encompass 0-15 GGGGS repeating
                        units
SEQUENCE: 138
GGGGSGGGGS GGGGSGGGGS GGGGSGGGGS GGGGSGGGGS GGGGSGGGGS GGGGSGGGGS  60
GGGGSGGGGS GGGGS                                                   75

SEQ ID NO: 139         moltype = AA  length = 4
FEATURE                Location/Qualifiers
source                 1..4
                       mol_type = protein
                       organism = synthetic construct
SEQUENCE: 139
IRQE                                                               4

SEQ ID NO: 140         moltype = AA  length = 4
FEATURE                Location/Qualifiers
source                 1..4
                       mol_type = protein
                       organism = synthetic construct
SEQUENCE: 140
YGGT                                                               4

SEQ ID NO: 141         moltype = DNA  length = 23
FEATURE                Location/Qualifiers
source                 1..23
                       mol_type = other DNA
                       organism = synthetic construct
SEQUENCE: 141
tttgtagcct ctcccgctct ggt                                          23
```

COMPOSITIONS COMPRISING A CAS12I POLYPEPTIDE AND USES THEREOF

CROSS REFERENCE TO RELATED APPLICATION

This application claims the benefit of U.S. Provisional Application No. 63/242,940, filed Sep. 10, 2021 and U.S. Provisional Application No. 63/270,513 filed Oct. 21, 2021. The contents of the aforementioned applications are hereby incorporated by reference in their entirety.

SEQUENCE LISTING

The instant application contains a Sequence Listing which has been submitted electronically in XML file format and is hereby incorporated by reference in its entirety. Said XML copy, created on Nov. 17, 2022, is named A2186-704110_SL.xml and is 184,137 bytes in size. No new matter has been added.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

It is against the above background that the present invention provides certain advantages and advancements over the prior art. Although this invention disclosed herein is not limited to specific advantages or functionalities, the invention provides Cas12i fusion proteins, compositions, systems, and methods of using the Cas12i fusion proteins. In particular, such Cas12i fusion proteins contain one or more domains, wherein at least one of the domains is a deaminase domain and wherein at least one of the domains is a Cas12i domain or biologically active portion thereof. The Cas12i domain in the Cas12i fusion proteins may bind to a target sequence on a target nucleic acid specified by an RNA guide. While the amino acid numbering system used herein is in relation to SEQ ID NO: 2, other Cas12i sequences can be used. One of ordinary skill in the art can identify the corresponding amino acid positions in another Cas12i sequences using available tools, such as sequence alignment algorithms.

In one aspect, the disclosure provides a Cas12i fusion protein comprising:

i) a Cas12i polypeptide comprising an alteration (e.g., comprising a plurality of alterations) relative to the amino acid sequence of SEQ ID NOs: 2, wherein the alteration is selected from the group comprising G587R, G624R, F626R, E833Q, E833N, D1019K, D1019N, D581R, D911R, I926R, V1030G, E1035R, S1046G, and P868T, and wherein the Cas12i2 polypeptide comprises at least 80%, at least 85%, at least 90%, at least 95%, at least 97%, or at least 99% identity to the amino acid sequence of SEQ ID NO: 2; and ii) a heterologous sequence comprising a deaminase domain.

In one aspect, the disclosure provides a Cas12i fusion protein comprising:

i) a Cas12i polypeptide comprising an alteration (e.g., comprising a plurality of alterations) relative to the amino acid sequence of SEQ ID NO: 2, wherein the alteration (e.g., plurality of alterations) is selected from the group comprising D581R, D911R, I926R, V1030G, S1046G, G624R, F626R, E1035R, and P868T, wherein the Cas12i2 polypeptide comprises at least 90% identity to the amino acid sequence of SEQ ID NO: 2; and ii) a heterologous sequence comprising a deaminase domain.

In one aspect, the disclosure provides a Cas12i fusion protein comprising:

i) a Cas12i polypeptide comprising an alteration (e.g., comprising a plurality of alterations) relative to the amino acid sequence of SEQ ID NO: 2, wherein the alteration (e.g., plurality of alterations) is selected from the group comprising D581R, D911R, I926R, V1030G, S1046G, G624R, F626R, E1035R, and P868T, wherein the Cas12i2 polypeptide comprises at least 90% identity to the amino acid sequence of SEQ ID NO: 2, and wherein the Cas12i polypeptide has reduced nuclease activity or is a nuclease dead Cas12i polypeptide; and ii) a heterologous sequence comprising a deaminase domain.

In some embodiments the Cas12i polypeptide comprises one or more alterations in a catalytic residue, wherein the one or more catalytic residues are selected from D599, E833, and D1019.

In certain embodiments, the Cas12i polypeptide comprises one or more alterations in a catalytic residue, wherein the one or more alterations are selected from D599A, D599K, E833Q, E833N, D1019K, and D1019N.

In some embodiments, the alteration in a catalytic residue comprises D599A. In certain embodiments, the alteration in a catalytic residue comprises D599K. In some embodiments, the alteration in a catalytic residue comprises E833Q. In one embodiment, the alteration in a catalytic residue comprises E833N. In certain embodiments, the alteration in a catalytic residue comprises D1019K. In some embodiments, the alteration in a catalytic residue comprises D1019N.

In one embodiment, the one or more alterations in a catalytic residue comprises D1019K and D599K.

In certain embodiments, the one or more alterations in the catalytic residue comprises D1019N and D599K.

In one embodiment, the one or more alterations in the catalytic residue comprises D1019K, E833N, and D599K.

In certain embodiments, the plurality of alterations further comprises G587R.

In some embodiments, the alteration comprises G624R. In some embodiments, the alteration comprises F626R. In some embodiments, the alteration comprises D581R. In certain embodiments, the alteration comprises D911R. In some embodiments, the alteration comprises I926R. In certain embodiments, the alteration comprises V1030G. In some embodiments, the alteration comprises S1046G. In certain embodiments, the alteration comprises E1035R. In one embodiment, the alteration comprises P868T.

In certain embodiments, the plurality of alterations further comprise a second alteration relative to the amino acid sequence of SEQ ID NO: 2.

In certain embodiments, the second alteration comprises a substitution, insertion, or deletion.

In some embodiments, the Cas12i polypeptide further comprises a third alteration relative to the amino acid sequence of SEQ ID NO: 2, and optionally further comprises a fourth, a fifth, a sixth, a seventh, eighth, ninth, and tenth alteration relative to the amino acid sequence of SEQ ID NO: 2.

In certain embodiments, the third, fourth, fifth, sixth, seventh, eighth, ninth, and tenth alterations, if present, each independently comprises a substitution, insertion, or deletion.

In some embodiments, the plurality of alterations comprise one or more of (e.g., 2, 3, or all of) D581R, D911R, I926R, and V1030G.

In certain embodiments, the plurality of alterations comprise one or more of (e.g., 2 or all of) D581R, I926R, and V1030G.

In certain embodiments, the plurality of alterations comprise one or more of (e.g., 2, 3, or all of) D581R, I926R, V1030G, and S1046G.

In some embodiments, the plurality of alterations comprise one or more of (e.g., 2, 3, 4, 5, 6, or all of) D581R, G624R, F626R, I926R, V1030G, E1035R, and S1046G.

In certain embodiments, the plurality of alterations comprise one or more of (e.g., 2, 3, 4, 5, 6, or all of) D581R, G624R, F626R, P868T, I926R, V1030G, E1035R, and S1046G.

In one embodiment, the plurality of alterations comprise:

i) D581R, D911R, I926R, and V1030G;

ii) D581R, I926R, and V1030G;

iii) D581R, I926R, V1030G, and S1046G;

iv) D581R, G624R, F626R, I926R, V1030G, E1035R, and S1046G; or v) D581R, G624R, F626R, P868T, I926R, V1030G, E1035R, and S1046G.

In certain embodiments the Cas12i polypeptide comprises at least 95% or 99% identity to the amino acid sequence of SEQ ID NO: 2.

In certain embodiments, an amino acid sequence according to SEQ ID NO: 41, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In some embodiments, the Cas12i fusion protein comprises an amino acid sequence according to SEQ ID NO: 42, or a sequence having at least 80%, 5%, 90%, 95%, 97%, 98%, or 99% identity thereto, wherein the fusion protein, when bound to a RNA guide, can introduce a substitution in a target sequence of a target nucleic acid.

In one embodiment, the Cas12i fusion protein comprises an amino acid sequence according to SEQ ID NO: 43, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the Cas12i fusion protein comprises an amino acid sequence according to SEQ ID NO: 44, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In some embodiments, the Cas12i fusion protein comprises an amino acid sequence according to SEQ ID NO: 45, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the Cas12i fusion protein comprises an amino acid sequence according to SEQ ID NO: 46, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In one aspect, the disclosure provides a Cas12i polypeptide comprising an alteration relative to the amino acid sequence of SEQ ID NO: 2, wherein the alteration is selected from D1019K or D1019N.

In one aspect, the disclosure provides a Cas12i fusion protein comprising the Cas12i polypeptide of the immediate preceding aspect and a heterologous sequence comprising a deaminase domain.

In one aspect, the disclosure provides a Cas12i fusion protein comprising:

i) a Cas12i polypeptide comprising an alteration (e.g., a plurality of alterations) relative to the amino acid sequence of SEQ ID NO: 9, wherein the alteration (e.g., plurality of alterations) is selected from the group comprising E480R, G564R, V592R, or E1042R, wherein the Cas12i polypeptide comprises at least 90% identity to the amino acid sequence of SEQ ID NO: 9, and wherein the Cas12i polypeptide has reduced nuclease activity or is a nuclease dead Cas12i polypeptide; and ii) a heterologous sequence comprising a deaminase domain.

In some embodiments, the alteration comprises E480R. In one embodiment, the alteration comprises G564R. In certain embodiments, the alteration comprises V592R. In some embodiments, the alteration comprises E1042R.

In certain embodiments, the Cas12i polypeptide comprises an alteration in a catalytic residue, wherein optionally the alteration comprises an alteration at one or more of D608 (e.g., D608A), E844, and D1022.

In certain embodiments, the Cas12i polypeptide further comprises a second alteration relative to the amino acid sequence of SEQ ID NO: 9.

In some embodiments, the second alteration comprises a substitution, insertion, or deletion.

In certain embodiments, the Cas12i polypeptide further comprises a third alteration, and optionally further comprises a fourth, a fifth, a sixth, a seventh, eighth, ninth, and tenth alteration.

In certain embodiments, the third, fourth, fifth, sixth, seventh, eighth, ninth, and tenth alterations, if present, each independently comprises a substitution, insertion, or deletion.

In certain embodiments, the plurality of alterations comprise E480R, G564R, V592R, and E1042R.

In some embodiments, the Cas12i polypeptide further comprises an alteration in a catalytic residue, wherein the alteration comprises D608A.

In certain embodiments, the Cas12i fusion protein an amino acid sequence according to SEQ ID NO: 60, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the Cas12i fusion protein comprises an amino acid sequence according to SEQ ID NO: 61, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In some embodiments, the Cas12i fusion protein comprises an amino acid sequence according to SEQ ID NO: 62, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the Cas12i fusion protein comprises an amino acid sequence according to SEQ ID NO: 63, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the Cas12i fusion protein comprises an amino acid sequence according to SEQ ID NO: 64, or a sequence having at least 80%, 85%, 90%, 95%, 97%, 98%, or 99% identity thereto, wherein the fusion protein, when bound to a RNA guide, can introduce a substitution in a target sequence of a target nucleic acid.

In certain embodiments, the heterologous sequence is N-terminal or C-terminal of the Cas12i polypeptide. In some embodiments, the heterologous sequence is N-terminal of the Cas12i polypeptide. In certain embodiments, the heterologous sequence is C-terminal of the Cas12i polypeptide.

In some embodiments, the deaminase domain is chosen from a human APOBEC3 family deaminase, an Activation Induced Deaminase (AID), or an ABE8 deaminase, or a functional fragment or variant thereof, or a deaminase domain having at least 80% amino acid sequence identity thereto.

In certain embodiments, the human APOBEC3 family deaminase is A3A comprising an amino acid sequence of SEQ ID NO: 29, the AID deaminase comprises an amino acid sequence of SEQ ID NO: 28, or the ABE8 is ABE8_20 (SEQ ID NO: 30), or a functional fragment or variant thereof, or a deaminase domain having at least 80% amino acid sequence identity thereto.

In some embodiments, the deaminase domain is chosen from humanAPOBEC3a (A3A; SEQ ID NO: 29) or Activation Induced Deaminase (AID; SEQ ID NO: 28), or a functional fragment or variant thereof, or a deaminase domain having at least 80% amino acid sequence identity thereto.

In certain embodiments, the deaminase domain is chosen from an APOBEC3 family deaminase or ABE8_20, or a functional fragment or variant thereof, or a deaminase domain having at least 80% amino acid sequence identity thereto.

In certain embodiments, the heterologous sequence further comprises at least one peptide linker. In some embodiments, the peptide linker comprises between 3 and 70 (e.g., 3-10, 10-15, 15-20, 20-25, 25-30, 30-35, 35-40, 40-45, 45-50, 50-55, 55-60, 60-65, or 65-70) amino acid residues. In certain embodiments, the peptide linker comprises one or more Gly residues and one or more Ser residues. In some embodiments, the peptide linker comprises (GSG)x, (GGGS)x, or (GSSG)x, wherein x is an integer between 0 and 15 (e.g., 0, 1, 2, 3, 4, 5, 6, 7, 8, 9, 10, 11, 12, 13, 14, or 15). In certain embodiments, the peptide linker comprises one or more proline residues.

In some embodiments, the peptide linker comprises the structure of:

$L_1$-$L_2$-$L_3$ wherein $L_1$ and $L_3$ are each independently chosen from $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15), and $L_2$ is a polypeptide comprising between 0-40 (e.g., 0-5, 5-10, 10-15, 15-20, 20-25, 25-30, 30-35, or 35-40) amino acid residues. In certain embodiments, $L_2$ is an amino acid sequence comprising at least 80% (e.g., 85%, 90%, 95%, 99% or 100%) sequence identity to SGSETPGTSESATPES (SEQ ID NO: 106). In certain embodiments, the peptide linker comprises an amino acid sequence comprising at least 80% (e.g., 85%, 90%, 95%, 99% or 100%) sequence identity to SEQ ID NO: 40.

In some embodiments, the Cas12i fusion protein does not comprise a linker sequence.

In some embodiments, heterologous sequence is heterologous to both the Cas12i polypeptide and the deaminase domain.

In certain embodiments, the heterologous sequence comprises a Uracil Glycosylase Inhibitor (UGI) polypeptide.

In some embodiments, the heterologous sequence comprises a nuclear localization sequence (NLS) polypeptide.

In some embodiments, the Cas12i fusion protein forms a complex with a ribonucleic acid (RNA) guide wherein the RNA guide comprises a nuclease binding sequence (e.g., a direct repeat sequence) and a DNA-binding sequence (e.g., a spacer sequence).

In one aspect, the disclosure provides a method of introducing a substitution in a target sequence of a target nucleic acid in a cell, the method comprising:

contacting the cell with: (i) a Cas12i domain, (ii) an RNA guide, and (iii) a deaminase domain, or nucleic acid encoding (i), (ii), and (iii), wherein the target nucleic acid comprises a nucleotide position 0, wherein nucleotide position 0 of the target strand hybridizes with the direct repeat-proximal end of the spacer sequence of the RNA guide, and a position x (wherein optionally x=20), wherein position x of the target strand hybridizes with the direct repeat-distal end of the spacer sequence of the RNA guide, and wherein the target nucleic acid comprises an A or a C between positions 5-16 (e.g., between positions 7-12, e.g., between positions 8-11) on the target strand or the non-target strand, wherein the A is substituted to a inosine (I) (e.g., converts an A:T base pair to an I:C, I:U, or I:A base pair) or a guanine (G) or the C is substituted to a U or T (e.g., converts a C:G base pair to a T:A base pair).

In one aspect, the disclosure provides a method of introducing a substitution in a target sequence of a target nucleic acid in a cell, the method comprising:

contacting the cell with (i) a Cas12i fusion protein described herein, and (ii) an RNA guide, or a nucleic acid encoding (i) and (ii), thereby introducing the substitution.

In certain embodiments, the cell is in vivo.

In some embodiments, the cell is ex vivo.

In one aspect, the disclosure provides a composition comprising:

a) the Cas12i fusion protein described herein; and b) an RNA guide or a nucleic acid encoding the RNA guide, wherein the RNA guide comprises a nuclease binding sequence (e.g., a direct repeat sequence) and a DNA-binding sequence (e.g., a spacer sequence).

In some embodiments of the aspects or embodiments described herein, the spacer sequence comprises about 10 nucleotides to about 50 nucleotides in length. In some embodiments, the spacer sequence comprises about 15 nucleotides and about 35 nucleotides in length.

In certain embodiments, the spacer sequence is substantially identical to a target sequence of a target nucleic acid.

In some embodiments, the target sequence is adjacent to a protospacer adjacent motif (PAM) sequence. In certain embodiments, the PAM sequence comprises a sequence set forth as 5'-NTTN-3', wherein N is any nucleotide.

In one aspect, the disclosure provides Cas12i fusion protein comprising, in an N-terminal to C-terminal direction:

(a) an N-terminal portion of a Cas12i polypeptide, wherein the N-terminal portion of the Cas12i polypeptide comprises a Cas12i sequence from the N-terminus to a loop, or a functional fragment or variant thereof;
(b) a heterologous sequence comprising a deaminase domain, and
(c) a C-terminal portion of the Cas12i polypeptide, wherein the C-terminal portion of the Cas12i polypeptide comprises a Cas12i sequence from the loop to the C-terminus, or a fragment or variant thereof.

In some embodiments, the N-terminal portion of the Cas12i polypeptide comprises amino acids 1-n of any one of SEQ ID NOs: 2-7, or a sequence having at least 80%, 85%, 90%, 95%, 96%, 97%, 98%, or 99% identity thereto; and the C-terminal portion of the Cas12i polypeptide comprises amino acids m-1054 of SEQ ID NO: 2, or a sequence having at least 80%, 85%, 90%, 95%, 96%, 97%, 98%, or 99% identity thereto.

In some embodiments, n and m are each independently a number between:

i) 342-358 (e.g., 342, 343, 344, 345, 346, 347, 348, 349, 350, 351, 352, 353, 354, 355, 356, 357, or 358);
ii) 373-378 (e.g., 373, 374, 375, 376, 377, or 378);
iii) 408-413 (e.g., 408, 409, 410, 411, 412, or 413);
iv) 677-685 (e.g., 677, 678, 679, 680, 681, 682, 683, 684, or 685);
v) 718-723 (e.g., 718, 719, 720, 721, 722, or 723);
vi) 771-782 (e.g., 771, 772, 773, 774, 775, 776, 777, 778, 779, 780, 781, or 782);
vii) 953-965 (e.g., 953, 954, 955, 956, 957, 958, 959, 960, 961, 962, 963, 964, or 965);
viii) 55-65 (e.g., 55, 56, 57, 58, 59, 60, 61, 62, 63, 64, or 65);
ix) 99-105 (e.g., 99, 100, 101, 102, 103, 104, or 105);
x) 112-120 (e.g., 112, 113, 114, 115, 116, 117, 118, 119, or 120);
xi) 195-206 (e.g., 195, 196, 197, 198, 199, 200, 201, 202, 203, 204, 205, or 206);
xii) 241-250 (e.g., 241, 242, 243, 244, 245, 246, 247, 248, 249, or 250);
xiii) 583-594 (e.g., 583, 584, 585, 586, 587, 588, 589, 590, 591, 592, 593, or 594);
xiv) 877-901 (e.g., 877, 878, 879, 880, 881, 882, 883, 884, 885, 886, 887, 888, 889, 890, 891, 892, 893, 894, 895, 896, 897, 898, 899, 900, or 901); or
xv) 386-397 (e.g., residue 386, 387, 388, 389, 390, 391, 392, 393, 394, 395, 396, or 397).

In certain embodiments, n<m. In some embodiments, m=n+1.

In particular embodiments, the Cas12i polypeptide is a Cas12i4 polypeptide.

In some embodiments, the heterologous sequence comprises at least one linker (e.g., any linker described herein).

In certain embodiments, the heterologous sequence comprises a first linker (e.g., a first peptide linker) and a second linker (e.g., a second peptide linker). In some embodiments, the first linker and the second linker each independently comprise between 3 and 70 (e.g., 3-10, 10-15, 15-20, 20-25, 25-30, 30-35, 35-40, 40-45, 45-50, 50-55, 55-60, 60-65, or 65-70) amino acid residues. In certain embodiments, the first linker and the second linker each independently comprise (GSG)x, (GGGS)x, or (GSSG)x, wherein x is an integer between 0 and 15 (e.g., 0, 1, 2, 3, 4, 5, 6, 7, 8, 9, 10, 11, 12, 13, 14, or 15). In some embodiments, the first linker and the second linker independently comprise amino acid sequence comprising at least 80% (e.g., 85%, 90%, 95%, 99% or 100%) sequence identity to SEQ ID NO: 40. In some embodiments, the first linker and the second linker each independently comprise one or more proline residues. In certain embodiments, the first linker is N-terminal of the deaminase domain and the second linker is C-terminal of the deaminase domain. In some embodiments, the first linker and the second linker have the same sequence. In certain embodiments, the first linker and the second linker have different sequences.

In one aspect, the disclosure provides a fusion protein comprising:

(a) a Cas12i4 polypeptide,
(b) a deaminase domain chosen from APOBEC3 or ABE8_20, or a biologically active portion or variant thereof.

In one embodiments, the deaminase domain is N-terminal or C-terminal of the Cas12i4 polypeptide. In certain embodiments, the deaminase domain is N-terminal of the Cas12i4 polypeptide. In certain embodiments, the deaminase domain is C-terminal of the Cas12i4 polypeptide. In some embodiments, the fusion protein does not comprise a linker sequence.

In certain embodiments, the fusion protein further comprises at least one heterologous sequence, which is heterologous to both the Cas12i4 domain and the deaminase domain.

In certain embodiments, the heterologous sequence comprises a Uracil Glycosylase Inhibitor (UGI) polypeptide.

In some embodiments, the heterologous sequence comprises a nuclear localization sequence (NLS) polypeptide.

In some embodiments, the fusion protein comprises, one, two, or three of:

i) a first heterologous sequence situated between the Cas12i4 domain and the deaminase domain;
ii) a second heterologous sequence situated between the Cas12i4 domain and the terminus nearest the Cas12i4 domain; or
iii) a third heterologous sequence situated between the deaminase domain and the terminus nearest the deaminase domain.

In some embodiments, the deaminase domain is N-terminal of the Cas12i4 domain and the UGI domain. In certain embodiments, the deaminase domain is C-terminal of the Cas12i4 domain.

In some embodiments, the deaminase domain is N-terminal of the Cas12i4 domain, the first heterologous sequence comprises the UGI domain, the second heterologous sequence comprises an NLS polypeptide (e.g., a bpNLS or an npNLS polypeptide), and the third heterologous sequence comprises an NLS polypeptide (e.g., a bpNLS or an npNLS polypeptide).

In some embodiments, the deaminase domain is C-terminal of the Cas12i4 domain, the first heterologous sequence comprises a linker, the second heterologous sequence comprises an NLS polypeptide (e.g., a bpNLS or an npNLS polypeptide) and the UGI domain, and the third heterologous sequence comprises an NLS polypeptide (e.g., a bpNLS or an npNLS polypeptide).

In some embodiments, the deaminase domain is C-terminal of the Cas12i4 domain, the first heterologous sequence comprises an NLS polypeptide (e.g., a bpNLS or an npNLS polypeptide), the second heterologous sequence is absent or comprises a peptide tag (e.g., a peptide purification tag), and the third heterologous sequence comprises a UGI domain and an NLS polypeptide (e.g., a bpNLS or an npNLS polypeptide).

In certain embodiments, the first heterologous sequence comprises the UGI polypeptide. In some embodiments, the UGI polypeptide is flanked by peptide linkers.

In some embodiments, the second and third heterologous sequence each independently comprise an NLS polypeptide.

In some embodiments, the first heterologous sequence comprises a peptide linker and, when present, the second heterologous sequence or the third heterologous sequence comprises an NLS polypeptide, one or more linkers, and a UGI polypeptide.

In certain embodiments, the NLS polypeptide is N-terminal of the UGI polypeptide. In certain embodiments, the NLS polypeptide is C-terminal of the UGI polypeptide.

In some embodiments, one of the one or more linkers is situated between the NLS polypeptide and the UGI polypeptide.

In certain embodiments, the third heterologous sequence comprises a first and a second linker, wherein the first linker is situated N-terminal the NLS polypeptide and the UGI polypeptide and the second linker is situated between the NLS polypeptide and the UGI polypeptide.

In some embodiments, the first heterologous sequence further comprises an NLS sequence. In certain embodiments, the NLS polypeptide is situated N-terminal of the linker.

In some embodiments, the fusion protein does not comprise the second heterologous sequence.

In one aspect, the disclosure provides a fusion protein comprising:

(a) a Cas12i4 polypeptide, (b) a deaminase domain; and (c) a UGI polypeptide.

In some embodiments, the deaminase domain is N-terminal or C-terminal of the Cas12i4 polypeptide. In some embodiments, the deaminase domain is N-terminal of the Cas12i4 polypeptide. In certain embodiments, the deaminase domain is C-terminal of the Cas12i4 polypeptide.

In some embodiments, the fusion protein does not comprise a linker sequence.

In certain embodiments, the fusion protein further comprises at least one heterologous sequence, which is heterologous to each of the Cas12i4 domain, the deaminase domain, and the UGI polypeptide.

In one embodiments, the heterologous sequence comprises a nuclear localization sequence (NLS) polypeptide.

In certain embodiments, the fusion protein comprises, one, two, or three of:

i) a first heterologous sequence situated between the Cas12i4 domain and the deaminase domain;

ii) a second heterologous sequence situated between the Cas12i4 domain and the terminus nearest the Cas12i4 domain; or iii) a third heterologous sequence situated between the deaminase domain and the terminus nearest the deaminase domain.

In certain embodiments, the deaminase domain is N-terminal of the Cas12i4 domain and the UGI domain.

In some embodiments, the deaminase domain is C-terminal of the Cas12i4 domain.

In certain embodiments, the fusion protein does not comprise the first heterologous sequence, and wherein the UGI domain is situated between the deaminase domain and the Cas12i4 domain.

In some embodiments, UGI domain is situated C-terminal of both the deaminase domain and the Cas12i4 domain.

In certain embodiments, the UGI domain is flanked by peptide linkers.

In certain embodiments, when present, the first and second heterologous sequence each independently comprise an NLS polypeptide.

In some embodiments, the one, two, or three of the first, the second, and the third heterologous sequence each independently comprise one or more peptide linkers and the third heterologous sequence comprises an NLS polypeptide. In some embodiments, the NLS polypeptide is N-terminal of the UGI polypeptide. In certain embodiments, the NLS polypeptide is C-terminal of the UGI polypeptide.

In some embodiments, at least one (e.g., one) of the one or more of the linkers is situated between the NLS polypeptide and the UGI polypeptide.

In certain embodiments, the third heterologous sequence comprises a first and a second linker, wherein the first linker is situated N-terminal the NLS polypeptide and the UGI polypeptide and the second linker is situated between the NLS polypeptide and the UGI polypeptide.

In some embodiments, the first heterologous sequence further comprises an NLS sequence. In certain embodiments, the NLS polypeptide is situated N-terminal of the linker.

In some embodiments, the NLS polypeptide is selected from a nuclear plasma NLS (npNLS) polypeptide or a bipartite NLS (bpNLS) polypeptide. In certain embodiments, the fusion protein comprises an npNLS polypeptide and a bpNLS polypeptide.

In some embodiments, the npNLS polypeptide is situated N-terminal of the bpNLS polypeptide.

In certain embodiments, the npNLS polypeptide is situated C-terminal of the bpNLS polypeptide.

In some embodiments, the npNLS polypeptide comprises an amino acid sequence comprising at least 80% (e.g., 85%, 90%, 95%, 99% or 100%) sequence identity to SEQ ID NO: 36. In certain embodiments, the bpNLS polypeptide comprises an amino acid sequence having at least 80% (e.g., 85%, 90%, 95%, 99% or 100%) sequence identity to SEQ ID NO: 38.

In some embodiments, the npNLS polypeptide comprises an amino acid sequence comprising at least 80% (e.g., 85%, 90%, 95%, 99% or 100%) sequence identity to SEQ ID NO: 36, and the bpNLS polypeptide comprises an amino acid sequence having at least 80% (e.g., 85%, 90%, 95%, 99% or 100%) sequence identity to SEQ ID NO: 38.

In certain embodiments, each peptide linker independently comprises between 2 and 200 amino acid residues. In some embodiments, each peptide linker independently comprises one or more Gly residues and one or more Ser residues. In certain embodiments, each peptide linker independently comprises $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15).

In particular embodiments, the peptide linker comprises the structure of:

$$L_1\text{-}L_2\text{-}L_3$$

wherein $L_1$ and $L_3$ are each independently chosen from $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15), and $L_2$ is a polypeptide comprising between 0-40 (e.g., 0-5, 5-10, 10-15, 15-20, 20-25, 25-30, 30-35, or 35-40) amino acid residues.

In certain embodiments, $L_2$ is an amino acid sequence comprising at least 80% (e.g., 85%, 90%, 95%, 99% or 100%) sequence identity to SGSETPGTSESATPES (SEQ ID NO: 106).

In some embodiments, the peptide linker comprises an amino acid sequence comprising at least 80% (e.g., 85%, 90%, 95%, 99% or 100%) sequence identity to SEQ ID NO: 40.

In certain embodiments, at least one of the first, second, or third heterologous sequence comprises a linker comprising an amino acid sequence comprising at least 80% (e.g., 85%, 90%, 95%, 99% or 100%) sequence identity to SEQ ID NO: 40.

In some embodiments, the fusion protein comprises an N-terminal or C-terminal peptide tag.

In one aspect, the disclosure provides a fusion protein comprising an amino acid sequence according to SEQ ID NO: 60, or a sequence having at least 80%, 85%, 90%, 95%, 97%, 98%, or 99% identity thereto, wherein the fusion protein, when bound to a gRNA, can introduce a substitution in a target sequence of a target nucleic acid.

In one aspect, the disclosure provides a fusion protein comprising an amino acid sequence according to SEQ ID NO: 61, or a sequence having at least 80%, 85%, 90%, 95%, 97%, 98%, or 99% identity thereto, wherein the fusion protein, when bound to a gRNA, can introduce a substitution in a target sequence of a target nucleic acid.

In one aspect, the disclosure provides a fusion protein comprising an amino acid sequence according to SEQ ID NO: 62, or a sequence having at least 80%, 85%, 90%, 95%, 97%, 98%, or 99% identity thereto, wherein the fusion protein, when bound to a gRNA, can introduce a substitution in a target sequence of a target nucleic acid.

In one aspect, the disclosure provides a fusion protein comprising an amino acid sequence according to SEQ ID NO: 63, or a sequence having at least 80%, 85%, 90%, 95%, 97%, 98%, or 99% identity thereto, wherein the fusion protein, when bound to a gRNA, can introduce a substitution in a target sequence of a target nucleic acid.

In one aspect, the disclosure provides a fusion protein comprising an amino acid sequence according to SEQ ID NO: 64, or a sequence having at least 80%, 85%, 90%, 95%, 97%, 98%, or 99% identity thereto, wherein the fusion protein, when bound to a gRNA, can introduce a substitution in a target sequence of a target nucleic acid.

In certain embodiments, the fusion protein forms a complex with a ribonucleic acid (RNA) guide wherein the RNA guide comprises a nuclease binding sequence (e.g., a direct repeat sequence) and a DNA-binding sequence (e.g., a spacer sequence).

In one aspect, the disclosure provides a polypeptide system comprising:

(a) a first polypeptide comprising a Cas12i domain and a first dimerization domain, and (b) a second polypeptide comprising a deaminase domain and a second, compatible dimerization domain.

In certain embodiments, the first polypeptide comprises a first peptide linker situated between the Cas12i domain and the first dimerization domain.

In some embodiments, the second polypeptide comprises a second peptide linker situated between the Cas12i domain and the second dimerization domain.

In certain embodiments, each peptide linker independently comprises between 2 and 200 amino acid residues.

In some embodiments, each peptide linker independently comprises one or more Gly residues and one or more Ser residues.

In certain embodiments, each peptide linker independently comprises $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15).

In some embodiments, each peptide linker independently comprises one or more proline residues.

In particular embodiments, the peptide linker comprises the structure of:

$$L_1\text{-}L_2\text{-}L_3$$

wherein $L_1$ and $L_3$ are each independently chosen from $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15), and $L_2$ is a polypeptide comprising between 0-40 (e.g., 0-5, 5-10, 10-15, 15-20, 20-25, 25-30, 30-35, or 35-40) amino acid residues.

In some embodiments, the first polypeptide and the second polypeptide form a complex upon dimerization of the of the first dimerization domain and the second dimerization domain.

In certain embodiments, the Cas12i domain comprises a Cas12i1 polypeptide, a Cas12i2 polypeptide, a Cas12i3 polypeptide, or a Cas12i4 polypeptide, and wherein:

(a) the Cas12i1 polypeptide comprises an amino acid sequence with at least 80% (e.g., 85%, 90%, 95%, 97%, 98%, or 99%) identity to SEQ ID NO: 8;

(b) the Cas12i2 polypeptide comprises an amino acid sequence with at least 80% (e.g., 85%, 90%, 95%, 97%, 98%, or 99%) identity to any one of SEQ ID NOs: 2-7;

(c) the Cas12i3 polypeptide comprises an amino acid sequence with at least 80% (e.g., 85%, 90%, 95%, 97%, 98%, or 99%) identity to SEQ ID NO: 11; and (d) the Cas12i4 polypeptide comprises an amino acid sequence with at least 80% (e.g., 85%, 90%, 95%, 97%, 98%, or 99%) identity to SEQ ID NO: 9 or SEQ ID NO: 10.

In some embodiments, the Cas12i domain forms a complex with an RNA guide, wherein the RNA guide comprises a nuclease binding sequence (e.g., a direct repeat sequence) and a DNA-binding sequence (e.g., a spacer sequence).

In certain embodiments, the first dimerization domain and the second dimerization domain are identical (e.g., a homodimer). In some embodiments, the first dimerization domain and the second dimerization domain are not identical (e.g., a heterodimer). In certain embodiments, the first dimerization domain is chosen from leucine zipper, nanobody, antibody, or coiled-coil domain. In certain embodiments, the first and second dimerization domains are chemically inducible dimerization domains (e.g., a rapamycin sensitive dimerization domain) that can be regulated by the presence of a small molecule.

In one aspect, the disclosure provides a fusion protein comprising:

a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, wherein the first portion and second portion together bind to an RNA guide comprising a direct repeat sequence and a spacer sequence.

In some embodiments, the fusion protein is capable of specifically binding a target nucleic acid complementary to the spacer sequence.

In certain embodiments, the first portion and the second portion are linked by a heterologous sequence.

In some embodiments, the heterologous sequence comprises one or more of:

a) a first linker (e.g., a first peptide linker);
b) a second linker (e.g., a second peptide linker); and
c) an effector domain.

In certain embodiments, the C-terminal most amino acid of the first portion is any amino acid residue of any one of SEQ ID NOs: 2-7 chosen from residues:

a) 342-358 (e.g., residue 342, 343, 344, 345, 346, 347, 348, 349, 350, 351, 352, 353, 354, 355, 356, 357, or 358);
b) 373-378 (e.g., residue 373, 374, 375, 376, 377, or 378);
c) 408-413 (e.g., residue 408, 409, 410, 411, 412, or 413);
d) 677-685 (e.g., residue 677, 678, 679, 680, 681, 682, 683, 684, or 685);
e) 718-723 (e.g., residue 718, 719, 720, 721, 722, or 723);
f) 771-782 (e.g., residue 771, 772, 773, 774, 775, 776, 777, 778, 779, 780, 781, or 782);
g) 953-965 (e.g., residue 953, 954, 955, 956, 957, 958, 959, 960, 961, 962, 963, 964, or 965);
h) 55-65 (e.g., residue 55, 56, 57, 58, 59, 60, 61, 62, 63, 64, or 65);
i) 99-105 (e.g., residue 99, 100, 101, 102, 103, 104, or 105);
j) 112-120 (e.g., residue 112, 113, 114, 115, 116, 117, 118, 119, or 120);
k) 195-206 (e.g., residue 195, 196, 197, 198, 199, 200, 201, 202, 203, 204, 205, or 206);
l) 241-250 (e.g., residue 241, 242, 243, 244, 245, 246, 247, 248, 249, or 250);
m) 583-594 (e.g., residue 583, 584, 585, 586, 587, 588, 589, 590, 591, 592, 593, or 594);
n) 877-901 (e.g., residue 877, 878, 879, 880, 881, 882, 883, 884, 885, 886, 887, 888, 889, 890, 891, 892, 893, 894, 895, 896, 897, 898, 899, 900, or 901);
o) 173-179 (e.g., residue 173, 174, 175, 176, 177, 178, or 179);
p) 216-221 (e.g., residue 216, 217, 218, 219, 220, or 221);
q) 265-272 (e.g., residue 265, 266, 267, 268, 269, 270, 271, or 272);
r) 456-468 (e.g., residue 456, 457, 458, 459, 460, 461, 462, 463, 464, 465, 466, 467, or 468);
s) 476-482 (e.g., residue 476, 477, 478, 479, 480, 481, or 482);
t) 498-513 (e.g., residue 498, 499, 500, 501, 502, 503, 504, 505, 506, 507, 508, 509, 510, 511, 512, or 513);
u) 614-625 (e.g., residue 614, 615, 616, 617, 618, 619, 620, 621, 622, 623, 624, or 625);
v) 977-982 (e.g., residue 977, 978, 979, 980, 981, or 982);
w) 1007-1012 (e.g., residue 1007, 1008, 1009, 1010, 1011, or 1012);
x) 386-397 (e.g., residue 386, 387, 388, 389, 390, 391, 392, 393, 394, 395, 396, or 397); or
y) 831-844 (e.g., residue 831, 832, 833, 834, 835, 836, 837, 838, 839, 840, 841, 842, 843, or 844).

In some embodiments, the first portion further comprises a fusion domain, the second portion comprises a fusion domain, or the first portion and the second portion comprise a fusion domain.

In certain embodiments, the fusion domain is a deaminase.

In some embodiments, the fusion domain is a UGI polypeptide and/or an NLS.

In certain embodiments, the fusion domain is a FokI nuclease domain.

In some embodiments, the FokI nuclease domain is a catalytically active FokI nuclease domain or a catalytically inactive FokI nuclease domain.

In certain embodiments, the FokI nuclease domain is fused to a deaminase.

In some embodiments, the FokI nuclease domain is fused to a UGI polypeptide and/or an NLS.

In some embodiments, the first portion comprises a catalytically active FokI nuclease domain and the second portion comprises a catalytically inactive FokI nuclease domain, or the first portion comprises a catalytically inactive FokI nuclease domain and the second portion comprises a catalytically active FokI nuclease domain.

In certain embodiments, the fusion protein comprises a catalytically inactive RuvC domain.

In some embodiments, the fusion protein comprises nickase activity.

In one aspect, the disclosure provides a method of producing a substitution in a target sequence of a target nucleic acid in a cell, the method comprising:

contacting the cell with: (i) a Cas12i domain, (ii) an RNA guide, and (iii) a deaminase domain, or nucleic acid encoding (i), (ii), and (iii), wherein the target sequence comprises a nucleotide position 0, wherein nucleotide position 0 of the target strand hybridizes with the direct repeat-proximal end of the spacer sequence of the RNA guide, and a position x (wherein optionally x=20), wherein position x of the target strand hybridizes with the direct repeat-distal end of the spacer sequence of the RNA guide, and wherein the target sequence comprises an A or a C between positions 5-16 (e.g., between positions 7-12, e.g., between positions 8-11)) on the target strand or the non-target strand, wherein the A is substituted to a inosine (I) (e.g., converts an A:T base pair to an I:C, I:U, or I:A base pair) or a guanine (G) or the C is substituted to a U or T (e.g., converts a C:G base pair to a T:A base pair).

In one aspect, the disclosure provides a method of introducing a substitution in a target sequence of a target nucleic acid in a cell, the method comprising:

contacting the cell with (i) a fusion protein described herein or the polypeptide system described herein, and (ii) an RNA guide, or a nucleic acid encoding (i) and (ii), thereby introducing the substitution.

In certain embodiments, the target sequence comprises a nucleotide position 0, wherein nucleotide position 0 of the target strand hybridizes with the direct repeat-proximal end of the spacer sequence of the RNA guide, and a position x (wherein optionally x=20), wherein position x of the target strand hybridizes with the direct repeat-distal end of the spacer sequence of the RNA guide, and wherein the target sequence comprises an A or a C between positions 5-16 (e.g., between positions 7-12, e.g., between positions 8-11) on the target strand or the non-target strand, wherein the A is substituted to a inosine (I) (e.g., an A:T base pair is converted to an I:C, I:U, or I:A base pair) or to guanine (G), or the C is substituted to a U (e.g., converts a C:G base pair to a T:A base pair).

In some embodiments, the method converts a C:G base pair to a T:A base pair alteration in the target sequence.

In some embodiments, the alteration occurs at one or more C:G base pairs between positions 7-12 (e.g., between positions 8-11) of the target sequence. In certain embodiments, the cell is selected from a eukaryotic cell, a mammalian cell, or a human cell. In some embodiments, the cell is in vivo. In certain embodiments, the cell is ex vivo. In some embodiments, the cell is in vitro.

In one aspect, the disclosure provides a composition comprising:

a) the fusion protein described herein, or the polypeptide system described herein; and b) an RNA guide or a nucleic acid encoding the RNA guide, wherein the RNA guide comprises a nuclease binding sequence (e.g., a direct repeat sequence) and a DNA-binding sequence (e.g., a spacer sequence).

In some embodiments, the Cas12i polypeptide is a Cas12i1 polypeptide, a Cas12i2 polypeptide, a Cas12i3 polypeptide, or a Cas12i4 polypeptide, and wherein:

(a) the Cas12i1 polypeptide comprises an amino acid sequence with at least 80% identity to SEQ ID NO: 8;

(b) the Cas12i2 polypeptide comprises an amino acid sequence with at least 80% identity to any one of SEQ ID NOs: 2-7;

(c) the Cas12i3 polypeptide comprises an amino acid sequence with at least 80% identity to SEQ ID NO: 11; and (d) the Cas12i4 polypeptide comprises an amino acid sequence with at least 80% identity to SEQ ID NO: 9 or SEQ ID NO: 10.

In some embodiments of the compositions, methods, or systems described herein:

(a) the Cas12i1 polypeptide comprises an amino acid sequence with at least 95% identity to SEQ ID NO: 8;

(b) the Cas12i2 polypeptide comprises an amino acid sequence with at least 95% identity to any one of SEQ ID NOs: 2-7;

(c) the Cas12i3 polypeptide comprises an amino acid sequence with at least 95% identity to SEQ ID NO: 11; and (d) the Cas12i4 polypeptide comprises an amino acid sequence with at least 95% identity to SEQ ID NO: 9 or SEQ ID NO: 10.

In some embodiments of the compositions, methods, or systems described herein:

(a) the Cas12i1 polypeptide comprises the amino acid sequence set forth in SEQ ID NO: 8;

(b) the Cas12i2 polypeptide comprises the amino acid sequence set forth in any one of SEQ ID NOs: 2-7;

(c) the Cas12i3 polypeptide comprises the amino acid sequence set forth in SEQ ID NO: 11; and (d) the Cas12i4 polypeptide comprises the amino acid sequence set forth in SEQ ID NO: 9 or SEQ ID NO: 10.

In certain embodiments, the Cas12i2 polypeptide comprises at least 80% identity to any one of SEQ ID NOs: 2-7, and wherein the Cas12i2 polypeptide further comprises one or more of the following substitutions: G587R, D599A, D599K, F626R, E833Q, E833N, D1019K, and D1019N.

In some embodiments, the Cas12i2 polypeptide comprises at least 95% identity to any one of SEQ ID NOs: 2-7, and wherein the Cas12i2 polypeptide further comprises one or more of the following substitutions: G587R, D599A, D599K, F626R, E833Q, E833N, D1019K, and D1019N.

In certain embodiments, the fusion protein or first polypeptide comprises at least one of an epitope peptide, a nuclear localization signal, and a nuclear export signal.

In some embodiments of the compositions, methods, or systems described herein:

(a) the Cas12i1 polypeptide comprises an amino acid sequence with at least 80% identity to SEQ ID NO: 8 and the direct repeat sequence comprises a nucleotide sequence with at least 90% identity to any one of SEQ ID NOs: 12-14;

(b) the Cas12i2 polypeptide comprises an amino acid sequence with at least 80% identity to any one of SEQ ID NOs: 2-7 and the direct repeat sequence comprises a nucleotide sequence with at least 90% identity to any one of SEQ ID NOs: 15-17;

(c) the Cas12i3 polypeptide comprises an amino acid sequence with at least 80% identity to SEQ ID NO: 11 and the direct repeat sequence comprises a nucleotide sequence with at least 90% identity to any one of SEQ ID NOs: 18-20; and (d) the Cas12i4 polypeptide comprises an amino acid sequence with at least 80% identity to SEQ ID NO: 9 or SEQ ID NO: 10 and the direct repeat sequence comprises a nucleotide sequence with at least 90% identity to any one of SEQ ID NOs: 21-24.

In some embodiments of the compositions, methods, or systems described herein:

(a) the Cas12i1 polypeptide comprises an amino acid sequence with at least 95% identity to SEQ ID NO: 8 and the direct repeat sequence comprises a nucleotide sequence with at least 90% identity to any one of SEQ ID NOs: 12-14;

(b) the Cas12i2 polypeptide comprises an amino acid sequence with at least 95% identity to any one of SEQ ID NOs: 2-7 and the direct repeat sequence comprises a nucleotide sequence with at least 90% identity to any one of SEQ ID NOs: 15-17;

(c) the Cas12i3 polypeptide comprises an amino acid sequence with at least 95% identity to SEQ ID NO: 11 and the direct repeat sequence comprises a nucleotide sequence with at least 90% identity to any one of SEQ ID NOs: 18-20; and (d) the Cas12i4 polypeptide comprises an amino acid sequence with at least 95% identity to SEQ ID NO: 9 or SEQ ID NO: 10 and the direct repeat sequence comprises a nucleotide sequence with at least 90% identity to any one of SEQ ID NOs: 21-24.

In some embodiments of the compositions, methods, or systems described herein:

(a) the Cas12i1 polypeptide comprises an amino acid sequence with at least 95% identity to SEQ ID NO: 8 and the direct repeat sequence comprises a nucleotide sequence with at least 95% identity to any one of SEQ ID NOs: 12-14;

(b) the Cas12i2 polypeptide comprises an amino acid sequence with at least 95% identity to any one of SEQ ID NOs: 2-7 and the direct repeat sequence comprises a nucleotide sequence with at least 95% identity to any one of SEQ ID NOs: 15-17;

(c) the Cas12i3 polypeptide comprises an amino acid sequence with at least 95% identity to SEQ ID NO: 11 and the direct repeat sequence comprises a nucleotide sequence with at least 95% identity to any one of SEQ ID NOs: 18-20; and (d) the Cas12i4 polypeptide comprises an amino acid sequence with at least 95% identity to SEQ ID NO: 9 or SEQ ID NO: 10 and the direct repeat sequence comprises a nucleotide sequence with at least 95% identity to any one of SEQ ID NOs: 21-24.

In certain embodiments, the spacer sequence comprises about 10 nucleotides to about 50 (e.g., about 10 to about 20, about 20 to about 30, about 30 to about 40, or about 40 to about 50) nucleotides in length. In some embodiments, the spacer sequence comprises about 15 nucleotides and about 35 (e.g., about 15 to about 20, about 20 to about 25, about 25 to about 30, or about 30 to about 35) nucleotides in length.

In some embodiments, the spacer sequence is substantially complementary to a target sequence of a target nucleic acid.

In certain embodiments, the target sequence is adjacent to a protospacer adjacent motif (PAM) sequence. In some embodiments, the PAM sequence comprises a sequence set forth as 5'-NTTN-3', wherein N is any nucleotide.

In one aspect, the disclosure provides a modified cell comprising a target sequence adjacent to a 5'-NTTN-3' sequence, wherein the 3' N is designated as position 0 and position numbers increase in the 3' direction, wherein the target nucleic acid comprises a nucleotide substitution between positions 5-16 (e.g., between positions 7-12 (e.g., 7, 8, 9, 10, 11, or 12)) relative to an unmodified cell from which the modified cell was produced.

In one aspect, the disclosure provides a modified cell comprising a target sequence comprising a nucleotide position 1 at the 3' end of a 5'-NTTN-3' sequence (e.g., positions −3 to −0) and a position x (wherein optionally x=20) nucleotides downstream from position 1, wherein the target sequence comprises a nucleotide substitution between positions 5-16 (e.g., between positions 7-12 (e.g., 7, 8, 9, 10, 11, or 12)) relative to an unmodified cell from which the modified cell was produced.

In certain embodiments, the unmodified cell comprises at least one C between 5-16 (e.g., between positions 7-12, e.g., between positions 8-11) nucleotides downstream from position 0.

In some embodiments, the at least one C is substituted to a U or a T (e.g., a C:G base pair is converted to a T:A base pair).

In certain embodiments, the unmodified cell comprises at least one A between 5-16 (e.g., between positions 7-12, e.g., between positions 8-11) nucleotides downstream from position 0.

In some embodiments, the at least one A is substituted to inosine (I) (e.g., an A:T base pair is converted to an I:C, I:U, or I:A base pair) or to guanine (G).

In certain embodiments, the cell is modified by a fusion protein or polypeptide system any method, or any composition described herein.

In some embodiments, the modified cell comprises 2, 3, or more nucleotide substitutions between nucleotide positions 5-16.

In some embodiments of any of the compositions described herein, the system is present in a delivery composition comprising a virus, a nanoparticle, a liposome, an exosome, a microvesicle, or a gene-gun.

In some embodiments of any of the compositions described herein, the compositions are within a cell. In some embodiments, the cell is a eukaryotic cell. In some embodiments, the cell is a mammalian cell. In some embodiments, the cell is a human cell. In some embodiments, the cell is a prokaryotic cell.

Other features and advantages of the invention will be apparent from the following detailed description and from the claims.

Definitions

The present invention will be described with respect to particular embodiments and with reference to certain Figures, but the invention is not limited thereto but only by the claims. Terms as set forth hereinafter are generally to be understood in their common sense unless indicated otherwise.

As used herein, the term "activity" refers to a biological activity. In some embodiments, the activity refers to effector activity. In some embodiments, activity includes enzymatic activity, e.g., catalytic ability of an effector. For example, activity can include nuclease activity. In another example, activity refers to the ability of an enzyme to generate DNA from RNA or to introduce an edit into a target sequence.

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences. In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides.

As used herein, a "biologically active portion" of a polypeptide is a portion of a polypeptide that maintains a function (e.g., completely, partially, or minimally) of the polypeptide (e.g., a Cas12i domain (e.g., a "minimal" or "core" domain) or a deaminase domain).

As used herein, the term "Cas12i polypeptide" (also referred to herein as Cas12i) refers to a polypeptide that binds to a target sequence on a target nucleic acid specified by an RNA guide, wherein the polypeptide has at least some amino acid sequence homology to a wild-type Cas12i polypeptide. In some embodiments, the Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 1-5 and 11-18 of U.S. Pat. No. 10,808,245, which is incorporated by reference herein in its entirety. In some embodiments, a Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NO: 3 (Cas12i1), SEQ ID NO: 5 (Cas12i2), SEQ ID NO: 14 (Cas12i3), or SEQ ID NO: 16 (Cas12i4) of U.S. Pat. No. 10,808,245, corresponding to SEQ ID NOs: 8, 2, 11, and 9 of the present application. In some embodiments, a Cas12i polypeptide of the disclosure is a Cas12i1 polypeptide or Cas12i2 polypeptide as described in PCT/US2021/025257. In some embodiments, the Cas12i polypeptide cleaves a target nucleic acid (e.g., as a nick or a double strand break).

The term "Cas12i fusion protein," as used herein, refers to a polypeptide having: i) one or more domains, wherein at least one of the domains includes a portion of a Cas12i domain and ii) a fusion domain such as a deaminase domain, wherein the Cas12i fusion protein binds to a target sequence on a target nucleic acid specified by an RNA guide. In some embodiments, the Cas12i fusion protein has enzymatic (e.g., nuclease) activity. In some embodiments, an enzymatic activity (e.g., nuclease activity) can be carried out by the Cas12i domain. In some instances, the Cas12i domain comprises an amino acid sequence having at least 80% (e.g., 80%, 85%, 90%, 95%, 96%, 97%, 98%, or 99%) sequence identity to any one of SEQ ID NOs: 2-11 or a portion thereof. In some instances, the Cas12i domain has the sequence of SEQ ID NO: 2 or a portion thereof. In some instances, the Cas12i domain has the sequence of SEQ ID NO: 4 or a portion thereof. While the amino acid numbering system used herein is in relation to SEQ ID NO: 2, other Cas12i2 sequences can be used. One of ordinary skill in the art can identify the corresponding amino acid positions in another Cas12i2 sequences using available tools, such as sequence alignment algorithms. In some embodiments, the Cas12i fusion protein was produced by translation of a single nucleic acid encoding the fusion protein. In some embodiments, the Cas12i domain and the heterologous domain were produced separately (e.g., from separate genes) and then covalently linked.

As used herein, the term "complex" refers to a grouping of two or more molecules. In some embodiments, the complex comprises a polypeptide and a nucleic acid molecule interacting with (e.g., binding to, coming into contact with, adhering to) one another. In some embodiments, the term "complex" is used to refer to association of a Cas12i polypeptide and a deaminase polypeptide. In some embodiments, the term "complex" is used to refer to association of an RNA guide and a Cas12i polypeptide. In some embodiments, the term "complex" is used to refer to association of a Cas12i polypeptide, a deaminase polypeptide, and an RNA guide.

As used herein, the term "deaminase" or "deaminase domain", refers to a polypeptide or polypeptide domain capable of removing an amino group from a substrate molecule (such as a nucleotide base). In some embodiments, the deaminase domain is an enzyme. In some embodiments, the deaminase domain is an enzyme classified in EC 3.5.4.

As used herein, the term "dimerization domain," refers to a polypeptide domain capable of specifically binding a separate, and compatible, polypeptide domain (e.g., a second compatible dimerization domain). In some embodiments, the dimer is formed by a non-covalent bond between the first dimerization domain and the second compatible dimerization domain. In some embodiments, the first dimerization domain and the second compatible dimerization domain have identical sequences (e.g., form a homodimer). In some embodiments, the first dimerization domain and the second dimerization domain do not have identical sequences (e.g., form a heterodimer). In some embodiments, a dimerization domain is a leucine zipper. In some instances, the dimerization domain is a nanobody, antibody, or coiled-coil domain. In some instances, the dimerization domain is a chemically inducible dimerization domain (e.g., a rapamycin sensitive dimerization domain) that can be regulated by the presence of a small molecule.

As used herein, the terms "domain" and "protein domain" refer to a distinct functional and/or structural unit of a polypeptide. In some embodiments, a domain may comprise a conserved amino acid sequence.

The term "fusion domain," as used herein, refers to a polypeptide domain that is operably linked to a second, heterologous domain. In some embodiments, the fusion domain is about 10-20, 20-50, 50-100, 100-200, or 200-300 amino acids in length.

The term "heterologous," when used to describe a first element in reference to a second element means that the first element and second element do not exist in nature disposed as described. For example, a heterologous polypeptide sequence refers to (a) a polypeptide, or portion of a polypeptide that is operably linked to a second polypeptide sequence to which it is not operably linked in nature, (b) a polypeptide or portion of a polypeptide that is not native to a cell in which it is expressed, (c) a polypeptide or portion of a polypeptide that has been altered or mutated relative to its native state, or (d) a polypeptide with an altered expression as compared to the native expression levels under similar conditions. As an example, a heterologous sequence of a polypeptide may be a different sequence or from a different source, relative to other domains or portions of a polypeptide. In some instances, the heterologous sequence includes a protein domain and at least one linker sequence.

The term "loop," as used herein, refers to a consecutive group of amino acids in an amino acid sequence of a polypeptide, comprising substantially no regular secondary structure, that connects two regular secondary structure elements when the polypeptide is under physiological conditions. In some embodiments, the loop is located on the surface in a solvent exposed area of a polypeptide, protein, or fragment thereof. In some embodiments, the loop comprises at least 3 amino acids. In some embodiments, loops are identified using analytical methods, such as X-ray crystallography, nuclear magnetic resonance (NMR), and small-angle X-ray scattering (SAXS). In some embodiments, loops can be determined using molecular modeling techniques.

The term "polypeptide linker," as used herein refers to a linker that comprises amino acids and links together two amino acid sequences (e.g., domains). In some embodiments, the polypeptide linker comprises glycine and/or serine residues used alone or in combination. In some embodiments, the peptide linker connects two portions of the Cas12i fusion protein together.

As used herein, the term "protospacer adjacent motif" or "PAM sequence" refers to a DNA sequence adjacent to a target sequence to which a binary complex comprising a Cas12i polypeptide and an RNA guide binds. In some embodiments, a PAM sequence is required for enzyme activity. In the case of a double-stranded target, the RNA guide binds to a first strand of the target, and a PAM sequence as described herein is present in the second, complementary strand. For example, in some embodiments, the RNA guide binds to the target strand (TS) (e.g., the spacer-complementary strand), and the PAM sequence as described herein is present in the non-target strand (i.e., the non-spacer-complementary strand). In a double-stranded DNA molecule, the strand containing the PAM motif is called the "PAM-strand" and the complementary strand is called the "non-PAM strand." The RNA guide binds to a site in the non-PAM strand that is complementary to a target sequence disclosed herein. In some embodiments, the PAM strand is a coding (e.g., sense) strand. In other embodiments, the PAM strand is a non-coding (e.g., antisense strand). Since an RNA guide binds the non-PAM strand via base-pairing, the non-PAM strand is also known as the target strand, while the PAM strand is also known as the non-target strand.

As used herein, the terms "RNA guide" or "RNA guide sequence" refer to any RNA molecule that facilitates the targeting of a Cas12i polypeptide described herein to a target sequence. For example, an RNA guide can be a molecule that recognizes (e.g., binds to) a target sequence. An RNA guide may be designed to be complementary to a specific nucleic acid sequence. An RNA guide comprises a DNA-targeting sequence (e.g., a DNA-binding sequence or a spacer) and a nuclease binding sequence (e.g. direct repeat (DR) sequence). The terms CRISPR RNA (crRNA), pre-crRNA and mature crRNA are also used herein to refer to an RNA guide. In some instances, the RNA guide can be a modified RNA molecule comprising one or more deoxyribonucleotides, for example, in a DNA-binding sequence contained in the RNA guide, which binds the non-PAM strand of a target nucleic acid. In some examples, the DNA-binding sequence may contain a DNA sequence or a DNA/RNA hybrid sequence.

As used herein, the term "substantially complementary" refers to a polynucleotide (e.g., a spacer sequence of an RNA guide) that has a certain level of complementarity to a target sequence. In some embodiments, the level of complementarity is such that the polynucleotide can hybridize to the target sequence with sufficient affinity to permit a Cas12i polypeptide that is complexed with the polynucleotide to act on (e.g., cleave) the target sequence.

As used herein, the term "substitution" refers to a replacement of a nucleotide or nucleotides with a different nucleotide or nucleotides, relative to a reference sequence. No particular process is implied in how to make a sequence comprising a substitution. For instance, a sequence comprising a substitution can be synthesized directly from individual nucleotides. In other embodiments, a substitution is made by providing and then altering a reference sequence. The nucleic acid sequence can be in a genome of an organism. The nucleic acid sequence can be in a cell. The nucleic acid sequence can be a DNA sequence. The substitution described herein refers to a substitution of up to several kilobases.

As used herein, the term "target sequence" refers to a sequence to which an RNA guide specifically binds. In some embodiments, the DNA-binding sequence of an RNA guide (e.g., the spacer) binds to a target sequence. In some embodiments, the term "target nucleic acid" is used to refer to a nucleic acid such as a chromosome where a target sequence can be found. For example, a target nucleic acid comprises the target sequence and additional coding or non-coding sequences. In some embodiments, an edit is introduced into a target sequence or target nucleic acid by a composition described herein. In some embodiments, the target sequence is a segment of DNA adjacent to a PAM motif (on the PAM strand). The complementary region of the target sequence is on the non-PAM strand. A target sequence may be immediately adjacent to the PAM motif. Alternatively, the target sequence and the PAM may be separated by a small sequence segment (e.g., up to 5 nucleotides, for example, up to 4, 3, 2, or 1 nucleotide). A target sequence may be located at the 3' end of the PAM motif or at the 5' end of the PAM motif, depending upon the CRISPR nuclease that recognizes the PAM motif, which is known in the art. For example, a target sequence is located at the 3' end of a PAM motif for a Cas12i polypeptide (e.g., a Cas12i2 polypeptide such as those disclosed herein). It is of course understood that DNA is often double stranded, and that a RNA guide will bind to one of the two strands, to which it is complementary. The location in the DNA where the RNA guide binds can be conveniently described by either providing the sequence of the strand to which the RNA guide binds (the non-PAM strand) or the sequence of the strand to which the RNA guide does not bind (the PAM strand). Thus, as is clear from context throughout the application, a target nucleic acid sequence may be described by providing the nucleic acid sequence of either strand of the double stranded DNA targeted by a RNA guide described herein.

It is understood that, herein, when a nucleic is said to comprise a particular nucleotide between specified positions, the end positions are included. For example, a nucleic acid comprising A between positions 8-11 could comprise the A at position 8, 9, 10, or 11.

BRIEF DESCRIPTION OF THE DRAWINGS

FIG. 12A depicts the positions of flexible loops in the Helical II domain (loops at residues 342-358, 373-378, and 386-397), the Helical III domain (loops at residues 677-685 and 771-782), the RuvC II motif (loop at residues 831-844), and the Nuc domain (loop at residues 953-965). FIG. 12B depicts the positions of the loops at residues 373-378, 677-685, and 953-965. FIG. 12C depicts the positions of the loops at residues 342-358 and 386-397. In some embodiments, a FokI nuclease domain is introduced by way of linker in the loop at residues 342-358 and in the loop at residues 386-397. For example, in some embodiments, a catalytically active FokI nuclease domain is introduced into the loop at residues 342-358 and a catalytically inactive FokI nuclease domain is introduced into the loop at residues 386-397. In another example, in some embodiments, a catalytically inactive FokI nuclease domain is introduced into the loop at residues 342-358 and a catalytically active FokI nuclease domain is introduced into the loop at residues 386-397. FIG. 12D depicts the positions of the loops at residues 342-358 and 386-397 as well as the helices between the two loops. In some instances, a circular permutation is introduced at any one of the indicated loops. In some instances, the portion of the Helical II domain positioned from about residue 342 to about 397 is deleted.

DETAILED DESCRIPTION

Figure 1:
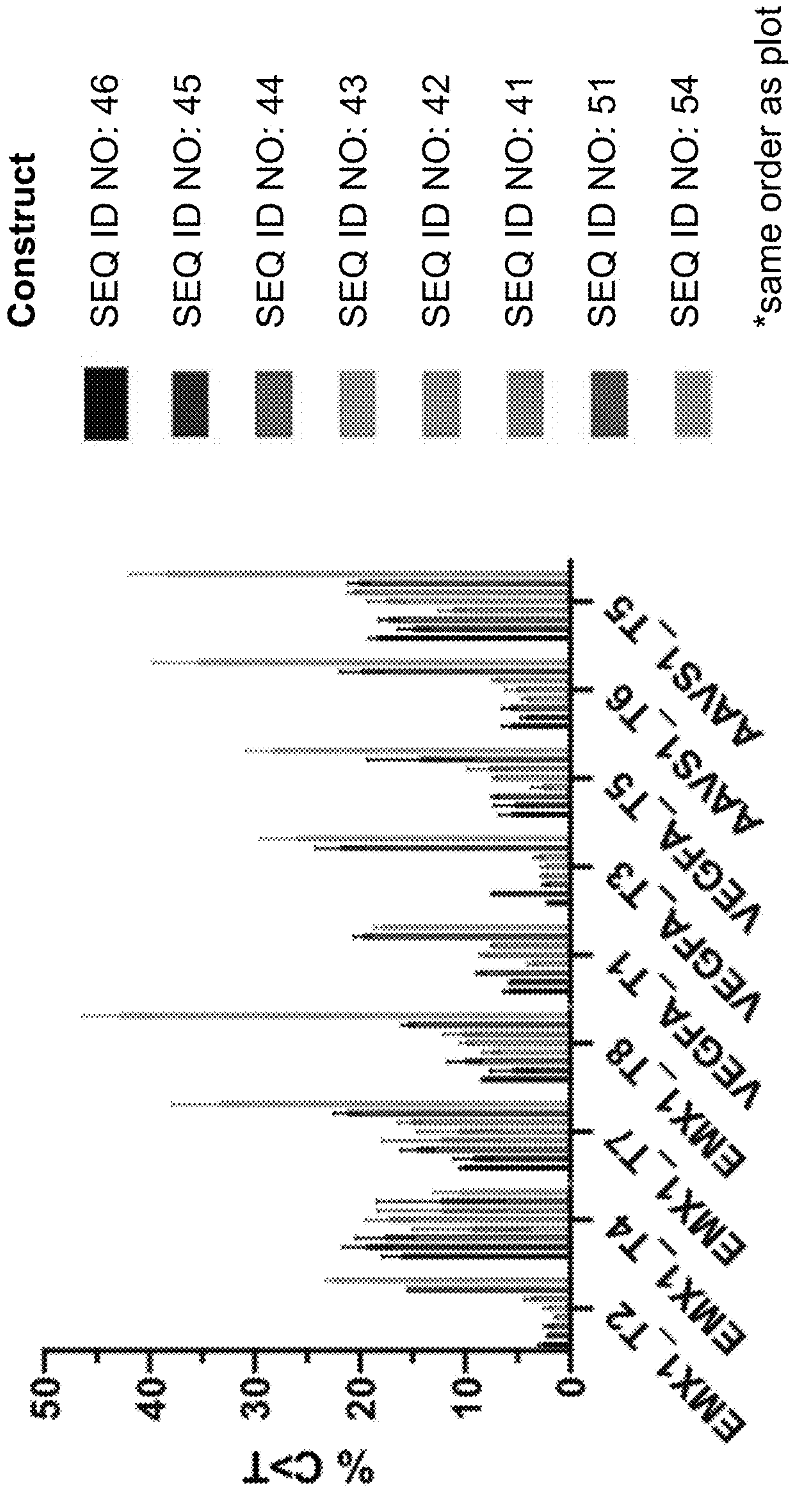
FIG. 1 is a bar graph that shows % C>T edits for AAVS1, EMX1, and VEGFA targets by Cas12i2-deaminase and Cas9-deaminase fusion polypeptides.

The present disclosure relates to a compositions comprising a Cas12i polypeptide, a deaminase, and an RNA guide. In some aspects, a composition having one or more characteristics is described herein. In some aspects, a method of producing the composition is described. In some aspects, a method of delivering the composition is described.

Composition

In some embodiments, a composition of the present invention comprises at least one protein component. In some embodiments, the at least one protein component is a Cas12i polypeptide, a deaminase polypeptide, or a Cas12i fusion protein (e.g., Cas12i-deaminase fusion polypeptide).

In some embodiments, a composition of the present invention is capable of binding to a target sequence of a target nucleic acid. In some embodiments, the target nucleic acid is DNA. In some embodiments, a composition of the present invention modifies a target nucleic acid. In some embodiments, a composition of a present invention introduces a substitution into a target sequence of a target nucleic acid. In some embodiments, a composition of a present invention is capable of introducing a substitution into the target strand of a target nucleic acid. In some embodiments, a composition of a present invention is capable of introducing a substitution into the non-target strand of a target nucleic acid.

Cas12i Domains and Polypeptides

In some embodiments, a composition of the present invention comprises a Cas12i polypeptide. In some embodiments, the Cas12i polypeptide is an RNA-guided nuclease. In some embodiments, the Cas12i polypeptide is a DNA-targeting nuclease.

In some embodiments, the Cas12i polypeptide is encoded by a nucleotide sequence such as SEQ ID NO: 1 or comprises an amino acid sequence such as SEQ ID NO: 2. In some embodiments, the Cas12i polypeptide of the present invention is a variant of a parent Cas12i polypeptide, wherein the parent comprises a nucleotide sequence such as SEQ ID NO: 1 or is encoded by a polypeptide that comprises an amino acid sequence such as SEQ ID NO: 2. See Table 1.

TABLE 1

Cas12i sequences.

| SEQ ID NO | Sequence | Description |
|---|---|---|
| 1 | ATGAGCAGCGCGATCAAAAGCTACAAGAGCGTTCTGCGTCCGAACGAGC<br>GTAAGAACCAACTGCTGAAAAGCACCATTCAGTGCCTGGAAGACGGTAG<br>CGCGTTCTTTTTCAAGATGCTGCAAGGCCTGTTTGGTGGCATCACCCCG<br>GAGATTGTTCGTTTCAGCACCGAACAGGAGAAACAGCAACAGGATATCG<br>CGCTGTGGTGCGCGGTTAACTGGTTCCGTCCGGTGAGCCAAGACAGCCT<br>GACCCACACCATTGCGAGCGATAACCTGGTGGAGAAGTTTGAGGAATAC<br>TATGGTGGCACCGCGAGCGACGCGATCAAACAGTACTTCAGCGCGAGCA<br>TTGGCGAAAGCTACTATTGGAACGACTGCCGTCAACAGTACTATGATCT<br>GTGCCGTGAGCTGGGTGTTGAGGTGAGCGACCTGACCCATGATCTGGAG<br>ATCCTGTGCCGTGAAAAGTGCCTGGCGGTTGCGACCGAGAGCAACCAGA<br>ACAACAGCATCATTAGCGTTCTGTTTGGCACCGGCGAAAAAGAGGACCG<br>TAGCGTGAAACTGCGTATCACCAAGAAAATTCTGGAGGCGATCAGCAAC<br>CTGAAAGAAATCCCGAAGAACGTTGCGCCGATTCAAGAGATCATTCTGA<br>ACGTGGCGAAAGCGACCAAGGAAACCTTCCGTCAGGTGTATGCGGGTAA<br>CCTGGGTGCGCCGAGCACCCTGGAGAAATTTATCGCGAAGGACGGCCAA<br>AAAGAGTTCGATCTGAAGAAACTGCAGACCGACCTGAAGAAAGTTATTC<br>GTGGTAAAAGCAAGGAGCGTGATTGGTGCTGCCAGGAAGAGCTGCGTAG<br>CTACGTGGAGCAAAACACCATCCAGTATGACCTGTGGGCGTGGGGCGAA<br>ATGTTCAACAAAGCGCACACCGCGCTGAAAATCAAGAGCACCCGTAACT<br>ACAACTTTGCGAAGCAACGTCTGGAACAGTTCAAAGAGATTCAGAGCCT | Nucleotide sequence encoding Cas12i2 |

TABLE 1-continued

Cas12i sequences.

| SEQ ID NO | Sequence | Description |
|---|---|---|
| | GAACAACCTGCTGGTTGTGAAGAAGCTGAACGACTTTTTCGATAGCGAA<br>TTTTTCAGCGGCGAGGAAACCTACACCATCTGCGTTCACCATCTGGGTG<br>GCAAGGACCTGAGCAAACTGTATAAGGCGTGGGAGGATGATCCGGCGGA<br>CCCGGAAAACGCGATTGTGGTTCTGTGCGACGATCTGAAAAACAACTTT<br>AAGAAAGAGCCGATCCGTAACATTCTGCGTTACATCTTCACCATTCGTC<br>AAGAATGCAGCGCGCAGGACATCCTGGCGGCGGCGAAGTACAACCAACA<br>GCTGGATCGTTATAAAAGCCAAAAGGCGAACCCGAGCGTTCTGGGTAAC<br>CAGGGCTTTACCTGGACCAACGCGGTGATCCTGCCGGAGAAGGCGCAGC<br>GTAACGACCGTCCGAACAGCCTGGATCTGCGTATTTGGCTGTACCTGAA<br>ACTGCGTCACCCGGACGGTCGTTGGAAGAAACACCATATCCCGTTCTAC<br>GATACCCGTTTCTTCCAAGAAATTTATGCGGCGGGCAACAGCCCGGTTG<br>ACACCTGCCAGTTTCGTACCCCGCGTTTCGGTTATCACCTGCCGAAACT<br>GACCGATCAGACCGCGATCCGTGTTAACAAGAAACATGTGAAAGCGGCG<br>AAGACCGAGGCGCGTATTCGTCTGGCGATCCAACAGGGCACCCTGCCGG<br>TGAGCAACCTGAAGATCACCGAAATTAGCGCGACCATCAACAGCAAAGG<br>TCAAGTGCGTATTCCGGTTAAGTTTGACGTGGGTCGTCAAAAAGGCACC<br>CTGCAGATCGGTGACCGTTTCTGCGGCTACGATCAAAACCAGACCGCGA<br>GCCACGCGTATAGCCTGTGGGAAGTGGTTAAAGAGGGTCAATACCATAA<br>AGAGCTGGGCTGCTTTGTTCGTTTCATCAGCAGCGGTGACATCGTGAGC<br>ATTACCGAGAACCGTGGCAACCAATTTGATCAGCTGAGCTATGAAGGTC<br>TGGCGTACCCGCAATATGCGGACTGGCGTAAGAAAGCGAGCAAGTTCGT<br>GAGCCTGTGGCAGATCACCAAGAAAAACAAGAAAAAGGAAATCGTGACC<br>GTTGAAGCGAAAGAGAAGTTTGACGCGATCTGCAAGTACCAGCCGCGTC<br>TGTATAAATTCAACAAGGAGTACGCGTATCTGCTGCGTGATATTGTTCG<br>TGGCAAAAGCCTGGTGGAACTGCAACAGATTCGTCAAGAGATCTTTCGT<br>TTCATTGAACAGGACTGCGGTGTTACCCGTCTGGGCAGCCTGAGCCTGA<br>GCACCCTGGAAACCGTGAAAGCGGTTAAGGGTATCATTTACAGCTATTT<br>TAGCACCGCGCTGAACGCGAGCAAGAACAACCCGATCAGCGACGAACAG<br>CGTAAAGAGTTTGATCCGGAACTGTTCGCGCTGCTGGAAAAGCTGGAGC<br>TGATTCGTACCCGTAAAAAGAAACAAAAAGTGGAACGTATCGCGAACAG<br>CCTGATTCAGACCTGCCTGGAGAACAACATCAAGTTCATTCGTGGTGAA<br>GGCGACCTGAGCACCACCAACAACGCGACCAAGAAAAAGGCGAACAGCC<br>GTAGCATGGATTGGTTGGCGCGTGGTGTTTTTAACAAAATCCGTCAACT<br>GGCGCCGATGCACAACATTACCCTGTTCGGTTGCGGCAGCCTGTACACC<br>AGCCACCAGGACCCGCTGGTGCATCGTAACCCGGATAAAGCGATGAAGT<br>GCCGTTGGGCGGCGATCCCGGTTAAGGACATTGGCGATTGGGTGCTGCG<br>TAAGCTGAGCCAAAACCTGCGTGCGAAAAACATCGGCACCGGCGAGTAC<br>TATCACCAAGGTGTTAAAGAGTTCCTGAGCCATTATGAACTGCAGGACC<br>TGGAGGAAGAGCTGCTGAAGTGGCGTAGCGATCGTAAAAGCAACATTCC<br>GTGCTGGGTGCTGCAGAACCGTCTGGCGGAGAAGCTGGGCAACAAAGAA<br>GCGGTGGTTTACATCCCGGTTCGTGGTGGCCGTATTTATTTTGCGACCC<br>ACAAGGTGGCGACCGGTGCGGTGAGCATCGTTTTCGACCAAAAACAAGT<br>GTGGGTTTGCAACGCGGATCATGTTGCGGCGGCGAACATCGCGCTGACC<br>GTGAAGGGTATTGGCGAACAAAGCAGCGACGAAGAGAACCCGGATGGTA<br>GCCGTATCAAACTGCAGCTGACCAGC | |
| 2 | MSSAIKSYKSVLRPNERKNQLLKSTIQCLEDGSAFFFKMLQGLFGGITP<br>EIVRFSTEQEKQQQDIALWCAVNWFRPVSQDSLTHTIASDNLVEKFEEY<br>YGGTASDAIKQYFSASIGESYYWNDCRQQYYDLCRELGVEVSDLTHDLE<br>ILCREKCLAVATESNQNNSIISVLFGTGEKEDRSVKLRITKKILEAISN<br>LKEIPKNVAPIQEIILNVAKATKETFRQVYAGNLGAPSTLEKFIAKDGQ<br>KEFDLKKLQTDLKKVIRGKSKERDWCCQEELRSYVEQNTIQYDLWAWGE<br>MFNKAHTALKIKSTRNYNFAKQRLEQFKEIQSLNNLLVVKKLNDFFDSE<br>FFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGN<br>QGFTWTNAVILPEKAQRNDRPNSLDLRIWLYLKLRHPDGRWKKHHIPFY<br>DTRFFQEIYAAGNSPVDTCQFRTPRFGYHLPKLTDQTAIRVNKKHVKAA<br>KTEARIRLAIQQGTLPVSNLKITEISATINSKGQVRIPVKFDVGRQKGT<br>LQIGDRFCGYDQNQTASHAYSLWEVVKEGQYHKELGCFVRFISSGDIVS<br>ITENRGNQFDQLSYEGLAYPQYADWRKKASKFVSLWQITKKNKKKEIVT<br>VEAKEKFDAICKYQPRLYKFNKEYAYLLRDIVRGKSLVELQQIRQEIFR<br>FIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGE<br>GDLSTTNNATKKKANSRSMDWLARGVFNKIRQLAPMHNITLFGCGSLYT<br>SHQDPLVHRNPDKAMKCRWAAIPVKDIGDWVLRKLSQNLRAKNIGTGEY<br>YHQGVKEFLSHYELQDLEEELLKWRSDRKSNIPCWVLQNRLAEKLGNKE<br>AVVYIPVRGGRIYFATHKVATGAVSIVFDQKQVWVCNADHVAAANIALT<br>VKGIGEQSSDEENPDGSRIKLQLTS | Cas12i2 amino acid sequence |
| 3 | MSSAIKSYKSVLRPNERKNQLLKSTIQCLEDGSAFFFKMLQGLFGGITP<br>EIVRFSTEQEKQQQDIALWCAVNWFRPVSQDSLTHTIASDNLVEKFEEY<br>YGGTASDAIKQYFSASIGESYYWNDCRQQYYDLCRELGVEVSDLTHDLE<br>ILCREKCLAVATESNQNNSIISVLFGTGEKEDRSVKLRITKKILEAISN<br>LKEIPKNVAPIQEIILNVAKATKETFRQVYAGNLGAPSTLEKFIAKDGQ<br>KEFDLKKLQTDLKKVIRGKSKERDWCCQEELRSYVEQNTIQYDLWAWGE | Variant Cas12i2 of SEQ ID NO: 3 of PCT/US2021/025257 |

TABLE 1-continued

Cas12i sequences.

| SEQ ID NO | Sequence | Description |
|---|---|---|
| | MFNKAHTALKIKSTRNYNFAKQRLEQFKEIQSLNNLLVVKKLNDFFDSE<br>FFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGN<br>QGFTWTNAVILPEKAQRNDRPNSLDLRIWLYLKLRHPDGRWKKHHIPFY<br>DTRFFQEIYAAGNSPVDTCQFRTPRFGYHLPKLTDQTAIRVNKKHVKAA<br>KTEARIRLAIQQGTLPVSNLKITEISATINSKGQVRIPVKFRVGRQKGT<br>LQIGDRFCGYDQNQTASHAYSLWEVVKEGQYHKELGCFVRFISSGDIVS<br>ITENRGNQFDQLSYEGLAYPQYADWRKKASKFVSLWQITKKNKKKEIVT<br>VEAKEKFDAICKYQPRLYKFNKEYAYLLRDIVRGKSLVELQQIRQEIFR<br>FIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGE<br>GDLSTTNNATKKKANSRSMDWLARGVFNKIRQLAPMHNITLFGCGSLYT<br>SHQDPLVHRNPDKAMKCRWAAIPVKDIGRWVLRKLSQNLRAKNRGTGEY<br>YHQGVKEFLSHYELQDLEEELLKWRSDRKSNIPCWVLQNRLAEKLGNKE<br>AVVYIPVRGGRIYFATHKVATGAVSIVFDQKQVWVCNADHVAAANIALT<br>GKGIGEQSSDEENPDGSRIKLQLTS | |
| 4 | MSSAIKSYKSVLRPNERKNQLLKSTIQCLEDGSAFFFKMLQGLFGGITP<br>EIVRFSTEQEKQQQDIALWCAVNWFRPVSQDSLTHTIASDNLVEKFEEY<br>YGGTASDAIKQYFSASIGESYYWNDCRQQYYDLCRELGVEVSDLTHDLE<br>ILCREKCLAVATESNQNNSIISVLFGTGEKEDRSVKLRITKKILEAISN<br>LKEIPKNVAPIQEIILNVAKATKETFRQVYAGNLGAPSTLEKFIAKDGQ<br>KEFDLKKLQTDLKKVIRGKSKERDWCCQEELRSYVEQNTIQYDLWAWGE<br>MFNKAHTALKIKSTRNYNFAKQRLEQFKEIQSLNNLLVVKKLNDFFDSE<br>FFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGN<br>QGFTWTNAVILPEKAQRNDRPNSLDLRIWLYLKLRHPDGRWKKHHIPFY<br>DTRFFQEIYAAGNSPVDTCQFRTPRFGYHLPKLTDQTAIRVNKKHVKAA<br>KTEARIRLAIQQGTLPVSNLKITEISATINSKGQVRIPVKFRVGRQKGT<br>LQIGDRFCGYDQNQTASHAYSLWEVVKEGQYHKELGCFVRFISSGDIVS<br>ITENRGNQFDQLSYEGLAYPQYADWRKKASKFVSLWQITKKNKKKEIVT<br>VEAKEKFDAICKYQPRLYKFNKEYAYLLRDIVRGKSLVELQQIRQEIFR<br>FIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGE<br>GDLSTTNNATKKKANSRSMDWLARGVFNKIRQLAPMHNITLFGCGSLYT<br>SHQDPLVHRNPDKAMKCRWAAIPVKDIGDWVLRKLSQNLRAKNRGTGEY<br>YHQGVKEFLSHYELQDLEEELLKWRSDRKSNIPCWVLQNRLAEKLGNKE<br>AVVYIPVRGGRIYFATHKVATGAVSIVFDQKQVWVCNADHVAAANIALT<br>GKGIGEQSSDEENPDGSRIKLQLTS | Variant Cas12i2 of SEQ ID NO: 4 of PCT/US2021/ 025257 |
| 5 | MSSAIKSYKSVLRPNERKNQLLKSTIQCLEDGSAFFFKMLQGLFGGITP<br>EIVRFSTEQEKQQQDIALWCAVNWFRPVSQDSLTHTIASDNLVEKFEEY<br>YGGTASDAIKQYFSASIGESYYWNDCRQQYYDLCRELGVEVSDLTHDLE<br>ILCREKCLAVATESNQNNSIISVLFGTGEKEDRSVKLRITKKILEAISN<br>LKEIPKNVAPIQEIILNVAKATKETFRQVYAGNLGAPSTLEKFIAKDGQ<br>KEFDLKKLQTDLKKVIRGKSKERDWCCQEELRSYVEQNTIQYDLWAWGE<br>MFNKAHTALKIKSTRNYNFAKQRLEQFKEIQSLNNLLVVKKLNDFFDSE<br>FFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGN<br>QGFTWTNAVILPEKAQRNDRPNSLDLRIWLYLKLRHPDGRWKKHHIPFY<br>DTRFFQEIYAAGNSPVDTCQFRTPRFGYHLPKLTDQTAIRVNKKHVKAA<br>KTEARIRLAIQQGTLPVSNLKITEISATINSKGQVRIPVKFRVGRQKGT<br>LQIGDRFCGYDQNQTASHAYSLWEVVKEGQYHKELGCFVRFISSGDIVS<br>ITENRGNQFDQLSYEGLAYPQYADWRKKASKFVSLWQITKKNKKKEIVT<br>VEAKEKFDAICKYQPRLYKFNKEYAYLLRDIVRGKSLVELQQIRQEIFR<br>FIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGE<br>GDLSTTNNATKKKANSRSMDWLARGVFNKIRQLAPMHNITLFGCGSLYT<br>SHQDPLVHRNPDKAMKCRWAAIPVKDIGDWVLRKLSQNLRAKNRGTGEY<br>YHQGVKEFLSHYELQDLEEELLKWRSDRKSNIPCWVLQNRLAEKLGNKE<br>AVVYIPVRGGRIYFATHKVATGAVSIVFDQKQVWVCNADHVAAANIALT<br>GKGIGEQSSDEENPDGGRIKLQLTS | Variant Cas12i2 of SEQ ID NO: 5 of PCT/US2021/ 025257 |
| 6 | MSSAIKSYKSVLRPNERKNQLLKSTIQCLEDGSAFFFKMLQGLFGGITP<br>EIVRFSTEQEKQQQDIALWCAVNWFRPVSQDSLTHTIASDNLVEKFEEY<br>YGGTASDAIKQYFSASIGESYYWNDCRQQYYDLCRELGVEVSDLTHDLE<br>ILCREKCLAVATESNQNNSIISVLFGTGEKEDRSVKLRITKKILEAISN<br>LKEIPKNVAPIQEIILNVAKATKETFRQVYAGNLGAPSTLEKFIAKDGQ<br>KEFDLKKLQTDLKKVIRGKSKERDWCCQEELRSYVEQNTIQYDLWAWGE<br>MFNKAHTALKIKSTRNYNFAKQRLEQFKEIQSLNNLLVVKKLNDFFDSE<br>FFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGN<br>QGFTWTNAVILPEKAQRNDRPNSLDLRIWLYLKLRHPDGRWKKHHIPFY<br>DTRFFQEIYAAGNSPVDTCQFRTPRFGYHLPKLTDQTAIRVNKKHVKAA<br>KTEARIRLAIQQGTLPVSNLKITEISATINSKGQVRIPVKFRVGRQKGT | Variant Cas12i2 of SEQ ID NO: 495 of PCT/US2021/ 025257 |

TABLE 1-continued

| SEQ ID NO | Sequence | Description |
|---|---|---|
| | Cas12i sequences. | |
| | LQIGDRFCGYDQNQTASHAYSLWEVVKEGQYHKELRCRVRFISSGDIVS ITENRGNQFDQLSYEGLAYPQYADWRKKASKFVSLWQITKKNKKKEIVT VEAKEKFDAICKYQPRLYKFNKEYAYLLRDIVRGKSLVELQQIRQEIFR FIEQDCGVTRLGSLSLSTLETVKAVKGIIYSYFSTALNASKNNPISDEQ RKEFDPELFALLEKLELIRTRKKKQKVERIANSLIQTCLENNIKFIRGE GDLSTTNNATKKKANSRSMDWLARGVFNKIRQLAPMHNITLFGCGSLYT SHQDPLVHRNPDKAMKCRWAAIPVKDIGDWVLRKLSQNLRAKNRGTGEY YHQGVKEFLSHYELQDLEEELLKWRSDRKSNIPCWVLQNRLAEKLGNKE AVVYIPVRGGRIYFATHKVATGAVSIVFDQKQVWVCNADHVAAANIALT GKGIGRQSSDEENPDGGRIKLQLTS | |
| 7 | MSSAIKSYKSVLRPNERKNQLLKSTIQCLEDGSAFFFKMLQGLFGGITP EIVRFSTEQEKQQQDIALWCAVNWFRPVSQDSLTHTIASDNLVEKFEEY YGGTASDAIKQYFSASIGESYYWNDCRQQYYDLCRELGVEVSDLTHDLE ILCREKCLAVATESNQNNSIISVLFGTGEKEDRSVKLRITKKILEAISN LKEIPKNVAPIQEIILNVAKATKETFRQVYAGNLGAPSTLEKFIAKDGQ KEFDLKKLQTDLKKVIRGKSKERDWCCQEELRSYVEQNTIQYDLWAWGE MFNKAHTALKIKSTRNYNFAKQRLEQFKEIQSLNNLLVVKKLNDFFDSE FFSGEETYTICVHHLGGKDLSKLYKAWEDDPADPENAIVVLCDDLKNNF KKEPIRNILRYIFTIRQECSAQDILAAAKYNQQLDRYKSQKANPSVLGN QGFTWTNAVILPEKAQRNDRPNSLDLRIWLYLKLRHPDGRWKKHHIPFY DTRFFQEIYAAGNSPVDTCQFRTPRFGYHLPKLTDQTAIRVNKKHVKAA KTEARIRLAIQQGTLPVSNLKITEISATINSKGQVRIPVKFRVGRQKGT LQIGDRFCGYDQNQTASHAYSLWEVVKEGQYHKELRCRVRFISSGDIVS ITENRGNQFDQLSYEGLAYPQYADWRKKASKFVSLWQITKKNKKKEIVT VEAKEKFDAICKYQPRLYKFNKEYAYLLRDIVRGKSLVELQQIRQEIFR FIEQDCGVTRLGSLSLSTLETVKAVKGIIYSYFSTALNASKNNPISDEQ RKEFDPELFALLEKLELIRTRKKKQKVERIANSLIQTCLENNIKFIRGE GDLSTTNNATKKKANSRSMDWLARGVFNKIRQLATMHNITLFGCGSLYT SHQDPLVHRNPDKAMKCRWAAIPVKDIGDWVLRKLSQNLRAKNRGTGEY YHQGVKEFLSHYELQDLEEELLKWRSDRKSNIPCWVLQNRLAEKLGNKE AVVYIPVRGGRIYFATHKVATGAVSIVFDQKQVWVCNADHVAAANIALT GKGIGRQSSDEENPDGGRIKLQLTS | Variant Cas12i2 of SEQ ID NO: 496 of PCT/US2021/ 025257 |
| 8 | MSNKEKNASETRKAYTTKMIPRSHDRMKLLGNFMDYLMDGTPIFFELWN QFGGGIDRDIISGTANKDKISDDLLLAVNWFKVMPINSKPQGVSPSNLA NLFQQYSGSEPDIQAQEYFASNFDTEKHQWKDMRVEYERLLAELQLSRS DMHHDLKLMYKEKCIGLSLSTAHYITSVMFGTGAKNNRQTKHQFYSKVI QLLEESTQINSVEQLASIILKAGDCDSYRKLRIRCSRKGATPSILKIVQ DYELGTNHDDEVNVPSLIANLKEKLGRFEYECEWKCMEKIKAFLASKVG PYYLGSYSAMLENALSPIKGMTTKNCKFVLKQIDAKNDIKYENEPFGKI VEGFFDSPYFESDTNVKWVLHPHHIGESNIKTLWEDLNAIHSKYEEDIA SLSEDKKEKRIKVYQGDVCQTINTYCEEVGKEAKTPLVQLLRYLYSRKD DIAVDKIIDGITFLSKKHKVEKQKINPVIQKYPSFNFGNNSKLLGKIIS PKDKLKHNLKCNRNQVDNYIWIEIKVLNTKTMRWEKHHYALSSTRFLEE VYYPATSENPPDALAARFRTKTNGYEGKPALSAEQIEQIRSAPVGLRKV KKRQMRLEAARQQNLLPRYTWGKDFNINICKRGNNFEVTLATKVKKKKE KNYKVVLGYDANIVRKNTYAAIEAHANGDGVIDYNDLPVKPIESGFVTV ESQVRDKSYDQLSYNGVKLLYCKPHVESRRSFLEKYRNGTMKDNRGNNI QIDFMKDFEAIADDETSLYYFNMKYCKLLQSSIRNHSSQAKEYREEIFE LLRDGKLSVLKLSSLSNLSFVMFKVAKSLIGTYFGHLLKKPKNSKSDVK APPITDEDKQKADPEMFALRLALEEKRLNKVKSKKEVIANKIVAKALEL RDKYGPVLIKGENISDTTKKGKKSSTNSFLMDWLARGVANKVKEMVMMH QGLEFVEVNPNFTSHQDPFVHKNPENTFRARYSRCTPSELTEKNRKEIL SFLSDKPSKRPTNAYYNEGAMAFLATYGLKKNDVLGVSLEKFKQIMANI LHQRSEDQLLFPSRGGMFYLATYKLDADATSVNWNGKQFWVCNADLVAA YNVGLVDIQKDFKKK | Cas12i1 (SEQ ID NO: 3 of U.S. Pat. No. 10,808,245) |
| 9 | MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENIT WEQYREALKNQLNAKNLEQVVANYKGNAGGADPFFKYSFSKEGMVSKKE HAQQLDKFKTVLKNKARDLNFPNKEKLKQYLEAEIGIPVDANVYSQMFS NGVSEVQPKTTRNMSFSNEKLDLLTELKDLNKGDGFEYAREVLNGFFDS ELHTTEDKFNITSRYLGGDKSNRLSKLYKIWKKEGVDCEEGIQQFCEAV KDKMGQIPIRNVLKYLWQFRETVSAEDFEAAAKANHLEEKISRVKAHPI VISNRYWAFGTSALVGNIMPADKRHQGEYAGQNFKMWLEAELHYDGKKA KHHLPFYNARFFEEVYCYHPSVAEITPFKTKQFGCEIGKDIPDYVSVAL KDNPYKKATKRILRAIYNPVANTTGVDKTTNCSFMIKRENDEYKLVINR KISVDRPKRIEVGRTIMGYDRNQTASDTYWIGRLVPPGTRGAYRIGEWS VQYIKSGPVLSSTQGVNNSTTDQLVYNGMPSSSERFKAWKKARMAFIRK LIRQLNDEGLESKGQDYIPENPSSFDVRGETLYVFNSNYLKALVSKHRK AKKPVEGILDEIEAWTSKDKDSCSLMRLSSLSDASMQGIASLKSLINSY FNKNGCKTIEDKEKFNPVLYAKLVEVEQRRTNKRSEKVGRIAGSLEQLA | Cas12i4 (SEQ ID NO: 16 of U.S. Pat. No. 10,808,245) |

TABLE 1-continued

Cas12i sequences.

| SEQ ID NO | Sequence | Description |
|---|---|---|
| | LLNGVEVVIGEADLGEVEKGKSKKQNSRNMDWCAKQVAQRLEYKLAFHG<br>IGYFGVNPMYTSHQDPFEHRRVADHIVMRARFEEVNVENIAEWHVRNFS<br>NYLRADSGTGLYYKQATMDFLKHYGLEEHAEGLENKKIKFYDFRKILED<br>KNLTSVIIPKRGGRIYMATNPVTSDSTPITYAGKTYNRCNADEVAAANI<br>VISVLAPRSKKNEEQDDIPLITKKAESKSPPKDRKRSKTSQLPQK | |
| 10 | MASISRPYGTKLRPDARKKEMLDKFFNTLTKGQRVFADLALCIYGSLTL<br>EMAKSLEPESDSELVCAIGWFRLVDKTIWSKDGIKQENLVKQYEAYSGK<br>EASEVVKTYLNSPSSDKYVWIDCRQKFLRFQRELGTRNLSEDFECMLFE<br>QYIRLTKGEIEGYAAISNMFGNGEKEDRSKKRMYATRMKDWLEANENIT<br>WEQYREALKNQLNAKNLEQVVANYKGNAGGADPFFKYSFSKEGMVSKKE<br>HAQQLDKFKTVLKNKARDLNFPNKEKLKQYLEAEIGIPVDANVYSQMFS<br>NGVSEVQPKTTRNMSFSNEKLDLLTELKDLNKGDGFEYAREVLNGFFDS<br>ELHTTEDKFNITSRYLGGDKSNRLSKLYKIWKKEGVDCEEGIQQFCEAV<br>KDKMGQIPIRNVLKYLWQFRETVSAEDFEAAAKANHLEEKISRVKAHPI<br>VISNRYWAFGTSALVGNIMPADKRHQGEYAGQNFKMWLRAELHYDGKKA<br>KHHLPFYNARFFEEVYCYHPSVAEITPFKTKQFGCEIGKDIPDYVSVAL<br>KDNPYKKATKRILRAIYNPVANTTRVDKTTNCSFMIKRENDEYKLVINR<br>KISRDRPKRIEVGRTIMGYDRNQTASDTYWIGRLVPPGTRGAYRIGEWS<br>VQYIKSGPVLSSTQGVNNSTTDQLVYNGMPSSSERFKAWKKARMAFIRK<br>LIRQLNDEGLESKGQDYIPENPSSFDVRGETLYVFNSNYLKALVSKHRK<br>AKKPVEGILDEIEAWTSKDKDSCSLMRLSSLSDASMQGIASLKSLINSY<br>FNKNGCKTIEDKEKFNPVLYAKLVEVEQRRTNKRSEKVGRIAGSLEQLA<br>LLNGVEVVIGEADLGEVEKGKSKKQNSRNMDWCAKQVAQRLEYKLAFHG<br>IGYFGVNPMYTSHQDPFEHRRVADHIVMRARFEEVNVENIAEWHVRNFS<br>NYLRADSGTGLYYKQATMDFLKHYGLEEHAEGLENKKIKFYDFRKILED<br>KNLTSVIIPKRGGRIYMATNPVTSDSTPITYAGKTYNRCNADEVAAANI<br>VISVLAPRSKKNREQDDIPLITKKAESKSPPKDRKRSKTSQLPQK | Variant Cas12i4 |
| 11 | MSISNNNILPYNPKLLPDDRKHKMLVDTFNQLDLIRNNLHDMIIALYGA<br>LKYDNIKQFASKEKPHISADALCSINWFRLVKTNERKPAIESNQIISKF<br>IQYSGHTPDKYALSHITGNHEPSHKWIDCREYAINYARIMHLSFSQFQD<br>LATACLNCKILILNGTLTSSWAWGANSALFGGSDKENFSVKAKILNSFI<br>ENLKDEMNTTKFQVVEKVCQQIGSSDAADLFDLYRSTVKDGNRGPATGR<br>NPKVMNLFSQDGEISSEQREDFIESFQKVMQEKNSKQIIPHLDKLKYHL<br>VKQSGLYDIYSWAAAIKNANSTIVASNSSNLNTILNKTEKQQTFEELRK<br>DEKIVACSKILLSVNDTLPEDLHYNPSTSNLGKNLDVFFDLLNENSVHT<br>IENKEEKNKIVKECVNQYMEECKGLNKPPMPVLLTFISDYAHKHQAQDF<br>LSAAKMNFIDLKIKSIKVVPTVHGSSPYTWISNLSKKNKDGKMIRTPNS<br>SLIGWIIPPEEIHDQKFAGQNPIIWAVLRVYCNNKWEMHHFPFSDSRFF<br>TEVYAYKPNLPYLPGGENRSKRFGYRHSTNLSNESRQILLDKSKYAKAN<br>KSVLRCMENMTHNVVFDPKTSLNIRIKTDKNNSPVLDDKGRITFVMQIN<br>HRILEKYNNTKIEIGDRILAYDQNQSENHTYAILQRTEEGSHAHQFNGW<br>YVRVLETGKVTSIVQGLSGPIDQLNYDGMPVTSHKFNCWQADRSAFVSQ<br>FASLKISETETFDEAYQAINAQGAYTWNLFYLRILRKALRVCHMENINQ<br>FREEILAISKNRLSPMSLGSLSQNSLKMIRAFKSIINCYMSRMSFVDEL<br>QKKEGDLELHTIMRLTDNKLNDKRVEKINRASSFLTNKAHSMGCKMIVG<br>ESDLPVADSKTSKKQNVDRMDWCARALSHKVEYACKLMGLAYRGIPAYM<br>SSHQDPLVHLVESKRSVLRPRFVVADKSDVKQHHLDNLRRMLNSKTKVG<br>TAVYYREAVELMCEELGIHKTDMAKGKVSLSDFVDKFIGEKAIFPQRGG<br>RFYMSTKRLTTGAKLICYSGSDVWLSDADEIAAINIGMFVVCDQTGAFK<br>KKKKEKLDDEECDILPFRPM | Cas12i3 (SEQ ID NO: 14 of U.S. Pat. No. 10,808,245) |

A nucleic acid sequence encoding the Cas12i polypeptide described herein may be substantially identical to a reference nucleic acid sequence, e.g., SEQ ID NO: 1. In some embodiments, the Cas12i polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., nucleic acid sequence encoding the parent polypeptide, e.g., SEQ ID NO: 1. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions (e.g., within a range of medium to high stringency).

In some embodiments, the Cas12i polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., nucleic acid sequence encoding the Cas12i polypeptide, e.g., SEQ ID NO: 1.

In some embodiments, the Cas12i polypeptide of the present invention comprises a polypeptide sequence having 50%, 60%, 65%, 70%, 75%, 80%, 85%, 90%, 91%, 92%, 93%, 94%, 95%, 96%, 97%, 98%, 99%, or 100% identity to SEQ ID NO: 2. In some embodiments, the Cas12i polypeptide of the present invention comprises a sequence having greater than 50%, 60%, 65%, 70%, 75%, 80%, 85%, 90%, 91%, 92%, 93%, 94%, 95%, 96%, 97%, 98%, or 99%, but not 100%, identity to SEQ ID NO: 2.

In some embodiments, the present invention describes a Cas12i polypeptide having a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 2. Homology or identity can be determined by amino acid sequence alignment, e.g., using a program such as BLAST, ALIGN, or CLUSTAL, as described herein.

In some embodiments, the Cas12i polypeptide is a variant Cas12i2 polypeptide described in PCT/US2021/025257, which is incorporated by reference in its entirety. In some embodiments, the variant Cas12i2 polypeptide comprises one or more of the amino acid substitutions listed in Table 2 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to the amino acid sequence of SEQ ID NO: 3 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to the amino acid sequence of SEQ ID NO: 4 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to the amino acid sequence of SEQ ID NO: 495 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to the amino acid sequence of SEQ ID NO: 496 of PCT/US2021/025257. In some embodiments, the Cas12i polypeptide is a variant Cas12i2 polypeptide having at least 90%, at least 91%, at least 92%, at least 93%, at least 94%, at least 95%, at least 96%, at least 97%, at least 98%, at least 99%, or 100% sequence identity to any one of SEQ ID NOs: 3-146 and 495-512 of PCT/US2021/025257.

In some embodiments, a Cas12i2 polypeptide further comprises one or more of the following substitutions: G587R, D599A, D599K, F626R, E833Q, E833N, D1019K, or D1019N.

In some embodiments, the Cas12i polypeptide is a Cas12i1 polypeptide. In some embodiments, the Cas12i1 polypeptide of the present invention comprises a polypeptide sequence having 50%, 60%, 65%, 70%, 75%, 80%, 85%, 90%, 91%, 92%, 93%, 94%, 95%, 96%, 97%, 98%, 99%, or 100% identity to SEQ ID NO: 8. In some embodiments, the Cas12i1 polypeptide of the present invention comprises a polypeptide sequence having greater than 50%, 60%, 65%, 70%, 75%, 80%, 85%, 90%, 91%, 92%, 93%, 94%, 95%, 96%, 97%, 98%, 99%, or 100% identity to SEQ ID NO: 8.

In some embodiments, the Cas12i polypeptide has a specified degree of amino acid sequence identity to one or more reference polypeptides, e.g., a Casil polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 8. Homology or identity can be determined by amino acid sequence alignment, e.g., using a program such as BLAST, ALIGN, or CLUSTAL, as described herein.

In some embodiments, a nucleic acid encoding the Cas12i1 polypeptide as described herein encodes an amino acid sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 8. In some embodiments, the Cas12i1 polypeptide has a sequence greater than 50%, 60%, 65%, 70%, 75%, 80%, 85%, 90%, 91%, 92%, 93%, 94%, 95%, 96%, 97%, 98%, 99%, or 100% identity to SEQ ID NO: 8.

In some embodiments, a Cas12i1 polypeptide described herein having enzymatic activity, e.g., nuclease or endonuclease activity, comprises an amino acid sequence which differs from the amino acid sequences of any one of a Cas12i polypeptide and SEQ ID NO: 8 by 100, 95, 90, 85, 80, 75, 70, 65, 60, 55, 50, 40, 35, 30, 25, 20, 19, 18, 17, 16, 15, 14, 13, 12, 11, 10, 9, 8, 7, 6, 5, 4, 3, 2, or 1 amino acid residue(s), when aligned using any of the previously described alignment methods.

In some embodiments, the Cas12i polypeptide is a Cas12i3 polypeptide. In some embodiments, the Cas12i3 polypeptide of the present invention comprises a polypeptide sequence having 50%, 60%, 65%, 70%, 75%, 80%, 85%, 90%, 91%, 92%, 93%, 94%, 95%, 96%, 97%, 98%, 99%, or 100% identity to SEQ ID NO: 11. In some embodiments, the Cas12i3 polypeptide of the present invention comprises a polypeptide sequence having greater than 50%, 60%, 65%, 70%, 75%, 80%, 85%, 90%, 91%, 92%, 93%, 94%, 95%, 96%, 97%, 98%, 99%, or 100% identity to SEQ ID NO: 11.

In some embodiments, the Cas12i3 polypeptide has a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 11. Homology or identity can be determined by amino acid sequence alignment, e.g., using a program such as BLAST, ALIGN, or CLUSTAL, as described herein.

In some embodiments, a nucleic acid encoding the Cas12i3 polypeptide as described herein encodes an amino acid sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 11. In some embodiments, the Cas12i3 polypeptide has a sequence greater than 50%, 60%, 65%, 70%, 75%, 80%, 85%, 90%, 91%, 92%, 93%, 94%, 95%, 96%, 97%, 98%, 99%, or 100% identity to SEQ ID NO: 11.

In some embodiments, a Cas12i3 polypeptide described herein having enzymatic activity, e.g., nuclease or endonuclease activity, comprises an amino acid sequence which differs from the amino acid sequences of any one of a Cas12i polypeptide and SEQ ID NO: 11 by 100, 95, 90, 85, 80, 75, 70, 65, 60, 55, 50, 40, 35, 30, 25, 20, 19, 18, 17, 16, 15, 14, 13, 12, 11, 10, 9, 8, 7, 6, 5, 4, 3, 2, or 1 amino acid residue(s), when aligned using any of the previously described alignment methods.

In some embodiments, the Cas12i polypeptide is a Cas12i4 polypeptide. In some embodiments, the Cas12i4 polypeptide of the present invention comprises a polypeptide sequence having 50%, 60%, 65%, 70%, 75%, 80%, 85%, 90%, 91%, 92%, 93%, 94%, 95%, 96%, 97%, 98%, 99%, or 100% identity to SEQ ID NO: 9 or SEQ ID NO: 10. In some embodiments, the Cas12i4 polypeptide of the present invention comprises a polypeptide sequence having greater than 50%, 60%, 65%, 70%, 75%, 80%, 85%, 90%, 91%, 92%, 93%, 94%, 95%, 96%, 97%, 98%, 99%, or 100% identity to SEQ ID NO: 9 or SEQ ID NO: 10.

In some embodiments, the Cas12i4 polypeptide has a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 9 or SEQ ID NO: 10. Homology or identity can be determined by amino acid sequence alignment, e.g., using a program such as BLAST, ALIGN, or CLUSTAL, as described herein.

In some embodiments, a nucleic acid encoding the Cas12i4 polypeptide as described herein encodes an amino acid sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 9 or SEQ ID NO: 10. In some embodiments, the Cas12i4 polypeptide has a sequence greater than 50%, 60%, 65%, 70%, 75%, 80%, 85%, 90%, 91%, 92%, 93%, 94%, 95%, 96%, 97%, 98%, 99%, or 100% identity to SEQ ID NO: 9 or SEQ ID NO: 10.

In some embodiments, a Cas12i4 polypeptide described herein having enzymatic activity, e.g., nuclease or endonuclease activity, comprises an amino acid sequence which differs from the amino acid sequences of any one of a Cas12i polypeptide and SEQ ID NO: 9 or SEQ ID NO: 10 by 100, 95, 90, 85, 80, 75, 70, 65, 60, 55, 50, 40, 35, 30, 25, 20, 19, 18, 17, 16, 15, 14, 13, 12, 11, 10, 9, 8, 7, 6, 5, 4, 3, 2, or 1 amino acid residue(s), when aligned using any of the previously described alignment methods.

In some embodiments, the Cas12i polypeptide comprises an alteration at one or more (e.g., several) amino acids of a parent polypeptide, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 162, 164, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 200, or more are altered.

An alteration may comprise a substitution, an insertion, deletion, addition, or fusion of an amino acid or amino acids in a peptide or polypeptide or a nucleotide or nucleotides in a nucleotide or nucleotides relative to a reference sequence. No particular process is implied in how to make a sequence comprising an alteration. For instance, a sequence comprising an alteration can be synthesized directly from individual nucleotides. In other embodiments, an alteration is made by providing and then altering a reference sequence.

In some embodiments, the nucleotide sequence encoding the Cas12i polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at kazusa.orjp/codon/and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

Although the changes described herein may be one or more amino acid changes, changes to the Cas12i polypeptide may also be of a structural or substantive nature, such as fusion of polypeptides as amino- and/or carboxyl-terminal extensions. For example, the Cas12i polypeptide may contain additional peptides, e.g., one or more peptides. Examples of additional peptides may include epitope peptides for labelling, such as a polyhistidine tag (His-tag), Myc, and FLAG. In some embodiments, the Cas12i polypeptide described herein can be fused to a detectable moiety such as a fluorescent protein (e.g., green fluorescent protein (GFP) or yellow fluorescent protein (YFP)).

In some embodiments, the Cas12i polypeptide as in any one of the embodiments described herein comprises at least one (e.g., two, three, four, five, six, or more) nuclear localization signal (NLS). In some embodiments, the Cas12i polypeptide comprises at least one (e.g., two, three, four, five, six, or more) nuclear export signal (NES). In some embodiments, the Cas12i polypeptide comprises at least one (e.g., two, three, four, five, six, or more) NLS and at least one (e.g., two, three, four, five, six, or more) NES.

In some embodiments, the Cas12i polypeptide comprises at least a RuvC domain but less than the whole Cas12i polypeptide. In some embodiments, the Cas12i polypeptide is a truncated Cas12i polypeptide relative to a wild-type Cas12i polypeptide. In some embodiments, the truncated Cas12i polypeptide comprises a RuvC domain. In some embodiments, the Cas12i polypeptide comprises at least one functional domain of the whole Cas12i polypeptide. In some embodiments, the Cas12i polypeptide comprises at least two RuvC domains or at least two RuvC motifs. In some embodiments, the Cas12i polypeptide comprises at least three RuvC domains or at least three RuvC motifs. In some embodiments, the Cas12i polypeptide comprises at least one catalytically dead RuvC domain and at least one catalytically active RuvC domain. In some embodiments, the Cas12i polypeptide comprises two RuvC domains from one or more Type V or Type II nucleases. In some embodiments, the Cas12i polypeptide comprises at least a RuvC domain and a dimerization domain.

In some embodiments, the Cas12i polypeptide as described in any one of the previous embodiments is fused to a deaminase polypeptide. In some embodiments, the Cas12i polypeptide comprises an N-terminal deaminase polypeptide. In some embodiments, the Cas12i polypeptide comprises a C-terminal deaminase polypeptide. In some embodiments, the Cas12i polypeptide comprises a deaminase polypeptide at an intramolecular position within the Cas12i polypeptide (e.g., the deaminase is within a loop of the Cas12i polypeptide.

In some embodiments, the Cas12i polypeptide as in any one of the embodiments described herein interacts with a deaminase polypeptide (e.g., through electrostatic interactions). In some embodiments, the Cas12i polypeptide comprises a dimerization domain. In some embodiments, the dimer is formed by a non-covalent bond between the first dimerization domain and the second compatible dimerization domain. In some embodiments, a dimerization domain is a leucine zipper, nanobody, or antibody. In some embodiments, the dimerization domain recruits a deaminase polypeptide. In some embodiments, the Cas12i polypeptide and the deaminase polypeptide interact through coiled-coil peptide heterodimers.

Deaminase Domains

In some embodiments, the deaminase domain comprises an enzyme classified in EC 3.5.4 (e.g., cytosine deaminase (EC 3.5.4.1), adenine deaminase (EC 3.5.4.2), guanine deaminase (EC 3.5.4.3), adenosine deaminase (EC 3.5.4.4), cytidine deaminase (EC 3.5.4.5), AMP deaminase (EC 3.5.4.6), ADP deaminase (EC 3.5.4.7), aminoimidazolase (EC 3.5.4.8), methenyltetrahydrofolate cyclohydrolase (EC 3.5.4.9), IMP cyclohydrolase (EC 3.5.4.10), pterin deaminase (EC 3.5.4.11), dCMP deaminase (EC 3.5.4.12), dCTP deaminase (EC 3.5.4.13), EC 3.5.4.14 (dCTP deaminase), EC 3.5.4.5, (deoxy)cytidine deaminase (EC 3.5.4.14), guanosine deaminase (EC 3.5.4.15), adenosine-phosphate deaminase (EC 3.5.4.17), ATP deaminase (EC 3.5.4.18), phosphoribosyl-AMP cyclohydrolase (EC 3.5.4.19), pyrithiamine deaminase (EC 3.5.4.20), creatinine deaminase (EC 3.5.4.21), 1-pyrroline-4-hydroxy-2-carboxylate deaminase (EC 3.5.4.22), blasticidin-S deaminase (EC 3.5.4.23), sepiapterin deaminase (EC 3.5.4.24), GTP cyclohydrolase II (EC 3.5.4.25), diaminohydroxyphosphoribosylaminopyrimidine deaminase (EC 3.5.4.26), methenyltetrahydromethanopterin cyclohydrolase (EC 3.5.4.27), GTP cyclohydrolase ha (EC 3.5.4.29), dCTP deaminase (dUMP-forming) (EC 3.5.4.30), S-methyl-5'-thioadenosine deaminase (EC 3.5.4.31), 8-oxoguanine deaminase (EC 3.5.4.32), tRNAAla(adenine37) deaminase (EC 3.5.4.34), tRNA(cytosine8) deaminase (EC 3.5.4.35), mRNA(cytosine6666) deaminase (EC 3.5.4.36), double-stranded RNA adenine deaminase (EC 3.5.4.37), single-stranded DNA cytosine deaminase (EC 3.5.4.38), GTP cyclohydrolase IV (EC 3.5.4.39), aminodeoxyfutalosine deaminase (EC 3.5.4.40), 5'-deoxyadenosine deaminase (EC 3.5.4.41), N-isopropylammelide isopropylaminohydrolase (EC 3.5.4.42), hydroxydechloroatrazine ethylaminohydrolase (EC 3.5.4.43), ectoine hydrolase (EC 3.5.4.44), melamine deaminase (EC 3.5.4.45), cAMP deaminase (EC 3.5.4.46), EC 3.5.4.31 (EC 3.5.4.n1), EC 3.5.4.39 (EC 3.5.4.n2), and EC 3.5.4.45 (EC 3.5.4.n3)), or any biologically active portion thereof.

In particular embodiments, the deaminase domain is a cytidine deaminase domain. In certain embodiments, the cytidine deaminase domain is an apolipoprotein B mRNA-editing complex (APOBEC) family deaminase. In certain embodiments, the cytidine deaminase is an APOBEC1 (UniprotKB—P41238), an APOBEC2 (UniprotKB—Q9Y235), an APOBEC3 (e.g., APOBEC3A (UniprotKB—P31941), APOBEC3B (UniprotKB—Q9UH17), APOBEC3C (UniprotKB—Q9NRW3), APOBEC3D (Q96AK3), APOBEC3E, APOBEC3F (UniprotKB—Q8IUX4), APOBEC3G (UniprotKB—Q9HC16), or APOBEC3H (UniprotKB—Q6NTF7)), an APOBEC4 (UniprotKB—Q8WW27) deaminase, or an Activation-induced (cytidine) deaminase (AID) (UniprotKB—Q9GZX7), or a biologically active portion or variant thereof. In certain embodiments, the cytidine deaminase is APOBEC3a (A3A) (e.g., human APOBEC3a), or a biologically active portion thereof. In certain embodiments, the cytidine deaminase is Activation Induced Deaminase (AID), or a biologically active portion thereof.

In certain embodiments, the deaminase domain is an adenine deaminase domain. In certain embodiments, the deaminase domain is an ABE8 deaminase. In certain embodiments, the ABE8 selected from ABE8.1, ABE8.2, ABE8.3, ABE8.4, ABE8.5, ABE8.6, ABE8.7, ABE8.8, ABE8.9, ABE8.10, ABE8.11, ABE8.12, ABE8.13, ABE8.17, or ABE8.20.

In some embodiments, the deaminase domain is an adenosine deaminase domain. In some embodiments, the adenosine deaminase is a TadA deaminase. In some embodiments, the TadA deaminase is TadA variant. In some embodiments, the TadA variant is a TadA*8. In some embodiments, the deaminase or deaminase domain is a variant of a naturally occurring deaminase from an organism, such as a human, chimpanzee, gorilla, monkey, cow, dog, rat, or mouse. In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identical to a naturally occurring deaminase. For example, deaminase domains are described in International PCT Application Nos. PCT/2017/045381 (WO 2018/027078) and PCT/US2016/058344 (WO 2017/070632), each of which is incorporated herein by reference for its entirety. Also, see Komor, A. C., et al., "Programmable editing of a target base in genomic DNA without double-stranded DNA cleavage" Nature 533, 420-424 (2016); Gaudelli, N. M., et al., "Programmable base editing of A·T to G·C in genomic DNA without DNA cleavage" Nature 551, 464-471 (2017); Komor, A. C., et al., "Improved base excision repair inhibition and bacteriophage Mu Gam protein yields C:G-to-T:A base editors with higher efficiency and product purity" Science Advances 3:eaao4774 (2017)), and Rees, H. A., et al., "Base editing: precision chemistry on the genome and transcriptome of living cells." Nat Rev Genet. 2018 December; 19(12):770-788. Doi: 10.1038/s41576-018-0059-1, the entire contents of which are hereby incorporated by reference.

Cas12i-Deaminase Fusion Polypeptides

The present disclosure provides Cas12i fusion proteins comprising a Cas12i domain (e.g., a Cas12i1, Cas12i2, Cas12i3, or Cas12i4 domain) and a deaminase domain as described herein wherein the Cas12i fusion protein binds to a target on a nucleic acid specified by an RNA guide. In some embodiments, the Cas12i2 fusion protein has enzymatic activity. In some embodiments, the enzymatic activity can be carried out by the Cas12i2 domain. In some embodiments, the enzymatic activity is carried out by the deaminase domain. In some embodiments, the deaminase domain is fused N-terminally to the Cas12i domain. In some embodiments, the deaminase domain is fused C-terminally to the Cas12i domain. In certain embodiments, the deaminase domain is fused directed to the Cas12i domain. In some embodiments, the Cas12i fusion proteins comprise a first deaminase domain fused N-terminally to the Cas12i domain and a second deaminase domain fused C-terminally to the Cas12i domain. In some embodiments, the deaminase domain is fused to the Cas12i through a linker. In some embodiments, the linker is a peptide linker as described herein.

In one aspect, the disclosure provides a Cas12i fusion protein comprising, in an N-terminal to C-terminal direction:

(a) a first, N-terminal portion of a Cas12i polypeptide, wherein the N-terminal portion of the Cas12i polypeptide comprises a Cas12i sequence from the N-terminus to a loop, or a functional fragment or variant thereof;
(b) a heterologous sequence comprising a deaminase domain, and
(c) a second, C-terminal portion of the Cas12i polypeptide, wherein the C-terminal portion of the Cas12i polypeptide comprises a Cas12i sequence from the loop to the C-terminus, or a fragment or variant thereof.

In one aspect, the disclosure provides a Cas12i fusion protein, wherein the N-terminal portion of the Cas12i polypeptide comprises amino acids 1-n of any one of SEQ ID NOs: 2-7, or a sequence having at least 80%, 85%, 90%, 95%, 96%, 97%, 98%, or 99% identity thereto; and the C-terminal portion of the Cas12i polypeptide comprises amino acids m-1054 of SEQ ID NO: 1, or a sequence having at least 80%, 85%, 90%, 95%, 96%, 97%, 98%, or 99% identity thereto.

In some embodiments, n and m are each independently a number between:

i) 342-358 (e.g., 342, 343, 344, 345, 346, 347, 348, 349, 350, 351, 352, 353, 354, 355, 356, 357, or 358);
ii) 373-378 (e.g., 373, 374, 375, 376, 377, or 378);
iii) 408-413 (e.g., 408, 409, 410, 411, 412, or 413);
iv) 677-685 (e.g., 677, 678, 679, 680, 681, 682, 683, 684, or 685);
v) 718-723 (e.g., 718, 719, 720, 721, 722, or 723);
vi) 771-782 (e.g., 771, 772, 773, 774, 775, 776, 777, 778, 779, 780, 781, or 782);
vii) 953-965 (e.g., 953, 954, 955, 956, 957, 958, 959, 960, 961, 962, 963, 964, or 965);
viii) 55-65 (e.g., 55, 56, 57, 58, 59, 60, 61, 62, 63, 64, or 65);
ix) 99-105 (e.g., 99, 100, 101, 102, 103, 104, or 105);
x) 112-120 (e.g., 112, 113, 114, 115, 116, 117, 118, 119, or 120);
xi) 195-206 (e.g., 195, 196, 197, 198, 199, 200, 201, 202, 203, 204, 205, or 206);
xii) 241-250 (e.g., 241, 242, 243, 244, 245, 246, 247, 248, 249, or 250);
xiii) 583-594 (e.g., 583, 584, 585, 586, 587, 588, 589, 590, 591, 592, 593, or 594).
xiv) 877-901 (e.g., 877, 878, 879, 880, 881, 882, 883, 884, 885, 886, 887, 888, 889, 890, 891, 892, 893, 894, 895, 896, 897, 898, 899, 900, or 901); or
xv) 386-397 (e.g., residue 386, 387, 388, 389, 390, 391, 392, 393, 394, 395, 396, or 397).

In some embodiments, n<m. In some embodiments, m=n+1. In certain embodiments, the Cas12i fusion protein comprises a component of Table 3.

Exemplary Cas12i2 Fusion Proteins Having a Heterologous Sequence at the Loop Region of Amino Acids S342-L358

In some embodiments of any Cas12i2 fusion protein described herein, a) n is 342 and m is 343, or b) n is 347 and m is 348. In some embodiments, the first portion comprises at least 273, 280, 290, 300, 310, 320, 330, 340, 341, or 342 amino acids. In certain embodiments, the second portion comprises at least 570, 580, 590, 600, 610, 620, 630, 640, 650, 660, 670, 680, 690, 700, 710, 711, or 712 amino acids. In certain embodiments, the C-terminal amino acid(s) of the first portion comprise FDS, DS, or S. In some embodiments, the N-terminal amino acid(s) of the second portion comprise EFS, EF, or E. In some embodiments, the heterologous moiety is situated between any two adjacent amino acids of SEFFSGEETYTICV (SEQ ID NO: 107), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, 11 and 12, 12 and 13, or 13 and 14 of SEQ ID NO: 107. In certain embodiments, one or more amino acids of SEQ ID NO: 107 are absent from the Cas12i2 fusion protein. In other embodiments, 1, 2, 3, 4, 5, 6, 7, 8, 9, 10, 11, 12, or 13 sequential amino acids of SEQ ID NO: 107 that are N-terminal to the heterologous sequence are absent from the Cas12i2 fusion protein. In certain embodiments, 1, 2, 3, 4, 5, 6, 7, 8, 9, 10, 11, 12, or 13 sequential amino acids of SEQ ID NO: 107 that are C-terminal to the heterologous sequence are absent from the Cas12i2 fusion protein.

Exemplary Cas12i2 Fusion Proteins Having a Heterologous Sequence at the Loop Region of Amino Acids D373-E378

In certain embodiments, n is 374 and m is 375. In some embodiments, the first portion comprises at least 300, 310, 320, 330, 340, 350, 360, 370, 373, 374, 375, 376, or 377 amino acids. In certain embodiments, the second portion comprises at least 544, 560, 570, 580, 590, 600, 610, 620, 630, 640, 650, 660, 670, or 680 amino acids. In some embodiments, the C-terminal amino acid(s) of the first portion comprise DDP, DP, or P. In some embodiments, the N-terminal amino acid(s) of the second portion comprise ADP, AD, or A. In certain embodiments, the heterologous moiety is situated between any two adjacent amino acids of DPADPE (SEQ ID NO: 108), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, or 5 and 6 of SEQ ID NO: 108. In some embodiments, one or more amino acids of SEQ ID NO: 108 are absent from the Cas12i2 fusion protein. In some embodiments, 1, 2, 3, 4, 5, or 6 sequential amino acids of SEQ ID NO: 108 that are N-terminal to the heterologous sequence are absent from the Cas12i2 fusion protein. In some embodiments, 1, 2, 3, 4, 5, or 6 sequential amino acids of SEQ ID NO: 108 that are C-terminal to the heterologous sequence are absent from the Cas12i2 fusion protein.

Exemplary Cas12i2 Fusion Proteins Having a Heterologous Sequence at the Loop Region of Amino Acids D386-I397

In some embodiments of any Cas12i2 fusion protein described herein, a) n is 386 and m is 387, b) n is 387 and m is 388, c) n is 388 and m is 389, d) n is 389 and m is 390, e) n is 390 and m is 391, f) n is 391 and m is 392, g) n is 392 and m is 393, h) n is 393 and m is 394, i) n is 394 and m is 395, j) n is 395 and m is 396, or k) n is 396 and m is 397. In some embodiments, the first portion comprises at least 308, 310, 320, 330, 340, 350, 360, 370, 380, or 390 amino acids. In certain embodiments, the second portion comprises at least 530, 540, 550, 560, 570, 580, 590, 600, 610, 620, 630, 640, 650, 660, 670, or 680 amino acids. In some embodiments, the heterologous moiety is situated between any two adjacent amino acids of DDLKNNFKKEPI (SEQ ID NO: 131), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, or 11 and 12 of SEQ ID NO: 131. In certain embodiments, one or more amino acids of SEQ ID NO: 107 are absent from the Cas12i2 fusion protein. In other embodiments, 1, 2, 3, 4, 5, 6, 7, 8, 9, 10, 11, or 12 sequential amino acids of SEQ ID NO: 131 that are N-terminal to the heterologous sequence are absent from the Cas12i2 fusion protein. In certain embodiments, 1, 2, 3, 4, 5, 6, 7, 8, 9, 10, 11, or 12 sequential amino acids of SEQ ID NO: 131 that are C-terminal to the heterologous sequence are absent from the Cas12i2 fusion protein.

Exemplary Cas12i2 Fusion Proteins Having a Heterologous Sequence at the Loop Region of Amino Acids R408-A413

In some embodiments of the fusion Cas12i2 proteins described herein, a) n is 409 and m is 410 or b) n is 410 and m is 411. In certain embodiments, the first portion comprises at least 328, 330, 340, 350, 360, 370, 380, 390, 400, 405, 406, 407, 408, 409, or 410 amino acids. In some embodiments, the second portion comprises at least 516, 520, 530, 540, 550, 560, 570, 580, 590, 600, 610, 620, 630, 640, 641, 642, 643, 644, or 645 amino acids. In certain embodiments, the C-terminal amino acid(s) of the first portion comprise IRQE, RQ, Q, or E. In some embodiments, the N-terminal amino acid(s) of the second portion comprise ECS, EC, E, or C. In some embodiments, the heterologous moiety is situated between any two adjacent amino acids of RQECSA (SEQ ID NO: 109), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, or 5 and 6 of SEQ ID NO: 109. In some embodiments, one or more amino acids of SEQ ID NO: 109 are absent from the Cas12i2 fusion protein. In some embodiments, 1, 2, 3, 4, 5, or 6 sequential amino acids of SEQ ID NO: 109 that are N-terminal to the heterologous sequence are absent from the Cas12i2 fusion protein. In certain embodiments, 1, 2, 3, 4, 5, or 6 sequential amino acids of SEQ ID NO: 109 that are C-terminal to the heterologous sequence are absent from the Cas12i2 fusion protein.

Exemplary Cas12i2 Fusion Proteins Having a Heterologous Sequence at the Loop Region of Amino Acids K677-V685

In some embodiments, n is 682 and m is 683. In some embodiments, the first portion comprises at least 546, 550, 560, 570, 580, 590, 600, 610, 620, 630, 640, 650, 660, 670, 680, 681, or 682 amino acids. In certain embodiments, the second portion comprises at least 298, 300, 310, 320, 330, 340, 350, 360, 370, 371, or 372 amino acids. In some embodiments, the C-terminal amino acid(s) of the first portion comprise KKK, KK, or K. In some embodiments, the N-terminal amino acid(s) of the second portion comprise EIV, EI, or E. In certain embodiments, the heterologous moiety is situated between any two adjacent amino acids of KKNKKKEIV (SEQ ID NO: 110), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 7 and 8, or 8 and 9 of SEQ ID NO: 110. In some embodiments, one or more amino acids of SEQ ID NO: 110 are absent from the Cas12i2 fusion protein. In some embodiments, 1, 2, 3, 4, 5, 6, 7, 8, or 9 sequential amino acids of SEQ ID NO: 110 that are N-terminal to the heterologous sequence are absent from the Cas12i2 fusion protein. In some embodiments, 1, 2, 3, 4, 5, 6, 7, 8, or 9 sequential amino acids of SEQ ID NO: 110 that are C-terminal to the heterologous sequence are absent from the Cas12i2 fusion protein.

Exemplary Cas12i2 Fusion Proteins Having a Heterologous Sequence at the Loop Region of Amino Acids V718-L723

In some embodiments, n is 721 and m is 722. In some embodiments, the first portion comprises at least 577, 580, 590, 600, 610, 620, 630, 640, 650, 660, 670, 680, 690, 700, 710, 720, or 721 amino acids. In certain embodiments, the second portion comprises at least 266, 270, 280, 290, 300, 310, 320, 330, 331, 332, or 333 amino acids. In some embodiments, the C-terminal amino acid(s) of the first portion comprise RGK, GK, or K. In some embodiments, the N-terminal amino acid(s) of the second portion comprise SLV, SL, or S. In certain embodiments, the heterologous moiety is situated between any two adjacent amino acids of VRGKSL (SEQ ID NO: 111), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, or 5 and 6 of SEQ ID NO: 111. In some embodiments, one or more amino acids of SEQ ID NO: 111 are absent from the Cas12i2 fusion protein. In some embodiments, 1, 2, 3, 4, 5, or 6 sequential amino acids of SEQ ID NO: 111 that are N-terminal to the heterologous sequence are absent from the Cas12i2 fusion protein. In certain embodiments, 1, 2, 3, 4, 5, or 6 sequential amino acids of SEQ ID NO: 111 that are C-terminal to the heterologous sequence are absent from the Cas12i2 fusion protein.

Exemplary Cas12i2 Fusion Proteins Having a Heterologous Sequence at the Loop Region of Amino Acids A771-D782

In some embodiments, n is 778 and m is 779. In certain embodiments, the first portion comprises at least 622, 630, 640, 650, 660, 670, 680, 690, 700, 710, 720, 730, 740, 750, 760, 770, 775, 776, 777 or 778 amino acids. In certain embodiments, the second portion comprises at least 221, 225, 230, 240, 250, 260, 270, 275, or 276 amino acids. In some embodiments, the C-terminal amino acid(s) of the first portion comprise KNN, NN, or N. In certain embodiments, the N-terminal amino acid(s) of the second portion comprise PIS, PI, or P. In some embodiments, the heterologous moiety is situated between any two adjacent amino acids of ALNASKNNPISD (SEQ ID NO: 112), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, or 11 and 12 of SEQ ID NO: 112. In some embodiments, one or more amino acids of SEQ ID NO: 112 are absent from the Cas12i2 fusion protein. In certain embodiments, 1, 2, 3, 4, 5, 6, 7, 8, 9, 10, 11, or 12 sequential amino acids of SEQ ID NO: 112 that are N-terminal to the heterologous sequence are absent from the Cas12i2 fusion protein. In some embodiments, 1, 2, 3, 4, 5, 6, 7, 8, 9, 10, 11, or 12 sequential amino acids of SEQ ID NO: 112 that are C-terminal to the heterologous sequence are absent from the Cas12i2 fusion protein.

Exemplary Cas12i2 Fusion Proteins Having a Heterologous Sequence at the Loop Region of Amino Acids L953-C965

In some embodiments, n is 960 and m is 961. In certain embodiments, the first portion comprises at least 768, 770, 780, 790, 800, 810, 820, 830, 840, 850, 860, 870, 880, 890, 900, 910, 920, 930, 940, 950, or 960 amino acids. In certain embodiments, the second portion comprises at least 75, 80, 85, 90, 91, 92, 93, or 94 amino acids. In some embodiments, the C-terminal amino acid(s) of the first portion comprise DRK, RK, or K. In certain embodiments, the N-terminal amino acid(s) of the second portion comprise SNI, SN, or S.

In some embodiments, the heterologous moiety is situated between any two adjacent amino acids of LKWRS-DRKSNIPC (SEQ ID NO: 113), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, 11 and 12, or 12 and 13 of SEQ ID NO: 113. In certain embodiments, one or more amino acids of SEQ ID NO: 113 are absent from the Cas12i2 fusion protein. In some embodiments, 1, 2, 3, 4, 5, 6, 7, 8, 9, 10, 11, 12, or 13 sequential amino acids of SEQ ID NO: 113 that are N-terminal to the heterologous sequence are absent from the Cas12i2 fusion protein. In certain embodiments, 1, 2, 3, 4, 5, 6, 7, 8, 9, 10, 11, 12, or 13 sequential amino acids of SEQ ID NO: 113 that are C-terminal to the heterologous sequence are absent from the Cas12i2 fusion protein.

Exemplary Cas12i2 Fusion Proteins Having a Heterologous Sequence at the Loop Region of Amino Acids S55-I65

In some embodiments of the Cas12i2 fusion protein described herein, a) n is 61 and m is 62, orb) n is 62 and m is 63. In some embodiments, the first portion comprises at least 49, 50, 51, 52, 53, 54, 55, 56, 57, 58, 59, 60, or 61 amino acids. In certain embodiments, the second portion comprises at least 795, 800, 810, 820, 830, 840, 850, 860, 870, 880, 890, 900, 910, 920, 930, 940, 950, 960, 970, 980, 990, or 991 amino acids. In some embodiments, the C-terminal amino acid(s) of the first portion comprise EKQ, KQ, or Q. In certain embodiments, the N-terminal amino acid(s) of the second portion comprise QQD, QQ, or Q. In some embodiments, the heterologous moiety is situated between any two adjacent amino acids of STEQEKQQQDI (SEQ ID NO: 114), e.g., between positions 1 and 2, 2 and 3, 3 and 4, 4 and 5, 5 and 6, 6 and 7, 7 and 8, or 8 and 9 of SEQ ID NO: 114. In certain embodiments, one or more amino acids of SEQ ID NO: 114 are absent from the Cas12i2 fusion protein. In some embodiments, 1, 2, 3, 4, 5, 6, 7, 8, or 9 amino acids of SEQ ID NO: 114 that are N-terminal to the heterologous sequence are absent from the Cas12i2 fusion protein. In some embodiments, 1, 2, 3, 4, 5, 6, 7, 8, or 9 sequential amino acids of SEQ ID NO: 114 that are C-terminal to the heterologous sequence are absent from the Cas12i2 fusion protein.

Exemplary Cas12i2 Fusion Proteins Having a Heterologous Sequence at the Loop Region of Amino Acids Y99-D105

In certain embodiments of the Cas12i2 fusion protein described herein, a) n is 101 and m is 102, orb) n is 102 and m is 103. In certain embodiments, the first portion comprises at least 81, 90, 100, or 101 amino acids. In certain embodiments, the second portion comprises at least 762, 770, 780, 790, 800, 810, 820, 830, 840, 850, 860, 870, 880, 890, 900, 910, 920, 930, 940, 950, 951, 952, or 953 amino acids. In some embodiments, the C-terminal amino acid(s) of the first portion comprise YGGT, YGG, GG, G, or T. In some embodiments, the N-terminal amino acid(s) of the second portion comprise TAS, TA, AS, T, or A. In some embodiments, the heterologous moiety is situated between any two adjacent amino acids of YGGTASD (SEQ ID NO: 115), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, or 6 and 7 of SEQ ID NO: 115. In some embodiments, one or more amino acids of SEQ ID NO: 115 are absent from the Cas12i2 fusion protein. In certain embodiments, 1, 2, 3, 4, 5, 6, or 7 sequential amino acids of SEQ ID NO: 115 that are N-terminal to the heterologous sequence are absent from the Cas12i2 fusion protein. In some embodiments, 1, 2, 3, 4, 5, 6, or 7 sequential amino acids of SEQ ID NO: 115 that are C-terminal to the heterologous sequence are absent from the Cas12i2 fusion protein.

Exemplary Cas12i2 Fusion Proteins Having a Heterologous Sequence at the Loop Region of Amino Acids S112-Y120

In some embodiments, n is 116 and m is 117. In certain embodiments, the first portion comprises at least 81, 90, 100, or 101 amino acids. In some embodiments, the second portion comprises at least 762, 780, 790, 800, 810, 820, 830, 840, 850, 860, 870, 880, 890, 900, 910, 920, 930, 940, 950, 951, 952, or 953 amino acids. In other embodiments, the C-terminal amino acid(s) of the first portion comprise SIG, IG, or G. In certain embodiments, the N-terminal amino acid(s) of the second portion comprise ESY, ES, or E. In other embodiments, the heterologous moiety is situated between any two adjacent amino acids of SASIGESYY (SEQ ID NO: 116), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, or 8 and 9 of SEQ ID NO: 116. In some embodiments, one or more amino acids of SEQ ID NO: 116 are absent from the Cas12i2 fusion protein. In other embodiments, 1, 2, 3, 4, 5, 6, 7, 8, or 9 sequential amino acids of SEQ ID NO: 116 that are N-terminal to the heterologous sequence are absent from the Cas12i2 fusion protein. In certain embodiments, 1, 2, 3, 4, 5, 6, 7, 8, or 9 sequential amino acids of SEQ ID NO: 116 that are C-terminal to the heterologous sequence are absent from the Cas12i2 fusion protein.

Exemplary Cas12i2 Fusion Proteins Having a Heterologous Sequence at the Loop Region of Amino Acids S195-P206

In some embodiments, n is 199 and m is 200. In other embodiments, the first portion comprises at least 160, 170, 180, 190, 195, 196, 197, 198, or 199 amino acids. In certain embodiments, the second portion comprises at least 684, 690, 700, 710, 720, 730, 740, 750, 760, 780, 790, 800, 810, 820, 830, 840, 850, or 855 amino acids. In some embodiments, the C-terminal amino acid(s) of the first portion comprise LKE, KE, or E. In some embodiments, the N-terminal amino acid(s) of the second portion comprise IPK, IP, or I. In some embodiments, the heterologous moiety is situated between any two adjacent amino acids of SNLKEIPKNVAP (SEQ ID NO: 117), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, or 11 and 12 of SEQ ID NO: 117. In some embodiments, one or more amino acids of SEQ ID NO: 117 are absent from the Cas12i2 fusion protein. In other embodiments, 1, 2, 3, 4, 5, 6, 7, 8, 9, 10, 11, or 12 sequential amino acids of SEQ ID NO: 117 that are N-terminal to the heterologous sequence are absent from the Cas12i2 fusion protein. In other embodiments, 1, 2, 3, 4, 5, 6, 7, 8, 9, 10, 11, or 12 sequential amino acids of SEQ ID NO: 117 that are C-terminal to the heterologous sequence are absent from the Cas12i2 fusion protein.

Exemplary Cas12i2 Fusion Proteins Having a Heterologous Sequence at the Loop Region of Amino Acids K241-L250

In some embodiments, n is 246 and m is 247. In other embodiments, the first portion comprises at least 197, 200, 210, 220, 230, 240, 245, or 246 amino acids. In certain embodiments, the second portion comprises at least 646, 650, 670, 680, 690, 700, 710, 720, 730, 740, 750, 760, 780, 790, 800, 805, 806, 807, or 808 amino acids. In yet another embodiment, the C-terminal amino acid(s) of the first portion comprise GQK, QK, or K. In certain embodiments, the N-terminal amino acid(s) of the second portion comprise EFD, EF, or E. In some embodiments, the heterologous moiety is situated between any two adjacent amino acids of KDGQKEFDL (SEQ ID NO: 118), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, or 8 and 9 of SEQ ID NO: 118. In some embodiments, one or more amino acids of SEQ ID NO: 118 are absent from the Cas12i2 fusion protein. In certain embodiments, 1, 2, 3, 4, 5, 6, 7, 8, or 9 sequential amino acids of SEQ ID NO: 118 that are N-terminal to the heterologous sequence are absent from the Cas12i2 fusion protein. In certain embodiments, 1, 2, 3, 4, 5, 6, 7, 8, or 9 sequential amino acids of SEQ ID NO: 118 that are C-terminal to the heterologous sequence are absent from the Cas12i2 fusion protein.

Exemplary Cas12i2 Fusion Proteins Having a Heterologous Sequence at the Loop Region of Amino Acids G583-R594

In some embodiments of the Cas12i2 fusion protein described herein, a) n is 587 and m is 588, or b) n is 590 and m is 591. In other embodiments, the first portion comprises at least 470, 472, 480, 490, 500, 510, 520, 530, 540, 550, 560, 570, 580, 585, 587, or 590 amino acids. In certain embodiments, the second portion comprises at least 371, 374, 380, 390, 400, 410, 420, 430, 440, 450, 460, 464, or 467 amino acids. In some embodiments, the C-terminal amino acid(s) of the first portion comprise: a) QKG, KG, or G; or b) TLQ, LQ, or Q. In some embodiments, the N-terminal amino acid(s) of the second portion comprise: a) TLQ, TL, or T; orb) IGD, IG, or I. In some embodiments, the heterologous moiety is situated between any two adjacent amino acids of GRQKGTLQIGDR (SEQ ID NO: 119), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, or 11 and 12 of SEQ ID NO: 119. In certain embodiments, one or more amino acids of SEQ ID NO: 119 are absent from the Cas12i2 fusion protein. In some embodiments, 1, 2, 3, 4, 5, 6, 7, 8, 9, 10, 11, or 12 sequential amino acids of SEQ ID NO: 119 that are N-terminal to the heterologous sequence are absent from the Cas12i2 fusion protein. In some embodiments, 1, 2, 3, 4, 5, 6, 7, 8, 9, 10, 11, or 12 sequential amino acids of SEQ ID NO: 119 that are C-terminal to the heterologous sequence are absent from the Cas12i2 fusion protein.

Exemplary Cas12i2 Fusion Proteins Having a Heterologous Sequence at Loop the Region of Amino Acids C877-W901

In some embodiments of the Cas12i2 fusion protein described herein, a) n is 893 and m is 894, or b) n is 894 and m is 895. In other embodiments, the first portion comprises at least 715, 716, 720, 730, 740, 750, 760, 770, 780, 790, 800, 810, 820, 830, 840, 850, 860, 870, 880, 890, 891, 892, 893, or 894 amino acids. In some embodiments, the second portion comprises at least 128, 129, 130, 140, 150, 160, or 161 amino acids. In certain embodiments, the C-terminal amino acid(s) of the first portion comprise: a) RNP, NP, or P; or b) NPD, PD, or D. In some embodiments, the N-terminal amino acid(s) of the second portion comprise: a) DKA, DK, or D; orb) KAM, KA, or K. In some embodiments, the heterologous moiety is situated between any two adjacent amino acids of CGSLYTSHQDPLVHRNPDKA-MKCRW (SEQ ID NO: 120), or an amino acid sequence having at least 80% (e.g., at least 80%, 85%, 90%, 95%, 96%, 97%, 98%, or 99%) identity thereto, e.g., between positions 1 and 2, 2 and 3, 3 and 4, 4 and 5, 5 and 6, 6 and 7, 7 and 8, 8 and 9, 9 and 10, 10 and 11, 11 and 12, 12 and 13, 13 and 14, 14 and 15, 15 and 16, 16 and 17, 17 and 18, 18 and 19, 19 and 20, 20 and 21, 21 and 22, 22 and 23, 23 and 24, 24 and 25, of SEQ ID NO: 120. In other embodiments, one or more amino acids of SEQ ID NO: 120 are absent from the Cas12i2 fusion protein. In some embodiments, 1, 2, 3, 4, 5, 6, 7, 8, 9, 10, 11, 12, 13, 14, 15, 16, 17, 18, 19, 20, 21, 22, 23, or 24 sequential amino acids of SEQ ID NO: 120 that are N-terminal to the heterologous sequence are absent from the Cas12i2 fusion protein. In other embodiments, 1, 2, 3, 4, 5, 6, 7, 8, 9, 10, 11, 12, 13, 14, 15, 16, 17, 18, 19, 20, 21, 22, 23, or 24 sequential amino acids of SEQ ID NO: 120 that are C-terminal to the heterologous sequence are absent from the Cas12i2 fusion protein.

In certain embodiments, the heterologous sequence comprises at least one linker sequence. In some embodiments, the heterologous sequence comprises a first linker (e.g., a first peptide linker) and a second linker (e.g., a second peptide linker). In some embodiments, the first linker and the second linker each independently comprise between 3 and 70 amino acid residues (e.g., 5, 10, 15, 20, 25, 30, 35, 40, 50, 55, 60, 65, or 70, between 3-10, between 10-15, between 15-20, between 20-25, between 25-30, between 30-35, between 35-40, between 40-45, between 45-50, between 50-55, between 55-60, between 60-65, or between 65-70). In some embodiments, the first linker and the second linker each independently comprise one or more Gly residues and/or one or more Ser residues. In other embodiments, the first linker and the second peptide linker each independently comprise $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15). In certain embodiments, the first linker and the second linker each independently comprise one or more proline residues. In some embodiments, the first linker is N-terminal of the deaminase domain, and the second linker is C-terminal of the deaminase domain. In certain embodiments, the first linker and the second linker have the same sequence. In some embodiments, the first linker and the second linker have different sequences.

In one aspect, the Cas12i fusion protein comprises (a) a Cas12i (e.g., a Cas12i1, Cas12i2, Cas12i3, or Cas12i4) polypeptide, (b) a deaminase domain (e.g., any deaminase described herein), or a biologically active portion or variant thereof.

In some embodiments, the Cas12i polypeptide is a Cas12i1 polypeptide. In some embodiments, the Cas12i polypeptide is a Cas12i2 polypeptide. In some embodiments, the Cas12i polypeptide is a Cas12i3 polypeptide. In some embodiments, the Cas12i polypeptide is a Cas12i4 polypeptide.

In some embodiments, the deaminase domain is N-terminal of the Cas12i polypeptide. In certain embodiments, the deaminase domain is C-terminal of the Cas12i polypeptide.

In certain embodiments, the fusion protein does not comprise a linker sequence.

In some embodiments, the fusion protein further comprises at least one heterologous sequence, which is heterologous to both the Cas12i domain and the deaminase domain. In certain embodiments, the heterologous sequence comprises a Uracil Glycosylase Inhibitor (UGI) polypeptide. In some embodiments, the heterologous sequence comprises a nuclear localization sequence (NLS) polypeptide.

In some embodiments, the fusion protein comprises, one, two, or three of:

i. a first heterologous sequence situated between the Cas12i domain and the deaminase domain;

ii. a second heterologous sequence situated between the Cas12i domain and the terminus nearest the Cas12i domain; or iii) a third heterologous sequence situated between the deaminase domain and the terminus nearest the deaminase domain.

In certain embodiments, the deaminase domain is N-terminal of the Cas12i domain and the UGI domain. In certain embodiments, the deaminase domain is C-terminal of the Cas12i domain. In some embodiments, the deaminase domain is N-terminal of the Cas12i domain, the first heterologous sequence comprises the UGI domain, the second heterologous sequence comprises an NLS polypeptide (e.g., a bpNLS or an npNLS polypeptide), and the third heterologous sequence comprises an NLS polypeptide (e.g., a bpNLS or an npNLS polypeptide).

In some embodiments, the deaminase domain is C-terminal of the Cas12i domain, the first heterologous sequence comprises a linker, the second heterologous sequence comprises an NLS polypeptide (e.g., a bpNLS or an npNLS polypeptide) and the UGI domain, and the third heterologous sequence comprises an NLS polypeptide (e.g., a bpNLS or an npNLS polypeptide).

In certain embodiments, the deaminase domain is C-terminal of the Cas12i domain, the first heterologous sequence comprises an NLS polypeptide (e.g., a bpNLS or an npNLS polypeptide), the second heterologous sequence is absent or comprises a peptide tag (e.g., a peptide purification tag), and the third heterologous sequence comprises a UGI domain and an NLS polypeptide (e.g., a bpNLS or an npNLS polypeptide).

In some embodiments, the first heterologous sequence comprises the UGI polypeptide. In certain embodiments, the UGI polypeptide is flanked by peptide linkers. In some embodiments, the second and third heterologous sequence each independently comprise an NLS polypeptide.

In some embodiments, the first heterologous sequence comprises a peptide linker and, when present, the second heterologous sequence or the third heterologous sequence comprises an NLS polypeptide, one or more linkers, and a UGI polypeptide. In certain embodiments, the NLS polypeptide is N-terminal of the UGI polypeptide.

In some embodiments, the NLS polypeptide is C-terminal of the UGI polypeptide.

In certain embodiments, one of the one or more linkers is situated between the NLS polypeptide and the UGI polypeptide. In certain embodiments, the third heterologous sequence comprises a first and a second linker, wherein the first linker is situated N-terminal the NLS polypeptide and the UGI polypeptide and the second linker is situated between the NLS polypeptide and the UGI polypeptide. In some embodiments, the first heterologous sequence further comprises an NLS sequence. In certain embodiments, the NLS polypeptide is situated N-terminal of the linker.

In some embodiments, the fusion protein does not comprise the second heterologous sequence.

In one aspect, the disclosure provides a fusion protein comprising:

(a) a Cas12i (e.g., a Cas12i1, Cas12i2, Cas12i3, or Cas12i4) polypeptide, (b) a deaminase domain; and (c) a UGI polypeptide.

In some embodiments, the deaminase domain is N-terminal of the Cas12i domain and the UGI domain. In certain embodiments, the deaminase domain is C-terminal of the Cas12i domain. In some embodiments, the deaminase domain is N-terminal of the Cas12i4 polypeptide. In some embodiments, the deaminase domain is C-terminal of the Cas12i4 domain.

In some embodiments, the fusion protein does not comprise a linker sequence.

In some embodiments, the fusion protein comprises at least one heterologous sequence. In certain embodiments, the heterologous sequence is heterologous to each of the Cas12i domain (e.g., Cas12i4 domain), the deaminase domain, and the UGI polypeptide. In certain embodiments, the heterologous sequence comprises a nuclear localization sequence (NLS) polypeptide.

In some embodiments, the fusion protein comprises, one, two, or three of:

i. a first heterologous sequence situated between the Cas12i domain and the deaminase domain;

ii. a second heterologous sequence situated between the Cas12i domain and the terminus nearest the Cas12i domain; or iii) a third heterologous sequence situated between the deaminase domain and the terminus nearest the deaminase domain.

In some embodiments, the fusion protein does not comprise the first heterologous sequence, and the UGI domain is situated between the deaminase domain and the Cas12i domain.

In certain embodiments, UGI domain is situated C-terminal of both the deaminase domain and the Cas12i domain.

In certain embodiments, the UGI domain is flanked by peptide linkers.

In some embodiments, when present, the first and second heterologous sequence each independently comprise an NLS polypeptide.

In certain embodiments, the one, two, or three of the first, the second, and the third heterologous sequence each independently comprise one or more peptide linkers and the third heterologous sequence comprises an NLS polypeptide. In certain embodiments, NLS polypeptide is N-terminal of the UGI polypeptide. In some embodiments, the NLS polypeptide is C-terminal of the UGI polypeptide. In some embodiments, one of the one or more of the linkers is situated between the NLS polypeptide and the UGI polypeptide.

In certain embodiments, the third heterologous sequence comprises a first and a second linker, wherein the first linker is situated N-terminal the NLS polypeptide and the UGI polypeptide and the second linker is situated between the NLS polypeptide and the UGI polypeptide.

In some embodiments, the first heterologous sequence comprises an NLS sequence. In certain embodiments, the NLS polypeptide is situated N-terminal of the linker.

In some embodiments, the Cas12i fusion protein is a is a fusion protein of Table 4. In some embodiments, a Cas12i fusion protein comprises an amino acid sequence of any one of SEQ ID NOs: 41-46.

In some embodiments, a Cas12i fusion protein is a polypeptide of Table 8. In some embodiments, a Cas12i fusion protein comprises an amino acid sequence of any one of SEQ ID NOs: 60-65.

In one aspect, the disclosure provides a fusion protein comprising an amino acid sequence according to SEQ ID NO: 60, or a sequence having at least 80%, 85%, 90%, 95%, 97%, 98%, or 99% identity thereto, wherein the fusion protein, when bound to a gRNA, can produce a substitution in a target sequence of a target nucleic acid.

In one aspect, the disclosure provides a fusion protein comprising an amino acid sequence according to SEQ ID NO: 61, or a sequence having at least 80%, 85%, 90%, 95%, 97%, 98%, or 99% identity thereto, wherein the fusion protein, when bound to a gRNA, can produce a substitution in a target sequence of a target nucleic acid.

In one aspect, the disclosure provides a fusion protein comprising an amino acid sequence according to SEQ ID NO: 62, or a sequence having at least 80%, 85%, 90%, 95%, 97%, 98%, or 99% identity thereto, wherein the fusion protein, when bound to a gRNA, can produce a substitution in a target sequence of a target nucleic acid.

In one aspect, the disclosure provides a fusion protein comprising an amino acid sequence according to SEQ ID NO: 63, or a sequence having at least 80%, 85%, 90%, 95%, 97%, 98%, or 99% identity thereto, wherein the fusion protein, when bound to a gRNA, can produce a substitution in a target sequence of a target nucleic acid.

In one aspect, the disclosure provides a fusion protein comprising an amino acid sequence according to SEQ ID NO: 64, or a sequence having at least 80%, 85%, 90%, 95%, 97%, 98%, or 99% identity thereto, wherein the fusion protein, when bound to a gRNA, can produce a substitution in a target sequence of a target nucleic acid.

In one aspect, the disclosure provides a fusion protein that forms a complex with a ribonucleic acid (RNA) guide wherein the RNA guide comprises a nuclease binding sequence (e.g., a direct repeat sequence) and a DNA-binding sequence (e.g., a spacer sequence).

Exemplary Circularly Permuted Cas12i2 Fusion Proteins

In another aspect, the disclosure provides an engineered, non-naturally occurring Cas12i2 protein comprising:

a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, wherein the first portion and second portion together bind to an RNA guide comprising a direct repeat sequence and a spacer sequence. In some embodiments, the circularly permuted Cas12i2 protein is capable of specifically binding a target nucleic acid complementary to the spacer sequence.

In certain embodiments, the first portion and the second portion are linked by a heterologous sequence. In some embodiments, the heterologous sequence comprises one or more of:

a) a first linker (e.g., a first peptide linker);

b) a second linker (e.g., a second peptide linker); and c) a fusion domain.

In some embodiments, the heterologous sequence comprises each of a first linker (e.g., a first peptide linker), a second linker (e.g., a second peptide linker), and a fusion domain, wherein the fusion domain is disposed between the first linker and the second linker. In certain embodiments, the first linker and the second linker, when present, comprise between 3 and 60 amino acid residues. In some embodiments, the first linker and the second linker each independently comprise the amino acid sequence $(GSG)_x$, $(GGGS)_x$, or $(GSSG)_x$, wherein X is an integer between 0 and 15 (e.g., 0, 1, 2, 3, 4, 5, 6, 7, 8, 9, 10, 11, 12, 13, 14, or 15).

In some embodiments, the C-terminal most amino acid of the first portion is any amino acid residue of any one of SEQ ID NOs: 2-7 chosen from residues:

a) 342-358 (e.g., residue 342, 343, 344, 345, 346, 347, 348, 349, 350, 351, 352, 353, 354, 355, 356, 357, or 358);

b) 373-378 (e.g., residue 373, 374, 375, 376, 377, or 378);

c) 408-413 (e.g., residue 408, 409, 410, 411, 412, or 413);

d) 677-685 (e.g., residue 677, 678, 679, 680, 681, 682, 683, 684, or 685);

e) 718-723 (e.g., residue 718, 719, 720, 721, 722, or 723);

f) 771-782 (e.g., residue 771, 772, 773, 774, 775, 776, 777, 778, 779, 780, 781, or 782);

g) 953-965 (e.g., residue 953, 954, 955, 956, 957, 958, 959, 960, 961, 962, 963, 964, or 965);

h) 55-65 (e.g., residue 55, 56, 57, 58, 59, 60, 61, 62, 63, 64, or 65);

i) 99-105 (e.g., residue 99, 100, 101, 102, 103, 104, or 105);

j) 112-120 (e.g., residue 112, 113, 114, 115, 116, 117, 118, 119, or 120);

k) 195-206 (e.g., residue 195, 196, 197, 198, 199, 200, 201, 202, 203, 204, 205, or 206);

l) 241-250 (e.g., residue 241, 242, 243, 244, 245, 246, 247, 248, 249, or 250);

m) 583-594 (e.g., residue 583, 584, 585, 586, 587, 588, 589, 590, 591, 592, 593, or 594);

n) 877-901 (e.g., residue 877, 878, 879, 880, 881, 882, 883, 884, 885, 886, 887, 888, 889, 890, 891, 892, 893, 894, 895, 896, 897, 898, 899, 900, or 901);

o) 173-179 (e.g., residue 173, 174, 175, 176, 177, 178, or 179);

p) 216-221 (e.g., residue 216, 217, 218, 219, 220, or 221);

q) 265-272 (e.g., residue 265, 266, 267, 268, 269, 270, 271, or 272);

r) 456-468 (e.g., residue 456, 457, 458, 459, 460, 461, 462, 463, 464, 465, 466, 467, or 468);

s) 476-482 (e.g., residue 476, 477, 478, 479, 480, 481, or 482);

t) 498-513 (e.g., residue 498, 499, 500, 501, 502, 503, 504, 505, 506, 507, 508, 509, 510, 511, 512, or 513);

u) 614-625 (e.g., residue 614, 615, 616, 617, 618, 619, 620, 621, 622, 623, 624, or 625);

v) 977-982 (e.g., residue 977, 978, 979, 980, 981, or 982);

w) 1007-1012 (e.g., residue 1007, 1008, 1009, 1010, 1011, or 1012);

x) 386-397 (e.g., residue 386, 387, 388, 389, 390, 391, 392, 393, 394, 395, 396, or 397); or y) 831-844 (e.g., residue 831, 832, 833, 834, 835, 836, 837, 838, 839, 840, 841, 842, 843, or 844).

In some embodiments, the N-terminal most amino acid of the second portion is any amino acid residue of any one of SEQ ID NOs: 2-7 chosen from residues:

a) 342-358 (e.g., residue 342, 343, 344, 345, 346, 347, 348, 349, 350, 351, 352, 353, 354, 355, 356, 357, or 358);

b) 373-378 (e.g., residue 373, 374, 375, 376, 377, or 378);

c) 408-413 (e.g., residue 408, 409, 410, 411, 412, or 413);

d) 677-685 (e.g., residue 677, 678, 679, 680, 681, 682, 683, 684, or 685);

e) 718-723 (e.g., residue 718, 719, 720, 721, 722, or 723);

f) 771-782 (e.g., residue 771, 772, 773, 774, 775, 776, 777, 778, 779, 780, 781, or 782);

g) 953-965 (e.g., residue 953, 954, 955, 956, 957, 958, 959, 960, 961, 962, 963, 964, or 965);

h) 55-65 (e.g., residue 55, 56, 57, 58, 59, 60, 61, 62, 63, 64, or 65);

i) 99-105 (e.g., residue 99, 100, 101, 102, 103, 104, or 105);

j) 112-120 (e.g., residue 112, 113, 114, 115, 116, 117, 118, 119, or 120);

k) 195-206 (e.g., residue 195, 196, 197, 198, 199, 200, 201, 202, 203, 204, 205, or 206);

l) 241-250 (e.g., residue 241, 242, 243, 244, 245, 246, 247, 248, 249, or 250);

m) 583-594 (e.g., residue 583, 584, 585, 586, 587, 588, 589, 590, 591, 592, 593, or 594);

n) 877-901 (e.g., residue 877, 878, 879, 880, 881, 882, 883, 884, 885, 886, 887, 888, 889, 890, 891, 892, 893, 894, 895, 896, 897, 898, 899, 900, or 901);

o) 173-179 (e.g., residue 173, 174, 175, 176, 177, 178, or 179);

p) 216-221 (e.g., residue 216, 217, 218, 219, 220, or 221);

q) 265-272 (e.g., residue 265, 266, 267, 268, 269, 270, 271, or 272);

r) 456-468 (e.g., residue 456, 457, 458, 459, 460, 461, 462, 463, 464, 465, 466, 467, or 468);

s) 476-482 (e.g., residue 476, 477, 478, 479, 480, 481, or 482);

t) 498-513 (e.g., residue 498, 499, 500, 501, 502, 503, 504, 505, 506, 507, 508, 509, 510, 511, 512, or 513);

u) 614-625 (e.g., residue 614, 615, 616, 617, 618, 619, 620, 621, 622, 623, 624, or 625);

v) 977-982 (e.g., residue 977, 978, 979, 980, 981, or 982);

w) 1007-1012 (e.g., residue 1007, 1008, 1009, 1010, 1011, or 1012);

x) 386-397 (e.g., residue 386, 387, 388, 389, 390, 391, 392, 393, 394, 395, 396, or 397); or y) 831-844 (e.g., residue 831, 832, 833, 834, 835, 836, 837, 838, 839, 840, 841, 842, 843, or 844).

In any of the embodiments described herein, the circularly permuted Cas12i2 protein further comprises a second heterologous sequence at its N-terminus. In some embodiments, the circularly permuted Cas12i2 protein further comprises an additional heterologous sequence at its C-terminus. In some embodiments, the second heterologous sequence and/or the additional heterologous sequence a chosen from a deaminase, a purification tag, a stability tag, or a restriction endonuclease or restriction endonuclease domain.

In some embodiments, a circularly permutated Cas12i2 protein comprises a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, and wherein the C-terminal most amino acid of the first portion is an amino acid residue of a flexible loop within the Helical II, Helical III, Nuc, or RuvC II domain. In some embodiments, the flexible loop is in proximity to or in contact with target DNA, such as a loop depicted in FIG. 12A-D.

In some embodiments, a circularly permutated Cas12i2 protein comprises a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, and wherein the N-terminal most amino acid of the second portion is an amino acid residue of a flexible loop within the Helical II, Helical III, Nuc, or RuvC II domain. In some embodiments, the flexible loop is in proximity to or in contact with target DNA, such as a loop depicted in FIG. 12A-D.

In some embodiments, a circularly permutated Cas12i2 protein comprises a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, and wherein the C-terminal most amino acid of the first portion is any amino acid residue of any one of SEQ ID NOs: 2-7 chosen from residues a) 342-358 (e.g., residue 342, 343, 344, 345, 346, 347, 348, 349, 350, 351, 352, 353, 354, 355, 356, 357, or 358); b) 373-378 (e.g., residue 373, 374, 375, 376, 377, or 378); c) 386-397 (e.g., residue 386, 387, 388, 389, 390, 391, 392, 393, 394, 395, 396, or 397); d) 677-685 (e.g., residue 677, 678, 679, 680, 681, 682, 683, 684, or 685); e) 771-782 (e.g., residue 771, 772, 773, 774, 775, 776, 777, 778, 779, 780, 781, or 782); f) 831-844 (e.g., residue 831, 832, 833, 834, 835, 836, 837, 838, 839, 840, 841, 842, 843, or 844), or g) 953-965 (e.g., residue 953, 954, 955, 956, 957, 958, 959, 960, 961, 962, 963, 964, or 965). The positions of the residues are indicated in FIG. 12A-D.

In some embodiments, a circularly permutated Cas12i2 protein comprises a) a first portion comprising an amino acid sequence of an N-terminal portion of any one of SEQ ID NOs: 2-7, or a sequence having at least 80%, 85%, 90%, 95%, 96%, 97%, 98%, or 99% identity thereto; and b) a second portion comprising an amino acid sequence of a C-terminal portion of any one of SEQ ID NOs: 2-7, or a sequence having at least 80%, 85%, 90%, 95%, 96%, 97%, 98%, or 99% identity thereto, wherein the second portion is N-terminal of the first portion, and wherein the N-terminal most amino acid of the second portion is any amino acid residue of any one of SEQ ID NOs: 2-7 chosen from residues a) 342-358 (e.g., residue 342, 343, 344, 345, 346, 347, 348, 349, 350, 351, 352, 353, 354, 355, 356, 357, or 358); b) 373-378 (e.g., residue 373, 374, 375, 376, 377, or 378); c) 386-397 (e.g., residue 386, 387, 388, 389, 390, 391, 392, 393, 394, 395, 396, or 397); d) 677-685 (e.g., residue 677, 678, 679, 680, 681, 682, 683, 684, or 685); e) 771-782 (e.g., residue 771, 772, 773, 774, 775, 776, 777, 778, 779, 780, 781, or 782); f) 831-844 (e.g., residue 831, 832, 833, 834, 835, 836, 837, 838, 839, 840, 841, 842, 843, or 844), or g) 953-965 (e.g., residue 953, 954, 955, 956, 957, 958, 959, 960, 961, 962, 963, 964, or 965). The positions of the residues are indicated in FIG. 12A-D.

In some embodiments, a circularly permuted Cas12i2 protein is truncated relative to a Cas12i2 protein of any one of SEQ ID NOs: 2-7. In some embodiments, a circularly permuted Cas12i2 protein has a modified Helical II domain relative to the Cas12i2 protein of any one of SEQ ID NOs: 2-7. For example, in some embodiments, the circularly permuted Cas12i2 protein comprises substitutions or deletions in the Helical II domain relative to the sequence of any one of SEQ ID NOs: 2-7. In some embodiments, a circularly permuted Cas12i2 protein comprises a truncated Helical II domain. For example, in some embodiments, the circularly permuted Cas12i2 protein does not comprise one or more flexible loops or alpha helices of the Helical II domain. For example, in some embodiments, the circularly permuted Cas12i2 protein does not comprise the loop of residues 342-358 (or 343-357), the loop of residues 386-397 (or 387-396), or the alpha helices of residues 359-385 (or 358-386).

Figure 11:
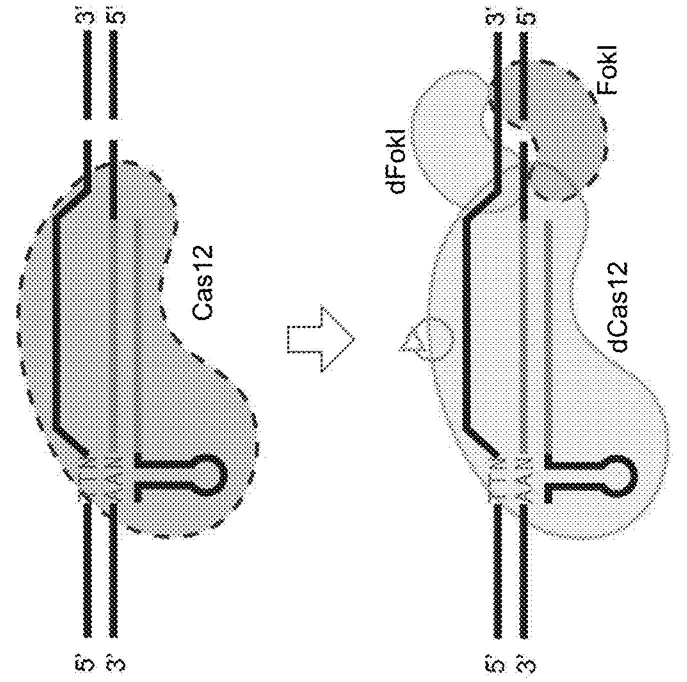
FIG. 11 depicts a schematic representation of a Cas12i2 fusion protein comprising a FokI nuclease domain. In some instances, the FokI nuclease domain is a heterodimeric FokI nuclease domain. In this exemplary schematic, the heterodimeric FokI nuclease domain comprises a catalytically active FokI nuclease domain and a catalytically inactive FokI nuclease domain. In some aspects, a FokI domain as depicted in FIG. 11 is further fused to a deaminase. In some aspects, the Cas12i2 protein as depicted in FIG. 11 is further fused to a deaminase.
Figure 12A:
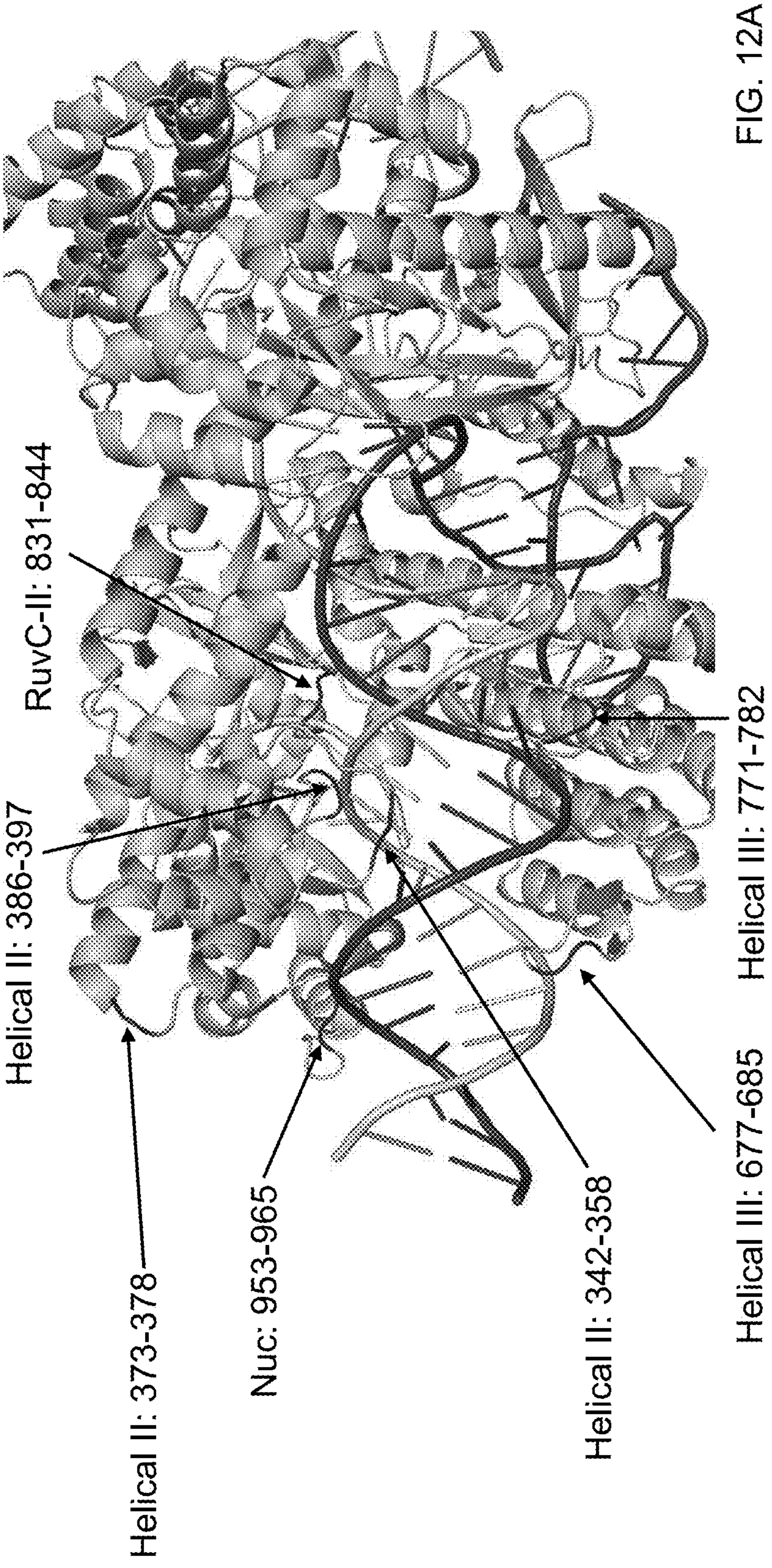
FIGS. 12A, 12B, 12C, and 12D depict flexible loops of the Cas12i2 protein in proximity to target DNA.
Figure 12B:
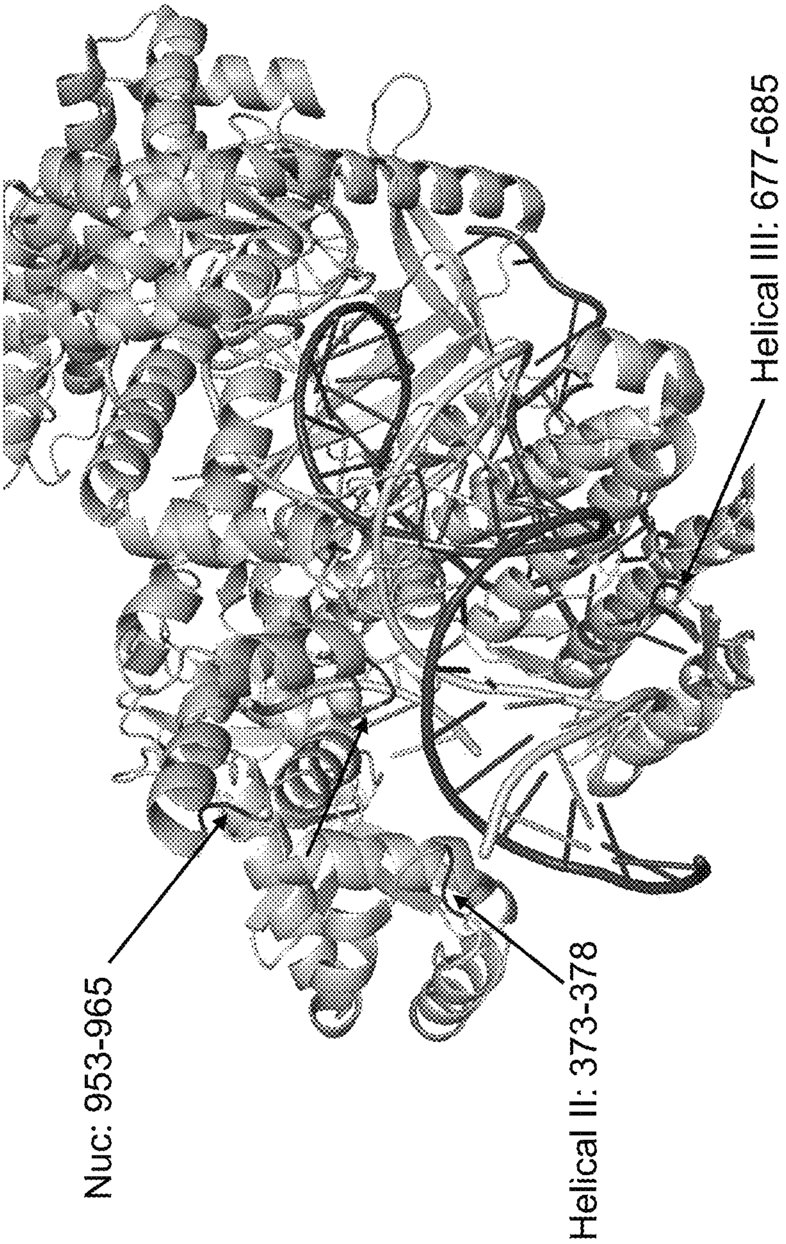
Figure 12C:
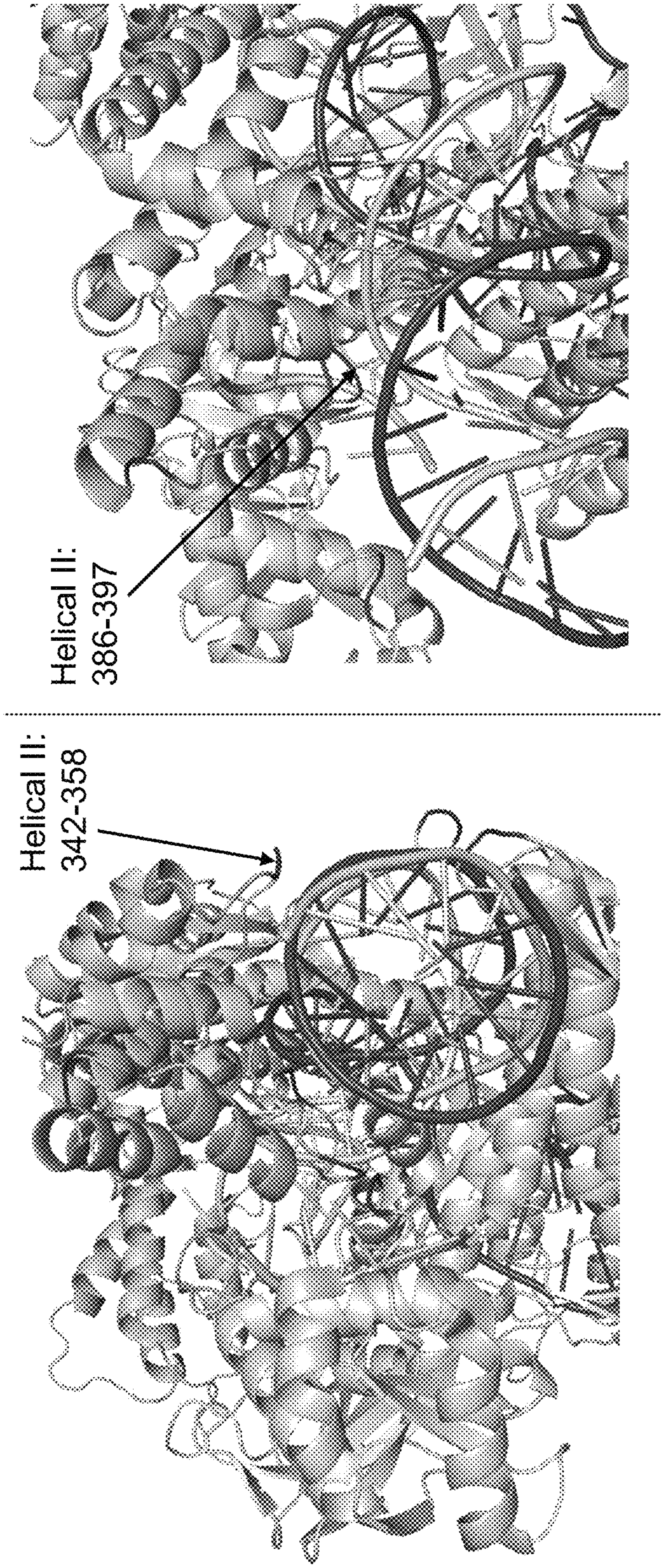
Figure 12D:
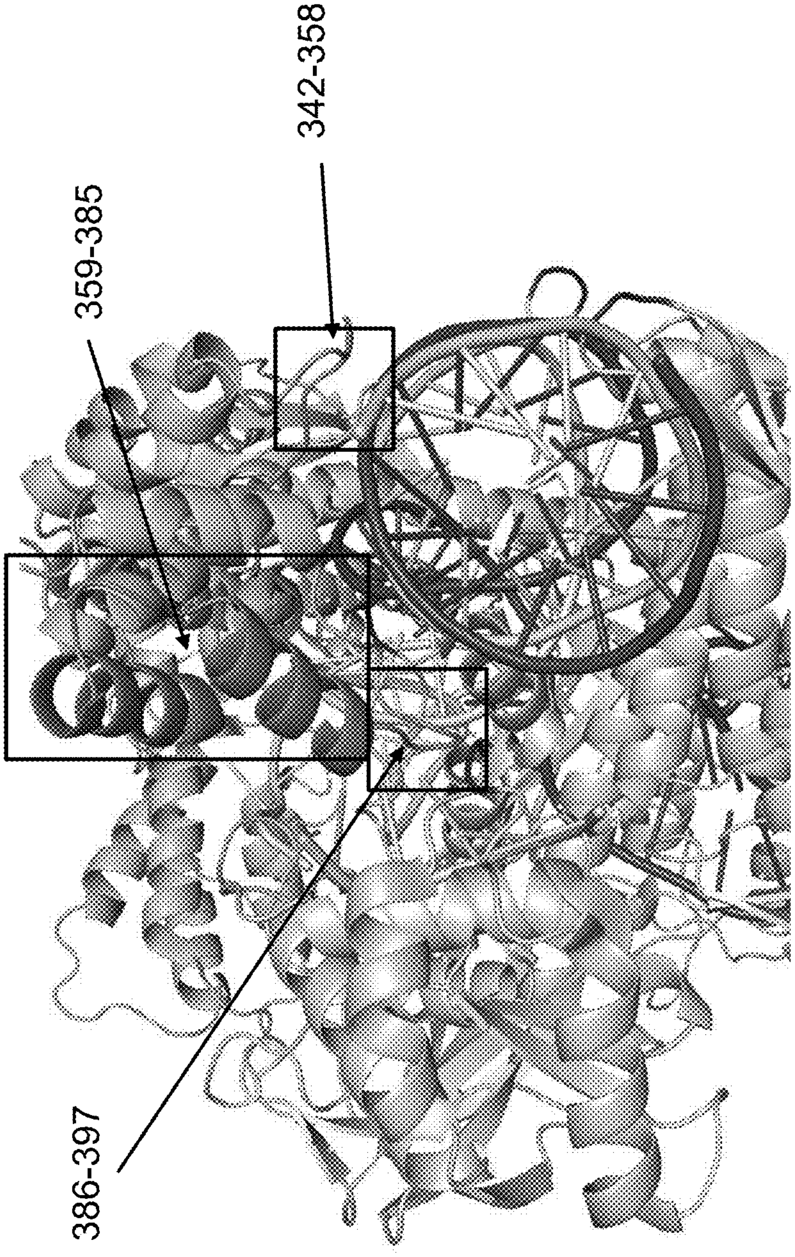
Figure 13A:
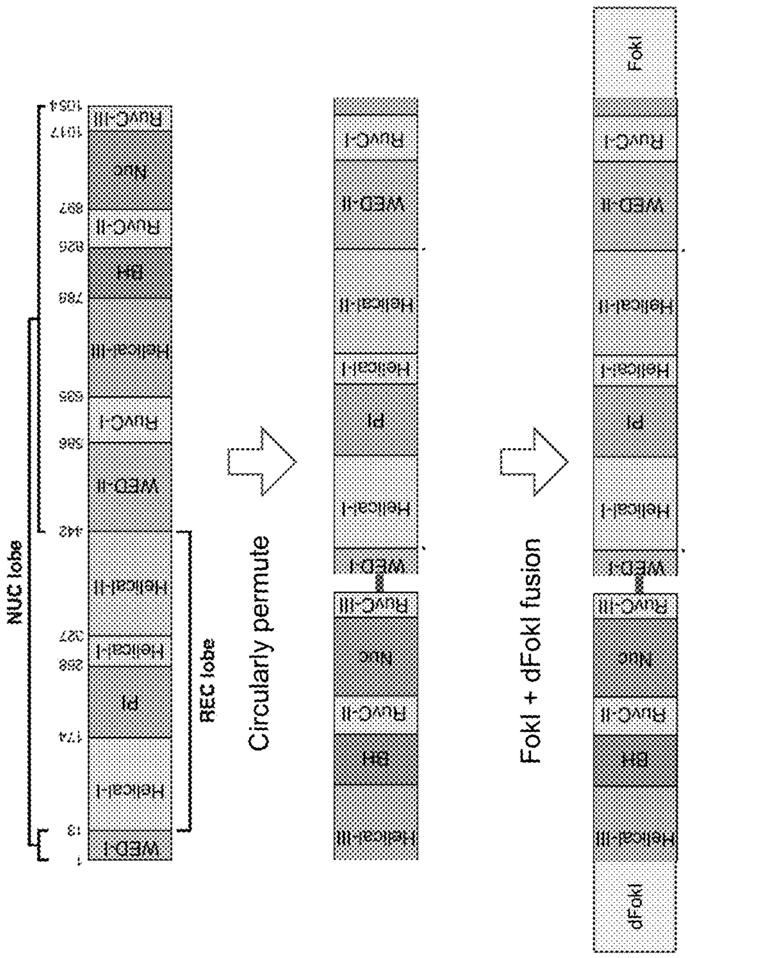
FIG. 13A depicts a schematic representation for the engineering a circularly permuted, non-naturally occurring Cas12i2 protein. The top panel depicts the domains of a reference Cas12i2 protein. In the middle panel of this exemplary schematic, the N-terminus and the C-terminus of the Cas12i2 protein are linked by way of a heterologous sequence (e.g., a linker), and a new N-terminus and C-terminus are located at a loop of interest (e.g., a loop within the Helical II domain). In some instances, the new N-terminus and/or C-terminus comprise a fusion domain. In some instances, the fusion domain is a FokI nuclease domain. As depicted in this exemplary schematic, the new N-terminus can be fused to a dead FokI nuclease domain, and the new C-terminus can be fused to an active FokI nuclease domain. In some aspects, a FokI domain as depicted in FIG. 13A is further fused to a deaminase. In some aspects, the Cas12i2 protein as depicted in FIG. 13A is further fused to a deaminase.
Figure 13B:
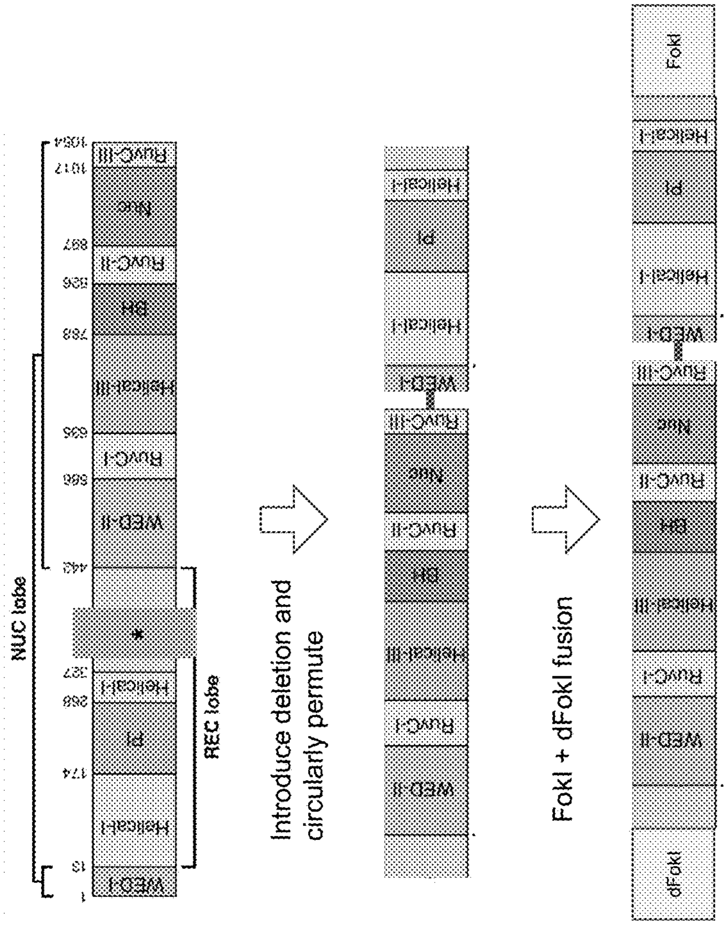
FIG. 13B depicts a schematic representation for the engineering a circularly permuted, non-naturally occurring Cas12i2 protein. The top panel depicts the domains of a reference Cas12i2 protein and a portion of the Helical II domain that can be mutated or deleted (see asterisk). In the middle panel of this exemplary schematic, the N-terminus and the C-terminus of the Cas12i2 protein are linked by way of a heterologous sequence (e.g., a linker), a portion of the Helical II domain is deleted (e.g., the portion from about residue 342 to about 397), and a new N-terminus and C-terminus are located within the Helical II domain. In some instances, the new N-terminus and/or C-terminus comprise a fusion domain. In some instances, the fusion domain is a FokI nuclease domain. As depicted in this exemplary schematic, the new N-terminus can be fused to a dead FokI nuclease domain, and the new C-terminus can be fused to an active FokI nuclease domain. In some aspects, a FokI domain as depicted in FIG. 13B is further fused to a deaminase. In some aspects, the Cas12i2 protein as depicted in FIG. 13B is further fused to a deaminase.

In some embodiments, the N-terminus of a circularly permutated Cas12i2 protein comprises at least one fusion domain. In some embodiments, the fusion domain is a FokI nuclease domain. See e.g., Ramirez et al., Nucleic Acids Res. 40(12): 5560-8 (2012) and Guilinger et al., Nature Biotechnology 32: 577-82 (2014). In some embodiments, the FokI nuclease domain is a catalytically active FokI nuclease domain. In some embodiments, the FokI nuclease domain is a dead (e.g., a catalytically inactive) FokI nuclease domain. In some embodiments, the circularly permuted Cas12i2 protein comprises a FokI nuclease domain at its N-terminus (e.g., a catalytically active FokI nuclease domain or a catalytically inactive FokI nuclease domain). In some embodiments, the circularly permuted Cas12i2 protein comprises a FokI nuclease domain at its C-terminus (e.g., a catalytically active FokI nuclease domain or a catalytically inactive FokI nuclease domain). In some embodiments, the circularly permuted Cas12i2 protein comprises a FokI nuclease domain at its N-terminus and at its C-terminus. In some embodiments, the circularly permuted Cas12i2 protein comprises a catalytically active FokI nuclease domain at its N-terminus and a catalytically active FokI nuclease domain at its C-terminus. In some embodiments, the circularly permuted Cas12i2 protein comprises a catalytically active FokI nuclease domain at its N-terminus and a catalytically inactive FokI nuclease domain at its C-terminus. In some embodiments, the circularly permuted Cas12i2 protein comprises a catalytically inactive FokI nuclease domain at its N-terminus and a catalytically active FokI nuclease domain at its C-terminus. In some embodiments, the circularly permuted Cas12i2 protein comprises a catalytically inactive FokI nuclease domain at its N-terminus and a catalytically inactive FokI nuclease domain at its C-terminus. In some embodiments wherein a circularly permuted Cas12i2 protein comprises a FokI nuclease domain at its N-terminus and at its C-terminus, the FokI nuclease domains form a dimer (e.g., a homodimer or a heterodimer). See, e.g., FIG. 11, FIG. 13A, and FIG. 13B.

In some embodiments, the FokI nuclease domain further comprises an additional fusion domain. In some embodiments, the FokI nuclease domain is a catalytically active FokI nuclease domain, and the additional fusion domain is a deaminase. In some embodiments, the FokI nuclease domain is a catalytically inactive FokI nuclease domain and the additional fusion domain is a deaminase.

In some embodiments, the circularly permuted Cas12i2 fusion protein further comprises an additional fusion domain. In some embodiments, the additional fusion domain is a deaminase. In some embodiments, the deaminase is fused to the N-terminus of the circularly permuted Cas12i2 fusion protein. In some embodiments, the deaminase is fused to the C-terminus of the circularly permuted Cas12i2 fusion protein. In some embodiments, the deaminase is inserted at an internal residue (e.g., a residue of a loop) of the circularly permuted Cas12i2 fusion protein.

In some embodiments, the circularly permuted Cas12i2 fusion protein further comprises a UGI polypeptide. In some embodiments, the UGI polypeptide is fused to the N-terminus of the circularly permuted Cas12i2 fusion protein. In some embodiments, the UGI polypeptide is fused to the C-terminus of the circularly permuted Cas12i2 fusion protein. In some embodiments, the UGI polypeptide is inserted at an internal residue (e.g., a residue of a loop) of the circularly permuted Cas12i2 fusion protein. In some embodiments, the UGI polypeptide is fused to a FokI nuclease domain (e.g., a catalytically active FokI nuclease domain or a catalytically inactive FokI nuclease domain). In some embodiments, the circularly permuted Cas12i2 fusion protein does not comprise a UGI polypeptide.

In some embodiments, the circularly permuted Cas12i2 fusion protein further comprises at least one NLS. In some embodiments, the NLS is fused to the N-terminus of the circularly permuted Cas12i2 fusion protein. In some embodiments, the NLS is fused to the C-terminus of the circularly permuted Cas12i2 fusion protein. In some embodiments, the NLS polypeptide is inserted at an internal residue (e.g., a residue of a loop) of the circularly permuted Cas12i2 fusion protein. In some embodiments, the NLS is fused to a FokI nuclease domain (e.g., a catalytically active FokI nuclease domain or a catalytically inactive FokI nuclease domain).

In certain embodiments, the N-terminal Met residue of any of any one of SEQ ID NOs: 2-7 is absent. In some embodiments, the N-terminal residue of a circularly permuted Cas12i2 protein is a Met residue. In some embodiments, the Met residue is added to the N-terminus of any one of the circularly permuted Cas12i2 proteins described herein.

In some embodiments, the circularly permuted Cas12i2 protein is capable of binding an RNA guide comprising a direct repeat sequence and a spacer sequence, wherein the spacer sequence is capable of hybridizing to a target nucleic acid.

In any of the aspects described herein, the circularly permuted Cas12i2 protein comprises a catalytic residue (e.g., D599, E833, and D1019). In certain embodiments, the circularly permuted Cas12i2 protein comprises a mutation (e.g., an alanine mutation) at any one of amino acid residue D599, E833, or D1019 of any one of SEQ ID NOs: 2-7. In certain embodiments, the circularly permuted Cas12i2 protein is a dead Cas12i2 protein (e.g., a catalytically inactive Cas12i2 protein).

In some embodiments, a circularly permuted Cas12i2 protein described herein comprises nickase activity. In some embodiments, a circularly permuted Cas12i2 protein described herein nicks the target strand of a target nucleic acid. In some embodiments, a circularly permuted Cas12i2 protein described herein nicks the non-target strand of a target nucleic acid. In some embodiments, a circularly permuted Cas12i2 protein described herein nicks a target sequence adjacent to a Cas12i2 PAM sequence (e.g., a 5'-NTTN-3' sequence). See, e.g., FIG. 11.

NLS Polypeptides

In some embodiments, Cas12i2 fusion protein comprises a nuclear localization sequence (also known as a nuclear localization signal) that promotes translocation through the nuclear envelope via nuclear pore complexes. The nuclear pore complex is composed of nucleoporins. Nucleoporins interact with transport molecules known as karyopherins. Karyopherins bind to proteins containing a nuclear localization sequence and transport the protein across the nuclear pore complex. In some embodiments a nuclear localization sequence consists of one or more short (e.g., <50 amino-acid residues) sequence of basic amino acids. In some embodiments a nuclear localization sequence consists of one or more short (e.g., <50 amino-acid residues) sequence of lysines or arginines. In some embodiments the nuclear localization sequence is monopartite or bipartite.

In some embodiments, the NLS polypeptide is selected from nuclear plasma NLS (npNLS) polypeptide or a bipartite NLS (bpNLS) polypeptide. In some embodiments, the npNLS polypeptide comprises an amino acid sequence comprising at least 80% (e.g., 85%, 90%, 95%, 99% or 100%) sequence identity to SEQ ID NO: 36. In some embodiments, the bpNLS polypeptide comprises an amino acid sequence having at least 80% (e.g., 85%, 90%, 95%, 99% or 100%) sequence identity to SEQ ID NO: 38.

In some embodiments the nuclear localization sequence is disposed in the middle of the Cas12i2 fusion protein and is exposed on the fusion protein surface. In some embodiments a nuclear localization sequence is recognized by a karyopherin. In some embodiment the nuclear localization sequence interacts with one or more karyopherin. In some embodiments the karyopherin recognizes a nuclear localization sequence as it emerges from a ribosome. In some embodiments the karyopherin recognizes a nuclear localization sequence on a fully translated protein.

In some embodiments, the nuclear localization sequence is defined as the nuclear localization sequence from the proteins listed in Table 6 of US 2015-0246139, which is incorporated by reference herein.

Cas12i Polypeptide Systems

Also provided within this disclosure is a polypeptide system comprising:

(a) a first polypeptide comprising a Cas12i domain and a first dimerization domain, and (b) a second polypeptide comprising a deaminase domain and a second, compatible dimerization domain.

In some embodiments, the first polypeptide comprises a first peptide linker situated between the Cas12i domain and the first dimerization domain.

In certain embodiments, the second polypeptide comprises a second peptide linker situated between the Cas12i domain and the second dimerization domain.

In some embodiments, the first polypeptide and the second polypeptide form a complex.

In some embodiments, the disclosure provides a first nucleic acid sequence encoding the first polypeptide and a second nucleic acid sequence encoding the second polypeptide. The first and second nucleic acid sequences may be in the same or different nucleic acid molecules.

Dimerization Domains

In some embodiments, a protein described herein, e.g., a polypeptide comprising a Cas12i domain, a polypeptide comprising a deaminase domain, or a Cas12i fusion protein, comprises a dimerization domain. Typically, a dimerization domain is a polypeptide domain capable of specifically binding a separate, and compatible, polypeptide domain (e.g., a second compatible dimerization domain). In some embodiments, the dimer is formed by a non-covalent bond between the first dimerization domain and the second compatible dimerization domain. In some embodiments, the first dimerization domain and the second compatible dimerization domain have identical sequences (e.g., form a homodimer). In some embodiments, the first dimerization domain and the second dimerization domain do not have identical sequences (e.g., form a heterodimer). In some embodiments, a dimerization domain is a leucine zipper. In some instances, the dimerization domain is a nanobody, antibody, or coiled-coil domain. In some instances, the dimerization domain is a chemically inducible dimerization domain (e.g., a rapamycin sensitive dimerization domain) that can be regulated by the presence of a small molecule. In some embodiments, the dimerization domain is a light inducible dimerization domain (e.g., a far-red light inducible) that can be regulated by light exposure.

Linkers

In some instances, a linker is a covalent linkage or connection between two or more components described herein. In some embodiments, the linker comprises a chemical linker. In some embodiments, a linker is a peptide linker. In some instances, the linker(s) is located N-terminal of the fusion domain. In some instances, the linker(s) is located C-terminal of the fusion domain. In some instances, a first linker is located N-terminal of the fusion domain and the second linker is located C-terminal of the fusion domain. In some embodiments, a first linker(s) is located C-terminal of a first fusion domain and a second linker is located N-terminal of a second fusion domain.

In some embodiments, a heterologous sequence comprises one or more linkers (e.g., peptide linkers) of at least 1, 2, 3, 4, 5, 6, 7, 8, 9, 10, 11, 12, 13, 14, 15, 16, 17, 18, 19, 20, 25, 30, 35, 40, 45, 50, or more amino acid residues. In some embodiments, the linker can be located N-terminal of a fusion domain. In certain embodiments, the linker can be located C-terminal of a fusion domain. The linker sequence may comprise any naturally occurring amino acid. In some embodiments, the linker sequence may comprise between 2 and 200 amino acid residues. In some embodiments, the linker comprises amino acids glycine and serine. In some embodiments, the linker comprises sets of glycine and serine repeats such as $(G_4S)_x$, where x is a positive integer between 0 and 15 (e.g., 1, 2, 3, 4, 5, 6, 7, 8, 9, 10, 11, 12, 13, 14, or 15). In some embodiments, the linker comprises an amino acid sequence of $(GSG)_x$, wherein X is an integer between 0 and 15 (e.g., 0, 1, 2, 3, 4, 5, 6, 7, 8, 9, 10, 11, 12, 13, 14, or 15). In some embodiments, the linker comprises an amino acid sequence of $(GSSG)_x$, wherein X is an integer between 0 and 15 (e.g., 0, 1, 2, 3, 4, 5, 6, 7, 8, 9, 10, 11, 12, 13, 14, or 15). In some embodiments, the linker can comprise the amino acid sequence of any of the following:

| Linker Amino Acid Sequence | SEQ ID NO |
|---|---|
| GGGGS | SEQ ID NO: 121 |
| GGGGSGGGGSGGGGSGGGGSGGGGSGGGGS | SEQ ID NO: 122 |
| GGGGSGGGGSGGGGS | SEQ ID NO: 123 |
| GSSG | SEQ ID NO: 124 |
| GSSGGSSG | SEQ ID NO: 125 |
| GSSGGSSGGSSG | SEQ ID NO: 126 |
| GSSGGSSGGSSGGSSG | SEQ ID NO: 127 |
| GSG | SEQ ID NO: 128 |
| GSGGSGGSGGSG | SEQ ID NO: 129 |
| GGGS | SEQ ID NO: 130 |

In some embodiments, the linker comprises the 16 residue "XTEN" linker, or a variant thereof (see, e.g., Schellenberger et al. (Nat. Biotechnol. 27: 1186-1190, 2009), the entirety of which is incorporated herein by reference.

In some embodiments, any peptide linker described herein may further comprise between 1-5 (e.g., 1, 2, 3, 4, or 5) amino acid residues N-terminal or C-terminal of the peptide linker. The 1-5 amino acids residues N-terminal or C-terminal of the peptide linker can comprise any naturally occurring or modified amino acid residue.

Also included within the scope of the invention are linkers described in WO2012/138475, incorporated herein by reference in its entirety.

In some embodiments, the peptide linker comprises the structure of:

$L_1$-$L_2$-$L_3$ wherein $L_1$ and $L_3$ are each independently chosen from $(GSG)_x$, $(GGGS)_x$, or $(GSSG)_x$, wherein x is an integer between 0 and 15 (e.g., 0, 1, 2, 3, 4, 5, 6, 7, 8, 9, 10, 11, 12, 13, 14, or 15), and $L_2$ is a polypeptide comprising between 0-40 (e.g., 0-5, 5-10, 10-15, 15-20, 20-25, 25-30, 30-35, or 35-40) amino acid residues.

In certain embodiments, $L_2$ is an amino acid sequence comprising at least 80% (e.g., 85%, 90%, 95%, 99% or 100%) sequence identity to SGSETPGTSESATPES (SEQ ID NO: 106).

In certain embodiments, the peptide linker comprises an amino acid sequence comprising at least 80% (e.g., 85%, 90%, 95%, 99% or 100%) sequence identity to SEQ ID NO: 40 or 106.

RNA Guide

In some embodiments, a composition as described herein comprises a nuclease binding sequence and a DNA-binding sequence. In some embodiments, an RNA guide comprises a nuclease binding sequence and a DNA-binding sequence. The RNA guide can bind any one of the Cas12i polypeptides described herein with specific binding affinity. In some embodiments, the RNA guide further comprises specific binding affinity to a target sequence. In some embodiments, a composition described herein comprises two or more RNA guides (e.g., 2, 3, 4, 5, 6, 7, 8, 9, or more). In some embodiments, the RNA guide is encoded in a vector. In some embodiments, the vector comprises a Pol II promoter or a Pol III promoter.

In some embodiments, the RNA guide can associate with a Cas12i polypeptide described herein. In some embodiments, the RNA guide directs the polypeptide to a target nucleic acid sequence (e.g., DNA).

Nuclease Binding Sequence

In some embodiments, the nuclease binding sequence comprises a direct repeat sequence. In certain embodiments, the nuclease binding sequence includes a direct repeat sequence linked to a DNA-binding sequence (e.g., a DNA-targeting sequence or spacer). In some embodiments, the nuclease binding sequence includes a direct repeat sequence and a DNA-binding sequence or a direct repeat-DNA-binding sequence-direct repeat sequence. In some embodiments, the nuclease binding sequence includes a truncated direct repeat sequence and a DNA-binding sequence, which is typical of processed or mature crRNA.

In some embodiments, the direct repeat sequence comprises at least 90% identity to any one of SEQ ID NOs: 12-24. In some embodiments, the direct repeat sequence comprises at least 95% (e.g., at least 97%, at least 99%, or at least 100%) identity to any one of SEQ ID NOs: 12-24. In some embodiments, the direct repeat sequence comprises any one of SEQ ID NOs: 12-24. In some embodiments, the direct repeat sequence comprises a portion of any one of SEQ ID NOs: 12-24.

TABLE 2

Direct repeat sequences.

| Sequence identifier | Direct Repeat Sequence | Cas12i Description |
|---|---|---|
| SEQ ID NO: 12 | GUUGGAAUGACUAAUUUUUGUGCCCACCGUUGGCAC | Cas 12i1 (SEQ ID NO: 3 of U.S. Pat. No. 10,808,245, SEQ ID NO: 8 of present application) |
| SEQ ID NO: 13 | AAUUUUUGUGCCCAUCGUUGGCAC | Cas12i1 (SEQ ID NO: 3 of U.S. Pat. No. 10,808,245, SEQ ID NO: 8 of present application) |
| SEQ ID NO: 14 | AUUUUUGUGCCCAUCGUUGGCAC | Cas12i1 (SEQ ID NO: 3 of U.S. Pat. No. 10,808,245, SEQ ID NO: 8 of present application) |
| SEQ ID NO: 15 | GUUGCAAAACCCAAGAAAUCCGUCUUUCAUUGACGG | Cas12i2 (SEQ ID NO: 5 of U.S. Pat. No. 10,808,245 or SEQ ID NOs: 2-7 of present application) |
| SEQ ID NO: 16 | GCAACACCUAAGAAAUCCGUCUUUCAUUGACGGG | Cas12i2 (SEQ ID NO: 5 of U.S. Pat. No. 10,808,245 or SEQ ID NOs: 2-7 of present application) |
| SEQ ID NO: 17 | AGAAAUCCGUCUUUCAUUGACGG | Cas 12i2 (SEQ ID NO: 5 of U.S. Pat. No. 10,808,245 or SEQ ID NOs: 2-7 of present application) |
| SEQ ID NO: 18 | CUAGCAAUGACCUAAUAGUGUGUCCUUAGUUGACAU | Cas 12i3 (SEQ ID NO: 14 of U.S. Pat. No. 10,808,245 or SEQ ID NO: 11 or present application) |

TABLE 2-continued

| Direct repeat sequences. | | |
|---|---|---|
| Sequence identifier | Direct Repeat Sequence | Cas12i Description |
| SEQ ID NO: 19 | CCUACAAUACCUA AGAAAUCCGUCCU AAGUUGACGG | Cas12i3 (SEQ ID NO: 14 of U.S. Pat. No. 10,808,245 or SEQ ID NO: 11 or present application) |
| SEQ ID NO: 20 | AUAGUGUGUCCUU AGUUGACAU | Cas 12i3 (SEQ ID NO: 14 of U.S. Pat. No. 10,808,245 or SEQ ID NO: 11 or present application) |
| SEQ ID NO: 21 | GUUGGAAUGACUA AUUUUUGUGCCCA CCGUUGGCAC | Cas 12i4 (SEQ ID NO: 16 of U.S. Pat. No. 10,808,245, SEQ ID NOs: 9 or 10 of present application) |
| SEQ ID NO: 22 | CCCACAAUACCUG AGAAAUCCGUCCU ACGUUGACGG | Cas 12i4 (SEQ ID NO: 16 of U.S. Pat. No. 10,808,245, SEQ ID NOs: 9 or 10 of present application) |
| SEQ ID NO: 23 | UCUCAACGAUAGU CAGACAUGUGUCC UCAGUGACAC | Cas 12i4 (SEQ ID NO: 16 of U.S. Pat. No. 10,808,245, SEQ ID NOs: 9 or 10 of present application) |
| SEQ ID NO: 24 | AGACAUGUGUCCU CAGUGACAC | Cas 12i4 (SEQ ID NO: 16 of U.S. Pat. No. 10,808,245, SEQ ID NOs: 9 or 10 of present application) |

DNA-Binding Sequence

In some embodiments, the DNA-binding sequence is a DNA-targeting sequence (e.g., spacer) having a length of from about 7 nucleotides to about 100 nucleotides. For example, the spacer can have a length of from about 7 nucleotides to about 80 nucleotides, from about 7 nucleotides to about 50 nucleotides, from about 7 nucleotides to about 40 nucleotides, from about 7 nucleotides to about 30 nucleotides, from about 7 nucleotides to about 25 nucleotides, from about 7 nucleotides to about 20 nucleotides, or from about 7 nucleotides to about 19 nucleotides. For example, the spacer can have a length of from about 7 nucleotides to about 20 nucleotides, from about 7 nucleotides to about 25 nucleotides, from about 7 nucleotides to about 30 nucleotides, from about 7 nucleotides to about 35 nucleotides, from about 7 nucleotides to about 40 nucleotides, from about 7 nucleotides to about 45 nucleotides, from about 7 nucleotides to about 50 nucleotides, from about 7 nucleotides to about 60 nucleotides, from about 7 nucleotides to about 70 nucleotides, from about 7 nucleotides to about 80 nucleotides, from about 7 nucleotides to about 90 nucleotides, from about 7 nucleotides to about 100 nucleotides, from about 10 nucleotides to about 25 nucleotides, from about 10 nucleotides to about 30 nucleotides, from about 10 nucleotides to about 35 nucleotides, from about 10 nucleotides to about 40 nucleotides, from about 10 nucleotides to about 45 nucleotides, from about 10 nucleotides to about 50 nucleotides, from about 10 nucleotides to about 60 nucleotides, from about 10 nucleotides to about 70 nucleotides, from about 10 nucleotides to about 80 nucleotides, from about 10 nucleotides to about 90 nucleotides, or from about 10 nucleotides to about 100 nucleotides.

In some embodiments, the DNA-binding sequence may be generally designed to have a length of between 7 and 50 nucleotides or between 15 and 35 nucleotides (e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides) and be complementary to a specific target sequence. In some embodiments, the RNA guide may be designed to be complementary to a specific DNA strand, e.g., of a genomic locus. In some embodiments, the DNA-binding sequence is designed to be complementary to a specific DNA strand, e.g., of a genomic locus.

In some embodiments, the DNA-binding sequence has at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a specific DNA sequence.

In some embodiments, a spacer or spacer sequence (e.g., the DNA-binding sequence) is a portion in an RNA guide that is the RNA equivalent of the target sequence (a DNA sequence). Typically, the spacer contains a sequence capable of binding to the non-PAM strand via base-pairing at the site complementary to the target sequence (in the PAM strand). In some instances, the spacer may be at least 75% identical to the target sequence (e.g., at least 80%, at least 85%, at least 90%, at least 95%, at least 98%, or at least 99%), when considering T to be equivalent to U for the purpose of this comparison. In some instances, the spacer may be 100% identical to the target sequence when considering T to be equivalent to U for the purpose of this comparison.

In some instances, a polynucleotide is complementary to another when a first polynucleotide (e.g., a spacer sequence of an RNA guide) has a certain level of complementarity to a second polynucleotide (e.g., the complementary sequence of a target sequence) such that the first and second polynucleotides can form a double-stranded complex via base-pairing to permit an effector polypeptide that is complexed with the first polynucleotide to act on (e.g., cleave) the second polynucleotide. In some embodiments, the first polynucleotide may be substantially complementary to the second polynucleotide. In some embodiments, the first polynucleotide has at least about 80%, 81%, 82%, 83%, 84%, 85%, 86%, 87%, 88%, 89%, 90%, 91%, 92%, 93%, 94%, 95%, 96%, 97%, 98%, or 99% complementarity to the second polynucleotide. In some embodiments, the first polynucleotide is completely complementary to the second polynucleotide, i.e., having 100% complementarity to the second polynucleotide.

In some embodiments, the DNA-binding sequence and specific DNA sequence do not base pair with 100% complementarity (e.g., there are mismatches between the DNA-binding sequence and specific DNA sequence). In some embodiments, mismatches between the DNA-binding sequence and the specific DNA sequence prevent retargeting by the Cas12i polypeptide.

In some embodiments, the DNA-binding sequence comprises only RNA bases. In some embodiments, the DNA-binding sequence comprises a DNA base (e.g., the spacer comprises at least one thymine). In some embodiments, the DNA-binding sequence comprises RNA bases and DNA bases (e.g., the DNA-binding sequence comprises at least one thymine and at least one uracil).

Modifications

An RNA guide or a nucleic acid sequence encoding a Cas12i polypeptide, a deaminase polypeptide, or Cas12i-deaminase fusion polypeptide may include one or more covalent modifications with respect to a reference sequence, in particular the parent polyribonucleotide, which are included within the scope of this invention.

Exemplary modifications can include any modification to the sugar, the nucleobase, the internucleoside linkage (e.g. to a linking phosphate/to a phosphodiester linkage/to the phosphodiester backbone), and any combination thereof. Some of the exemplary modifications provided herein are described in detail below.

The RNA guide or any of the nucleic acid sequences encoding components of the variant polypeptides may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc.). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

Target Sequence

The compositions disclosed herein are applicable for editing a variety of target sequences. In some embodiments, the target sequence is a DNA molecule, such as a DNA locus (referred to herein as a target sequence or an on-target sequence). In some embodiments, the target sequence is an RNA, such as an RNA locus or mRNA. In some embodiments, the target sequence is single-stranded (e.g., single-stranded DNA). In some embodiments, the target sequence is double-stranded (e.g., double-stranded DNA). In some embodiments, the target sequence comprises both single-stranded and double-stranded regions. In some embodiments, the target sequence is linear. In some embodiments, the target sequence is circular. In some embodiments, the target sequence comprises one or more modified nucleotides, such as methylated nucleotides, damaged nucleotides, or nucleotides analogs. In some embodiments, the target sequence is not modified. In some embodiments, a single-stranded target sequence does not require a PAM sequence.

The target sequence may be of any length, such as about at least any one of 100 bp, 200 bp, 500 bp, 1000 bp, 2000 bp, 5000 bp, 10 kb, 20 kb, 50 kb, 100 kb, 200 kb, 500 kb, 1 Mb, or longer. The target sequence may also comprise any sequence. In some embodiments, the target sequence is GC-rich, such as having at least about any one of 40%, 45%, 50%, 55%, 60%, 65%, or higher GC content. In some embodiments, the target sequence has a GC content of at least about 70%, 80%, or more. In some embodiments, the target sequence is a GC-rich fragment in a non-GC-rich target sequence. In some embodiments, the target sequence is not GC-rich. In some embodiments, the target sequence has one or more secondary structures or higher-order structures. In some embodiments, the target sequence is not in a condensed state, such as in a chromatin, to render the target sequence inaccessible by ribonucleoprotein.

In some embodiments, the target sequence is present in a cell. In some embodiments, the target sequence is present in the nucleus of the cell. In some embodiments, the target sequence is endogenous to the cell. In some embodiments, the target sequence is a genomic DNA. In some embodiments, the target sequence is a chromosomal DNA. In some embodiments, the target sequence is a protein-coding gene or a functional region thereof, such as a coding region, or a regulatory element, such as a promoter, enhancer, a 5' or 3' untranslated region, etc. In some embodiments, the target sequence is a non-coding gene, such as transposon, miRNA, tRNA, ribosomal RNA, ribozyme, or lincRNA. In some embodiments, the target sequence is a plasmid.

In some embodiments, the target sequence is exogenous to a cell. In some embodiments, the target sequence is a viral nucleic acid, such as viral DNA or viral RNA. In some embodiments, the target sequence is a horizontally transferred plasmid. In some embodiments, the target sequence is integrated in the genome of the cell. In some embodiments, the target sequence is not integrated in the genome of the cell. In some embodiments, the target sequence is a plasmid in the cell. In some embodiments, the target sequence is present in an extrachromosomal array.

In some embodiments, the target sequence is an isolated nucleic acid, such as an isolated DNA or an isolated RNA. In some embodiments, the target sequence is present in a cell-free environment. In some embodiments, the target sequence is an isolated vector, such as a plasmid. In some embodiments, the target sequence is an ultrapure plasmid.

The target is a segment of the target sequence that hybridizes to the RNA guide. In some embodiments, the target sequence has only one copy of the target sequence. In some embodiments, the target sequence has more than one copy, such as at least about any one of 2, 3, 4, 5, 10, 100, or more copies of the target sequence. For example, a target sequence comprising a repeated sequence in a genome of a viral nucleic acid or a bacterium may be targeted by the Cas12i polypeptide.

In some embodiments, the target sequence is present in a readily accessible region of the target sequence. In some embodiments, the target sequence is in an exon of a target gene. In some embodiments, the target sequence is across an exon-intron junction of a target gene. In some embodiments, the target sequence is present in a non-coding region, such as a regulatory region of a gene. In some embodiments, wherein the target sequence is exogenous to a cell, the target sequence comprises a sequence that is not found in the genome of the cell.

Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target sequence that is complementary to and hybridizes with the RNA guide is referred to as the "complementary strand" and the strand of the target sequence that is complementary to the "complementary strand" (and is therefore not complementary to the RNA guide) is referred to as the "noncomplementary strand" or "non-complementary strand".

In some embodiments, the PAM sequence comprises 5'-NTTN-3' wherein N is any nucleotide (e.g., A, G, T, or C). In other embodiments, a PAM sequence of the disclosure comprises the sequence 5'-TTY-3' or 5'-TTB-3', wherein Y is C or T, and B is G, T, or C. The PAM sequence may be immediately adjacent to the target sequence or, for example, within a small number (e.g., 1, 2, 3, 4, or 5) of nucleotides of the target sequence. In the case of a double-stranded target, the RNA guide binds to a first strand of the target and a PAM sequence as described herein is present in the second, complementary strand. In such a case, the PAM sequence is immediately adjacent to (or within a small number, e.g., 1, 2, 3, 4, or 5 nucleotides of) a sequence in the second strand that is complementary to the sequence in the first strand to which the binding moiety binds.

In some embodiments, the target sequence is a gene that is involved in an immune response in a subject. In some embodiments, the target sequence is an immune checkpoint gene. In some embodiments, the target sequence is selected from the group consisting of: BCL11A intronic erythroid enhancer, CD3, Beta-2 microglobulin (B2M), T Cell Receptor Alpha Constant (TRAC), Programmed Cell Death 1 (PDCD1), T-cell receptor alpha, T-cell receptor beta, B-cell lymphoma/leukemia 11A (BCL11A), Cytotoxic T-Lymphocyte Antigen 4 (CTLA-4), chemokine (C—C motif) receptor 5 (gene/pseudogene) (CCR5), CXCR4 gene, CD160 molecule (CD160), adenosine A2a receptor (ADORA), CD276, B7-H3, B7-H4, BTLA, nicotinamide adenine dinucleotide phosphate NADPH oxidase isoform 2 (NOX2), V-domain Ig suppressor of T cell activation (VISTA), Sialic acid-binding immunoglobulin-type lectin 7 (SIGLEC7), Sialic acid-binding immunoglobulin-type lectin 9 (SIGLEC9), SIGLEC10, V-set domain containing T cell activation inhibitor 1 (VTCN1), B and T lymphocyte associated (BTLA), Indoleamine 2,3-dioxygenase (IDO), indoleamine 2,3-dioxygenase 1 (IDO1), Killer-cell Immunoglobulin-like Receptor (KIR), killer cell immunoglobulin-like receptor, three domains, long cytoplasmic tail, 1 (KIR3DL1), lymphocyte-activation gene 3 (LAG3), T-cell Immunoglobulin domain and Mucin domain 3 (TIM3), hepatitis A virus cellular receptor 2 (HAVCR2), natural killer cell receptor 2B4 (CD244), hypoxanthine phosphoribosyltransferase 1 (HPRT), T-cell immunoreceptor with Ig and ITIM domains (TIGIT), CD96 molecule (CD96), cytotoxic and regulatory T-cell molecule (CRTAM), leukocyte associated immunoglobulin like receptor 1 (LAIR1), adeno-associated virus integration site 1 (AAVS1), AAVS 2, AAVS3, AAVS4, AAVS5, AAVS6, AAVS7, AAVS8, transforming growth factor beta receptor II (TGFBRII), transforming growth factor beta receptor I (TGFBR1), SMAD family member 2 (SMAD2), SMAD family member 3 (SMAD3), SMAD family member 4 (SMAD4), SKI proto-oncogene (SKI), SKI-like proto-oncogene (SKIL), egl-9 family hypoxia-inducible factor 1 (EGLN1), egl-9 family hypoxia-inducible factor 2 (EGLN2), egl-9 family hypoxia-inducible factor 3 (EGLN3), protein phosphatase 1 regulatory subunit 12C (PPP1R12C), TGFB induced factor homeobox 1 (TGIF1), tumor necrosis factor receptor superfamily member, tumor necrosis factor receptor superfamily member 10b (TNFRSF10B), tumor necrosis factor receptor superfamily member 10a (TNFRSF10A), BY55, B7H5, caspase 8 (CASP8), caspase 10 (CASP10), caspase 3 (CASP3), caspase 6 (CASP6), caspase 7 (CASP7), Fas associated via death domain (FADD), Fas cell surface death receptor (FAS), interleukin 10 receptor subunit alpha (IL10RA), interleukin 10 receptor subunit beta (IL10RB), heme oxygenase 2 (HMOX2), interleukin 6 receptor (IL6R), interleukin 6 signal transducer (IL6ST), c-src tyrosine kinase (CSK), phosphoprotein membrane anchor with glycosphingolipid microdomains 1 (PAG1), guanylate cyclase 1, soluble, beta 3 (GUCY1B3), signaling threshold regulating transmembrane adaptor 1 (SIT1), forkhead box P3 (FOXP3), PR domain 1 (PRDM1), basic leucine zipper transcription factor, ATF-like (BATF), guanylate cyclase 1, soluble, alpha 2 (GUCY1A2), guanylate cyclase 1, soluble, alpha 3 (GUCY1A3), guanylate cyclase 1, soluble, beta 2 (GUCY1B2), prolyl hydroxylase domain (PHD1, PHD2, PHD3) family of proteins, CD27, CD28, CD40, CD122, CD137, OX40, GITR, and ICOS. In some embodiments, the modified gene is programmed death ligand 1 (PD-L1), class II major histocompatibility complex transactivator (CIITA), citramalyl-CoA lyase (CLYBL), transthyretin (TTR), lactate dehydrogenase-A (LDHA), dydroxyacid oxidase-1 (HAO1), alanine-glyoxylate and serine-pyruvate aminotransferase (AGXT), glyoxylate reductase/hydroxypyruvate reductase (GRHPR), 4-hydroxy-2-oxoglutarate aldolase (HOGA), polypyrimidine tract binding protein 1 (PTBP1), stathmin 2 (STMN2), or actin beta (ACTB).

Base Editing

In some embodiments, a composition described herein introduces at least one edit into a target sequence of a target nucleic acid. In some embodiments, the edit may include a substitution relative to a wild-type nucleic acid sequence. In some embodiments, the edit is a one-nucleotide substitution. In some embodiments, the edit is a two-nucleotide substitution. In some embodiments, the edit is a three-nucleotide substitution. In some embodiments, the edit is a four-nucleotide substitution. In some embodiments, the edit is a five-nucleotide substitution.

In aspect, the disclosure provides a method of producing an edit (e.g., a substitution) in a target sequence of a target nucleic acid (e.g., a target nucleic acid in a cell), the method comprising:

- contacting target nucleic acid (e.g., the target nucleic acid in the cell): (i) a Cas12i domain, (ii) an RNA guide, and (iii) a deaminase domain, or nucleic acid encoding (i), (ii), and (iii),
- wherein the target nucleic acid comprises a nucleotide position 0, wherein nucleotide position 0 of the target strand hybridizes with the direct repeat-proximal end of the spacer sequence of the RNA guide, and a position x (wherein optionally x=20), wherein position x of the target strand hybridizes with the direct repeat-distal end of the spacer sequence of the RNA guide,
- and wherein the target nucleic acid comprises an A or a C between positions 5-16 (e.g., between positions 7-12, e.g., between positions 8-11) on the target strand or the non-target strand,
- wherein the A is mutated to a inosine (I) (e.g., converts an A:T base pair to an I:C, I:U, or I:A base pair) or the C is mutated to a U or T (e.g., converts a C:G base pair to a T:A base pair).

In one aspect, the disclosure provides a method of producing an edit (e.g., a substitution) in a target sequence of a target nucleic acid (e.g., a target nucleic acid in a cell), the method comprising:

- contacting target nucleic acid (e.g., the target nucleic acid in the cell) (i) a fusion protein described herein or the polypeptide system described herein, and (ii) an RNA guide, or a nucleic acid encoding (i) and (ii),
- thereby introducing the substitution.

In certain embodiments, the target nucleic acid comprises a nucleotide position 0, wherein nucleotide position 0 of the target strand hybridizes with the direct repeat-proximal end of the spacer sequence of the RNA guide, and a position x (wherein optionally x=20), wherein position x of the target strand hybridizes with the direct repeat-distal end of the spacer sequence of the RNA guide,

- and wherein the target nucleic acid comprises an A or a C between positions 5-16 (e.g., between positions 7-12 (e.g., 7, 8, 9, 10, 11, or 12)) on the target strand or the non-target strand,
- wherein the A is mutated to a inosine (I) or the C is mutated to a U (e.g., converts a C:G base pair to a T:A base pair).

In some embodiments, the method converts a C:G base pair to a T:A base pair alteration in the target nucleic acid.

In certain embodiments, the alteration occurs at one or more C:G base pairs between positions 7-12 (e.g., 7, 8, 9, 10, 11, or 12) of the target nucleic acid.

It is understood that, herein, when a nucleic is said to comprise a particular nucleotide between specified positions, the end positions are included. For example, a nucleic acid comprising A between positions 8-11 could comprise the A at position 8, 9, 10, or 11.

In some embodiments wherein the Cas12i domain is a circularly permuted domain, the target nucleic acid comprises an alteration between positions 1-30. For example, in some embodiments, the alteration is between positions 1-30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30), positions 1-25 (e.g., 1, 2, 3, 4, 5, 6, 7, 8, 9, 10, 11, 12, 13, 14, 15, 16, 17, 18, 19, 20, 21, 22, 23, 24, or 25), positions 1-20 (e.g., 1, 2, 3, 4, 5, 6, 7, 8, 9, 10, 11, 12, 13, 14, 15, 16, 17, 18, 19, or 20), position 5-25 (e.g., 5, 6, 7, 8, 9, 10, 11, 12, 13, 14, 15, 16, 17, 18, 19, 20, 21, 22, 23, 24, or 25), or position 5-20 (e.g., 5, 6, 7, 8, 9, 10, 11, 12, 13, 14, 15, 16, 17, 18, 19, or 20). In some embodiments wherein the Cas12i domain comprises a FokI nuclease domain, the target nucleic acid comprises an alteration between positions 1-30. For example, in some embodiments, the alteration is between positions 1-30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30), positions 1-25 (e.g., 1, 2, 3, 4, 5, 6, 7, 8, 9, 10, 11, 12, 13, 14, 15, 16, 17, 18, 19, 20, 21, 22, 23, 24, or 25), positions 1-20 (e.g., 1, 2, 3, 4, 5, 6, 7, 8, 9, 10, 11, 12, 13, 14, 15, 16, 17, 18, 19, or 20), position 5-25 (e.g., 5, 6, 7, 8, 9, 10, 11, 12, 13, 14, 15, 16, 17, 18, 19, 20, 21, 22, 23, 24, or 25), or position 5-20 (e.g., 5, 6, 7, 8, 9, 10, 11, 12, 13, 14, 15, 16, 17, 18, 19, or 20). In some embodiments wherein the alteration between positions 1-30, the alteration is in the target strand. In some embodiments wherein the alteration between positions 1-30, the alteration is in the non-target strand.

In some embodiments, the cell is selected from a eukaryotic cell, a mammalian cell, or a human cell. In certain embodiments, the cell is in vivo. In some embodiments, the cell is ex vivo. In certain embodiments, the cell is in vitro.

Production

In some embodiments, a composition of the present invention comprising a Cas12i polypeptide and a deaminase or a Cas12i polypeptide-deaminase fusion can be prepared by (a) culturing bacteria which produce the Cas12i polypeptide and the deaminase polypeptide of the present invention, isolating the Cas12i polypeptide and the deaminase, optionally, purifying the Cas12i polypeptide and the deaminase, and complexing the Cas12i polypeptide and the deaminase with the RNA guide. The Cas12i polypeptide and the deaminase can be also prepared by (b) a known genetic engineering technique, specifically, by isolating a gene encoding the Cas12i polypeptide and the deaminase of the present invention from bacteria, constructing a recombinant expression vector, and then transferring the vector into an appropriate host cell that expresses the RNA guide for expression of a recombinant protein that complexes with the RNA guide in the host cell. Alternatively, the Cas12i polypeptide and the deaminase can be prepared by (c) an in vitro coupled transcription-translation system and then complexes with RNA guide. Bacteria that can be used for preparation of the Cas12i polypeptide and the deaminase of the present invention are not particularly limited as long as they can produce the Cas12i polypeptide and the deaminase of the present invention. Some nonlimiting examples of the bacteria include *E. coli* cells described herein.

Unless otherwise noted, all compositions and complexes and polypeptides provided herein are made in reference to the active level of that composition or complex or polypeptide, and are exclusive of impurities, for example, residual solvents or by-products, which may be present in commercially available sources. Enzymatic component weights are based on total active protein. All percentages and ratios are calculated by weight unless otherwise indicated. All percentages and ratios are calculated based on the total composition unless otherwise indicated. In the exemplified composition, the enzymatic levels are expressed by pure enzyme by weight of the total composition and unless otherwise specified, the ingredients are expressed by weight of the total compositions.

Vectors

The present invention provides a vector for expressing the Cas12i polypeptide and the deaminase described herein or nucleic acids encoding the composition components described herein may be incorporated into a vector. In some embodiments, a vector of the invention includes a nucleotide sequence encoding Cas12i polypeptide and the deaminase. In some embodiments, a vector of the invention includes a nucleotide sequence encoding the Cas12i polypeptide and the deaminase.

In some embodiments, the RNA guide or any portion thereof is encoded in a vector. In some embodiments, the vector comprises a Pol II promoter or a Pol III promoter.

The present invention also provides a vector that may be used for preparation of the Cas12i polypeptide and the deaminase and/or the RNA guide or compositions comprising the Cas12i polypeptide and the deaminase and/or the RNA guide as described herein. In some embodiments, the invention includes the composition or vector described herein in a cell. In some embodiments, the invention includes a method of expressing the composition comprising the Cas12i polypeptide and the deaminase and/or the RNA guide, or vector or nucleic acid encoding the Cas12i polypeptide and the deaminase and/or the RNA guide, in a cell. The method may comprise the steps of providing the composition, e.g., vector or nucleic acid, and delivering the composition to the cell.

Expression of natural or synthetic polynucleotides is typically achieved by operably linking a polynucleotide encoding the gene of interest, e.g., nucleotide sequence encoding the Cas12i polypeptide and the deaminase and/or the RNA guide, to a promoter and incorporating the construct into an expression vector. The expression vector is not particularly limited as long as it includes a polynucleotide encoding the Cas12i polypeptide and the deaminase and/or the RNA guide of the present invention and can be suitable for replication and integration in eukaryotic cells.

Typical expression vectors include transcription and translation terminators, initiation sequences, and promoters useful for expression of the desired polynucleotide. For example, plasmid vectors carrying a recognition sequence for RNA polymerase (pSP64, pBluescript, etc.) may be used. Vectors including those derived from retroviruses such as lentivirus are suitable tools to achieve long-term gene transfer since they allow long-term, stable integration of a transgene and its propagation in daughter cells. Examples of vectors include expression vectors, replication vectors, probe generation vectors, and sequencing vectors. The expression vector may be provided to a cell in the form of a viral vector.

Viral vector technology is well known in the art and described in a variety of virology and molecular biology manuals. Viruses which are useful as vectors include, but are not limited to phage viruses, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

The kind of the vector is not particularly limited, and a vector that can be expressed in host cells can be appropriately selected. To be more specific, depending on the kind of the host cell, a promoter sequence to ensure the expression of the effector polypeptide(s) from the polynucleotide is appropriately selected, and this promoter sequence and the polynucleotide are inserted into any of various plasmids etc. for preparation of the expression vector.

Additional promoter elements, e.g., enhancing sequences, regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription.

Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate transcriptional control sequences to enable expression in the host cells. Examples of such a marker include a dihydrofolate reductase gene and a neomycin resistance gene for eukaryotic cell culture; and a tetracycline resistance gene and an ampicillin resistance gene for culture of *E. coli* and other bacteria. By use of such a selection marker, it can be confirmed whether the polynucleotide encoding the effector polypeptide(s) of the present invention has been transferred into the host cells and then expressed without fail.

The preparation method for recombinant expression vectors is not particularly limited, and examples thereof include methods using a plasmid, a phage or a cosmid.

Methods of Expression

The present invention includes a method for protein expression, comprising translating the Cas12i polypeptide and the deaminase, and expressing the RNA guide described herein.

In some embodiments, a host cell described herein is used to express the Cas12i polypeptide and the deaminase and/or the RNA guide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the Cas12i polypeptide, the deaminase and/or the RNA guide. After expression of the Cas12i polypeptide, the deaminase and/or the RNA guide, the host cells can be collected and Cas12i polypeptide, the deaminase and/or the RNA guide purified from the cultures etc. according to conventional methods (for example, filtration, centrifugation, cell disruption, gel filtration chromatography, ion exchange chromatography, etc.).

In some embodiments, the methods for expression comprise translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the effector polypeptide(s). In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the Cas12i polypeptide and the deaminase.

A variety of methods can be used to determine the level of production of a mature Cas12i polypeptide, the deaminase and/or the RNA guide in a host cell. Such methods include, but are not limited to, for example, methods that utilize either polyclonal or monoclonal antibodies specific for the proteins or a labeling tag as described elsewhere herein. Exemplary methods include, but are not limited to, enzyme-linked immunosorbent assays (ELISA), radioimmunoassays (MA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the Cas12i polypeptide and the deaminase and/or the RNA guide in a cell, comprising providing a polyribonucleotide encoding the Cas12i polypeptide, the deaminase and/or the RNA guide to a host cell wherein the polyribonucleotide encodes the Cas12i polypeptide, the deaminase and/or the RNA guide, expressing the Cas12i polypeptide, the deaminase and/or the RNA guide in the cell, and obtaining the Cas12i polypeptide, the deaminase and/or the RNA guide from the cell.

Compositions and Formulations

The disclosure also provides a composition or formulation comprising a cell modified by a composition described herein. In some embodiments, the composition or formulation includes a cell or plurality of cells modified by a system described herein (e.g., (i) an RNA guide and (ii) a Cas12i fusion protein or a protein system comprising a Cas12i polypeptide and a deaminase polypeptide). In some embodiments, the composition or formulation includes a cell or plurality of cells comprising a substitution, insertion, or deletion described herein. In some embodiments, the composition or formulation includes a cell line modified by system described herein. In some embodiments, the composition or formulation includes a cell line comprising a substitution, insertion, or deletion described herein. The composition or formulation can additionally include, optionally, media and/or instructions for use of the modified cell or cell line.

In some embodiments, the composition is a pharmaceutical composition. A pharmaceutical composition that is useful may be prepared, packaged, or sold in a formulation suitable for oral, rectal, vaginal, parenteral, topical, pulmonary, intranasal, intra-lesional, buccal, ophthalmic, intravenous, intra-organ or another route of administration. A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined number of cells. The number of cells is generally equal to the dosage of the cells which would be administered to a subject or a convenient fraction of such a dosage such as, for example, one-half or one-third of such a dosage.

A formulation of a pharmaceutical composition suitable for parenteral administration may comprise the cells combined with a pharmaceutically acceptable carrier, such as sterile water or sterile isotonic saline. Such a formulation may be prepared, packaged, or sold in a form suitable for bolus administration or for continuous administration. Some injectable formulations may be prepared, packaged, or sold in unit dosage form, such as in ampules or in multi-dose containers containing a preservative. Some formulations for parenteral administration include, but are not limited to, suspensions, solutions, emulsions in oily or aqueous vehicles, pastes, and implantable sustained-release or biodegradable formulations. Some formulations may further comprise one or more additional ingredients including, but not limited to, suspending, stabilizing, or dispersing agents.

The pharmaceutical composition may be prepared, packaged, or sold in the form of a sterile injectable aqueous or oily suspension or solution. This suspension or solution may be formulated according to the known art, and may comprise, in addition to the cells, additional ingredients such as the dispersing agents, wetting agents, or suspending agents described herein. Such sterile injectable formulation may be prepared using a non-toxic parenterally-acceptable diluent or solvent, such as water or saline. Other acceptable diluents and solvents include, but are not limited to, Ringer's solution, isotonic sodium chloride solution, and fixed oils such as synthetic mono- or di-glycerides. Other parentally-administrable formulations which that are useful include those which may comprise the cells in a packaged form, in a liposomal preparation, or as a component of a biodegradable polymer system. Some compositions for sustained release or implantation may comprise pharmaceutically acceptable polymeric or hydrophobic materials such as an emulsion, an ion exchange resin, a sparingly soluble polymer, or a sparingly soluble salt.

Kits and Uses

The invention also provides kits or systems that can be used, for example, to carry out a method described herein. In some embodiments, the kits or systems include a Cas12i polypeptide and a deaminase. In some embodiments, the kits or systems include a polynucleotide that encodes a Cas12i polypeptide and deaminase, and optionally the polynucleotide is comprised within a vector, e.g., as described herein. In some embodiments, the kits or systems include a Cas12i-deaminase fusion polypeptide. The kits or systems also can include a deaminase, and an RNA guide as described herein. The RNA guide of the kits or systems of the invention can be designed to target a sequence of interest. The Cas12i polypeptide, deaminase, and RNA guide can be packaged within the same vial or other vessel within a kit or system or can be packaged in separate vials or other vessels, the contents of which can be mixed prior to use. The kits or systems can additionally include, optionally, a buffer and/or instructions for use of the Cas12i polypeptide and deaminase, along with the RNA guide.

In some embodiments, the kit may be useful for research purposes. For example, in some embodiments, the kit may be useful to study gene function.

Delivery

Compositions described herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, compositions are delivered using an AAV particle comprising an AAV vector. In some embodiments, the AAV particle is an AAV1, AAV2, AAV3, AAV4, AAV5, AAV6, AAV7, AAV8, AAV9, AAV10, or AAV11 particle (e.g., an AAV8, AAV3, or AAV2 particle). In some embodiments, the AAV particle comprises an AAV capsid. In some embodiments, the AAV capsid comprises one or more AAV1, AAV2, AAV3, AAV4, AAV5, AAV6, AAV7, AAV8, AAV9, AAV10, or AAV11 proteins. In some embodiments, all the protein components of the AAV capsid are proteins of the same AAV serotype (e.g., all AAV1, AAV2, AAV3, AAV4, AAV5, AAV6, AAV7, AAV8, AAV9, AAV10, or AAV11 proteins). In some embodiments, a first protein component of the AAV capsid is a protein of a first AAV serotype, and a second protein component of the AAV capsid is a protein of a second different AAV serotype. In some embodiments, the AAV particle is a pseudotype particle. In some embodiments, the first AAV ITR is from a different AAV serotype than the serotype of one or more of the proteins of the AAV capsid. In some embodiments, the second AAV ITR is from a different AAV serotype than the serotype of one or more of the proteins of the AAV capsid. In some embodiments, the first AAV ITR is from the same AAV serotype as the serotype of one or more of the proteins of the AAV capsid. In some embodiments, the second AAV ITR is from the same AAV serotype as the serotype of one or more of the proteins of the AAV capsid.

In some embodiments, the method comprises delivering one or more nucleic acids (e.g., nucleic acids encoding the Cas12i polypeptide, deaminase, RNA guide, one or more transcripts thereof, and/or a pre-formed ribonucleoprotein to a cell. Exemplary intracellular delivery methods, include, but are not limited to: viruses or virus-like agents; chemical-based transfection methods, such as those using calcium phosphate, dendrimers, liposomes, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnetofection or magnet assisted transfection, particle bombardment; and hybrid methods, such as nucleofection. In some embodiments, the present application further provides cells produced by such methods, and organisms (such as animals, plants, or fungi) comprising or produced from such cells. In some embodiments, a composition of the present invention is further delivered with an agent (e.g., compound, molecule, or biomolecule) that affects DNA repair or DNA repair machinery. In some embodiments, a composition of the present invention is further delivered with an agent (e.g., compound, molecule, or biomolecule) that affects the cell cycle.

Cells

In embodiments described herein the composition is delivered to or introduced into a cell. The cell described herein can be a variety of cells. In some embodiments, the cell is an isolated cell. In some embodiments, the cell is in cell culture or a co-culture of two or more cell types. In some embodiments, the cell is ex vivo. In some embodiments, the cell is obtained from a living organism and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the cell is an archaeal cell or derived from an archaeal cell.

In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a primate cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, CHO, and transgenic varieties thereof. Cell lines are available from a variety of sources known to those with skill in the art (see, e.g., the American Type Culture Collection (ATCC) (Manassas, Va.)). In some embodiments, the cell is an immortal or immortalized cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a mesenchymal stem cell. In some embodiments, the cell is an embryonic stem cell. In some embodiments, the cell is a hematopoietic stem cell. In some embodiments, the cell is a differentiated cell. For example, in some embodiments, the differentiated cell is a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a liver cell (e.g., a hepatocyte), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is a glial cell. In some embodiments, the cell is a pancreatic islet cell, including an alpha cell, beta cell, delta cell, or enterochromaffin cell. In some embodiments, the cell is an immune cell. In some embodiments, the immune cell is a T cell. In some embodiments, the immune cell is a B cell. In some embodiments, the immune cell is a Natural Killer (NK) cell. In some embodiments, the immune cell is a Tumor Infiltrating Lymphocyte (TIL). In some embodiments, the cell is a mammalian cell, e.g., a human cell or primate cell or a murine cell. In some embodiments, the murine cell is derived from a wild-type mouse, an immunosuppressed mouse, or a disease-specific mouse model. In some embodiments, the cell is a cell within a living tissue, organ, or organism.

In some embodiments, the cell is a primary cell. For example, cultures of primary cells can be passaged 0 times, 1 time, 2 times, 4 times, 5 times, 10 times, 15 times or more. In some embodiments, the primary cells are harvest from an individual by any known method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

In embodiments wherein a composition of the present invention is introduced into a plurality of cells, at least about 0.5% of the cells comprise the desired edit. In some embodiments, at least about 1% of the cells comprise the desired edit. In some embodiments, at least about 2% of the cells comprise the desired edit. In some embodiments, at least about 3% of the cells comprise the desired edit. In some embodiments, at least about 4% of the cells comprise the desired edit. In some embodiments, at least about 5% of the cells comprise the desired edit. In some embodiments, at least about 10% of the cells comprise the desired edit. In some embodiments, at least about 20% of the cells comprise the desired edit. In some embodiments, at least about 30% of the cells comprise the desired edit. In some embodiments, at least about 40% of the cells comprise the desired edit. In some embodiments, at least about 50% of the cells comprise the desired edit.

In some embodiments, the composition or formulation comprising a cell modified by a Cas12i polypeptide, deaminase, and RNA guide as described herein may be useful as an expression system to manufacture biomolecules. For example, in some embodiments, the composition or formulation comprising the modified cell may be useful to produce biomolecules such as proteins (e.g., cytokines, antibodies, antibody-based molecules), peptides, lipids, carbohydrates, nucleic acids, amino acids, and vitamins. In other embodiments, the composition or formulation comprising the modified cell may be useful in the production of a viral vector such as a lentivirus, adenovirus, adeno-associated virus, and oncolytic virus vector. In some embodiments, the composition or formulation comprising the modified cell may be useful in cytotoxicity studies. In some embodiments, the composition or formulation comprising the modified cell may be useful as a disease model. In some embodiments, the composition or formulation comprising the modified cell may be useful in vaccine production. In some embodiments, the composition or formulation comprising the modified cell may be useful in therapeutics. For example, in some embodiments, the composition or formulation comprising the modified cell may be useful in cellular therapies such as transfusions and transplantations.

In some embodiments, the composition or formulation comprising a cell modified by a Cas12i polypeptide, deaminase, and RNA guide as described herein may be useful to establish a new cell line comprising a modified genomic sequence. In some embodiments, a modified cell of the disclosure is a modified stem cell (e.g., a modified totipotent/omnipotent stem cell, a modified pluripotent stem cell, a modified multipotent stem cell, a modified oligopotent stem cell, or a modified unipotent stem cell) that differentiates into one or more cell lineages comprising the deletion of the modified stem cell. The disclosure further provides organisms (such as animals, plants, or fungi) comprising or produced from a modified cell of the disclosure.

All references and publications cited herein are hereby incorporated by reference.

EXAMPLES

The following examples are provided to further illustrate some embodiments of the present invention but are not intended to limit the scope of the invention; it will be understood by their exemplary nature that other procedures, methodologies, or techniques known to those skilled in the art may alternatively be used.

Example 1—Base Editing Mediated by Cas12i2

This Example describes editing of multiple mammalian targets using inactivated Cas12i2 fused to a deaminase.

To generate base editing fusion constructs, the variant Cas12i2 of SEQ ID NO: 4 was first deactivated by mutating the catalytic D599 residue to alanine. The deactivated Cas12i2 variant (referred to as dCas12i2 herein and having the sequence set forth in SEQ ID NO: 25) was then fused to one of the two cytidine deaminases—humanAPOBEC3a (A3A) (SEQ ID NO: 29) or Activation Induced Deaminase (AID) (SEQ ID NO: 28). In addition to fusing the deaminase, a copy of Uracyl Glycosylase Inhibitor (UGI) (SEQ ID NO: 31) was also fused. See Table 3. Various N- and C-terminal fusion combinations were generated, as shown in Table 4. Cas9 base editing constructs were also generated with either inactivated Cas9 (dCas9) or Cas9 nickase (nCas9) carrying the D10A mutation. Base editing constructs were cloned into a pcda3.1 backbone (Invitrogen).

TABLE 3

Base editing construct components

| Component | Sequence |
|---|---|
| Variant Cas12i2 (SEQ ID NO: 4) | MSSAIKSYKSVLRPNERKNQLLKSTIQCLEDGSAFFFKMLQGLFGGIT<br>PEIVRFSTEQEKQQQDIALWCAVNWFRPVSQDSLTHTIASDNLVEKF<br>EEYYGGTASDAIKQYFSASIGESYYWNDCRQQYYDLCRELGVEVSD<br>LTHDLEILCREKCLAVATESNQNNSIISVLFGTGEKEDRSVKLRITKKI<br>LEAISNLKEIPKNVAPIQEIILNVAKATKETFRQVYAGNLGAPSTLEKF<br>IAKDGQKEFDLKKLQTDLKKVIRGKSKERDWCCQEELRSYVEQNTI<br>QYDLWAWGEMFNKAHTALKIKSTRNYNFAKQRLEQFKEIQSLNNLL<br>VVKKLNDFFDSEFFSGEETYTICVHHLGGKDLSKLYKAWEDDPADP<br>ENAIVVLCDDLKNNFKKEPIRNILRYIFTIRQECSAQDILAAAKYNQQ<br>LDRYKSQKANPSVLGNQGFTWTNAVILPEKAQRNDRPNSLDLRIWL<br>YLKLRHPDGRWKKHHIPFYDTRFFQEIYAAGNSPVDTCQFRTPRFGY<br>HLPKLTDQTAIRVNKKHVKAAKTEARIRLAIQQGTLPVSNLKITEISA<br>TINSKGQVRIPVKFRVGRQKGTLQIGDRFCGYDQNQTASHAYSLWE<br>VVKEGQYHKELGCFVRFISSGDIVSITENRGNQFDQLSYEGLAYPQY<br>ADWRKKASKFVSLWQITKKNKKKEIVTVEAKEKFDAICKYQPRLYK<br>FNKEYAYLLRDIVRGKSLVELQQIRQEIFRFIEQDCGVTRLGSLSLSTL<br>ETVKAVKGIIYSYFSTALNASKNNPISDEQRKEFDPELFALLEKLELIR<br>TRKKKQKVERIANSLIQTCLENNIKFIRGEGDLSTTNNATKKKANSRS<br>MDWLARGVFNKIRQLAPMHNITLFGCGSLYTSHQDPLVHRNPDKA<br>MKCRWAAIPVKDIGDWVLRKLSQNLRAKNRGTGEYYHQGVKEFLS<br>HYELQDLEEELLKWRSDRKSNIPCWVLQNRLAEKLGNKEAVVYIPV<br>RGGRIYFATHKVATGAVSIVFDQKQVWVCNADHVAAANIALTGKGI<br>GEQSSDEENPDGSRIKLQLTS |
| dCas12i2(D599A) (SEQ ID NO: 25) | MSSAIKSYKSVLRPNERKNQLLKSTIQCLEDGSAFFFKMLQGLFGGIT<br>PEIVRFSTEQEKQQQDIALWCAVNWFRPVSQDSLTHTIASDNLVEKF<br>EEYYGGTASDAIKQYFSASIGESYYWNDCRQQYYDLCRELGVEVSD<br>LTHDLEILCREKCLAVATESNQNNSIISVLFGTGEKEDRSVKLRITKKI<br>LEAISNLKEIPKNVAPIQEIILNVAKATKETFRQVYAGNLGAPSTLEKF<br>IAKDGQKEFDLKKLQTDLKKVIRGKSKERDWCCQEELRSYVEQNTI<br>QYDLWAWGEMFNKAHTALKIKSTRNYNFAKQRLEQFKEIQSLNNLL<br>VVKKLNDFFDSEFFSGEETYTICVHHLGGKDLSKLYKAWEDDPADP<br>ENAIVVLCDDLKNNFKKEPIRNILRYIFTIRQECSAQDILAAAKYNQQ<br>LDRYKSQKANPSVLGNQGFTWTNAVILPEKAQRNDRPNSLDLRIWL<br>YLKLRHPDGRWKKHHIPFYDTRFFQEIYAAGNSPVDTCQFRTPRFGY<br>HLPKLTDQTAIRVNKKHVKAAKTEARIRLAIQQGTLPVSNLKITEISA<br>TINSKGQVRIPVKFRVGRQKGTLQIGDRFCGYAQNQTASHAYSLWE<br>VVKEGQYHKELGCFVRFISSGDIVSITENRGNQFDQLSYEGLAYPQY<br>ADWRKKASKFVSLWQITKKNKKKEIVTVEAKEKFDAICKYQPRLYK<br>FNKEYAYLLRDIVRGKSLVELQQIRQEIFRFIEQDCGVTRLGSLSLSTL<br>ETVKAVKGIIYSYFSTALNASKNNPISDEQRKEFDPELFALLEKLELIR<br>TRKKKQKVERIANSLIQTCLENNIKFIRGEGDLSTTNNATKKKANSRS<br>MDWLARGVFNKIRQLAPMHNITLFGCGSLYTSHQDPLVHRNPDKA<br>MKCRWAAIPVKDIGDWVLRKLSQNLRAKNRGTGEYYHQGVKEFLS<br>HYELQDLEEELLKWRSDRKSNIPCWVLQNRLAEKLGNKEAVVYIPV<br>RGGRIYFATHKVATGAVSIVFDQKQVWVCNADHVAAANIALTGKGI<br>GEQSSDEENPDGSRIKLQLTS |
| dCas9(D10A_H840A) (SEQ ID NO: 26) | MDKKYSIGLAIGTNSVGWAVITDEYKVPSKKFKVLGNTDRHSIKKN<br>LIGALLFDSGETAEATRLKRTARRRYTRRKNRICYLQEIFSNEMAKV<br>DDSFFHRLEESFLVEEDKKHERHPIFGNIVDEVAYHEKYPTIYHLRKK<br>LVDSTDKADLRLIYLALAHMIKFRGHFLIEGDLNPDNSDVDKLFIQL<br>VQTYNQLFEENPINASGVDAKAILSARLSKSRRLENLIAQLPGEKKN<br>GLFGNLIALSLGLTPNFKSNFDLAEDAKLQLSKDTYDDDLDNLLAQI<br>GDQYADLFLAAKNLSDAILLSDILRVNTEITKAPLSASMIKRYDEHH<br>QDLTLLKALVRQQLPEKYKEIFFDQSKNGYAGYIDGGASQEEFYKFI<br>KPILEKMDGTEELLVKLNREDLLRKQRTFDNGSIPHQIHLGELHAILR<br>RQEDFYPFLKDNREKIEKILTFRIPYYVGPLARGNSRFAWMTRKSEET<br>ITPWNFEEVVDKGASAQSFIERMTNFDKNLPNEKVLPKHSLLYEYFT<br>VYNELTKVKYVTEGMRKPAFLSGEQKKAIVDLLFKTNRKVTVKQLK<br>EDYFKKIECFDSVEISGVEDRFNASLGTYHDLLKIIKDKDFLDNEENE<br>DILEDIVLTLTLFEDREMIEERLKTYAHLFDDKVMKQLKRRRYTGW<br>GRLSRKLINGIRDKQSGKTILDFLKSDGFANRNFMQLIHDDSLTFKED<br>IQKAQVSGQGDSLHEHIANLAGSPAIKKGILQTVKVVDELVKVMGR<br>HKPENIVIEMARENQTTQKGQKNSRERMKRIEEGIKELGSQILKEHPV |

TABLE 3-continued

| Base editing construct components | |
|---|---|
| Component | Sequence |
| | ENTQLQNEKLYLYYLQNGRDMYVDQELDINRLSDYDVDAIVPQSFL KDDSIDNKVLTRSDKNRGKSDNVPSEEVVKKMKNYWRQLLNAKLI TQRKFDNLTKAERGGLSELDKAGFIKRQLVETRQITKHVAQILDSRM NTKYDENDKLIREVKVITLKSKLVSDFRKDFQFYKVREINNYHHAHD AYLNAVVGTALIKKYPKLESEFVYGDYKVYDVRKMIAKSEQEIGKA TAKYFFYSNIMNFFKTEITLANGEIRKRPLIETNGETGEIVWDKGRDF ATVRKVLSMPQVNIVKKTEVQTGGFSKESILPKRNSDKLIARKKDW DPKKYGGFDSPTVAYSVLVVAKVEKGKSKKLKSVKELLGITIMERSS FEKNPIDFLEAKGYKEVKKDLIIKLPKYSLFELENGRKRMLASAGEL QKGNELALPSKYVNFLYLASHYEKLKGSPEDNEQKQLFVEQHKHYL DEIIEQISEFSKRVILADANLDKVLSAYNKHRDKPIREQAENIIHLFTLT NLGAPAAFKYFDTTIDRKRYTSTKEVLDATLIHQSITGLYETRIDLSQ LGGD |
| nCas9(D10A) (SEQ ID NO: 27) | MDKKYSIGLAIGTNSVGWAVITDEYKVPSKKFKVLGNTDRHSIKKN LIGALLFDSGETAEATRLKRTARRRYTRRKNRICYLQEIFSNEMAKV DDSFFHRLEESFLVEEDKKHERHPIFGNIVDEVAYHEKYPTIYHLRKK LVDSTDKADLRLIYLALAHMIKFRGHFLIEGDLNPDNSDVDKLFIQL VQTYNQLFEENPINASGVDAKAILSARLSKSRRLENLIAQLPGEKKN GLFGNLIALSLGLTPNFKSNFDLAEDAKLQLSKDTYDDDLDNLLAQI GDQYADLFLAAKNLSDAILLSDILRVNTEITKAPLSASMIKRYDEHH QDLTLLKALVRQQLPEKYKEIFFDQSKNGYAGYIDGGASQEEFYKFI KPILEKMDGTEELLVKLNREDLLRKQRTFDNGSIPHQIHLGELHAILR RQEDFYPFLKDNREKIEKILTFRIPYYVGPLARGNSRFAWMTRKSEET ITPWNFEEVVDKGASAQSFIERMTNFDKNLPNEKVLPKHSLLYEYFT VYNELTKVKYVTEGMRKPAFLSGEQKKAIVDLLFKTNRKVTVKQLK EDYFKKIECFDSVEISGVEDRFNASLGTYHDLLKIIKDKDFLDNEENE DILEDIVLTLTLFEDREMIEERLKTYAHLFDDKVMKQLKRRRYTGW GRLSRKLINGIRDKQSGKTILDFLKSDGFANRNFMQLIHDDSLTFKED IQKAQVSGQGDSLHEHIANLAGSPAIKKGILQTVKVVDELVKVMGR HKPENIVIEMARENQTTQKGQKNSRERMKRIEEGIKELGSQILKEHPV ENTQLQNEKLYLYYLQNGRDMYVDQELDINRLSDYDVDHIVPQSFL KDDSIDNKVLTRSDKNRGKSDNVPSEEVVKKMKNYWRQLLNAKLI TQRKFDNLTKAERGGLSELDKAGFIKRQLVETRQITKHVAQILDSRM NTKYDENDKLIREVKVITLKSKLVSDFRKDFQFYKVREINNYHHAHD AYLNAVVGTALIKKYPKLESEFVYGDYKVYDVRKMIAKSEQEIGKA TAKYFFYSNIMNFFKTEITLANGEIRKRPLIETNGETGEIVWDKGRDF ATVRKVLSMPQVNIVKKTEVQTGGFSKESILPKRNSDKLIARKKDW DPKKYGGFDSPTVAYSVLVVAKVEKGKSKKLKSVKELLGITIMERSS FEKNPIDFLEAKGYKEVKKDLIIKLPKYSLFELENGRKRMLASAGEL QKGNELALPSKYVNFLYLASHYEKLKGSPEDNEQKQLFVEQHKHYL DEIIEQISEFSKRVILADANLDKVLSAYNKHRDKPIREQAENIIHLFTLT NLGAPAAFKYFDTTIDRKRYTSTKEVLDATLIHQSITGLYETRIDLSQ LGGD |
| AID (SEQ ID NO: 28) | MDPATFTYQFKNVRWAKGRRETYLCYVVKRRDSATSFSLDFGYLR NKNGCHVELLFLRYISDWDLDPGRCYRVTWFTSWSPCYDCARHVA DFLRGNPNLSLRIFTARLYFCEDRKAEPEGLRRLAEAGVQIAIMTFKD YFYCWNTFVENHERTFKAWEGLHENSVRLSRQLRRILQ |
| A3A (SEQ ID NO: 29) | MEASPASGPRHLMDPHIFTSNFNNGIGRHKTYLCYEVERLDNGTSVK MDQHRGFLHNQAKNLLCGFYGRHAELRFLDLVPSLQLDPAQIYRVT WFISWSPCFSAGCAGEVRAFLQENTHVRLRIFAARIYDYDYLYKEAL QMLRDAGAQVSIMTYDEFKHCWDTFVDHQGCPFQPWDGLDEHSQA LSGRLRAILQNQGN |
| ABE8_20 (SEQ ID NO: 30) | MSEVEFSHEYWMRHALTLAKRARDEREVPVGAVLVLNNRVIGEGW NRAIGLHDPTAHAEIMALRQGGLVMQNYRLYDATLYSTFEPCVMCA GAMIHSRIGRVVFGVRNAKTGAAGSLMDVLHHPGMNHRVEITEGIL ADECAALLCRFFRMPRRVFNAQKKAQSSTD |
| UGI (SEQ ID NO: 31) | MTNLSDIIEKETGKQLVIQESILMLPEEVEEVIGNKPESDILVHTAYDE STDENVMLLTSDAPEYKPWALVIQDSNGENKIKML |
| SGGS (SEQ ID NO: 32) | SGGS |
| SV40NLS (SEQ ID NO: 33) | PKKKRKV |
| mH6 (SEQ ID NO: 34) | MKIEEGKGHHHHHH |
| 3xGGGGS (SEQ ID NO: 35) | GGGGSGGGGSGGGGS |

TABLE 3-continued

| Base editing construct components | |
|---|---|
| Component | Sequence |
| Nuclear plasma NLS (npNLS) (SEQ ID NO: 36) | KRPAATKKAGQAKKKK |
| T2A (SEQ ID NO: 37) | EGRGSLLTCGDVEENPGP |
| bipartite NLS (bpNLS) (SEQ ID NO: 38) | MKRTADGSEFESPKKKRKV |
| P2A (SEQ ID NO: 39) | ATNFSLLKQAGDVEENPGP |
| 2xSGGS-XTEN-2xSGGS (SEQ ID NO: 40) | SGGSSGGSSGSETPGTSESATPESSGGSSGGS |

TABLE 4

| Base editing constructs. | |
|---|---|
| Construct | Sequence |
| bpNLS-AID-SGGS-UGI-2xSGGS-XTEN-2xSGGS-dCas12i2(D599A)-npNLS (SEQ ID NO: 41) | MKRTADGSEFESPKKKRKV-MDPATFTYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYFCEDRKAEPEGLRRLAEAGVQIAIMTFKDYFYCWNTFVENHERTFKAWEGLHENSVRLSRQLRRILQ-SGGS-MTNLSDIIEKETGKQLVIQESILMLPEEVEEVIGNKPESDILVHTAYDESTDENVMLLTSDAPEYKPWALVIQDSNGENKIKML-SGGSSGGSSGSETPGTSESATPESSGGSSGGS-MSSAIKSYKSVLRPNERKNQLLKSTIQCLEDGSAFFFKMLQGLFGGITPEIVRFSTEQEKQQQDIALWCAVNWFRPVSQDSLTHTIASDNLVEKFEEYYGGTASDAIKQYFSASIGESYYWNDCRQQYYDLCRELGVEVSDLTHDLEILCREKCLAVATESNQNNSIISVLFGTGEKEDRSVKLRITKKILEAISNLKEIPKNVAPIQEIILNVAKATKETFRQVYAGNLGAPSTLEKFIAKDGQKEFDLKKLQTDLKKVIRGKSKERDWCCQEELRSYVEQNTIQYDLWAWGEMFNKAHTALKIKSTRNYNFAKQRLEQFKEIQSLNNLLVVKKLNDFFDSEFFSGEETYTICVHHLGGKDLSKLYKAWEDDPADPENAIVVLCDDLKNNFKKEPIRNILRYIFTIRQECSAQDILAAAKYNQQLDRYKSQKANPSVLGNQGFTWTNAVILPEKAQRNDRPNSLDLRIWLYLKLRHPDGRWKKHHIPFYDTRFFQEIYAAGNSPVDTCQFRTPRFGYHLPKLTDQTAIRVNKKHVKAAKTEARIRLAIQQGTLPVSNLKITEISATINSKGQVRIPVKFRVGRQKGTLQIGDRFCGYAQNQTASHAYSLWEVVKEGQYHKELGCFVRFISSGDIVSITENRGNQFDQLSYEGLAYPQYADWRKKASKFVSLWQITKKNKKKEIVTVEAKEKFDAICKYQPRLYKFNKEYAYLLRDIVRGKSLVELQQIRQEIFRFIEQDCGVTRLGSLSLSTLETVKAVKGIIYSYFSTALNASKNNPISDEQRKEFDPELFALLEKLELIRTRKKKQKVERIANSLIQTCLENNIKFIRGEGDLSTTNNATKKKANSRSMDWLARGVFNKIRQLAPMHNITLFGCGSLYTSHQDPLVHRNPDKAMKCRWAAIPVKDIGDWVLRKLSQNLRAKNRGTGEYYHQGVKEFLSHYELQDLEEELLKWRSDRKSNIPCWVLQNRLAEKLGNKEAVVYIPVRGGRIYFATHKVATGAVSIVFDQKQVWVCNADHVAAANIALTGKGIGEQSSDEENPDGSRIKLQLTS-KRPAATKKAGQAKKKK |
| bpNLS-AID-2xSGGS-XTEN-2xSGGS-dCas12i2(D599A)-npNLS-3xGGGGS-UGI (SEQ ID NO: 42) | MKRTADGSEFESPKKKRKV-MDPATFTYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYFCEDRKAEPEGLRRLAEAGVQIAIMTFKDYFYCWNTFVENHERTFKAWEGLHENSVRLSRQLRRILQ-SGGSSGGSSGSETPGTSESATPESSGGSSGGS-MSSAIKSYKSVLRPNERKNQLLKSTIQCLEDGSAFFFKMLQGLFGGITPEIVRFSTEQEKQQQDIALWCAVNWFRPVSQDSLTHTIASDNLVEKFEEYYGGTASDAIKQYFSASIGESYYWNDCRQQYYDLCRELGVEVSDLTHDLEILCREKCLAVATESNQNNSIISVLFGTGEKEDRSVKLRITKKILEAISNLKEIPKNVAPIQEIILNVAKATKETFRQVYAGNLGAPSTLEKFIAKDGQKEFDLKKLQTDLKKVIRGKSKERDWCCQEELRSYVEQNTIQYDLWAWGEMFNKAHTALKIKSTRNYNFAKQRLEQFKEIQSLNNLLVVKKLNDFFDSEFFSGEETYTICVHHLGGKDLSKLYKAWEDDPADPENAIVVLCDDLKNNFKK |

TABLE 4-continued

| Base editing constructs. | |
|---|---|
| Construct | Sequence |
| | EPIRNILRYIFTIRQECSAQDILAAAKYNQQLDRYKSQKANPSVL GNQGFTWTNAVILPEKAQRNDRPNSLDLRIWLYLKLRHPDGRW KKHHIPFYDTRFFQEIYAAGNSPVDTCQFRTPRFGYHLPKLTDQ TAIRVNKKHVKAAKTEARIRLAIQQGTLPVSNLKITEISATINSK GQVRIPVKFRVGRQKGTLQIGDRFCGYAQNQTASHAYSLWEVV KEGQYHKELGCFVRFISSGDIVSITENRGNQFDQLSYEGLAYPQ YADWRKKASKFVSLWQITKKNKKKEIVTVEAKEKFDAICKYQP RLYKFNKEYAYLLRDIVRGKSLVELQQIRQEIFRFIEQDCGVTRL GSLSLSTLETVKAVKGIIYSYFSTALNASKNNPISDEQRKEFDPEL FALLEKLELIRTRKKKQKVERIANSLIQTCLENNIKFIRGEGDLST TNNATKKKANSRSMDWLARGVFNKIRQLAPMHNITLFGCGSLY TSHQDPLVHRNPDKAMKCRWAAIPVKDIGDWVLRKLSQNLRA KNRGTGEYYHQGVKEFLSHYELQDLEEELLKWRSDRKSNIPCW VLQNRLAEKLGNKEAVVYIPVRGGRIYFATHKVATGAVSIVFD QKQVWVCNADHVAAANIALTGKGIGEQSSDEENPDGSRIKLQL TS-KRPAATKKAGQAKKKK-GGGGSGGGGSGGGGS- MTNLSDIIEKETGKQLVIQESILMLPEEVEEVIGNKPESDILVHTA YDESTDENVMLLTSDAPEYKPWALVIQDSNGENKIKML |
| mH6-dCas12i2(D599A)-npNLS-2xSGGS-XTEN-2xSGGS-AID-SGGS-UGI-SGGS-bpNLS (SEQ ID NO: 43) | MKIEEGKGHHHHHH- MSSAIKSYKSVLRPNERKNQLLKSTIQCLEDGSAFFFKMLQGLF GGITPEIVRFSTEQEKQQQDIALWCAVNWFRPVSQDSLTHTIAS DNLVEKFEEYYGGTASDAIKQYFSASIGESYYWNDCRQQYYDL CRELGVEVSDLTHDLEILCREKCLAVATESNQNNSIISVLFGTGE KEDRSVKLRITKKILEAISNLKEIPKNVAPIQEIILNVAKATKETF RQVYAGNLGAPSTLEKFIAKDGQKEFDLKKLQTDLKKVIRGKS KERDWCCQEELRSYVEQNTIQYDLWAWGEMFNKAHTALKIKS TRNYNFAKQRLEQFKEIQSLNNLLVVKKLNDFFDSEFFSGEETY TICVHHLGGKDLSKLYKAWEDDPADPENAIVVLCDDLKNNFKK EPIRNILRYIFTIRQECSAQDILAAAKYNQQLDRYKSQKANPSVL GNQGFTWTNAVILPEKAQRNDRPNSLDLRIWLYLKLRHPDGRW KKHHIPFYDTRFFQEIYAAGNSPVDTCQFRTPRFGYHLPKLTDQ TAIRVNKKHVKAAKTEARIRLAIQQGTLPVSNLKITEISATINSK GQVRIPVKFRVGRQKGTLQIGDRFCGYAQNQTASHAYSLWEVV KEGQYHKELGCFVRFISSGDIVSITENRGNQFDQLSYEGLAYPQ YADWRKKASKFVSLWQITKKNKKKEIVTVEAKEKFDAICKYQP RLYKFNKEYAYLLRDIVRGKSLVELQQIRQEIFRFIEQDCGVTRL GSLSLSTLETVKAVKGIIYSYFSTALNASKNNPISDEQRKEFDPEL FALLEKLELIRTRKKKQKVERIANSLIQTCLENNIKFIRGEGDLST TNNATKKKANSRSMDWLARGVFNKIRQLAPMHNITLFGCGSLY TSHQDPLVHRNPDKAMKCRWAAIPVKDIGDWVLRKLSQNLRA KNRGTGEYYHQGVKEFLSHYELQDLEEELLKWRSDRKSNIPCW VLQNRLAEKLGNKEAVVYIPVRGGRIYFATHKVATGAVSIVFD QKQVWVCNADHVAAANIALTGKGIGEQSSDEENPDGSRIKLQL TS-KRPAATKKAGQAKKKK- SGGSSGGSSGSETPGTSESATPESSGGSSGGS- MDPATFTYQFKNVRWAKGRRETYLCYVVKRRDSATSFSLDFG YLRNKNGCHVELLFLRYISDWDLDPGRCYRVTWFTSWSPCYDC ARHVADFLRGNPNLSLRIFTARLYFCEDRKAEPEGLRRLAEAGV QIAIMTFKDYFYCWNTFVENHERTFKAWEGLHENSVRLSRQLR RILQ-SGGS- MTNLSDIIEKETGKQLVIQESILMLPEEVEEVIGNKPESDILVHTA YDESTDENVMLLTSDAPEYKPWALVIQDSNGENKIKML- SGGS-MKRTADGSEFESPKKKRKV |
| bpNLS-A3A-SGGS-UGI-2xSGGS-XTEN-2xSGGS-dCas12i2(D599A)-npNLS (SEQ ID NO: 44) | MKRTADGSEFESPKKKRKV- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGS- MTNLSDIIEKETGKQLVIQESILMLPEEVEEVIGNKPESDILVHTA YDESTDENVMLLTSDAPEYKPWALVIQDSNGENKIKML- SGGSSGGSSGSETPGTSESATPESSGGSSGGS- MSSAIKSYKSVLRPNERKNQLLKSTIQCLEDGSAFFFKMLQGLF GGITPEIVRFSTEQEKQQQDIALWCAVNWFRPVSQDSLTHTIAS DNLVEKFEEYYGGTASDAIKQYFSASIGESYYWNDCRQQYYDL CRELGVEVSDLTHDLEILCREKCLAVATESNQNNSIISVLFGTGE KEDRSVKLRITKKILEAISNLKEIPKNVAPIQEIILNVAKATKETF RQVYAGNLGAPSTLEKFIAKDGQKEFDLKKLQTDLKKVIRGKS KERDWCCQEELRSYVEQNTIQYDLWAWGEMFNKAHTALKIKS TRNYNFAKQRLEQFKEIQSLNNLLVVKKLNDFFDSEFFSGEETY TICVHHLGGKDLSKLYKAWEDDPADPENAIVVLCDDLKNNFKK EPIRNILRYIFTIRQECSAQDILAAAKYNQQLDRYKSQKANPSVL GNQGFTWTNAVILPEKAQRNDRPNSLDLRIWLYLKLRHPDGRW KKHHIPFYDTRFFQEIYAAGNSPVDTCQFRTPRFGYHLPKLTDQ |

TABLE 4-continued

| Base editing constructs. | |
|---|---|
| Construct | Sequence |
| | TAIRVNKKHVKAAKTEARIRLAIQQGTLPVSNLKITEISATINSK GQVRIPVKFRVGRQKGTLQIGDRFCGYAQNQTASHAYSLWEVV KEGQYHKELGCFVRFISSGDIVSITENRGNQFDQLSYEGLAYPQ YADWRKKASKFVSLWQITKKNKKKEIVTVEAKEKFDAICKYQP RLYKFNKEYAYLLRDIVRGKSLVELQQIRQEIFRFIEQDCGVTRL GSLSLSTLETVKAVKGIIYSYFSTALNASKNNPISDEQRKEFDPEL FALLEKLELIRTRKKKQKVERIANSLIQTCLENNIKFIRGEGDLST TNNATKKKANSRSMDWLARGVFNKIRQLAPMHNITLFGCGSLY TSHQDPLVHRNPDKAMKCRWAAIPVKDIGDWVLRKLSQNLRA KNRGTGEYYHQGVKEFLSHYELQDLEEELLKWRSDRKSNIPCW VLQNRLAEKLGNKEAVVYIPVRGGRIYFATHKVATGAVSIVFD QKQVWVCNADHVAAANIALTGKGIGEQSSDEENPDGSRIKLQL TS-KRPAATKKAGQAKKKK |
| bpNLS-A3A-2xSGGS-XTEN-2xSGGS-dCas12i2(D599A)-npNLS-3xGGGGS-UGI (SEQ ID NO: 45) | MKRTADGSEFESPKKKRKV-MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGSSGGSSGSETPGTSESATPESSGGSSGGS-MSSAIKSYKSVLRPNERKNQLLKSTIQCLEDGSAFFFKMLQGLF GGITPEIVRFSTEQEKQQQDIALWCAVNWFRPVSQDSLTHTIAS DNLVEKFEEYYGGTASDAIKQYFSASIGESYYWNDCRQQYYDL CRELGVEVSDLTHDLEILCREKCLAVATESNQNNSIISVLFGTGE KEDRSVKLRITKKILEAISNLKEIPKNVAPIQEIILNVAKATKETF RQVYAGNLGAPSTLEKFIAKDGQKEFDLKKLQTDLKKVIRGKS KERDWCCQEELRSYVEQNTIQYDLWAWGEMFNKAHTALKIKS TRNYNFAKQRLEQFKEIQSLNNLLVVKKLNDFFDSEFFSGEETY TICVHHLGGKDLSKLYKAWEDDPADPENAIVVLCDDLKNNFKK EPIRNILRYIFTIRQECSAQDILAAAKYNQQLDRYKSQKANPSVL GNQGFTWTNAVILPEKAQRNDRPNSLDLRIWLYLKLRHPDGRW KKHHIPFYDTRFFQEIYAAGNSPVDTCQFRTPRFGYHLPKLTDQ TAIRVNKKHVKAAKTEARIRLAIQQGTLPVSNLKITEISATINSK GQVRIPVKFRVGRQKGTLQIGDRFCGYAQNQTASHAYSLWEVV KEGQYHKELGCFVRFISSGDIVSITENRGNQFDQLSYEGLAYPQ YADWRKKASKFVSLWQITKKNKKKEIVTVEAKEKFDAICKYQP RLYKFNKEYAYLLRDIVRGKSLVELQQIRQEIFRFIEQDCGVTRL GSLSLSTLETVKAVKGIIYSYFSTALNASKNNPISDEQRKEFDPEL FALLEKLELIRTRKKKQKVERIANSLIQTCLENNIKFIRGEGDLST TNNATKKKANSRSMDWLARGVFNKIRQLAPMHNITLFGCGSLY TSHQDPLVHRNPDKAMKCRWAAIPVKDIGDWVLRKLSQNLRA KNRGTGEYYHQGVKEFLSHYELQDLEEELLKWRSDRKSNIPCW VLQNRLAEKLGNKEAVVYIPVRGGRIYFATHKVATGAVSIVFD QKQVWVCNADHVAAANIALTGKGIGEQSSDEENPDGSRIKLQL TS-KRPAATKKAGQAKKKK-GGGGSGGGGSGGGGS-MTNLSDIIEKETGKQLVIQESILMLPEEVEEVIGNKPESDILVHTA YDESTDENVMLLTSDAPEYKPWALVIQDSNGENKIKML |
| mH6-dCas12i2(D599A)-npNLS-2xSGGS-XTEN-2xSGGS-A3A-SGGS-UGI-SGGS-bpNLS (SEQ ID NO: 46) | MKIEEGKGHHHHHH-MSSAIKSYKSVLRPNERKNQLLKSTIQCLEDGSAFFFKMLQGLF GGITPEIVRFSTEQEKQQQDIALWCAVNWFRPVSQDSLTHTIAS DNLVEKFEEYYGGTASDAIKQYFSASIGESYYWNDCRQQYYDL CRELGVEVSDLTHDLEILCREKCLAVATESNQNNSIISVLFGTGE KEDRSVKLRITKKILEAISNLKEIPKNVAPIQEIILNVAKATKETF RQVYAGNLGAPSTLEKFIAKDGQKEFDLKKLQTDLKKVIRGKS KERDWCCQEELRSYVEQNTIQYDLWAWGEMFNKAHTALKIKS TRNYNFAKQRLEQFKEIQSLNNLLVVKKLNDFFDSEFFSGEETY TICVHHLGGKDLSKLYKAWEDDPADPENAIVVLCDDLKNNFKK EPIRNILRYIFTIRQECSAQDILAAAKYNQQLDRYKSQKANPSVL GNQGFTWTNAVILPEKAQRNDRPNSLDLRIWLYLKLRHPDGRW KKHHIPFYDTRFFQEIYAAGNSPVDTCQFRTPRFGYHLPKLTDQ TAIRVNKKHVKAAKTEARIRLAIQQGTLPVSNLKITEISATINSK GQVRIPVKFRVGRQKGTLQIGDRFCGYAQNQTASHAYSLWEVV KEGQYHKELGCFVRFISSGDIVSITENRGNQFDQLSYEGLAYPQ YADWRKKASKFVSLWQITKKNKKKEIVTVEAKEKFDAICKYQP RLYKFNKEYAYLLRDIVRGKSLVELQQIRQEIFRFIEQDCGVTRL GSLSLSTLETVKAVKGIIYSYFSTALNASKNNPISDEQRKEFDPEL FALLEKLELIRTRKKKQKVERIANSLIQTCLENNIKFIRGEGDLST TNNATKKKANSRSMDWLARGVFNKIRQLAPMHNITLFGCGSLY TSHQDPLVHRNPDKAMKCRWAAIPVKDIGDWVLRKLSQNLRA KNRGTGEYYHQGVKEFLSHYELQDLEEELLKWRSDRKSNIPCW VLQNRLAEKLGNKEAVVYIPVRGGRIYFATHKVATGAVSIVFD QKQVWVCNADHVAAANIALTGKGIGEQSSDEENPDGSRIKLQL TS-KRPAATKKAGQAKKKK-SGGSSGGSSGSETPGTSESATPESSGGSSGGS- |

TABLE 4-continued

| Base editing constructs. | |
|---|---|
| Construct | Sequence |
| | MEASPASGPRHLMDPHIFTSNFNNGIGRHKTYLCYEVERLDNGT<br>SVKMDQHRGFLHNQAKNLLCGFYGRHAELRFLDLVPSLQLDPA<br>QIYRVTWFISWSPCFSAGCAGEVRAFLQENTHVRLRIFAARIYD<br>YDYLYKEALQMLRDAGAQVSIMTYDEFKHCWDTFVDHQGCPF<br>QPWDGLDEHSQALSGRLRAILQNQGN-SGGS-<br>MTNLSDIIEKETGKQLVIQESILMLPEEVEEVIGNKPESDILVHTA<br>YDESTDENVMLLTSDAPEYKPWALVIQDSNGENKIKML-<br>SGGS-MKRTADGSEFESPKKKRKV |
| bpNLS-AID-SGGS-<br>UGI-2xSGGS-XTEN-<br>2xSGGS-<br>dCas9(D10A_H840A)-<br>npNLS<br>(SEQ ID NO: 47) | MKRTADGSEFESPKKKRKV-<br>MDPATFTYQFKNVRWAKGRRETYLCYVVKRRDSATSFSLDFG<br>YLRNKNGCHVELLFLRYISDWDLDPGRCYRVTWFTSWSPCYDC<br>ARHVADFLRGNPNLSLRIFTARLYFCEDRKAEPEGLRRLAEAGV<br>QIAIMTFKDYFYCWNTFVENHERTFKAWEGLHENSVRLSRQLR<br>RILQ-SGGS-<br>MTNLSDIIEKETGKQLVIQESILMLPEEVEEVIGNKPESDILVHTA<br>YDESTDENVMLLTSDAPEYKPWALVIQDSNGENKIKML-<br>SGGSSGGSSGSETPGTSESATPESSGGSSGGS-<br>MDKKYSIGLAIGTNSVGWAVITDEYKVPSKKFKVLGNTDRHSI<br>KKNLIGALLFDSGETAEATRLKRTARRRYTRRKNRICYLQEIFSN<br>EMAKVDDSFFHRLEESFLVEEDKKHERHPIFGNIVDEVAYHEKY<br>PTIYHLRKKLVDSTDKADLRLIYLALAHMIKFRGHFLIEGDLNP<br>DNSDVDKLFIQLVQTYNQLFEENPINASGVDAKAILSARLSKSR<br>RLENLIAQLPGEKKNGLFGNLIALSLGLTPNFKSNFDLAEDAKL<br>QLSKDTYDDDLDNLLAQIGDQYADLFLAAKNLSDAILLSDILRV<br>NTEITKAPLSASMIKRYDEHHQDLTLLKALVRQQLPEKYKEIFF<br>DQSKNGYAGYIDGGASQEEFYKFIKPILEKMDGTEELLVKLNRE<br>DLLRKQRTFDNGSIPHQIHLGELHAILRRQEDFYPFLKDNREKIE<br>KILTFRIPYYVGPLARGNSRFAWMTRKSEETITPWNFEEVVDKG<br>ASAQSFIERMTNFDKNLPNEKVLPKHSLLYEYFTVYNELTKVKY<br>VTEGMRKPAFLSGEQKKAIVDLLFKTNRKVTVKQLKEDYFKKI<br>ECFDSVEISGVEDRFNASLGTYHDLLKIIKDKDFLDNEENEDILE<br>DIVLTLTLFEDREMIEERLKTYAHLFDDKVMKQLKRRRYTGWG<br>RLSRKLINGIRDKQSGKTILDFLKSDGFANRNFMQLIHDDSLTFK<br>EDIQKAQVSGQGDSLHEHIANLAGSPAIKKGILQTVKVVDELVK<br>VMGRHKPENIVIEMARENQTTQKGQKNSRERMKRIEEGIKELGS<br>QILKEHPVENTQLQNEKLYLYYLQNGRDMYVDQELDINRLSDY<br>DVDAIVPQSFLKDDSIDNKVLTRSDKNRGKSDNVPSEEVVKKM<br>KNYWRQLLNAKLITQRKFDNLTKAERGGLSELDKAGFIKRQLV<br>ETRQITKHVAQILDSRMNTKYDENDKLIREVKVITLKSKLVSDF<br>RKDFQFYKVREINNYHHAHDAYLNAVVGTALIKKYPKLESEFV<br>YGDYKVYDVRKMIAKSEQEIGKATAKYFFYSNIMNFFKTEITLA<br>NGEIRKRPLIETNGETGEIVWDKGRDFATVRKVLSMPQVNIVKK<br>TEVQTGGFSKESILPKRNSDKLIARKKDWDPKKYGGFDSPTVAY<br>SVLVVAKVEKGKSKKLKSVKELLGITIMERSSFEKNPIDFLEAK<br>GYKEVKKDLIIKLPKYSLFELENGRKRMLASAGELQKGNELALP<br>SKYVNFLYLASHYEKLKGSPEDNEQKQLFVEQHKHYLDEIIEQI<br>SEFSKRVILADANLDKVLSAYNKHRDKPIREQAENIIHLFTLTNL<br>GAPAAFKYFDTTIDRKRYTSTKEVLDATLIHQSITGLYETRIDLS<br>QLGGD-KRPAATKKAGQAKKKK |
| bpNLS-AID-2xSGGS-<br>XTEN-2xSGGS-<br>dCas9(D10A_H840A)-<br>npNLS-3xGGGGS-UGI<br>(SEQ ID NO: 48) | MKRTADGSEFESPKKKRKV-<br>MDPATFTYQFKNVRWAKGRRETYLCYVVKRRDSATSFSLDFG<br>YLRNKNGCHVELLFLRYISDWDLDPGRCYRVTWFTSWSPCYDC<br>ARHVADFLRGNPNLSLRIFTARLYFCEDRKAEPEGLRRLAEAGV<br>QIAIMTFKDYFYCWNTFVENHERTFKAWEGLHENSVRLSRQLR<br>RILQ-SGGSSGGSSGSETPGTSESATPESSGGSSGGS-<br>MDKKYSIGLAIGTNSVGWAVITDEYKVPSKKFKVLGNTDRHSI<br>KKNLIGALLFDSGETAEATRLKRTARRRYTRRKNRICYLQEIFSN<br>EMAKVDDSFFHRLEESFLVEEDKKHERHPIFGNIVDEVAYHEKY<br>PTIYHLRKKLVDSTDKADLRLIYLALAHMIKFRGHFLIEGDLNP<br>DNSDVDKLFIQLVQTYNQLFEENPINASGVDAKAILSARLSKSR<br>RLENLIAQLPGEKKNGLFGNLIALSLGLTPNFKSNFDLAEDAKL<br>QLSKDTYDDDLDNLLAQIGDQYADLFLAAKNLSDAILLSDILRV<br>NTEITKAPLSASMIKRYDEHHQDLTLLKALVRQQLPEKYKEIFF<br>DQSKNGYAGYIDGGASQEEFYKFIKPILEKMDGTEELLVKLNRE<br>DLLRKQRTFDNGSIPHQIHLGELHAILRRQEDFYPFLKDNREKIE<br>KILTFRIPYYVGPLARGNSRFAWMTRKSEETITPWNFEEVVDKG<br>ASAQSFIERMTNFDKNLPNEKVLPKHSLLYEYFTVYNELTKVKY<br>VTEGMRKPAFLSGEQKKAIVDLLFKTNRKVTVKQLKEDYFKKI<br>ECFDSVEISGVEDRFNASLGTYHDLLKIIKDKDFLDNEENEDILE<br>DIVLTLTLFEDREMIEERLKTYAHLFDDKVMKQLKRRRYTGWG<br>RLSRKLINGIRDKQSGKTILDFLKSDGFANRNFMQLIHDDSLTFK<br>EDIQKAQVSGQGDSLHEHIANLAGSPAIKKGILQTVKVVDELVK<br>VMGRHKPENIVIEMARENQTTQKGQKNSRERMKRIEEGIKELGS<br>QILKEHPVENTQLQNEKLYLYYLQNGRDMYVDQELDINRLSDY |

TABLE 4-continued

| Base editing constructs. | |
|---|---|
| Construct | Sequence |
| | DVDAIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK-GGGGSGGGGSGGGGS- MTNLSDIIEKETGKQLVIQESILMLPEEVEEVIGNKPESDILVHTA YDESTDENVMLLTSDAPEYKPWALVIQDSNGENKIKML |
| mH6-dCas9(D10A_H840A)-npNLS-2xSGGS-XTEN-2xSGGS-AID-SGGS-UGI-SGGS-bpNLS (SEQ ID NO: 49) | MKIEEGKGHHHHHH- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDAIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK- SGGSSGGSSGSETPGTSESATPESSGGSSGGS- MDPATFTYQFKNVRWAKGRRETYLCYVVKRRDSATSFSLDFG YLRNKNGCHVELLFLRYISDWDLDPGRCYRVTWFTSWSPCYDC ARHVADFLRGNPNLSLRIFTARLYFCEDRKAEPEGLRRLAEAGV QIAIMTFKDYFYCWNTFVENHERTFKAWEGLHENSVRLSRQLR RILQ-SGGS- MTNLSDIIEKETGKQLVIQESILMLPEEVEEVIGNKPESDILVHTA YDESTDENVMLLTSDAPEYKPWALVIQDSNGENKIKML- SGGS-MKRTADGSEFESPKKKRKV |
| bpNLS-A3A-SGGS-UGI-2xSGGS-XTEN-2xSGGS-dCas9(D10A_H840A)-npNLS (SEQ ID NO: 50) | MKRTADGSEFESPKKKRKV- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGS- MTNLSDIIEKETGKQLVIQESILMLPEEVEEVIGNKPESDILVHTA YDESTDENVMLLTSDAPEYKPWALVIQDSNGENKIKML- SGGSSGGSSGSETPGTSESATPESSGGSSGGS- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF |

TABLE 4-continued

Base editing constructs.

| Construct | Sequence |
|---|---|
| | DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDAIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK |
| bpNLS-A3A-2xSGGS-XTEN-2xSGGS-dCas9(D10A_H840A)-npNLS-3xGGGGS-UGI (SEQ ID NO: 51) | MKRTADGSEFESPKKKRKV-MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGSSGGSSGSETPGTSESATPESSGGSSGGS-MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDAIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK-GGGGSGGGGSGGGGS-MTNLSDIIEKETGKQLVIQESILMLPEEVEEVIGNKPESDILVHTA YDESTDENVMLLTSDAPEYKPWALVIQDSNGENKIKML |
| mH6-dCas9(D10A_H840A)-npNLS-2xSGGS-XTEN-2xSGGS-A3A-SGGS-UGI-SGGS-bpNLS (SEQ ID NO: 52) | MKIEEGKGHHHHHH-MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF |

TABLE 4-continued

| Base editing constructs. | |
|---|---|
| Construct | Sequence |
| | DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDAIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK- SGGSSGGSSGSETPGTSESATPESSGGSSGGS- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGS- MTNLSDIIEKETGKQLVIQESILMLPEEVEEVIGNKPESDILVHTA YDESTDENVMLLTSDAPEYKPWALVIQDSNGENKIKML- SGGS-MKRTADGSEFESPKKKRKV |
| bpNLS-AID-SGGS-UGI-2xSGGS-XTEN-2xSGGS-nCas9(D10A)-npNLS (SEQ ID NO: 53) | MKRTADGSEFESPKKKRKV- MDPATFTYQFKNVRWAKGRRETYLCYVVKRRDSATSFSLDFG YLRNKNGCHVELLFLRYISDWDLDPGRCYRVTWFTSWSPCYDC ARHVADFLRGNPNLSLRIFTARLYFCEDRKAEPEGLRRLAEAGV QIAIMTFKDYFYCWNTFVENHERTFKAWEGLHENSVRLSRQLR RILQ-SGGS- MTNLSDIIEKETGKQLVIQESILMLPEEVEEVIGNKPESDILVHTA YDESTDENVMLLTSDAPEYKPWALVIQDSNGENKIKML- SGGSSGGSSGSETPGTSESATPESSGGSSGGS- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDHIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK |

TABLE 4-continued

Base editing constructs.

| Construct | Sequence |
|---|---|
| bpNLS-AID-2xSGGS-XTEN-2xSGGS-nCas9(D10A)-npNLS-3xGGGGS-UGI (SEQ ID NO: 54) | MKRTADGSEFESPKKKRKV-<br>MDPATFTYQFKNVRWAKGRRETYLCYVVKRRDSATSFSLDFG<br>YLRNKNGCHVELLFLRYISDWDLDPGRCYRVTWFTSWSPCYDC<br>ARHVADFLRGNPNLSLRIFTARLYFCEDRKAEPEGLRRLAEAGV<br>QIAIMTFKDYFYCWNTFVENHERTFKAWEGLHENSVRLSRQLR<br>RILQ-SGGSSGGSSGSETPGTSESATPESSGGSSGGS-<br>MDKKYSIGLAIGTNSVGWAVITDEYKVPSKKFKVLGNTDRHSI<br>KKNLIGALLFDSGETAEATRLKRTARRRYTRRKNRICYLQEIFSN<br>EMAKVDDSFFHRLEESFLVEEDKKHERHPIFGNIVDEVAYHEKY<br>PTIYHLRKKLVDSTDKADLRLIYLALAHMIKFRGHFLIEGDLNP<br>DNSDVDKLFIQLVQTYNQLFEENPINASGVDAKAILSARLSKSR<br>RLENLIAQLPGEKKNGLFGNLIALSLGLTPNFKSNFDLAEDAKL<br>QLSKDTYDDDLDNLLAQIGDQYADLFLAAKNLSDAILLSDILRV<br>NTEITKAPLSASMIKRYDEHHQDLTLLKALVRQQLPEKYKEIFF<br>DQSKNGYAGYIDGGASQEEFYKFIKPILEKMDGTEELLVKLNRE<br>DLLRKQRTFDNGSIPHQIHLGELHAILRRQEDFYPFLKDNREKIE<br>KILTFRIPYYVGPLARGNSRFAWMTRKSEETITPWNFEEVVDKG<br>ASAQSFIERMTNFDKNLPNEKVLPKHSLLYEYFTVYNELTKVKY<br>VTEGMRKPAFLSGEQKKAIVDLLFKTNRKVTVKQLKEDYFKKI<br>ECFDSVEISGVEDRFNASLGTYHDLLKIIKDKDFLDNEENEDILE<br>DIVLTLTLFEDREMIEERLKTYAHLFDDKVMKQLKRRRYTGWG<br>RLSRKLINGIRDKQSGKTILDFLKSDGFANRNFMQLIHDDSLTFK<br>EDIQKAQVSGQGDSLHEHIANLAGSPAIKKGILQTVKVVDELVK<br>VMGRHKPENIVIEMARENQTTQKGQKNSRERMKRIEEGIKELGS<br>QILKEHPVENTQLQNEKLYLYYLQNGRDMYVDQELDINRLSDY<br>DVDHIVPQSFLKDDSIDNKVLTRSDKNRGKSDNVPSEEVVKKM<br>KNYWRQLLNAKLITQRKFDNLTKAERGGLSELDKAGFIKRQLV<br>ETRQITKHVAQILDSRMNTKYDENDKLIREVKVITLKSKLVSDF<br>RKDFQFYKVREINNYHHAHDAYLNAVVGTALIKKYPKLESEFV<br>YGDYKVYDVRKMIAKSEQEIGKATAKYFFYSNIMNFFKTEITLA<br>NGEIRKRPLIETNGETGEIVWDKGRDFATVRKVLSMPQVNIVKK<br>TEVQTGGFSKESILPKRNSDKLIARKKDWDPKKYGGFDSPTVAY<br>SVLVVAKVEKGKSKKLKSVKELLGITIMERSSFEKNPIDFLEAK<br>GYKEVKKDLIIKLPKYSLFELENGRKRMLASAGELQKGNELALP<br>SKYVNFLYLASHYEKLKGSPEDNEQKQLFVEQHKHYLDEIIEQI<br>SEFSKRVILADANLDKVLSAYNKHRDKPIREQAENIIHLFTLTNL<br>GAPAAFKYFDTTIDRKRYTSTKEVLDATLIHQSITGLYETRIDLS<br>QLGGD-KRPAATKKAGQAKKKK-GGGGSGGGGSGGGGS-<br>MTNLSDIIEKETGKQLVIQESILMLPEEVEEVIGNKPESDILVHTA<br>YDESTDENVMLLTSDAPEYKPWALVIQDSNGENKIKML |
| mH6-nCas9(D10A)-npNLS-2xSGGS-XTEN-2xSGGS-AID-SGGS-UGI-SGGS-bpNLS (SEQ ID NO: 55) | MKIEEGKGHHHHHH-<br>MDKKYSIGLAIGTNSVGWAVITDEYKVPSKKFKVLGNTDRHSI<br>KKNLIGALLFDSGETAEATRLKRTARRRYTRRKNRICYLQEIFSN<br>EMAKVDDSFFHRLEESFLVEEDKKHERHPIFGNIVDEVAYHEKY<br>PTIYHLRKKLVDSTDKADLRLIYLALAHMIKFRGHFLIEGDLNP<br>DNSDVDKLFIQLVQTYNQLFEENPINASGVDAKAILSARLSKSR<br>RLENLIAQLPGEKKNGLFGNLIALSLGLTPNFKSNFDLAEDAKL<br>QLSKDTYDDDLDNLLAQIGDQYADLFLAAKNLSDAILLSDILRV<br>NTEITKAPLSASMIKRYDEHHQDLTLLKALVRQQLPEKYKEIFF<br>DQSKNGYAGYIDGGASQEEFYKFIKPILEKMDGTEELLVKLNRE<br>DLLRKQRTFDNGSIPHQIHLGELHAILRRQEDFYPFLKDNREKIE<br>KILTFRIPYYVGPLARGNSRFAWMTRKSEETITPWNFEEVVDKG<br>ASAQSFIERMTNFDKNLPNEKVLPKHSLLYEYFTVYNELTKVKY<br>VTEGMRKPAFLSGEQKKAIVDLLFKTNRKVTVKQLKEDYFKKI<br>ECFDSVEISGVEDRFNASLGTYHDLLKIIKDKDFLDNEENEDILE<br>DIVLTLTLFEDREMIEERLKTYAHLFDDKVMKQLKRRRYTGWG<br>RLSRKLINGIRDKQSGKTILDFLKSDGFANRNFMQLIHDDSLTFK<br>EDIQKAQVSGQGDSLHEHIANLAGSPAIKKGILQTVKVVDELVK<br>VMGRHKPENIVIEMARENQTTQKGQKNSRERMKRIEEGIKELGS<br>QILKEHPVENTQLQNEKLYLYYLQNGRDMYVDQELDINRLSDY<br>DVDHIVPQSFLKDDSIDNKVLTRSDKNRGKSDNVPSEEVVKKM<br>KNYWRQLLNAKLITQRKFDNLTKAERGGLSELDKAGFIKRQLV<br>ETRQITKHVAQILDSRMNTKYDENDKLIREVKVITLKSKLVSDF<br>RKDFQFYKVREINNYHHAHDAYLNAVVGTALIKKYPKLESEFV<br>YGDYKVYDVRKMIAKSEQEIGKATAKYFFYSNIMNFFKTEITLA<br>NGEIRKRPLIETNGETGEIVWDKGRDFATVRKVLSMPQVNIVKK<br>TEVQTGGFSKESILPKRNSDKLIARKKDWDPKKYGGFDSPTVAY<br>SVLVVAKVEKGKSKKLKSVKELLGITIMERSSFEKNPIDFLEAK<br>GYKEVKKDLIIKLPKYSLFELENGRKRMLASAGELQKGNELALP<br>SKYVNFLYLASHYEKLKGSPEDNEQKQLFVEQHKHYLDEIIEQI<br>SEFSKRVILADANLDKVLSAYNKHRDKPIREQAENIIHLFTLTNL<br>GAPAAFKYFDTTIDRKRYTSTKEVLDATLIHQSITGLYETRIDLS<br>QLGGD-KRPAATKKAGQAKKKK-<br>SGGSSGGSSGSETPGTSESATPESSGGSSGGS-<br>MDPATFTYQFKNVRWAKGRRETYLCYVVKRRDSATSFSLDFG |

TABLE 4-continued

Base editing constructs.

| Construct | Sequence |
|---|---|
| | YLRNKNGCHVELLFLRYISDWDLDPGRCYRVTWFTSWSPCYDC ARHVADFLRGNPNLSLRIFTARLYFCEDRKAEPEGLRRLAEAGV QIAIMTFKDYFYCWNTFVENHERTFKAWEGLHENSVRLSRQLR RILQ-SGGS- MTNLSDIIEKETGKQLVIQESILMLPEEVEEVIGNKPESDILVHTA YDESTDENVMLLTSDAPEYKPWALVIQDSNGENKIKML- SGGS-MKRTADGSEFESPKKKRKV |
| bpNLS-A3A-SGGS-UGI-2xSGGS-XTEN-2xSGGS-nCas9(D10A)-npNLS (SEQ ID NO: 56) | MKRTADGSEFESPKKKRKV- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGS- MTNLSDIIEKETGKQLVIQESILMLPEEVEEVIGNKPESDILVHTA YDESTDENVMLLTSDAPEYKPWALVIQDSNGENKIKML- SGGSSGGSSGSETPGTSESATPESSGGSSGGS- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDHIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK |
| bpNLS-A3A-2xSGGS-XTEN-2xSGGS-nCas9(D10A)-npNLS-3xGGGGS-UGI (SEQ ID NO: 57) | MKRTADGSEFESPKKKRKV- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN- SGGSSGGSSGSETPGTSESATPESSGGSSGGS- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY |

TABLE 4-continued

| Base editing constructs. | |
|---|---|
| Construct | Sequence |
| | DVDHIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK-GGGGSGGGGSGGGGS- MTNLSDIIEKETGKQLVIQESILMLPEEVEEVIGNKPESDILVHTA YDESTDENVMLLTSDAPEYKPWALVIQDSNGENKIKML |
| mH6-nCas9(D10A)-npNLS-2xSGGS-XTEN-2xSGGS-A3A-SGGS-UGI-SGGS-bpNLS (SEQ ID NO: 58) | MKIEEGKGHHHHHH- MDKKYSIGLAIGTNSVGWAVITDEYKVPSKKFKVLGNTDRHSI KKNLIGALLFDSGETAEATRLKRTARRRYTRRKNRICYLQEIFSN EMAKVDDSFFHRLEESFLVEEDKKHERHPIFGNIVDEVAYHEKY PTIYHLRKKLVDSTDKADLRLIYLALAHMIKFRGHFLIEGDLNP DNSDVDKLFIQLVQTYNQLFEENPINASGVDAKAILSARLSKSR RLENLIAQLPGEKKNGLFGNLIALSLGLTPNFKSNFDLAEDAKL QLSKDTYDDDLDNLLAQIGDQYADLFLAAKNLSDAILLSDILRV NTEITKAPLSASMIKRYDEHHQDLTLLKALVRQQLPEKYKEIFF DQSKNGYAGYIDGGASQEEFYKFIKPILEKMDGTEELLVKLNRE DLLRKQRTFDNGSIPHQIHLGELHAILRRQEDFYPFLKDNREKIE KILTFRIPYYVGPLARGNSRFAWMTRKSEETITPWNFEEVVDKG ASAQSFIERMTNFDKNLPNEKVLPKHSLLYEYFTVYNELTKVKY VTEGMRKPAFLSGEQKKAIVDLLFKTNRKVTVKQLKEDYFKKI ECFDSVEISGVEDRFNASLGTYHDLLKIIKDKDFLDNEENEDILE DIVLTLTLFEDREMIEERLKTYAHLFDDKVMKQLKRRRYTGWG RLSRKLINGIRDKQSGKTILDFLKSDGFANRNFMQLIHDDSLTFK EDIQKAQVSGQGDSLHEHIANLAGSPAIKKGILQTVKVVDELVK VMGRHKPENIVIEMARENQTTQKGQKNSRERMKRIEEGIKELGS QILKEHPVENTQLQNEKLYLYYLQNGRDMYVDQELDINRLSDY DVDHIVPQSFLKDDSIDNKVLTRSDKNRGKSDNVPSEEVVKKM KNYWRQLLNAKLITQRKFDNLTKAERGGLSELDKAGFIKRQLV ETRQITKHVAQILDSRMNTKYDENDKLIREVKVITLKSKLVSDF RKDFQFYKVREINNYHHAHDAYLNAVVGTALIKKYPKLESEFV YGDYKVYDVRKMIAKSEQEIGKATAKYFFYSNIMNFFKTEITLA NGEIRKRPLIETNGETGEIVWDKGRDFATVRKVLSMPQVNIVKK TEVQTGGFSKESILPKRNSDKLIARKKDWDPKKYGGFDSPTVAY SVLVVAKVEKGKSKKLKSVKELLGITIMERSSFEKNPIDFLEAK GYKEVKKDLIIKLPKYSLFELENGRKRMLASAGELQKGNELALP SKYVNFLYLASHYEKLKGSPEDNEQKQLFVEQHKHYLDEIIEQI SEFSKRVILADANLDKVLSAYNKHRDKPIREQAENIIHLFTLTNL GAPAAFKYFDTTIDRKRYTSTKEVLDATLIHQSITGLYETRIDLS QLGGD-KRPAATKKAGQAKKKK- SGGSSGGSSGSETPGTSESATPESSGGSSGGS- MEASPASGPRHLMDPHIFTSNFNNGIGRHKTYLCYEVERLDNGT SVKMDQHRGFLHNQAKNLLCGFYGRHAELRFLDLVPSLQLDPA QIYRVTWFISWSPCFSAGCAGEVRAFLQENTHVRLRIFAARIYD YDYLYKEALQMLRDAGAQVSIMTYDEFKHCWDTFVDHQGCPF QPWDGLDEHSQALSGRLRAILQNQGN-SGGS- MTNLSDIIEKETGKQLVIQESILMLPEEVEEVIGNKPESDILVHTA YDESTDENVMLLTSDAPEYKPWALVIQDSNGENKIKML- SGGS-MKRTADGSEFESPKKKRKV |

Each RNA guide sequence with a U6 promoter (Table 5) was cloned into a plasmid backbone and maxi-prepped. A working solution of 144 ng/μL effector plasmids was prepared in water (effector working solution), and a working solution of 50 ng/μL of corresponding guide RNA plasmids was prepared in water (guide working solution).

TABLE 5

| RNA guide sequences | | | |
|---|---|---|---|
| Target | Nuclease | Target Sequence | RNA Guide Sequence |
| AAVS1_T3 | Cas12i2 | GTGAGAATGGTGCGTCCTAG (SEQ ID NO: 66) | AGAAAUCCGUCUUUCAUUGAC GGGUGAGAAUGGUGCGUCCUAG (SEQ ID NO: 86) |

TABLE 5-continued

RNA guide sequences

| Target | Nuclease | Target Sequence | RNA Guide Sequence |
|---|---|---|---|
| AAVS1_T3 | Cas9 | TTGTGAGAATGGTGCGTCCT (SEQ ID NO: 67) | GUUUUAGAGCUAGAAAUAGCA AGUUAAAAUAAGGCUAGUCCG UUAUCAACUUGAAAAAGUGGC ACCGAGUCGGUGCUUGUGAGA AUGGUGCGUCCU (SEQ ID NO: 87) |
| AAVS1_T5 | Cas12i2 | AACTGGCCCTGGCTTTGGCA (SEQ ID NO: 68) | AGAAAUCCGUCUUUCAUUGAC GGAACUGGCCCUGGCUUUGGCA (SEQ ID NO: 88) |
| AAVS1_T5 | Cas9 | GCTTTAACTGGCCCTGGCTT (SEQ ID NO: 69) | GUUUUAGAGCUAGAAAUAGCA AGUUAAAAUAAGGCUAGUCCG UUAUCAACUUGAAAAAGUGGC ACCGAGUCGGUGCAACUGGCC CUGGCUUUGGCA (SEQ ID NO: 89) |
| AAVS1_T6 | Cas12i2 | GTAGCCTCTCCCGCTCTGGT (SEQ ID NO: 70) | AGAAAUCCGUCUUUCAUUGAC GGGUAGCCUCUCCCGCUCUGGU (SEQ ID NO: 90) |
| AAVS1_T6 | Cas9 | CTTTGTAGCCTCTCCCGCTC (SEQ ID NO: 71) | GUUUUAGAGCUAGAAAUAGCA AGUUAAAAUAAGGCUAGUCCG UUAUCAACUUGAAAAAGUGGC ACCGAGUCGGUGCCUUUGUAG CCUCUCCCGCUC (SEQ ID NO: 91) |
| EMX1_T2 | Cas12i2 | GGATGGCGACTTCAGGCACA (SEQ ID NO: 72) | AGAAAUCCGUCUUUCAUUGAC GGGGAUGGCGACUUCAGGCACA (SEQ ID NO: 92) |
| EMX1_T2 | Cas9 | TGGATGGCGACTTCAGGCAC (SEQ ID NO: 73) | GUUUUAGAGCUAGAAAUAGCA AGUUAAAAUAAGGCUAGUCCG UUAUCAACUUGAAAAAGUGGC ACCGAGUCGGUGCUGGAUGGC GACUUCAGGCAC (SEQ ID NO: 93) |
| EMX1_T4 | Cas12i2 | GGGGAGGCCTGGAGTCATGG (SEQ ID NO: 74) | AGAAAUCCGUCUUUCAUUGAC GGGGGGAGGCCUGGAGUCAUGG (SEQ ID NO: 94) |
| EMX1_T4 | Cas9 | TTTGGGGAGGCCTGGAGTCA (SEQ ID NO: 75) | GUUUUAGAGCUAGAAAUAGCA AGUUAAAAUAAGGCUAGUCCG UUAUCAACUUGAAAAAGUGGC ACCGAGUCGGUGCUUUGGGGA GGCCUGGAGUCA (SEQ ID NO: 95) |
| EMX1_T7 | Cas12i2 | AGCAAGGGACTATTCAGGGA (SEQ ID NO: 76) | AGAAAUCCGUCUUUCAUUGAC GGAGCAAGGGACUAUUCAGGGA (SEQ ID NO: 96) |
| EMX1_T7 | Cas9 | CTTTAGCAAGGGACTATTCA (SEQ ID NO: 77) | GUUUUAGAGCUAGAAAUAGCA AGUUAAAAUAAGGCUAGUCCG UUAUCAACUUGAAAAAGUGGC ACCGAGUCGGUGCCUUUAGCA AGGGACUAUUCA (SEQ ID NO: 97) |
| EMX1_T8 | Cas12i2 | AAAATTGAGCAATCTACCCT (SEQ ID NO: 78) | AGAAAUCCGUCUUUCAUUGAC GGAAAAUUGAGCAAUCUACCCU (SEQ ID NO: 98) |
| EMX1_T8 | Cas9 | TAAAATTGAGCAATCTACCC (SEQ ID NO: 79) | GUUUUAGAGCUAGAAAUAGCA AGUUAAAAUAAGGCUAGUCCG UUAUCAACUUGAAAAAGUGGC ACCGAGUCGGUGCUAAAAUUG AGCAAUCUACCC (SEQ ID NO: 99) |
| VEGFA_T1 | Cas12l2 | TGGGGGTGACCGCCGGAGCG (SEQ ID NO: 80) | AGAAAUCCGUCUUUCAUUGAC GGUGGGGGUGACCGCCGGAGCG (SEQ ID NO: 100) |

TABLE 5-continued

RNA guide sequences

| Target | Nuclease | Target Sequence | RNA Guide Sequence |
|---|---|---|---|
| VEGFA_T1 | Cas9 | TGGGGGTGACCGCCGGAGCG (SEQ ID NO: 81) | GUUUUAGAGCUAGAAAUAGCA AGUUAAAAUAAGGCUAGUCCG UUAUCAACUUGAAAAAGUGGC ACCGAGUCGGUGCUGGGGGUG ACCGCCGGAGCG (SEQ ID NO: 101) |
| VEGFA_T3 | Cas12i2 | GTTGACATTGTCCACACCTG (SEQ ID NO: 82) | AGAAAUCCGUCUUUCAUUGAC GGGUUGACAUUGUCCACACCUG (SEQ ID NO: 102) |
| VEGFA_T3 | Cas9 | TTGTTGACATTGTCCACACC (SEQ ID NO: 83) | GUUUUAGAGCUAGAAAUAGCA AGUUAAAAUAAGGCUAGUCCG UUAUCAACUUGAAAAAGUGGC ACCGAGUCGGUGCUUGUUGAC AUUGUCCACACC (SEQ ID NO: 103) |
| VEGFA_T5 | Cas12i2 | TTAAACTCTCCATGGACCAG (SEQ ID NO: 84) | AGAAAUCCGUCUUUCAUUGAC GGUUAAACUCUCCAUGGACCAG (SEQ ID NO: 104) |
| VEGFA_T5 | Cas9 | TTTTAAACTCTCCATGGACC (SEQ ID NO: 85) | GUUUUAGAGCUAGAAAUAGCA AGUUAAAAUAAGGCUAGUCCG UUAUCAACUUGAAAAAGUGGC ACCGAGUCGGUGCUUUUAAAC UCUCCAUGGACC (SEQ ID NO: 105) |

Approximately 16 hours prior to transfection, 100 μl of 25,000 HEK293T cells in DMEM/10% FBS+Pen/Strep were plated into each well of a 96-well plate. On the day of transfection, the cells were 70-90% confluent. For each well to be transfected, a mixture of 0.5 μl of Lipofectamine 2000 and 9.5 μl of Opti-MEM was prepared and then incubated at room temperature for 5-20 minutes (Solution 1). After incubation, the lipofectamine:OptiMEM mixture was added to a separate mixture containing 1 μL of the effector working solution, 1 μL of the guide working solution and 8 μL of the OptiMEM media (Solution 2). For apo controls the crRNA was not included in Solution 2. The solution 1 and solution 2 mixtures were mixed by pipetting up and down and then incubated at room temperature for 25 minutes. Following incubation, 20 μL of the Solution 1 and Solution 2 mixture were added dropwise to each well of a 96 well plate containing the cells. 72 hours post transfection, cells are trypsinized by adding 10 μL of TrypLE to the center of each well and incubated for approximately 5 minutes. 100 μL of D10 media was then added to each well and mixed to resuspend cells. The cells were then spun down at 500 g for 10 minutes, and the supernatant was discarded. QuickExtract buffer was added to ⅕ the amount of the original cell suspension volume. Cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. PCR1 products were purified by column purification. Round 2 PCR (PCR2) was done to add Illumina adapters and indexes. Reactions were then pooled and purified by column purification. Sequencing runs were done with a 150 cycle NextSeq v2.5 mid or high output kit.

For each target, the percentage of reads with C>T edits was measured for every C within the target. For all targets tested, each of the Cas12i2-deaminase fusions constructs demonstrated C>T editing at one or more cytosines within the target. FIG. 1 shows the highest C>T editing efficiency observed at different targets for each base editing construct. All the Cas12i2-deaminase fusion constructs had similar editing efficiencies at any given target. For EMX1_T4, EMX1_T7, EMX1_T8 and AAVS1_T5, the Cas12i2 base editing efficiency was comparable to that of the dCas9-A3A fusion construct.

Figure 2:
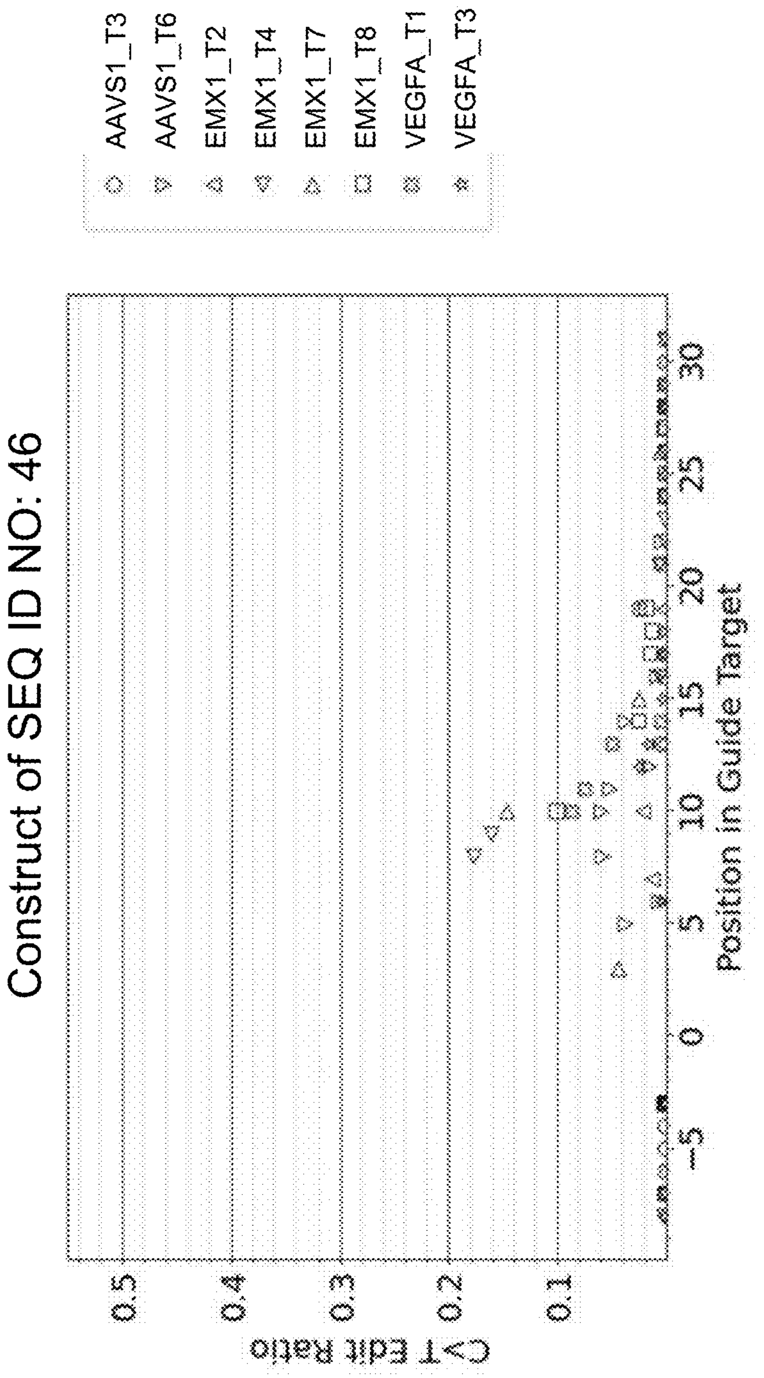
FIG. 2 is a graph that shows C>T base editing by a Cas12i2-NA3A-NUGI construct of SEQ ID NO: 46.
Figure 3:
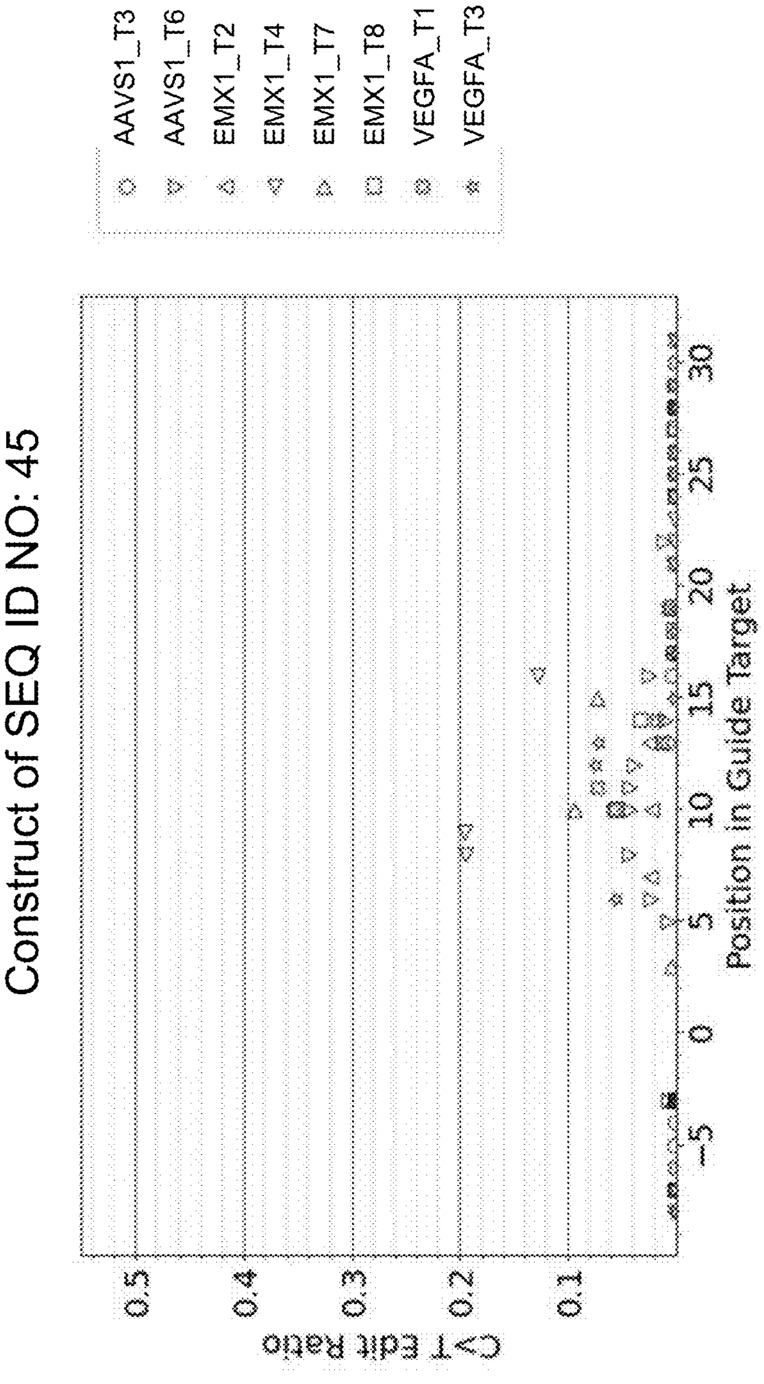
FIG. 3 is a graph that shows C>T base editing by a Cas12i2-NA3A-NUGI construct of SEQ ID NO: 45.
Figure 4:
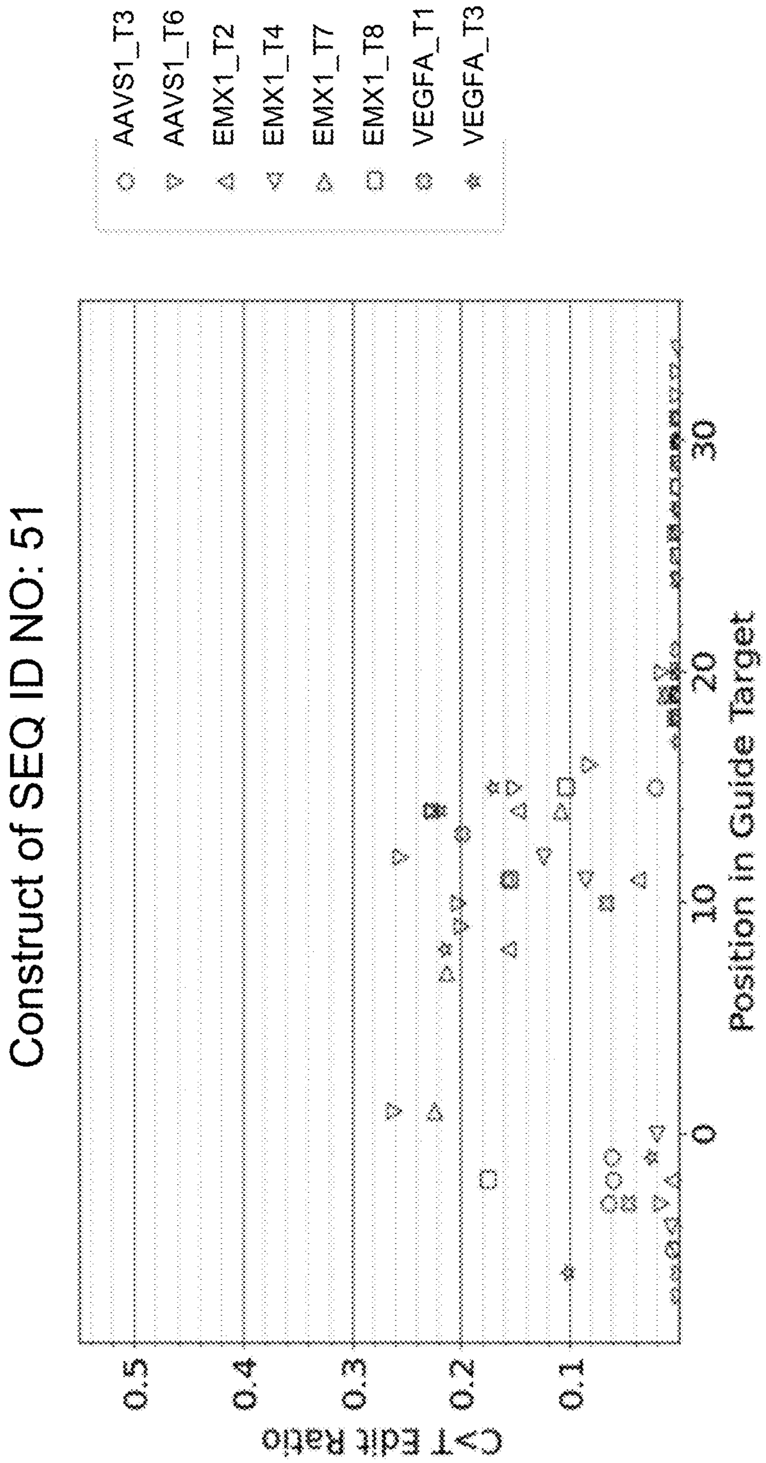
FIG. 4 is a graph that shows C>T base editing by a dCas9-NA3A-CUGI construct of SEQ ID NO: 51.
Figure 5:
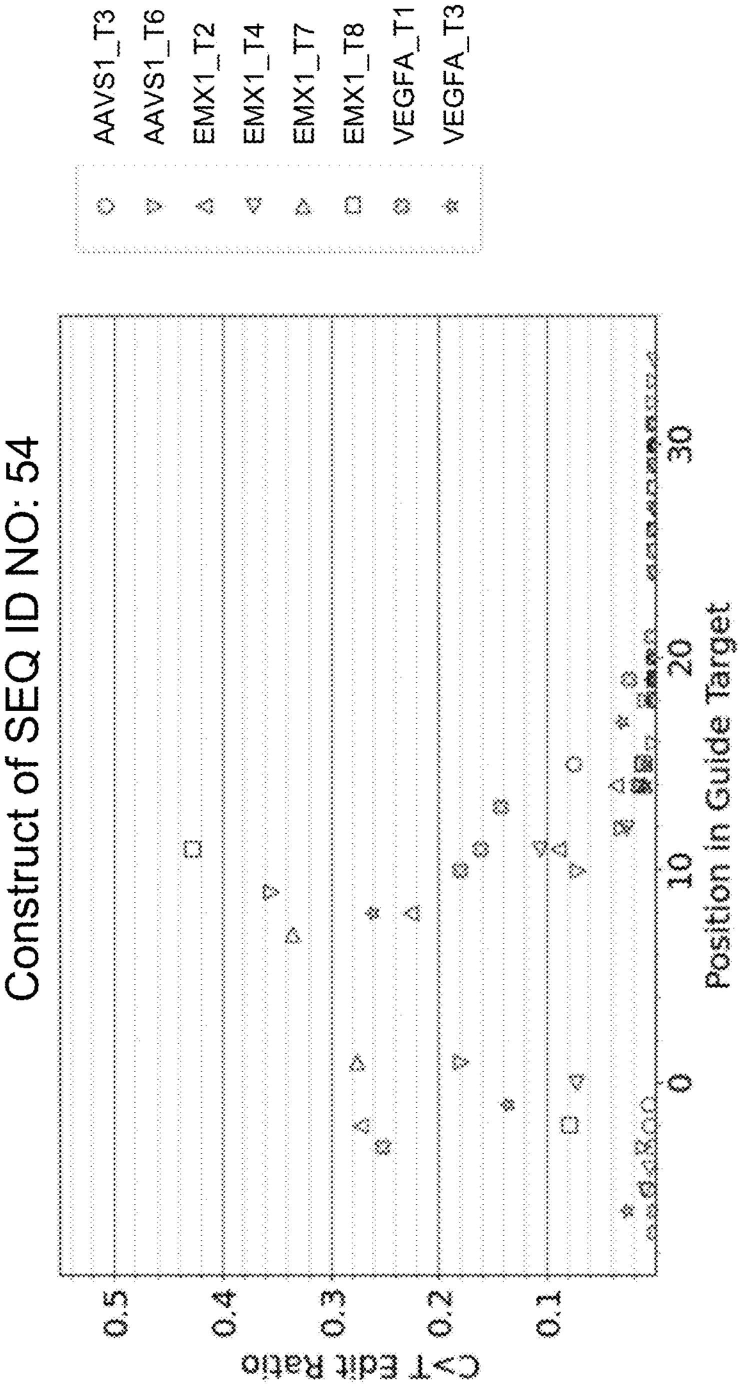
FIG. 5 is a graph that shows C>T base editing by an nCas9-NAID-CUGI construct of SEQ ID NO: 54.

FIG. 2 and FIG. 3 show base editing efficiencies of Cas12i2 constructs according to positions within the tested targets. Edit ratio is defined as the fraction of analyzed reads (typically N>=10K) aligning to the genomic reference sequence that also resulted in a gap in said sequence alignment. For each target, the position of C from the 5'-NTTN-3' PAM sequence (PAM is −3 to 0) is shown on the x-axis and the corresponding C>T editing efficiency at that C is plotted on the y-axis. These aggregated data sets show that for most Cas12i2-deaminase fusion constructs, the optimal editing window was 8-10 nucleotides from the PAM sequence. Compared to the Cas9 base editing constructs with the same deaminases, shown in FIG. 4 and FIG. 5, the Cas12i2 editing window was found to be narrower, potentially allowing for more specific editing compared to Cas9.

Figure 6A:
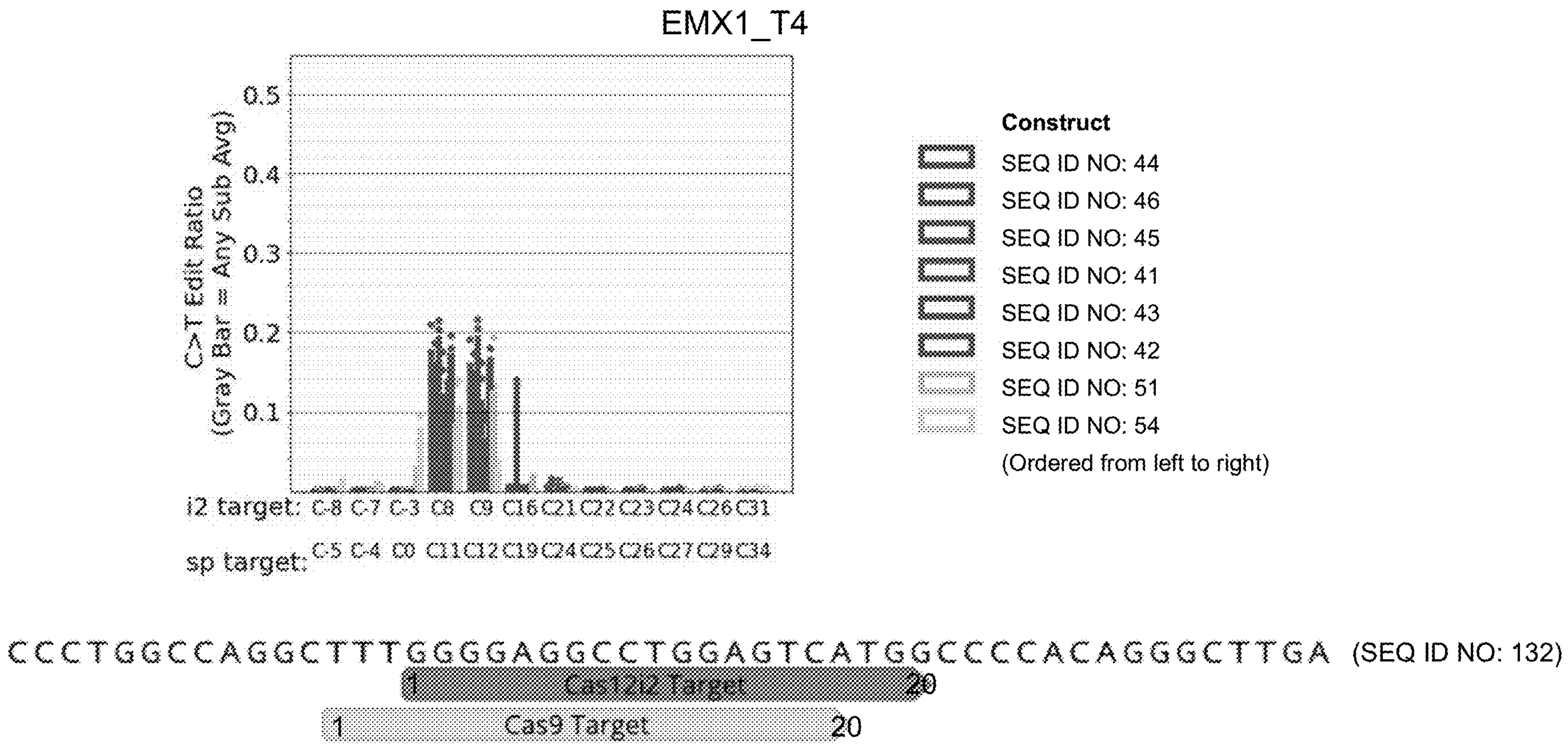
FIG. 6A is a bar graph that shows C>T base editing by Cas12i2-deaminase and Cas9-deaminase fusion polypeptides within an EMX1_T4 target. Positions of the Cas12i2 and Cas9 targets are shown in the schematic diagram below the graph.
Figure 6B:
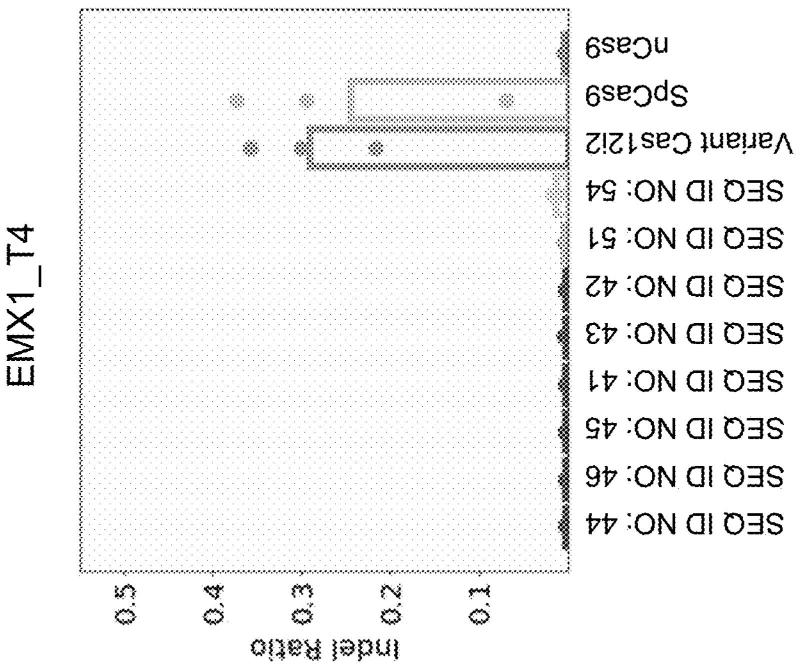
FIG. 6B is a bar graph that shows indel activity by Cas12i2 and Cas9 constructs within an EMX1_T4 target.
Figure 7A:
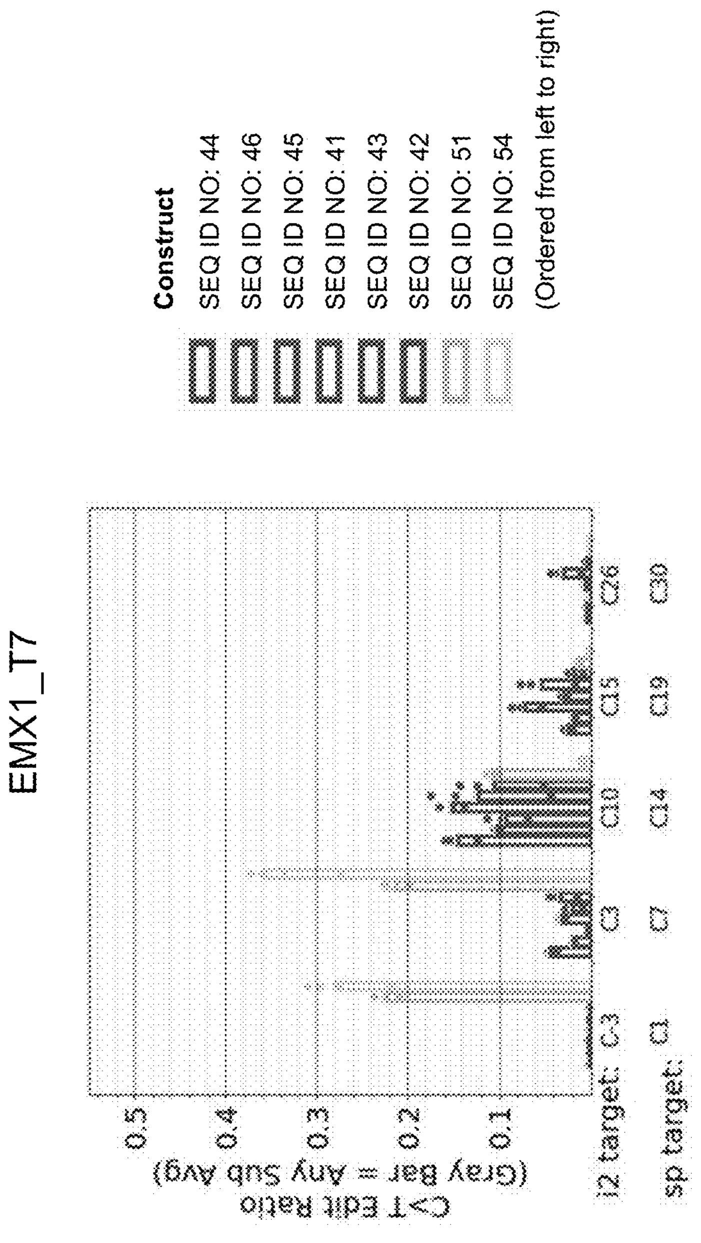
FIG. 7A is a bar graph that shows C>T base editing by Cas12i2-deaminase and Cas9-deaminase fusion polypeptides within an EMX1_T7 target. Positions of the Cas12i2 and Cas9 targets are shown.
Figure 7B:
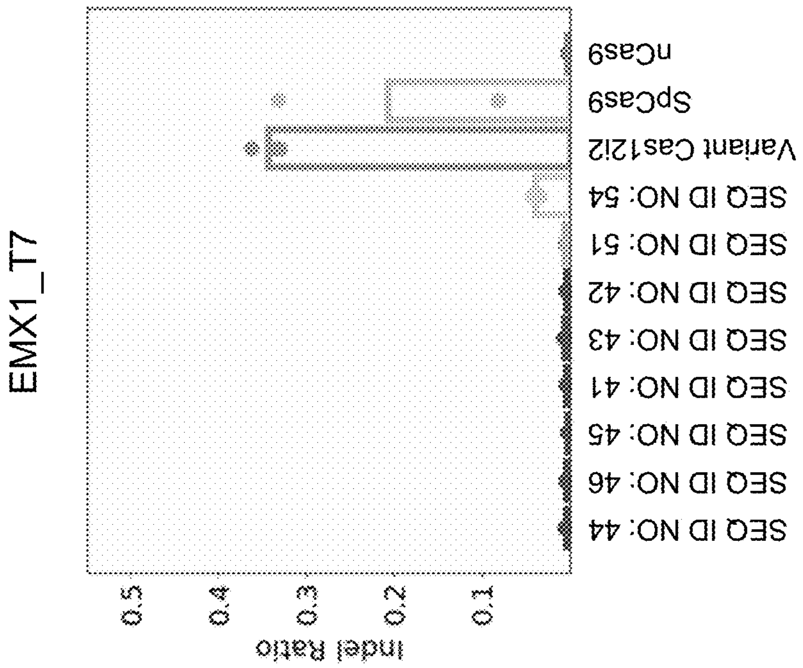
FIG. 7B is a bar graph that shows indel activity by Cas12i2 and Cas9 constructs within an EMX1_T7 target.

Comparisons of C>T base editing by Cas12i2- and Cas9-deaminase fusion constructs at various positions within the EMX1_T4 or EMX1_T7 targets are shown in FIG. 6A-B and FIG. 7A-B, respectively. As shown in FIG. 6A, dCas9-deaminase and nCas9-deaminase constructs induced C>T substitutions primarily at C-3, C8, and C9 (or C0, C10, and C11 according to Cas12i2 numbering). Cas12i2-deaminase constructs induced C>T substitutions primarily at positions C10 and C11, with Cas12i2-deaminase activity exceeding that of Cas9-deaminase activity. As shown in FIG. 7A, dCas9-deaminase and nCas9-deaminase fusion constructs favored C>T substitutions at positions Cl and C7 (or C-3 and C3 according to Cas12i2 numbering). Cas12i2-deaminase fusion constructs, however, favored C>T substitutions at positions C10 and C15. Additionally, as shown in both FIG. 6B and FIG. 7B, Cas12i2- and Cas9-deaminase fusion constructs did not demonstrate significant indel activity. Control sequences (e.g., variant Cas12i2 of SEQ ID NO: 4 and wild-type Cas9), however, were active nucleases.

Figure 8:
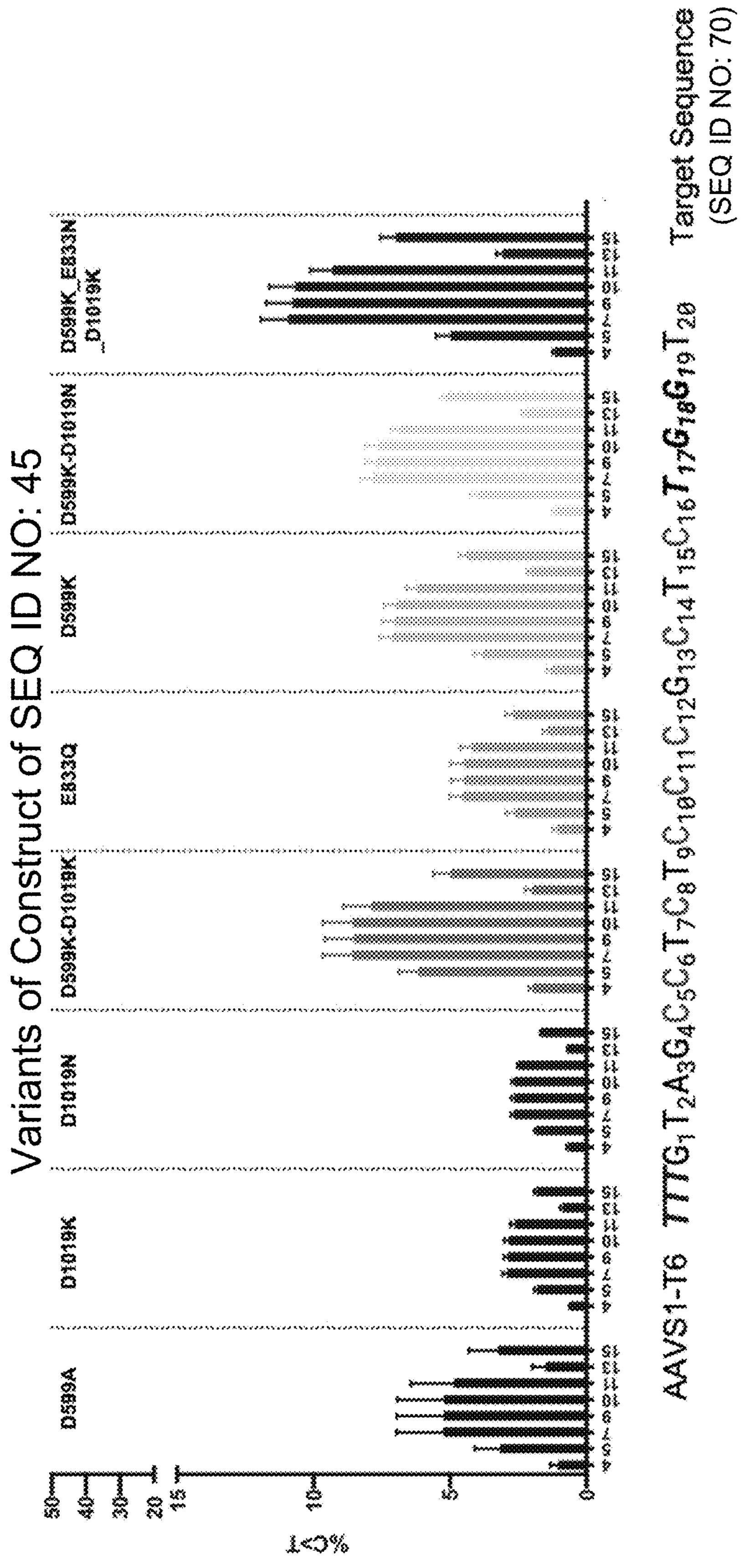
FIG. 8 is a bar graph that shows C>T base editing activity for variants of the Cas12i2-deaminase fusion polypeptide of SEQ ID NO: 45.
Figure 9:
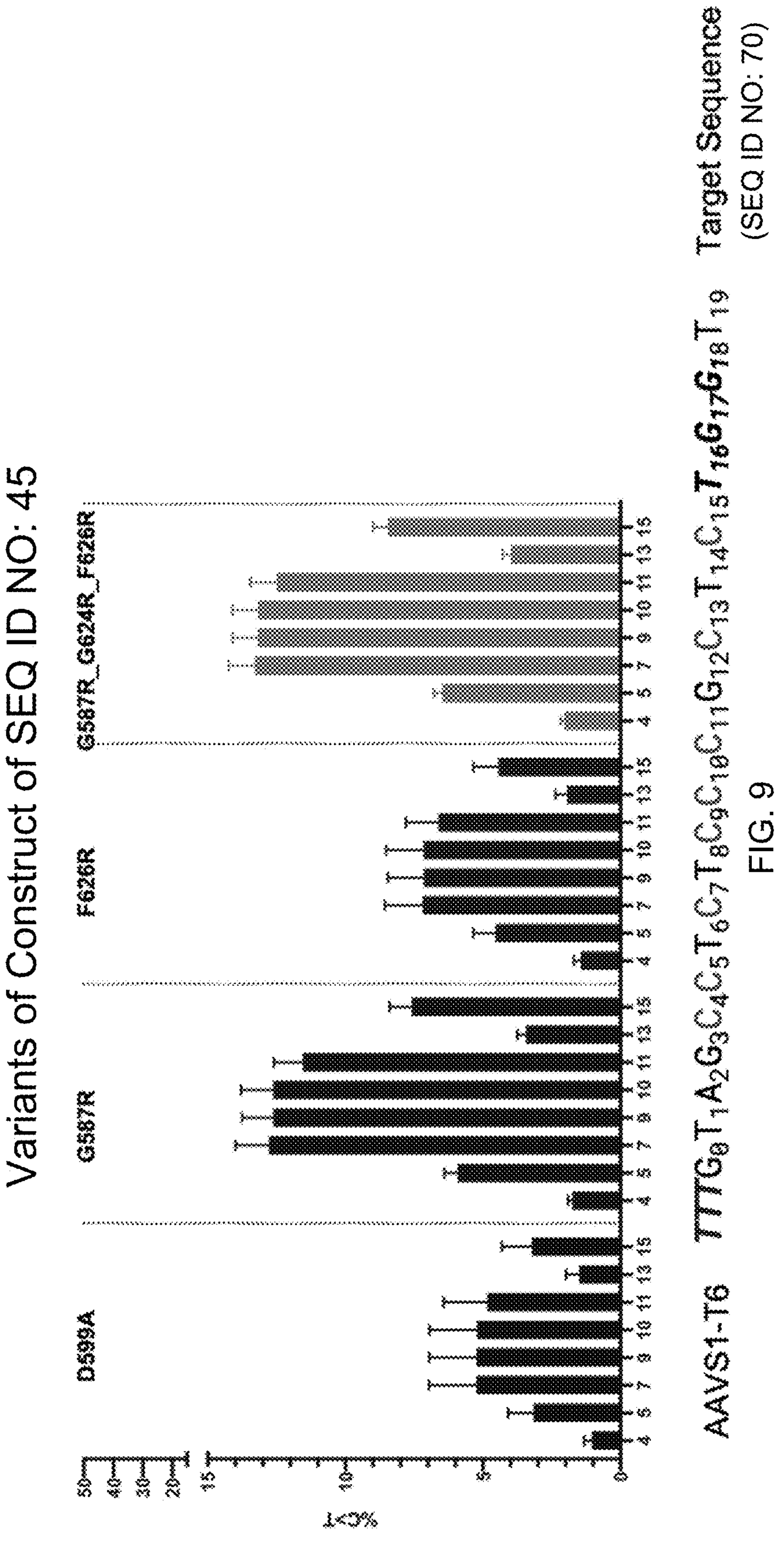
FIG. 9 is a bar graph that shows C>T base editing activity for variants of the Cas12i2-deaminase fusion polypeptide of SEQ ID NO: 45.

To increase base editing efficiency, several mutations were introduced into the dCas12i2-NA3A-CUGI fusion construct. These mutations are listed in Table 6. Most mutations substituted the catalytic site residues (D599, D1019 and E833) into negatively charged amino acid residues such as K, N or Q. Some additional mutations tested, such as F626R, G587R and G624R, were predicted from structural analysis to enhance the binding contacts with the dsDNA target. FIG. 8 and FIG. 9 show the raw editing efficiency for each of these variants. Two variants showed consistent fold improvement of 1.0-2.5 across most targets tested—the variant containing single point mutant G587R, and the variant containing combo mutations of G587R_G624R_F626R. In addition, some catalytic residue mutations such as D599K D1019K also showed an improvement over dCas12i2-NA3A-CUGI. Therefore, this result demonstrates that the base editing efficiency of dCas12i2 base editors can be improved significantly by engineering the dCas12i2 effector for improved substrate binding.

TABLE 6 dCas12i2 Variants for increased base editing activity.

| | Substitution(s) |
|---|---|
| Single Mutants | G587R<br>D599A<br>D599K<br>F626R<br>E833Q<br>E833N<br>D1019K<br>D1019N |
| Combination Mutants | D599K D1019K<br>D599K D1019N<br>D599K E833N D1019K<br>G587R G624R F626R |

Example 2—Base Editing Mediated by Cas12i4

This Example describes editing of multiple mammalian targets using inactivated Cas12i4 fused to a deaminase.

To generate base editing fusion constructs, the variant Cas12i4 of SEQ ID NO: 10 was first deactivated by mutating the catalytic D608 residue to alanine. See Table 7. The deactivated Cas12i4 variant (referred to as dCas12i4 herein and having the sequence set forth in SEQ ID NO: 59) was then fused to one of the two cytidine deaminases—humanAPOBEC3a (A3A) or Activation Induced Deaminase (AID). In addition to fusing the deaminase, a copy of Uracyl Glycosylase Inhibitor (UGI) was also fused. Various N- and C-terminal fusion combinations were generated, as shown in Table 8.

TABLE 7

Cas12i4 sequences.

| Cas12i4 | Sequence |
|---|---|
| Variant Cas12i4 (SEQ ID NO: 10) | MASISRPYGTKLRPDARKKEMLDKFFNTLTKGQRVFADLALCIYGSLT<br>LEMAKSLEPESDSELVCAIGWFRLVDKTIWSKDGIKQENLVKQYEAYS<br>GKEASEVVKTYLNSPSSDKYVWIDCRQKFLRFQRELGTRNLSEDFECM<br>LFEQYIRLTKGEIEGYAAISNMFGNGEKEDRSKKRMYATRMKDWLEA<br>NENITWEQYREALKNQLNAKNLEQVVANYKGNAGGADPFFKYSFSKE<br>GMVSKKEHAQQLDKFKTVLKNKARDLNFPNKEKLKQYLEAEIGIPVD<br>ANVYSQMFSNGVSEVQPKTTRNMSFSNEKLDLLTELKDLNKGDGFEY<br>AREVLNGFFDSELHTTEDKFNITSRYLGGDKSNRLSKLYKIWKKEGVD<br>CEEGIQQFCEAVKDKMGQIPIRNVLKYLWQFRETVSAEDFEAAAKAN<br>HLEEKISRVKAHPIVISNRYWAFGTSALVGNIMPADKRHQGEYAGQNF<br>KMWLRAELHYDGKKAKHHLPFYNARFFEEVYCYHPSVAEITPFKTKQ<br>FGCEIGKDIPDYVSVALKDNPYKKATKRILRAIYNPVANTTRVDKTTN<br>CSFMIKRENDEYKLVINRKISRDRPKRIEVGRTIMGYARNQTASDTYWI<br>GRLVPPGTRGAYRIGEWSVQYIKSGPVLSSTQGVNNSTTDQLVYNGM<br>PSSSERFKAWKKARMAFIRKLIRQLNDEGLESKGQDYIPENPSSFDVRG<br>ETLYVFNSNYLKALVSKHRKAKKPVEGILDEIEAWTSKDKDSCSLMRL<br>SSLSDASMQGIASLKSLINSYFNKNGCKTIEDKEKFNPVLYAKLVEVEQ<br>RRTNKRSEKVGRIAGSLEQLALLNGVEVVIGEADLGEVEKGKSKKQNS<br>RNMDWCAKQVAQRLEYKLAFHGIGYFGVNPMYTSHQDPFEHRRVAD<br>HIVMRARFEEVNVENIAEWHVRNFSNYLRADSGTGLYYKQATMDFLK<br>HYGLEEHAEGLENKKIKFYDFRKILEDKNLTSVIIPKRGGRIYMATNPV<br>TSDSTPITYAGKTYNRCNADEVAAANIVISVLAPRSKKNREQDDIPLIT<br>KKAESKSPPKDRKRSKTSQLPQK |
| dCas12i4(D608A) (SEQ ID NO: 59) | MASISRPYGTKLRPDARKKEMLDKFFNTLTKGQRVFADLALCIYGSLT<br>LEMAKSLEPESDSELVCAIGWFRLVDKTIWSKDGIKQENLVKQYEAYS<br>GKEASEVVKTYLNSPSSDKYVWIDCRQKFLRFQRELGTRNLSEDFECM<br>LFEQYIRLTKGEIEGYAAISNMFGNGEKEDRSKKRMYATRMKDWLEA<br>NENITWEQYREALKNQLNAKNLEQVVANYKGNAGGADPFFKYSFSKE<br>GMVSKKEHAQQLDKFKTVLKNKARDLNFPNKEKLKQYLEAEIGIPVD<br>ANVYSQMFSNGVSEVQPKTTRNMSFSNEKLDLLTELKDLNKGDGFEY<br>AREVLNGFFDSELHTTEDKFNITSRYLGGDKSNRLSKLYKIWKKEGVD<br>CEEGIQQFCEAVKDKMGQIPIRNVLKYLWQFRETVSAEDFEAAAKAN |

TABLE 7-continued

| Cas12i4 sequences. | |
|---|---|
| Cas12i4 | Sequence |
| | HLEEKISRVKAHPIVISNRYWAFGTSALVGNIMPADKRHQGEYAGQNF KMWLRAELHYDGKKAKHHLPFYNARFFEEVYCYHPSVAEITPFKTKQ FGCEIGKDIPDYVSVALKDNPYKKATKRILRAIYNPVANTTRVDKTTN CSFMIKRENDEYKLVINRKISRDRPKRIEVGRTIMGYDRNQTASDTYWI GRLVPPGTRGAYRIGEWSVQYIKSGPVLSSTQGVNNSTTDQLVYNGM PSSSERFKAWKKARMAFIRKLIRQLNDEGLESKGQDYIPENPSSFDVRG ETLYVFNSNYLKALVSKHRKAKKPVEGILDEIEAWTSKDKDSCSLMRL SSLSDASMQGIASLKSLINSYFNKNGCKTIEDKEKFNPVLYAKLVEVEQ RRTNKRSEKVGRIAGSLEQLALLNGVEVVIGEADLGEVEKGKSKKQNS RNMDWCAKQVAQRLEYKLAFHGIGYFGVNPMYTSHQDPFEHRRVAD HIVMRARFEEVNVENIAEWHVRNFSNYLRADSGTGLYYKQATMDFLK HYGLEEHAEGLENKKIKFYDFRKILEDKNLTSVIIPKRGGRIYMATNPV TSDSTPITYAGKTYNRCNADEVAAANIVISVLAPRSKKNREQDDIPLIT KKAESKSPPKDRKRSKTSQLPQK |

TABLE 8

| Cas12i4 base editing constructs. | |
|---|---|
| Construct | Sequence |
| bpNLS-AID-SGGS-UGI-2xSGGS-XTEN-2xSGGS-Cas12i4 (D608A)-npNLS (SEQ ID NO: 60) | MKRTADGSEFESPKKKRKV-MDPATFTYQFKNVRWAKGRRETYLCYVVKRRDSATSFSLDFGYLRNKN GCHVELLFLRYISDWDLDPGRCYRVTWFTSWSPCYDCARHVADFLRGN PNLSLRIFTARLYFCEDRKAEPEGLRRLAEAGVQIAIMTFKDYFYCWNTF VENHERTFKAWEGLHENSVRLSRQLRRILQ-SGGS-MTNLSDIIEKETGKQLVIQESILMLPEEVEEVIGNKPESDILVHTAYDEST DENVMLLTSDAPEYKPWALVIQDSNGENKIKML-SGGSSGGSSGSETPGTSESATPESSGGSSGGS-MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK-KRPAATKKAGQAKKKK |
| bpNLS-AID-2xSGGS-XTEN-2xSGGS-Cas12i4 (D608A)-npNLS-3xGGGGS-UGI (SEQ ID NO: 61) | MKRTADGSEFESPKKKRKV-MDPATFTYQFKNVRWAKGRRETYLCYVVKRRDSATSFSLDFGYLRNKN GCHVELLFLRYISDWDLDPGRCYRVTWFTSWSPCYDCARHVADFLRGN PNLSLRIFTARLYFCEDRKAEPEGLRRLAEAGVQIAIMTFKDYFYCWNTF VENHERTFKAWEGLHENSVRLSRQLRRILQ-SGGSSGGSSGSETPGTSESATPESSGGSSGGS-MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA |

TABLE 8-continued

Cas12i4 base editing constructs.

| Construct | Sequence |
|---|---|
| | FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK- KRPAATKKAGQAKKKK-GGGGSGGGGSGGGGS- MTNLSDIIEKETGKQLVIQESILMLPEEVEEVIGNKPESDILVHTAYDEST DENVMLLTSDAPEYKPWALVIQDSNGENKIKML |
| mH6-Cas12i4 (D608A)- npNLS-2xSGGS- XTEN-2xSGGS- AID-SGGS- UGI-SGGS- bpNLS (SEQ ID NO: 62) | MKIEEGKGHHHHHH- MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK- KRPAATKKAGQAKKKK- SGGSSGGSSGSETPGTSESATPESSGGSSGGS- MDPATFTYQFKNVRWAKGRRETYLCYVVKRRDSATSFSLDFGYLRNKN GCHVELLFLRYISDWDLDPGRCYRVTWFTSWSPCYDCARHVADFLRGN PNLSLRIFTARLYFCEDRKAEPEGLRRLAEAGVQIAIMTFKDYFYCWNTF VENHERTFKAWEGLHENSVRLSRQLRRILQ-SGGS- MTNLSDIIEKETGKQLVIQESILMLPEEVEEVIGNKPESDILVHTAYDEST DENVMLLTSDAPEYKPWALVIQDSNGENKIKML-SGGS- MKRTADGSEFESPKKKRKV |
| bpNLS-A3A- SGGS-UGI- 2xSGGS-XTEN- 2xSGGS-Cas12i4 (D608A)-npNLS (SEQ ID NO: 63) | MKRTADGSEFESPKKKRKV- MEASPASGPRHLMDPHIFTSNFNNGIGRHKTYLCYEVERLDNGTSVKMD QHRGFLHNQAKNLLCGFYGRHAELRFLDLVPSLQLDPAQIYRVTWFISW SPCFSAGCAGEVRAFLQENTHVRLRIFAARIYDYDYLYKEALQMLRDAG AQVSIMTYDEFKHCWDTFVDHQGCPFQPWDGLDEHSQALSGRLRAILQ NQGN-SGGS- MTNLSDIIEKETGKQLVIQESILMLPEEVEEVIGNKPESDILVHTAYDEST DENVMLLTSDAPEYKPWALVIQDSNGENKIKML- SGGSSGGSSGSETPGTSESATPESSGGSSGGS- MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF |

TABLE 8-continued

Cas12i4 base editing constructs.

| Construct | Sequence |
|---|---|
| | RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK-KRPAATKKAGQAKKKK |
| bpNLS-A3A-2xSGGS-XTEN-2xSGGS-Cas12i4 (D608A)-npNLS-3xGGGGS-UGI (SEQ ID NO: 64) | MKRTADGSEFESPKKKRKV-MEASPASGPRHLMDPHIFTSNFNNGIGRHKTYLCYEVERLDNGTSVKMD QHRGFLHNQAKNLLCGFYGRHAELRFLDLVPSLQLDPAQIYRVTWFISW SPCFSAGCAGEVRAFLQENTHVRLRIFAARIYDYDYLYKEALQMLRDAG AQVSIMTYDEFKHCWDTFVDHQGCPFQPWDGLDEHSQALSGRLRAILQ NQGN-SGGSSGGSSGSETPGTSESATPESSGGSSGGS-MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK-KRPAATKKAGQAKKKK-GGGGSGGGGSGGGGS-MTNLSDIIEKETGKQLVIQESILMLPEEVEEVIGNKPESDILVHTAYDEST DENVMLLTSDAPEYKPWALVIQDSNGENKIKML |
| mH6-Cas12i4 (D608A)-npNLS-2xSGGS-XTEN-2xSGGS-A3A-SGGS-UGI-SGGS-bpNLS (SEQ ID NO: 65) | MKIEEGKGHHHHHH-MASISRPYGTKLRPDARKKEMLDKFFNTLTKGQRVFADLALCIYGSLTL EMAKSLEPESDSELVCAIGWFRLVDKTIWSKDGIKQENLVKQYEAYSGK EASEVVKTYLNSPSSDKYVWIDCRQKFLRFQRELGTRNLSEDFECMLFE QYIRLTKGEIEGYAAISNMFGNGEKEDRSKKRMYATRMKDWLEANENI TWEQYREALKNQLNAKNLEQVVANYKGNAGGADPFFKYSFSKEGMVS KKEHAQQLDKFKTVLKNKARDLNFPNKEKLKQYLEAEIGIPVDANVYS QMFSNGVSEVQPKTTRNMSFSNEKLDLLTELKDLNKGDGFEYAREVLN GFFDSELHTTEDKFNITSRYLGGDKSNRLSKLYKIWKKEGVDCEEGIQQF CEAVKDKMGQIPIRNVLKYLWQFRETVSAEDFEAAAKANHLEEKISRVK AHPIVISNRYWAFGTSALVGNIMPADKRHQGEYAGQNFKMWLRAELHY DGKKAKHHLPFYNARFFEEVYCYHPSVAEITPFKTKQFGCEIGKDIPDYV SVALKDNPYKKATKRILRAIYNPVANTTRVDKTTNCSFMIKRENDEYKL VINRKISRDRPKRIEVGRTIMGYDRNQTASDTYWIGRLVPPGTRGAYRIG EWSVQYIKSGPVLSSTQGVNNSTTDQLVYNGMPSSSERFKAWKKARMA FIRKLIRQLNDEGLESKGQDYIPENPSSFDVRGETLYVFNSNYLKALVSK HRKAKKPVEGILDEIEAWTSKDKDSCSLMRLSSLSDASMQGIASLKSLIN SYFNKNGCKTIEDKEKFNPVLYAKLVEVEQRRTNKRSEKVGRIAGSLEQ LALLNGVEVVIGEADLGEVEKGKSKKQNSRNMDWCAKQVAQRLEYKL AFHGIGYFGVNPMYTSHQDPFEHRRVADHIVMRARFEEVNVENIAEWH VRNFSNYLRADSGTGLYYKQATMDFLKHYGLEEHAEGLENKKIKFYDF RKILEDKNLTSVIIPKRGGRIYMATNPVTSDSTPITYAGKTYNRCNADEV AAANIVISVLAPRSKKNREQDDIPLITKKAESKSPPKDRKRSKTSQLPQK-KRPAATKKAGQAKKKK-SGGSSGGSSGSETPGTSESATPESSGGSSGGS-MEASPASGPRHLMDPHIFTSNFNNGIGRHKTYLCYEVERLDNGTSVKMD QHRGFLHNQAKNLLCGFYGRHAELRFLDLVPSLQLDPAQIYRVTWFISW SPCFSAGCAGEVRAFLQENTHVRLRIFAARIYDYDYLYKEALQMLRDAG AQVSIMTYDEFKHCWDTFVDHQGCPFQPWDGLDEHSQALSGRLRAILQ NQGN-SGGS-MTNLSDIIEKETGKQLVIQESILMLPEEVEEVIGNKPESDILVHTAYDEST DENVMLLTSDAPEYKPWALVIQDSNGENKIKML-SGGS-MKRTADGSEFESPKKKRKV |

Each RNA guide sequence with a U6 promoter (Table 9) was cloned into a plasmid backbone and maxi-prepped. A working solution of 144 ng/μL effector plasmids was prepared in water (effector working solution), and a working solution of 50 ng/μL of corresponding guide RNA plasmids was prepared in water (guide working solution).

TABLE 9

RNA guide sequences

| Target | Nuclease | Target Sequence | RNA Guide Sequence |
|---|---|---|---|
| EMX1_T7 | Cas12i4 | AGCAAGGGACTATTCAGGGA (SEQ ID NO: 76) | AGACAUGUGUCCUCAGUGACA CAGCAAGGGACUAUUCAGGGA (SEQ ID NO: 121) |
| EMX1_T7 | Cas12i2 | AGCAAGGGACTATTCAGGGA (SEQ ID NO: 76) | AGAAAUCCGUCUUUCAUUGAC GGAGCAAGGGACUAUUCAGGGA (SEQ ID NO: 96) |
| EMX1_T7 | Cas9 | CTTTAGCAAGGGACTATTCA (SEQ ID NO: 77) | GUUUUAGAGCUAGAAAUAGCA AGUUAAAAUAAGGCUAGUCCG UUAUCAACUUGAAAAAGUGGC ACCGAGUCGGUGCCUUUAGCA AGGGACUAUUCA (SEQ ID NO: 97) |

Figure 10:
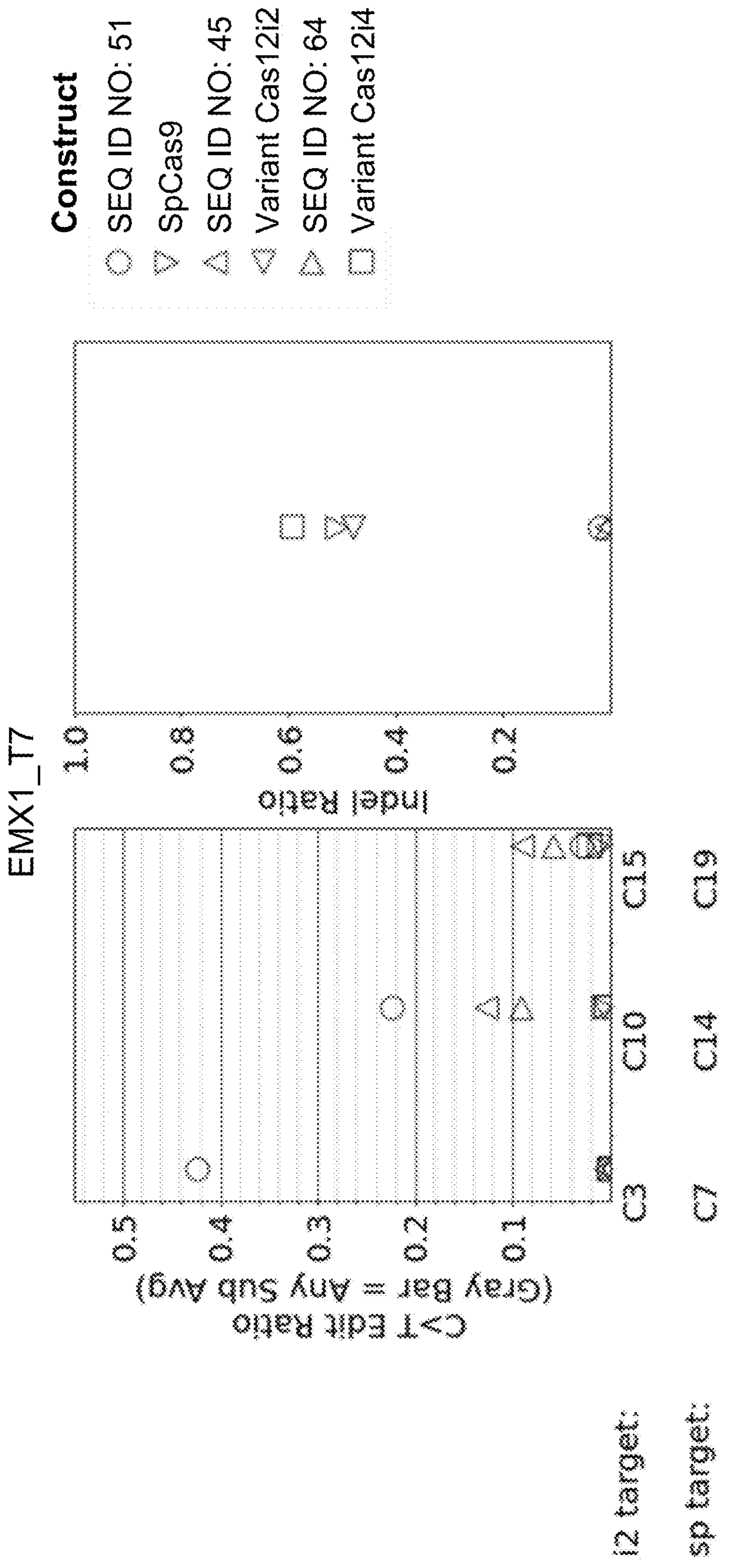
FIG. 10 is a graph that shows C>T base editing activity and indel activity by Cas12i2, Cas12i4, and Cas9 constructs of SEQ ID NO: 45, SEQ ID NO: 64, and SEQ ID NO: 51, respectively.

Cells were transfected and C>T reads were measured for every C within the target as described in Example 1. Each of the Cas12i4-deaminase fusions constructs demonstrated C>T editing at one or more cytosines within the EMX1_T7 target. FIG. 10 shows base editing efficiencies of Cas12i4, Cas12i2, and Cas9 constructs according to positions within the tested targets. As shown in FIG. 10, the Cas12i4-deaminase fusion construct of SEQ ID NO: 64 and the Cas12i2-deaminase fusion construct of SEQ ID NO: 45 each demonstrated C>T base editing activity at C10 and C15 within the Cas12i EMX1_T7 target, and the Cas9-deaminase fusion construct of SEQ ID NO: 51 demonstrated C>T base editing activity at C7 and C14 of the Cas9 EMX1_T7 target. Therefore, the fusion strategy used for Cas12i2 was compatible with Cas12i4, and Cas12i4-deaminase fusion constructs exhibited similar editing profiles as the Cas12i2-deaminase fusion constructs.

Therefore, this Example shows that like Cas12i4-deaminase constructs and Cas12i2-deaminase constructs introduced C>T edits in targets.

Other Embodiments

The disclosures of each and every patent, patent application, and publication cited herein are hereby incorporated herein by reference in their entirety. While this disclosure has been described with reference to specific embodiments, it is apparent that other embodiments and variations of this disclosure may be devised by others skilled in the art without departing from the true spirit and scope of the invention. The appended claims are intended to be construed to include all such embodiments and equivalent variations.

What is claimed is:

1. A Cas12i fusion protein comprising:

i) a Cas12i polypeptide comprising an alteration relative to the amino acid sequence of SEQ ID NO: 2, wherein the alteration is selected from the group comprising D581R, D911R, V1030G, S1046G, G624R, F626R, E1035R, and P868T, wherein the Cas12i polypeptide comprises at least 95% identity to the amino acid sequence of SEQ ID NO: 2, and wherein the Cas12i polypeptide has reduced nuclease activity or is a nuclease dead Cas12i polypeptide; and ii) a heterologous sequence comprising a deaminase domain.

2. The Cas12i fusion protein of claim 1, wherein the Cas12i polypeptide further comprises an alteration in one or more of D599, E833, and D1019.

3. The Cas12i fusion protein of claim 1, wherein the Cas12i polypeptide further comprises an alteration selected from the group comprising D599A, D599K, E833Q, E833N, D1019K, and D1019N.

4. The Cas12i fusion protein of claim 1, wherein the Cas12i polypeptide further comprises alterations selected from the group comprising:

(i) D1019K and D599K;

(ii) D1019N and D599K; or (iii) D1019K, E833N, and D599K.

5. The Cas12i fusion protein of claim 1, further comprising an alteration of G587R.

6. The Cas12i fusion protein of claim 1, which further comprises a second alteration relative to the amino acid sequence of SEQ ID NO: 2.

7. The Cas12i fusion protein of claim 6, wherein the second alteration comprises a substitution, insertion, or deletion.

8. The Cas12i fusion protein of claim 7, wherein the Cas12i polypeptide further comprises a third alteration relative to the amino acid sequence of SEQ ID NO: 2.

9. The Cas12i fusion protein of claim 1, which comprises a plurality of alterations relative to SEQ ID NO: 2, wherein the plurality of alterations comprises two or more of D581R, D911R, 1926R, and V1030G.

10. The Cas12i fusion protein of claim 1, which comprises a plurality of alterations relative to SEQ ID NO: 2, wherein the plurality of alterations comprises two or more of D581R, 1926R, and V1030G.

11. The Cas12i fusion protein of claim 1, which comprises a plurality of alterations relative to SEQ ID NO: 2, wherein the plurality of alterations comprises two or more of D581R, 1926R, V1030G, and S1046G.

12. The Cas12i fusion protein of claim 1, which comprises a plurality of alterations relative to SEQ ID NO: 2, wherein the plurality of alterations comprises two or more of D581R, G624R, F626R, 1926R, V1030G, E1035R, and S1046G.

13. The Cas12i fusion protein of claim 1, which comprises a plurality of alterations relative to SEQ ID NO: 2, wherein the plurality of alterations comprises two or more of D581R, G624R, F626R, P868T, 1926R, V1030G, E1035R, and S1046G.

14. The Cas12i fusion protein of claim 1, wherein the Cas12i polypeptide comprises at least 99% identity to the amino acid sequence of SEQ ID NO: 2.

15. The Cas12i fusion protein of claim 1, wherein the Cas12i fusion protein comprises an amino acid sequence according to SEQ ID NO: 45, or a sequence having at least 98% identity thereto, wherein the Cas12i fusion protein, when bound to an RNA guide, can introduce a substitution in a target sequence of a target nucleic acid.

16. The Cas12i fusion protein of claim 1, wherein the Cas12i fusion protein comprises an amino acid sequence according to SEQ ID NO: 41-44 or 46, or a sequence having at least 98% identity thereto, wherein the Cas12i fusion protein, when bound to an RNA guide, can introduce a substitution in a target sequence of a target nucleic acid.

17. The Cas12i fusion protein of claim 1, wherein the heterologous sequence is N-terminal of the Cas12i polypeptide.

18. The Cas12i fusion protein of claim 1, wherein the heterologous sequence is C-terminal of the Cas12i polypeptide.

19. The Cas12i fusion protein of claim 1, wherein the deaminase domain is chosen from a human APOBEC3 family deaminase, an Activation Induced Deaminase (AID), or an ABE8 deaminase, or a deaminase domain having at least 98% amino acid sequence identity thereto.

20. The Cas12i fusion protein of claim 19, wherein the human APOBEC3 family deaminase is A3A comprising an amino acid sequence of SEQ ID NO: 29, the AID comprises an amino acid sequence of SEQ ID NO: 28, or the ABE8 deaminase is ABE8_20 (SEQ ID NO: 30), or a deaminase domain having at least 98% amino acid sequence identity thereto.

21. The Cas12i fusion protein of claim 1, wherein the deaminase domain is chosen from human APOBEC3a (A3A; SEQ ID NO: 29) or Activation Induced Deaminase (AID; SEQ ID NO: 28), or a deaminase domain having at least 98% amino acid sequence identity thereto.

22. The Cas12i fusion protein of claim 1, wherein the heterologous sequence further comprises at least one peptide linker.

23. The Cas12i fusion protein of claim 22, wherein the at least one peptide linker comprises between 3 and 70 amino acid residues.

24. The Cas12i fusion protein of claim 22, wherein the at least one peptide linker comprises one or more Gly residues and one or more Ser residues.

25. The Cas12i fusion protein of claim 24, wherein the at least one peptide linker comprises a structure of:

$$L_1\text{-}L_2\text{-}L_3$$

wherein $L_1$ and $L_3$ are each independently chosen from SEQ ID NOs: 135-137, and $L_2$ is a polypeptide comprising between 0-40 amino acid residues.

26. The Cas12i fusion protein of claim 25, wherein $L_2$ is an amino acid sequence comprising at least 90% sequence identity to SGSETPGTSESATPES (SEQ ID NO: 106).

27. The Cas12i fusion protein of claim 22, wherein the at least one peptide linker comprises a sequence selected from SEQ ID NOs: 135-137.

28. The Cas12i fusion protein of claim 22, wherein the at least one peptide linker comprises one or more proline residues.

29. The Cas12i fusion protein of claim 22, wherein the at least one peptide linker comprises an amino acid sequence comprising at least 90% sequence identity to SEQ ID NO: 40.

30. The Cas12i fusion protein of claim 1, which does not comprise a linker sequence.

31. The Cas12i fusion protein of claim 1, wherein the fusion protein further comprises at least one additional heterologous sequence which is heterologous to both the Cas12i polypeptide and the deaminase domain.

32. The Cas12i fusion protein of claim 31, wherein the additional heterologous sequence comprises a Uracil Glycosylase Inhibitor (UGI) polypeptide.

33. The Cas12i fusion protein of claim 31, wherein the additional heterologous sequence comprises a nuclear localization sequence (NLS) polypeptide.

34. The Cas12i fusion protein of claim 1, wherein the Cas12i fusion protein forms a complex with a ribonucleic acid (RNA) guide wherein the RNA guide comprises a nuclease binding sequence and a DNA-binding sequence.

35. The Cas12i fusion protein of claim 34, wherein the DNA-binding sequence is a spacer sequence comprising 10 nucleotides to 50 nucleotides in length.

36. The Cas12i fusion protein of claim 34, wherein the DNA-binding sequence is a spacer sequence which is substantially identical to a target sequence of a target nucleic acid.

37. The Cas12i fusion protein of claim 36, wherein the target sequence is adjacent to a protospacer adjacent motif (PAM) sequence.

38. The Cas12i fusion protein of claim 37, wherein the PAM sequence comprises a sequence set forth as 5'-NTTN-3', wherein N is any nucleotide.

39. An in vitro or ex vivo method of introducing a substitution in a target sequence of a target nucleic acid in a cell, the method comprising:

contacting the cell with (i) a Cas12i fusion protein of claim 1, and (ii) an RNA guide, or a nucleic acid encoding (i) and (ii), thereby introducing the substitution.

40. A composition comprising:

a) the Cas12i fusion protein of claim 1; and b) an RNA guide or a nucleic acid encoding the RNA guide, wherein the RNA guide comprises a nuclease binding sequence and a DNA-binding sequence.

41. The Cas12i fusion protein of claim 1, further comprising an 1926R alteration relative to the amino acid sequence of SEQ ID NO: 2.

42. The Cas12i fusion protein of claim 1, wherein the N-terminal Met residue is absent.

* * * * *